(12) United States Patent
Kim et al.

(10) Patent No.: US 8,501,992 B2
(45) Date of Patent: Aug. 6, 2013

(54) HYDROXYPHENYL SULFONAMIDES AS ANTIAPOPTOTIC BCL INHIBITORS

(75) Inventors: Kyoung S. Kim, North Brunswick, NJ (US); Robert M. Borzilleri, New Hope, PA (US); Zhen-Wei Cai, Belle Mead, NJ (US); Kap-Sun Yeung, Madison, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 59 days.

(21) Appl. No.: 13/055,056

(22) PCT Filed: Jun. 8, 2009

(86) PCT No.: PCT/US2009/046579
§ 371 (c)(1),
(2), (4) Date: May 18, 2011

(87) PCT Pub. No.: WO2009/152082
PCT Pub. Date: Dec. 17, 2009

(65) Prior Publication Data
US 2011/0294793 A1 Dec. 1, 2011

Related U.S. Application Data

(60) Provisional application No. 61/059,853, filed on Jun. 9, 2008.

(51) Int. Cl.
*C07C 311/00* (2006.01)

(52) U.S. Cl.
USPC .................................. 564/80; 564/82; 564/93

(58) Field of Classification Search
USPC .............................................. 564/80, 82, 93
See application file for complete search history.

(56) References Cited

U.S. PATENT DOCUMENTS

| | | | |
|---|---|---|---|
| 6,727,264 | B1 | 4/2004 | Marzabadi et al. |
| 7,199,135 | B2 | 4/2007 | Marzabadi et al. |
| 7,759,518 | B2 * | 7/2010 | Maderna et al. ................ 564/84 |
| 2002/0086887 | A1 | 7/2002 | Augeri et al. |
| 2004/0186103 | A1 | 9/2004 | Mazabadi et al. |

FOREIGN PATENT DOCUMENTS

| | | |
|---|---|---|
| GB | 1556279 | 6/1977 |
| WO | WO 2004/026292 | 4/2004 |
| WO | WO 2004/073634 | 9/2004 |
| WO | WO 2005/049593 | 6/2005 |
| WO | WO 2007/040650 | 4/2007 |
| WO | WO 2007/076055 | 7/2007 |
| WO | WO2007/076055 A2 * | 7/2007 |
| WO | WO 2008/093919 | 8/2008 |
| WO | WO2008/129288 * | 10/2008 |

OTHER PUBLICATIONS

Database Chemcats Chemical Abstracts Service XP002545558 Database accession No. 2064116242 (2009).
Porter et al., Bioorganic & Medicinal Chemistry Letters 19 (2009) 230-233.
Dolezal et al., Archiv der Pharmazie (2009), 342(2), 113-119.
Supuran et al., Journal of Enzyme Inhibition and Medicinal Chemistry (2004), 19(3), 237-248.
Gupta et al., Bioorganic & Medicinal Chemistry (2003), 11(14), 3065-3071.
Kumar et al., Bioorganic & Medicinal Chemistry (2003), 11(3), 421-426.
You et al., Chemical Communications (2001), (17), 1546-1547.
Clare et al., Journal of Medicinal Chemistry (2001), 44(13), 2253-2258.
You et al., Chemical Communications (2000), (19), 1963-1964.
Scozzafava et al., European Journal of Pharmaceutical Sciences (2000), 11(1) 69-79.
Supuran et al., J. Enzyme Inhibition, 2000, vol. 15, pp. 111-128.
Scozzafava et al., European Journal of Medicinal Chemistry (2000), 35(3)) 299-307.
Scozzafava et al. Journal of Medicinal Chemistry (2000), 43(9), 1858-1865.
Scozzafava et al., Bioorganic & Medicinal Chemistry Letters 2000, 10(5), 499-502.
Scozzafava et al., Bioorganic & Medicinal Chemistry Letters 2000, 8(3), 637-640.
Supuran et al., European Journal of Pharmaceutical Sciences (2000), 10(1) 67-76.
Guo et al., Tetrahedron 53(12), 4145-4158 (1997).
Reed, Cell Death and Differentiation (2006) 13, 1378-1386.
Chan et al., Clinical and Experimental Pharmacology and Physiology (2004) 31, 119-128.
Degterev et al., Nature Cell Biology vol. 3 Feb. 2001 173-182.
Int'l Preliminary Report on Patentability, PCT/US2009/04679 (2010).
Written Opinion of the Int'l Searching Auth., PCT/US2009/046579 (2009).

* cited by examiner

*Primary Examiner* — Johann R Richter
*Assistant Examiner* — Pancham Bakshi
(74) *Attorney, Agent, or Firm* — Mary K. VanAtten; Gary D. Greenblatt

(57) ABSTRACT

The present invention provides compound of Formula (I): or a stereoisomer, tautomer, salt or solvate thereof, wherein the variables are defined herein. The compounds of formula (I) are inhibitors of Bcl-2 family antiapoptotic proteins, compositions containing the compounds and methods of treating diseases using the compounds.

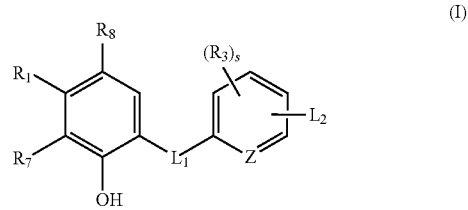

12 Claims, No Drawings

HYDROXYPHENYL SULFONAMIDES AS ANTIAPOPTOTIC BCL INHIBITORS

FIELD OF THE INVENTION

The invention relates to novel hydroxyphenylsulfonamide compounds that are useful as anti-cancer agents. This invention also relates to a method of using the compounds in the treatment of proliferative and other diseases and to pharmaceutical compositions containing the compounds.

BACKGROUND

Apoptosis, or programmed cell death, plays an important role ensuring a proper balance between cell proliferation and cell loss in multicellular organisms. Disruption of this pathway is implicated in many human diseases, including cancer (J. C. Reed, Cell Death and Differentiation 13 (2006) 1379-1386]. Targeting critical apoptosis regulators is an attractive approach for the development of anticancer therapeutics and therapies for other human diseases caused by biologically impaired apoptosis.

Proteins belonging to the Bcl-2 (B-cell lymphocyte/leukemia-2) family play a central role in regulating apoptosis [Chan, S-L and V. C. Yu, Clin. and Exper. Pharmacol. and Physiol. 31 (2004) 119-128]. This family contains proteins promoting cell survival (Bcl-2, Bcl-b, Bcl-Xl, Bcl-w, Mcl-1, A1) and proteins promoting cell death (i.e., Bak, Bax, Bim, Bid, etc). Family members share up to four Bcl-2 homology (BH) domains and formation of homo- or heterodimers via these BH domains modulates each other's function(s) as cell death agonists or antagonists. Cellular ratios between proapoptotic and prosurvival family members dictate cellular fate. For example, prosurvival Bcl-2 family protein levels are elevated in many cancers enabling tumor cells more resistant to apoptosis. Consequently, antagonizing prosurvival Bcl-2 family protein function in tumor cells is a promising strategy for the development of anticancer therapeutics. Conceptually this therapeutic strategy is also applicable towards other diseases brought about by the disrupted cellular balance of proapoptotic and prosurvival Bcl-2 family proteins.

The present invention describes discovery of small molecule Bcl-2 family prosurvival protein antagonists for cancer treatment and other diseases caused by impaired apoptosis.

SUMMARY OF THE INVENTION

The invention is directed to compounds of Formula I that which are useful as inhibitors of Bcl-2 family antiapoptotic proteins, and are useful for the treatment of cancer, or stereoisomers, tautomers, pharmaceutically acceptable slats, solvates or prodrugs thereof.

The present invention also provides processes and intermediates for making the compounds of the present invention or stereoisomers, tautomers, pharmaceutically acceptable salts, solvates, or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for inhibition of Bcl-2 family antiapoptotic proteins comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating cancers comprising administering to a host in need of such treatment a therapeutically effective amount of at least one of the compounds of the present invention or stereoisomers, tautomers, pharmaceutically acceptable salts, solvates, or prodrugs thereof.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment of cancers.

These and other features of the invention will be set forth in the expanded form as the disclosure continues.

DETAILED DESCRIPTION OF THE EMBODIMENTS OF THE INVENTION

The invention provides for compounds of formula I, pharmaceutical compositions employing such compounds and for methods of using such compounds.

In accordance with the invention, there are disclosed compounds of formula I

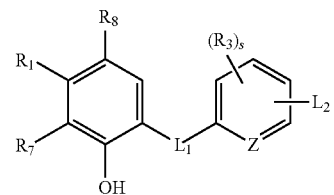

or salt thereof, wherein $L_1$ is —SO$_2$N(R$_2$)—CH$_2$—;

$L_2$ is R$_5$, —(CH$_2$)$_n$—N(R$_4$)—CO—(CH$_2$)$_l$R$_5$, —(CH$_2$)$_n$—N(R$_4$)—CO—O—C$_{1-6}$alkyl, —CH$_2$—N(R$_4$)—SO$_2$—R$_5$, —CH$_2$—N(R$_4$)—CO—N(R$_4$)—R$_5$, —CO—N(R$_4$)—(CHR)$_n$—R$_5$, —CH$_2$—N(R$_4$)—CH$_2$—R$_5$., —O—R$_{5a}$, —CH$_2$—S—(CH$_2$)$_l$—R$_5$, —(CH$_2$)$_n$—R$_{5a}$, —CO—R$_{5b}$;

n is 0, 1, 2, or 3;

l is 0, 1, 2, or 3;

Z is CH, N or N-oxide;

R, at each occurrence, is independently selected from H, C$_{1-6}$ alkyl, C$_{1-6}$ haloalkyl, and —(CH$_2$)$_r$-aryl;

R$_1$ is selected from hydrogen, F, Br, Cl, NO$_2$, CN, C$_{1-6}$ alkyl, —(CHR)$_r$-aryl substituted with 0-2 R$_{1a}$, alkoxy, aryloxy substituted with 0-2 R$_{1a}$, heterocyclyl substituted with 0-2 R$_{1a}$;

R$_{1a}$ is selected from H, C$_{1-6}$ alkyl, C$_{1-6}$ haloalkyl, Cl, Br, F, NO$_2$, CN, (CHR)$_r$OH, (CHR)$_r$SH, (CHR)$_r$OR$_b$, (CHR)$_r$S(O)$_p$R$_b$, (CHR)$_r$C(O)R$_d$, (CHR)$_r$NR$_a$R$_a$, (CHR)$_r$C(O)NR$_a$R$_a$, (CHR)$_r$C(O)NR$_a$OR$_b$, (CHR)$_r$NR$_a$C(O)R$_d$, (CHR)$_r$NR$_a$C(O)OR$_b$, (CHR)$_r$OC(O)NR$_a$R$_a$, (CHR)$_r$C(O)OR$_d$, (CHR)$_r$S(O)$_p$NR$_a$R$_a$, (CHR)$_r$NR$_a$S(O)$_p$R$_b$, and a (CHR)$_r$—C$_{3-6}$ carbocyclic residue substituted with 0-5 R$_e$;

R$_2$ is selected from hydrogen, C$_{1-9}$ alkyl, C$_{1-9}$ alkenyl, C$_{1-6}$ haloalkyl, —(CH$_2$)$_r$-cycloalkyl substituted with 0-5 R$_{2a}$, —(CH$_2$)$_r$-aryl substituted with 0-5 R$_{2a}$, —(CH$_2$)$_r$-heterocycloalkyl substituted with 0-3 R$_{2a}$, R$_{2a}$, at each occurrence, is selected from C$_{1-6}$ alkyl, C$_{2-6}$ alkenyl, C$_{2-6}$ alkynyl, C$_{1-6}$ haloalkyl, (C$_2$)$_r$C$_{3-6}$ cycloalkyl, Cl, Br, F, $NO_2$, CN, $(CHR)_rOH$, $(CHR)_rSH$, $(CHR)_rOR_b$, $(CHR)_rS(O)_pR_b$, $(CHR)_rC(O)R_d$, $(CHR)_rNR_aR_a$, $(CHR)_rC(O)NR_aR_a$, $(CHR)_rC(O)NR_aOR_b$, $(CHR)_rNR_aC(O)R_d$, $(CHR)_rNR_aC(O)OR_b$, $(CHR)_rOC(O)NR_aR_a$, $(CHR)_rC(O)OR_d$, $(CHR)_rS(O)_pNR_aR_a$, $(CHR)_rNR_aS(O)_pR_b$, and a $(CHR)_r$—$C_{3-10}$ carbocyclic residue substituted with 0-5 $R_e$;

$R_3$ is selected from hydrogen, F, Br, Cl, $C_{1-6}$ alkyl, $(CHR)_r$—$C_{3-6}$ cycloalkyl, $(CHR)_r$-aryl substituted with 0-3 $R_{3a}$, —O—$C_{1-6}$alkyl, —O—$(CHR)_r$-aryl substituted with 0-3 $R_{3a}$, and heterocycle substituted with 0-2 $R_{3a}$;

$R_{3a}$, at each occurrence, is selected from $C_{1-6}$ alkyl, $C_{2-6}$ alkenyl, $C_{2-6}$ alkynyl, $C_{1-6}$ haloalkyl, $(CH_2)_rC_{3-6}$ cycloalkyl, Cl, Br, F, $NO_2$, CN, $(CHR)_rOH$, $(CHR)_rSH$, $(CHR)_rOR_b$, $(CHR)_rS(O)_pR_b$, $(CHR)_rC(O)R_d$, $(CHR)_rNR_aR_a$, $(CHR)_rC(O)NR_aR_a$, $(CHR)_rC(O)NR_aOR_b$, $(CHR)_rNR_aC(O)R_d$, $(CHR)_rNR_aC(O)OR_b$, $(CHR)_rOC(O)NR_aR_a$, $(CHR)_rC(O)OR_d$, $(CHR)_rS(O)_pNR_aR_a$, $(CHR)_rNR_aS(O)_pR_b$, and a $(CHR)_r$—$C_{3-6}$ carbocyclic residue substituted with 0-5 $R_e$;

$R_4$ is selected from hydrogen, $C_{1-6}$ alkyl substituted with 0-3 $R_e$, $(CHR)_r$—$C_{3-6}$cycloalkyl, $(CHR)_r$-aryl substituted with 0-2 $R_{4a}$, and $(CHR)_r$-heterocycle substituted with 0-2 $R_{4a}$;

$R_{4a}$, at each occurrence, is selected from $C_{1-6}$ alkyl, $C_{2-6}$ alkenyl, $C_{2-6}$ alkynyl, $(CH_2)_rC_{3-6}$ cycloalkyl, Cl, Br, F, $NO_2$, CN, $(CHR)_rOH$, $(CHR)_rSH$, $(CHR)_rOR_b$, $(CHR)_rS(O)_pR_b$, $(CHR)_rC(O)R_d$, $(CHR)_rNR_aR_a$, $(CHR)_rC(O)NR_aR_a$, $(CHR)_r$ $C(O)NR_aOR_b$, $(CHR)_rNR_aC(O)R_d$, $(CHR)_rNR_aC(O)OR_b$, $(CHR)_rOC(O)NR_aR_a$, $(CHR)_rC(O)OR_d$, $(CHR)_rS(O)_pNR_aR_a$, $(CHR)_rNR_aS(O)_pR_b$, and a $(CHR)_r$—$C_{3-6}$ carbocyclic residue substituted with 0-5 $R_e$;

$R_5$ is selected from $C_{1-6}$ alkyl substituted with 0-3 $R_6$, $C_{3-10}$ carbocyclic residue substituted with 0-5 $R_6$, awl substituted with 0-5 $R_6$, and heterocyclyl substituted with 0-5 $R_6$;

$R_{5a}$ is aryl substituted with 0-5 $R_6$;

$R_{5b}$ is aryl substituted with 0-5 $R_6$ or heterocyclyl substituted with 0-5 $R_6$;

$R_6$ is selected from hydrogen, H, F, Cl, Br, $OCF_3$, $CF_3$, CN, $NO_2$, =O, $N_3$, $(CHR)_rOH$, $(CHR)_rSH$, $(CHR)_rOR_b$, $(CHR)_rS(O)_pR_b$, $(CHR)_rC(O)R_d$, $(CHR)_rNR_aR_a$, $(CHR)_rC(O)NR_aR_a$, $(CHR)_rC(O)NR_aOR_b$, $(CHR)_rNR_aC(O)R_d$, $(CHR)_rNR_aC(O)OR_b$, $(CHR)_rOC(O)NR_aR_a$, $(CHR)_rNR_aC(O)NR_aR_a$, $(CHR)_rC(O)OR_d$, $(CHR)_rS(O)_pNR_aR_a$, $(CHR)_rN-R_aS(O)_pR_b$, $SO_2F$, or $C_{1-6}$ alkyl substituted with 0-2 $R_e$, $C_{1-6}$ haloalkyl a $(CHR)_r$—$C_{3-6}$ carbocyclic residue substituted with 0-5 $R_e$, and a $(CHR)_r$-heterocyclyl substituted with 0-5 $R_e$;

$R_a$, at each occurrence, is independently selected from H, $C_{1-6}$ alkyl substituted with 0-2 $R_e$, $C_{1-6}$ haloalkyl, $C_{3-6}$ alkenyl substituted with 0-2 $R_e$, $C_{3-6}$ alkynyl substituted with 0-2 $R_e$, a $(CH_2)_r$—$C_{3-10}$ carbocyclic residue substituted with 0-5 $R_e$, and a $(CH_2)_r$— heterocyclyl substituted with 0-2 $R_e$;

$R_b$, at each occurrence, is independently selected from $C_{1-6}$ alkyl substituted with 0-2 $R_e$, $C_{1-6}$ haloalkyl, $C_{3-6}$ alkenyl substituted with 0-2 $R_e$, $C_{3-6}$ alkynyl substituted with 0-2 $R_e$, a $(CH_2)_r$—$C_{3-10}$ carbocyclic residue substituted with 0-5 $R_e$, and a $(CH_2)_r$— heterocyclyl substituted with 0-2 $R_e$;

$R_d$, at each occurrence, is independently selected from H, $C_{1-6}$ alkyl substituted with 0-2 $R_e$, $C_{1-6}$ haloalkyl, $C_{3-6}$ alkenyl substituted with 0-2 $R_e$, $C_{3-6}$ alkynyl substituted with 0-2 $R_e$, a $(CH_2)_r$—$C_{3-10}$ carbocyclic residue substituted with 0-5 $R_e$, and a $(CH_2)_r$-heterocyclyl substituted with 0-2 $R_e$;

$R_e$, at each occurrence, is independently selected from $C_{1-6}$ alkyl, $C_{2-6}$ alkenyl, $C_{2-6}$ alkynyl, $(CH_2)_rC_{3-6}$ cycloalkyl, Cl, F, Br, CN, $NO_2$, $CO_2H$, $CO_2C_{1-5}$alkyl, $(CF_2)_rCF_3$, $(CH_2)_rOC_{1-5}$alkyl, OH, SH, $(CH_2)_rSC_{1-5}$ alkyl, $(CH_2)_rNR_fR_f$, and $(CH_2)_r$phenyl;

$R_f$, at each occurrence, is independently selected from H, $C_{1-5}$ alkyl, and $C_{3-6}$ cycloalkyl, and phenyl;

$R_7$ is selected from F, Cl, $CF_3$, $C(O)NR_aR_a$, and $C(O)OR_b$;

$R_8$ is selected from hydrogen, F, Cl, $CF_3$, $C(O)NR_aR_a$, and $C(O)OR_b$;

p, at each occurrence, is independently selected from 0, 1, and 2;

r, at each occurrence, is independently selected from 0, 1, 2, 3, and 4;

s is selected from 0, 1, and 2.

In another embodiment, there is provided compounds of formula (I), wherein $R_1$ is selected from hydrogen, F, Br, Cl, $C_{1-6}$ alkyl, and —$(CHR)_r$-phenyl substituted with 0-2 $R_{1a}$;

$R_2$ is selected from hydrogen, $C_{1-9}$ alkyl, $C_{1-9}$ alkenyl, —$(CH_2)_r$-cyclohexyl substituted with 0-5 $R_{2a}$, —$(CH_2)_r$-phenyl substituted with 0-5 $R_{2a}$, and indolinyl substituted with 0-1 $R_{2a}$;

$R_{2a}$, at each occurrence is selected from $C_{1-6}$ alkyl, $C_{1-6}$ haloalkyl, $(CH_2)_rC_{3-6}$ cycloalkyl, Cl, Br, F, $NO_2$, CN, $(CHR)_rOH$, $(CHR)_rOR_b$, $(CHR)_rS(O)_pR_b$, and a $(CHR)_r$—$C_{3-6}$ carbocyclic residue substituted with 0-5 $R_e$.

In another embodiment, there is provided compounds of formula (I), wherein $R_3$ is selected from hydrogen, F, Br, Cl, $(CH_2)_r$-phenyl substituted with 0-3 $R_{3a}$, —O—$C_{1-6}$alkyl, and —$O(CH_2)_r$-phenyl substituted with 0-3 $R_{3a}$;

$R_{3a}$, at each occurrence is selected from $C_{1-6}$ alkyl, $(CH_2)_r$ $C_{3-6}$ cycloalkyl, $CF_3$, Cl, Br, F, $NO_2$, and CN;

$R_4$ is selected from hydrogen, $C_{1-6}$ alkyl substituted with 0-1 $R_e$, cyclopropyl, cyclopentyl, cyclohexyl, and $(CH_2)_r$-phenyl substituted with 0-2 $R_{4a}$ and $(CHR)_r$-heterocycle substituted with 0-2 $R_{4a}$;

$R_{4a}$, at each occurrence, is selected from $C_{1-6}$ alkyl, $(CH_2)_r$ $C_{3-6}$ cycloalkyl, Cl, Br, F, $NO_2$, CN, $(CH_2)_rS(O)_pR_b$, $(CHR)_r$ $C(O)R_d$, and a $(CHR)_r$—$C_{3-6}$ carbocyclic residue substituted with 0-5 $R_e$.

In another embodiment, there is provided compounds of formula (I), wherein $R_1$ is hydrogen;

$R_2$ is selected from hydrogen, $C_{1-9}$ alkyl, —$(CH_2)_r$-cyclohexyl substituted with 0-5 $R_{2a}$, —$(CH_2)_r$-phenyl substituted with 0-2 $R_{2a}$, and indolinyl;

$R_{2a}$, at each occurrence is selected from $C_{1-6}$ alkyl, $C_{1-2}$ haloalkyl, Cl, Br, F, $NO_2$, CN, $(CH_2)_rOH$, $(CH_2)_rOR_b$, $(CH_2)_rS(O)_pR_b$, and a $(CHR)_r$—$C_{3-6}$ carbocyclic residue substituted with 0-2 $R_e$.

In another embodiment, there is provided compounds of formula wherein $R_3$ is selected from hydrogen, F, Br, Cl, $(CH_2)_r$-phenyl substituted with 0-1 $R_{3a}$, and —$O(CH_2)_r$-phenyl substituted with 0-1 $R_{3a}$;

$R_4$ is selected from hydrogen, $C_{1-6}$ alkyl, and $(CH_2)_r$-phenyl substituted with 0-2 $R_{4a}$;

$R_{4a}$, at each occurrence, is selected from $C_{1-6}$ alkyl, Cl, Br, F, $NO_2$, CN, $(CH_2)_rS(O)_pR_b$, $(CHR)_rC(O)R_d$, and a $(CHR)_r$—$C_{3-6}$ carbocyclic residue substituted with 0-5 $R_e$.

In another embodiment, there is provided compounds of formula (I), wherein $R_5$ is selected from $C_{1-6}$ alkyl substituted with 0-3 $R_6$, cyclopropyl substituted with 0-3 $R_6$, aryl substituted with 0-3 $R_6$, wherein the aryl is selected from phenyl and naphthyl, and heterocyclyl substituted with 0-3 $R_6$, wherein the heterocyclyl is selected from pyrrolidinyl, piperidinyl, morpholinyl, pyridinyl, pyridinyl N-oxide, piperazinyl, thiazolyl, benzothiazolyl, benzodiazepinonyl, indolyl, and quinoxalinedionyl;

$R_{5a}$ is phenyl substituted with 0-3 $R_6$, or napthyl substituted with 0-3 $R_6$;

$R_{5b}$ is phenyl substituted with 0-3 $R_6$ or heterocyclyl substituted with 0-3 $R_6$, wherein the heterocyclyl is selected from piperidinyl, piperazinyl, morpholinyl and pyrrolidinyl.

In another embodiment, there is provided compounds of formula (I), wherein $R_6$ is selected from hydrogen, F, Cl, Br, $OCF_3$, $CF_3$, CN, $NO_2$, =O, $N_3$, $(CHR)_rOH$, $(CH_2)_rOR_b$, $(CH_2)_rS(O)_pR_b$, $(CH_2)_rC(O)R_d$, $(CH_2)_rNR_aR_a$, $(CH_2)_rC(O)NR_aR_a$, $(CH_2)_rNR_aC(O)R_d$, $(CH_2)_rNR_aC(O)OR_b$, $(CH_2)_rOC(O)NR_aR_a$, $(CH_2)_rNR_aC(O)NR_aR_a$, $(CH_2)_rC(O)OR_d$, $(CH_2)_rS(O)_pNR_aR_a$, $(CH_2)_rNR_aS(O)_pR_b$, $SO_2F$, or $C_{1-6}$ alkyl substituted with 0-2 $R_e$, a $(CHR)_r$—$C_{3-6}$ carbocyclic residue substituted with 0-5 $R_e$, wherein the carbocyclic residue is selected from phenyl and cyclohexyl, and a $(CHR)_r$-heterocyclyl substituted with 0-5 $R_e$, wherein the heterocyclyl is selected from piperidinyl, pyrazinyl, and pyridinyl.

In another embodiment, there is provided compounds of formula (I), wherein $R_6$ is selected from hydrogen, F, Cl, Br, $OCF_3$, $CF_3$, CN, $NO_2$, =O, $N_3$, $(CHR)_rOH$, $(CH_2)_rOR_b$, $S(O)_pR_b$, $NR_aR_a$, $NR_aC(O)NR_aR_a$, $C(O)OR_d$, $S(O)_pNR_aR_a$, $SO_2F$, or $C_{1-6}$ alkyl substituted with 0-2 $R_e$ wherein alkyl is selected from methyl, ethyl, propyl, i-propyl and t-butyl, a $(CHR)_r$—$C_{3-6}$ carbocyclic residue substituted with 0-5 $R_e$, wherein the carbocyclic residue is selected from phenyl and cyclohexyl, and a $(CHR)_r$-heterocyclyl substituted with 0-5 $R_e$, wherein the heterocyclyl is selected from piperidinyl, pyrazinyl, and pyridinyl.

In another embodiment, there is provided compounds of formula (I), wherein $R_7$ is selected from Cl, $CF_3$, $C(O)NR_aR_a$ and $C(O)OR_b$;

$R_8$ is selected from hydrogen and Cl, $CF_3$, $C(O)NR_aR_a$, and $C(O)OR_b$;

$R_a$, at each occurrence, is independently selected from H, $C_{1-6}$ alkyl substituted with 0-2 $R_e$, $C_{1-6}$ haloalkyl, and a $(CH_2)_r$—$C_{3-6}$ carbocyclic residue substituted with 0-3 $R_e$ wherein the carbocyclic residue is selected from phenyl and cyclohexyl, $(CH_2)_r$-indolyl, and $(CH_2)_r$-pyrazolyl;

$R_b$, at each occurrence, is independently selected from $C_{1-6}$ alkyl substituted with 0-2 $R_e$, $CF_3$, a $(CH_2)_r$—$C_{3-6}$ carbocyclic residue substituted with 0-3 $R_e$, wherein the carbocyclic residue is selected from phenyl and cyclohexyl;

$R_d$, at each occurrence, is independently selected from H, $C_{1-6}$ alkyl substituted with 0-2 $R_e$, $CF_3$, and a $(CH_2)_r$—$C_{3-6}$ carbocyclic residue substituted with 0-3 $R_e$, wherein the carbocyclic residue is selected from phenyl and cyclohexyl;

$R_e$, at each occurrence, is independently selected from $C_{1-6}$ alkyl, $C_{2-6}$ alkenyl, $C_{2-6}$ alkynyl, $(CH_2)_rC_{3-6}$ cycloalkyl, Cl, F, Br, CN, $NO_2$, $CO_2H$, $CO_2C_{1-5}$alkyl, $(CF_2)_rCF_3$, $(CH_2)_rOC_{1-5}$ alkyl, OH, SH, $(CH_2)_rSC_{1-5}$ alkyl, $(CH_2)_rNR_fR_f$, and $(CH_2)_r$phenyl.

In another embodiment, there is provided compounds of formula (I), wherein $R_2$ is selected from $C_{1-9}$ alkyl, $—(CH_2)_r$-cyclohexyl substituted with 0-5 $R_{2a}$, $—(CH_2)_r$-phenyl substituted with 0-2 $R_{2a}$, and indolinyl.

In another embodiment, there is provided compounds of formula (I), wherein $L_2$ is $C_{3-10}$ carbocyclic residue substituted with 0-5 $R_6$, aryl substituted with 0-5 $R_6$, and heterocyclyl substituted with 0-5 $R_6$, $—(CH_2)_n—N(R_4)—CO—(CH_2)_t—R_5$, $—(CH_2)_n—N(R_4)—CO—O—C_{1-6}$alkyl, $—CH_2—N(R_4)—SO_2—R_5$, $—CH_2—N(R_4)—CO—N(R_4)—R_5$, $—CO—N(R_4)—(CHR)_n—R_5$, $—CH_2—N(R_4)—CH_2—R_{5'}$, $—O—R_{5a}$, $—CH_2—S—(CH_2)_t—R_5$, $—(CH_2)_n—R_{5a}$, $—CO—R_{5b}$.

In another embodiment, there is provided compounds of formula (I), $L_2$ is cyclopropyl substituted with 0-3 $R_6$, aryl substituted with 0-3 $R_6$, wherein the aryl is selected from phenyl and naphthyl, and heterocyclyl substituted with 0-3 $R_6$, wherein the heterocycylyl is selected from pyrrolidinyl, piperidinyl, morpholinyl, pyridinyl, pyridinyl N-oxide, piperazinyl, thiazolyl, benzothiazolyl, benzodiazepinonyl, indolyl, and quinoxaline-dionyl; $—(CH_2)_n—N(R_4)—CO—(CH_2)_t—R_5$, $—(CH_2)_n—N(R_4)—CO—O—C_{1-6}$alkyl, $—CH_2—N(R_4)—SO_2—R_5$, $—CH_2—N(R_4)—CO—N(R_4)—R_5$, $—CO—N(R_4)—(CHR)_n—R_5$, $—CH_2—N(R_4)=CH_2—R_{5'}$, $—O—R_{5a}$, $—CH_2—S—(CH_2)_t—R_5$, $—(CH_2)_n R_{5a}$, $—CO—R_{5b}$.

In another embodiment, there is provided compounds of formula (I), $L_2$ is cyclopropyl substituted with 0-3 $R_6$, aryl substituted with 0-3 $R_6$ wherein the aryl is selected from phenyl and naphthyl, and heterocyclyl substituted with 0-3 $R_6$, wherein the heterocycylyl is pyridinyl; $—(CH_2)_n—N(R_4)—CO—(CH_2)_t—R_5$, $—(CH_2)_n—N(R_4)—CO—O—C_{1-6}$ alkyl, $—CH_2—N(R_4)—SO_2—R_5$, $—CH_2—N(R_4)—CO—N(R_4)—R_5$, $—CO—N(R_4)—(CHR)_n—R_5$, $—CH_2—N(R_4)—CH_2—R_{5'}$, $—O—R_{5a}$, $—CH_2—S—(CH_2)_t—R_5$, $—(CH_2)_n—R_{5a}$, $—CO—R_{5b}$.

In another embodiment, there is provided compounds of formula (I), $L_2$ is cyclopropyl substituted with 0-3 $R_6$, aryl substituted with 0-3 $R_6$, wherein the aryl is selected from phenyl and naphthyl; $—(CH_2)_n—N(R_4)—CO—(CH_2)_t—R_5$, $—(CH_2)_n—N(R_4)—CO—O—C_{1-6}$alkyl, $—CH_2—N(R_4)—SO_2—R_5$, $—CH_2—N(R_4)—CO—N(R_4)—R_5$, $—CO—N(R_4)—(CHR)$, $—R_5$, $—CH_2—N(R_4)—CH_2—R_{5'}$, $—O—R_{5a}$, $—CH_2—S—(CH_2)_t—R_5$, $—(CH_2)_n—R_{5a}$, $—CO—R_{5b}$.

In another embodiment, there is provided compounds of formula (I), wherein $R_5$ is selected from cyclopropyl substituted with 0-3 $R_6$, aryl substituted with 0-3 $R_6$, wherein the aryl is selected from phenyl and naphthyl, and heterocyclyl substituted with 0-3 $R_6$, wherein the heterocycylyl is selected from pyrrolidinyl, piperidinyl, morpholinyl, pyridinyl, pyridinyl N-oxide, piperazinyl, thiazolyl, benzothiazolyl, benzodiazepinonyl, indolyl, and quinoxaline-dionyl.

In another embodiment, the present invention is directed to examples 1-275 or salts thereof.

In another embodiment of the invention, there are disclosed compounds of formula

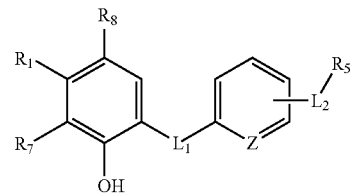

or salt thereof,
wherein
$L_1$ is $—Y—N(R_2)—CH_2—$ or $—CH_2—N(R_2)—Y$;
$L_2$ is $—CH_2—N(R_4)—X—$ or $—X—N(R_4)—CH_2—$;
X is $—SO_2—$, $—CO—$, or $—(CO)NR—$;
Y is $—SO_2—$ or $—CO—$;
Z is CH, N or N-oxide;
R, at each occurrence, is independently selected from H, $C_{1-6}$ alkyl, $C_{1-6}$ haloalkyl, and $—(CH_2)_r$-aryl;

R₁ is selected from hydrogen, F, Br, Cl, NO₂, CN, $C_{1-6}$ alkyl, —(CHR)$_r$-aryl substituted with 0-2 $R_{1a}$, alkoxy, aryloxy substituted with 0-2 $R_{1a}$, heterocyclyl substituted with 0-2 $R_{1a}$;

$R_{1a}$ is selected from H, $C_{1-6}$ alkyl, $C_{1-6}$ haloalkyl, Cl, Br, F, NO₂, CN, (CHR)$_r$OH, (CHR)$_r$SH, (CHR)$_r$OR$_b$, (CHR)$_r$S(O)$_p$ R$_b$, (CHR)$_r$C(O)R$_d$, (CHR)$_r$NR$_a$R$_a$, (CHR)$_r$C(O)NR$_a$R$_a$, (CHR)$_r$C(O)NR$_a$OR$_b$, (CHR)$_q$NR$_a$C(O)R$_d$, (CHR)$_r$NR$_a$C(O)OR$_b$, (CHR)$_r$OC(O)NR$_a$R$_a$, (CHR)$_r$C(O)OR$_d$, (CHR)$_r$S(O)$_p$NR$_a$R$_a$, (CHR)$_r$NR$_a$S(O)$_p$R$_b$, and a (CHR)$_r$—$C_{3-6}$ carbocyclic residue substituted with 0-5 R$_e$;

R₂ is selected from hydrogen, $C_{1-6}$ alkyl substituted with 0-3 $R_{2a}$, $C_{1-6}$ haloalkyl, —(CH₂)$_r$-aryl substituted with 0-5 $R_{2a}$, —(CH₂)-heterocycloalkyl substituted with 0-3 $R_{2a}$, $R_{2a}$, at each occurrence is selected from $C_{1-6}$ alkyl, $C_{2-6}$ alkenyl, $C_{2-6}$ alkynyl, $C_{1-6}$ haloalkyl, (CH₂)$_r$$C_{3-6}$ cycloalkyl, Cl, Br, F, NO₂, CN, (CHR)$_r$OH, (CHR)$_r$SH, (CHR)$_r$OR$_b$, (CHR)$_r$S(O)$_p$R$_b$, (CHR)$_r$C(O)R$_d$, (CHR)$_r$NR$_a$R$_a$, (CHR)$_r$C(O)NR$_a$R$_a$, (CHR)$_r$C(O)NR$_a$OR$_b$, (CHR)$_r$NR$_a$C(O)R$_d$, (CHR)$_r$NR$_a$C(O)OR$_b$, (CHR)$_r$OC(O)NR$_a$R$_a$, (CHR)$_r$C(O)OR$_d$, (CHR)$_r$S(O)$_p$NR$_a$R$_a$, (CHR)$_r$NR$_a$S(O)$_p$R$_b$, and a (CHR)$_r$—$C_{3-6}$ carbocyclic residue substituted with 0-5 R$_e$;

R₃ is selected from hydrogen, F, Br, Cl, $C_{1-6}$ alkyl, (CHR)$_r$—$C_{3-6}$ cycloalkyl, (CHR)$_r$-aryl substituted with 0-3 $R_{3a}$, —O—(CHR)$_r$-aryl substituted with 0-3 $R_{3a}$, and heterocycle substituted with 0-2 $R_{3a}$;

$R_{3a}$, at each occurrence, is selected from $C_{1-6}$ alkyl, $C_{2-6}$ alkenyl, $C_{2-6}$ alkynyl, (CH₂)$_r$$C_{3-6}$ cycloalkyl, Cl, Br, F, NO₂, CN, (CHR)$_r$OH, (CHR)$_r$SH, (CHR)$_r$OR$_b$, (CHR)$_r$S(O)$_p$R$_b$, (CHR)$_r$C(O)R$_d$, (CHR)$_r$NR$_a$R$_a$, (CHR)$_r$C(O)NR$_a$R$_a$, (CHR)$_r$ C(O)NR$_a$OR$_b$, (CHR)$_r$NR$_a$C(O)R$_d$, (CHR)$_r$NR$_a$C(O)OR$_b$, (CHR)$_r$OC(O)NR$_a$R$_a$, (CHR)$_r$C(O)OR$_d$, (CHR)$_r$S(O)$_p$NR$_a$R$_a$, (CHR)$_r$NR$_a$S(O)$_p$R$_b$, and a (CHR)$_r$—$C_{3-6}$ carbocyclic residue substituted with 0-5 R$_e$;

R₄ is selected from hydrogen, $C_{1-6}$ alkyl, (CHR) aryl substituted with 0-2 $R_{4a}$, and (CHR)$_r$-heterocycle substituted with 0-2 $R_{4a}$;

$R_{4a}$, at each occurrence, is selected from $C_{1-6}$ alkyl, $C_{2-6}$ alkenyl, $C_{2-6}$ alkynyl, (CH₂)$_r$$C_{3-6}$ cycloalkyl, Cl, Br, F, NO₂, CN, (CHR)$_r$OH, (CHR)$_r$SH, (CHR)$_r$OR$_b$, (CHR)$_r$S(O)$_p$R$_b$, (CHR)$_r$C(O)R$_d$, (CHR)$_r$NR$_a$R$_a$, (CHR)$_r$C(O)NR$_a$R$_a$, (CHR)$_r$ C(O)NR$_a$OR$_b$, (CHR)$_r$NR$_a$C(O)R$_d$, (CHR)$_r$NR$_a$C(O)OR$_b$, (CHR)$_r$OC(O)NR$_a$R$_a$, (CHR)$_r$C(O)OR$_d$, (CHR)$_r$S(O)$_p$NR$_a$R$_a$, (CHR)$_r$NR$_a$S(O)$_p$R$_b$, and a (CHR)$_r$—$C_{3-6}$ carbocyclic residue substituted with 0-5 R$_e$;

R₅ is selected from $C_{3-6}$ carbocyclic residue substituted with 0-5 R₆, aryl substituted with 0-5 R₆, and heterocyclyl substituted with 0-5 R₆;

R₆ is selected from hydrogen, H, F, Cl, Br, OCF₃, CF₃, CN, NO₂, =O, (CHR)$_r$OH, (CHR)$_r$SH, (CHR)$_r$OR$_b$, (CHR)$_r$S(O)$_p$R$_b$, (CHR)$_r$C(O)R$_d$, (CHR)$_r$NR$_a$R$_a$, (CHR)$_r$C(O)NR$_a$R$_a$, (CHR)$_r$C(O)NR$_a$OR$_b$, (CHR)$_r$NR$_a$C(O)R$_d$, (CHR)$_r$NR$_a$C(O)OR$_b$, (CHR)$_r$OC(O)NR$_a$R$_a$, (CHR)$_r$NR$_a$C(O)NR$_a$R$_a$, (CHR)$_r$C(O)OR$_d$, (CHR)$_r$S(O)$_p$NR$_a$R$_a$, (CHR)$_r$NR$_a$S(O)$_p$R$_b$, or $C_{1-6}$ alkyl substituted with 0-2 R$_e$, $C_{1-6}$ haloalkyl a (CHR)$_r$—$C_{3-6}$ carbocyclic residue substituted with 0-5 R$_e$, and a (CHR)$_r$-heterocyclyl substituted with 0-5 R$_e$;

R$_a$, at each occurrence, is independently selected from H, $C_{1-6}$ alkyl substituted with 0-2 R$_e$, $C_{1-6}$ haloalkyl, $C_{3-6}$ alkenyl substituted with 0-2 R$_e$, $C_{3-6}$ alkynyl substituted with 0-2 R$_e$, a (CH₂)$_r$—$C_{3-10}$ carbocyclic residue substituted with 0-5 R$_e$, and a (CH₂)$_r$-heterocyclyl substituted with 0-2 R$_e$;

R$_b$, at each occurrence, is independently selected from $C_{1-6}$ alkyl substituted with 0-2 R$_e$, $C_{1-6}$ haloalkyl, $C_{3-6}$ alkenyl substituted with 0-2 R$_e$, $C_{3-6}$ alkynyl substituted with 0-2 R$_e$, a (CH₂)$_r$—$C_{3-10}$ carbocyclic residue substituted with 0-5 R$_e$, and a (CH₂)$_r$-heterocyclyl substituted with 0-2 R$_e$;

R$_d$, at each occurrence, is independently selected from H, $C_{1-6}$ alkyl substituted with 0-2 R$_e$, $C_{1-6}$ haloalkyl, $C_{3-6}$ alkenyl substituted with 0-2 R$_e$, $C_{3-6}$ alkynyl substituted with 0-2 R$_e$, a (CH₂)$_r$—$C_{3-10}$ carbocyclic residue substituted with 0-5 R$_e$, and a (CH₂)$_r$-heterocyclyl substituted with 0-2 R$_e$;

R$_e$, at each occurrence, is independently selected from $C_{1-6}$ alkyl, $C_{2-6}$ alkenyl, $C_{2-6}$ alkynyl, (CH₂)$_r$$C_{3-6}$ cycloalkyl, Cl, F, Br, CN, NO₂, CO₂H, (CF₂)$_r$CF₃, (CH₂)$_r$OC$_{1-5}$ alkyl, OH, SH, (CH₂)$_r$SC$_{1-5}$ alkyl, (CH₂)$_r$NR$_f$R$_f$, and (CH₂)$_r$phenyl;

R$_f$, at each occurrence, is independently selected from H, $C_{1-5}$ alkyl, and $C_{3-6}$ cycloalkyl, and phenyl;

R₇ is selected from F and Cl;

R₈ is selected from hydrogen, F, and Cl;

p, at each occurrence, is independently selected from 0, 1, and 2;

r, at each occurrence, is independently selected from 0, 1, 2, 3, and 4.

In another embodiment,

R₁ is selected from hydrogen, F, Br, C₁, $C_{1-6}$ alkyl, and —(CHR)$_r$-phenyl substituted with 0-2 $R_{1a}$;

R₂ is selected from hydrogen, $C_{1-6}$ alkyl, —(CH₂)$_r$-aryl substituted with 0-5 $R_{2a}$;

$R_{2a}$, at each occurrence is selected from $C_{1-6}$ alkyl, $C_{1-6}$ haloalkyl, (CH₂)$_r$$C_{3-6}$ cycloalkyl, Cl, Br, F, NO₂, CN, (CHR)$_r$OH, (CHR)$_r$OR$_b$, (CHR)$_r$S(O)$_p$R$_b$, (CH₂)$_r$C(O)R$_d$, (CH₂)$_r$NR$_a$R$_a$, (CH₂)$_r$C(O)NR$_a$R$_a$, (CH₂)$_r$C(O)NR$_a$OR$_b$, (CH₂)$_r$NR$_a$C(O)R$_d$, (CH₂)$_r$NR$_a$C(O)OR$_b$, (CH₂)$_r$OC(O)NR$_a$R$_a$, (CH₂)$_r$C(O)OR$_d$, (CH₂)$_r$S(O)$_p$NR$_a$R$_a$, (CH₂)$_r$NR$_a$S(O)$_p$R$_b$, and a (CHR)$_r$—$C_{3-6}$ carbocyclic residue substituted with 0-5 R$_e$.

In accordance with the invention, there are disclosed compounds of formula Ia or salt thereof, wherein

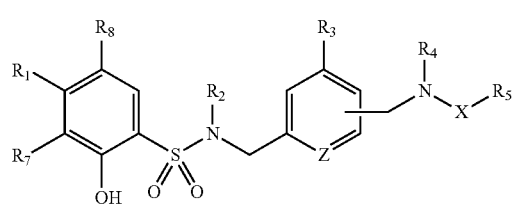

Ia wherein

R₃ is selected from hydrogen, F, Br, Cl, $C_{1-6}$ alkyl, (CH₂)$_r$—$C_{3-6}$ cycloalkyl, (CH₂)$_r$-aryl substituted with 0-3 $R_{3a}$, —O—$C_{1-6}$alkyl, and —O(CH₂)$_r$-aryl substituted with 0-3 $R_{3a}$;

$R_{3a}$, at each occurrence, is selected from $C_{1-6}$ alkyl, (CH₂)$_r$$C_{3-6}$ cycloalkyl, Cl, Br, F, NO₂, and CN;

R₄ is selected from hydrogen, $C_{1-6}$ alkyl, and (CH₂)$_r$-aryl substituted with 0-2 $R_{4a}$;

$R_{4a}$, at each occurrence, is selected from $C_{1-6}$ alkyl, (CH₂)$_r$$C_{3-6}$ cycloalkyl, Cl, Br, F, NO₂, CN, (CHR)$_r$OH, (CHR)$_r$OR$_b$, (CHR)$_r$S(O)$_p$R$_b$, (CHR)$_r$C(O)R$_d$, (CHR)$_r$NR$_a$R$_a$, (CHR)$_r$C(O)NR$_a$R$_a$, (CHR)$_r$C(O)NR$_a$OR$_b$, (CHR)$_r$NR$_a$C(O)R$_d$, (CHR)$_r$NR$_a$C(O)OR$_b$, (CHR)$_r$OC(O)NR$_a$R$_a$, (CHR)$_r$C(O)OR$_d$, (CHR)$_r$S(O)$_p$NR$_a$R$_a$, (CHR)$_r$NR$_a$S(O)$_p$R$_b$, and a (CHR)$_r$—$C_{3-6}$ carbocyclic residue substituted with 0-5 R$_e$.

In another embodiment, X is —SO₂—, —CO—, or —(CO)NH—;

Y is —SO₂—;

R₅ is selected from aryl substituted with 0-5 R₆, and

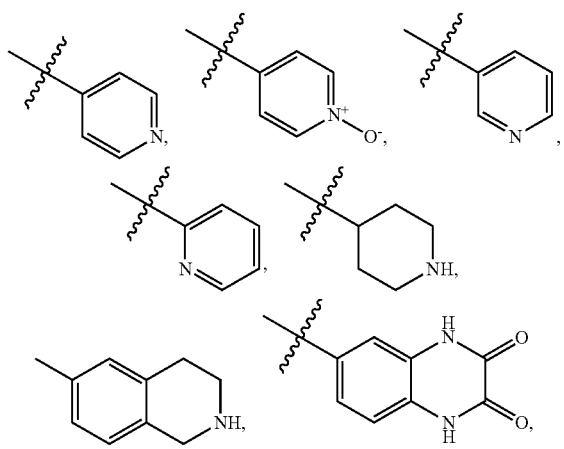

any of which is substituted with 0-5 $R_6$;

$R_6$ is selected from hydrogen, H, F, Cl, Br, $OCF_3$, $CF_3$, CN, $NO_2$, =O, $(CH_2)_rOH$, $(CH_2)_rSH$, $(CH_2)_rOR_b$, $(CH_2)_rS(O)_pR_b$, $(CH_2)_rC(O)R_d$, $(CH_2)_rNR_aR_a$, $(CH_2)_rC(O)NR_aR_a$, $(CH_2)_rC(O)NR_aOR_b$, $(CH_2)_rNR_aC(O)R_d$, $(CH_2)_rNR_aC(O)OR_b$, $(CH_2)_rOC(O)NR_aR_a$, $(CH_2)_rNR_aC(O)NR_aR_a$, $(CH_2)_rC(O)OR_d$, $(CH_2)_rS(O)_pNR_aR_a$, $(CH_2)_rNR_aS(O)_pR_b$, or $C_{1-6}$ alkyl substituted with 0-2 $R_e$, $C_{1-6}$ haloalkyl a $(CHR)_r$—$C_{3-6}$ carbocyclic residue substituted with 0-5 $R_e$, and a $(CHR)_r$-heterocyclyl substituted with 0-5 $R_e$.

In another embodiment, $R_1$ is selected from hydrogen, F, Br, Cl, and $C_{1-6}$ alkyl;

$R_2$ is selected from hydrogen, $C_{1-6}$ alkyl, —$(CH_2)_r$-phenyl substituted with 0-5 $R_{2a}$;

$R_{2a}$, at each occurrence is selected from $C_{1-6}$ alkyl, $C_{1-6}$ haloalkyl, Cl, Br, F, $NO_2$, CN, $(CH_2)_rOH$, $(CH_2)_rOR_b$, $(CH_2)_rS(P)_pR_b$, and a $(CHR)_r$—$C_{3-6}$ carbocyclic residue substituted with 0-2 $R_e$.

In another embodiment, $R_3$ is selected from hydrogen, F, Br, Cl, $C_{1-6}$ alkyl, $(CH_2)_r$—$C_{3-6}$ cycloalkyl, $(CH_2)_r$-phenyl substituted with 0-3 $R_{3a}$, and —$O(CH_2)_r$-phenyl substituted with 0-3 $R_{3a}$;

$R_4$ is selected from hydrogen, $C_{1-6}$ alkyl, and $(CH_2)_r$-phenyl substituted with 0-2 $R_{4a}$;

$R_{4a}$, at each occurrence, is selected from $C_{1-6}$ alkyl, Cl, Br, F, $NO_2$, CN, $(CH_2)_rS(O)_pR_b$, $(CHR)_rC(O)R_d$, and a $(CHR)_r$—$C_{3-6}$ carbocyclic residue substituted with 0-5 $R_e$.

In another embodiment, $R_6$ is selected from hydrogen, F, Cl, Br, $OCF_3$, $CF_3$, CN, $NO_2$, =O, $(CH_2)_rOH$, $(CH_2)_rOR_b$, $(CH_2)_rS(O)_pR_b$, $(CH_2)_rC(O)R_d$, $(CH_2)_rNR_aR_a$, $(CH_2)_rC(O)NR_aR_a$, $(CH_2)_rNR_aC(O)R_d$, $(CH_2)_rNR_aC(O)OR_b$, $(CH_2)_rOC(O)NR_aR_a$, $(CH_2)_rNR_aC(O)NR_aR_a$, $(CH_2)_rC(O)OR_d$, $(CH_2)_rS(O)_pNR_aR_a$, $(CH_2)_rNR_aS(O)_pR_b$, or $C_{1-6}$ alkyl substituted with 0-2 $R_e$, a $(CHR)_r$—$C_{3-6}$ carbocyclic residue substituted with 0-5 $R_e$.

In another embodiment, $R_7$ is selected from Cl;

$R_8$ is selected from hydrogen and Cl.

In another embodiment, $R_a$, at each occurrence, is independently selected from H, $C_{1-6}$ alkyl substituted with 0-2 $R_e$, $C_{1-6}$ haloalkyl, and a $(CH_2)_r$—$C_{3-6}$ carbocyclic residue substituted with 0-5 $R_e$;

$R_b$, at each occurrence, is independently selected from $C_{1-6}$ alkyl substituted with 0-2 $R_e$, $C_{1-6}$ haloalkyl, a $(CH_2)_r$—$C_{3-6}$ carbocyclic residue substituted with 0-5 $R_e$;

$R_d$, at each occurrence, is independently selected from H, $C_{1-6}$ alkyl substituted with 0-2 $R_e$, $C_{1-6}$ haloalkyl, and a $(CH_2)_r$—$C_{3-6}$ carbocyclic residue substituted with 0-5 $R_e$;

$R_e$, at each occurrence, is independently selected from $C_{1-6}$ alkyl, $C_{2-6}$ alkenyl, $C_{2-6}$ alkynyl, $(CH_2)_rC_{3-6}$ cycloalkyl, Cl, F, Br, CN, $NO_2$, $CO_2H$, $(CF_2)_rCF_3$, $(CH_2)_rOC_{1-5}$ alkyl, OH, SH, $(CH_2)_rSC_{1-5}$ alkyl, $(CH_2)_rNR_fR_f$, and $(CH_2)_r$phenyl.

In another embodiment, the compound of formula Ia or salt thereof,

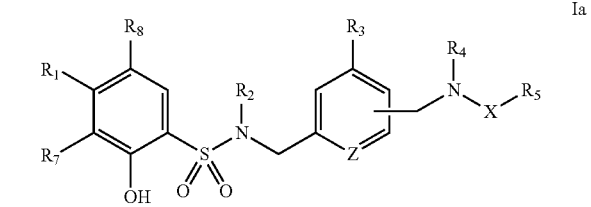

$R_1$ is hydrogen;

$R_2$ is selected from hydrogen, $C_{1-6}$ alkyl, —$(CH_2)_r$-phenyl substituted with 0-3 $R_{2a}$;

$R_{2a}$, at each occurrence is selected from $C_{1-4}$ alkyl, $C_{1-4}$ haloalkyl, Cl, Br, F, $NO_2$, CN, OH, SH, $OR_d$, $S(O)_pR_b$, and a $(CH_2)_r$-phenyl substituted with 0-1 $R_e$;

$R_3$ is selected from hydrogen, F, Br, Cl, $C_{1-4}$ alkyl, cyclopropyl, $(CH_2)_r$-phenyl substituted with 0-1 $R_{3a}$, and —$O(CH_2)_r$-phenyl substituted with 0-1 $R_{3a}$;

$R_{3a}$, at each occurrence, is selected from $C_{1-6}$ alkyl, Cl, Br, and F;

$R_4$ is selected from hydrogen, $C_{1-4}$ alkyl, and $(CH_2)$-phenyl substituted with 0-1 $R_{4a}$;

$R_{4a}$, at each occurrence, is selected from Cl, Br, F, $S(O)_2$—$C_{1-4}$ alkyl;

$R_5$ is selected from phenyl or napthyl either of which is substituted with 0-3 $R_6$, and

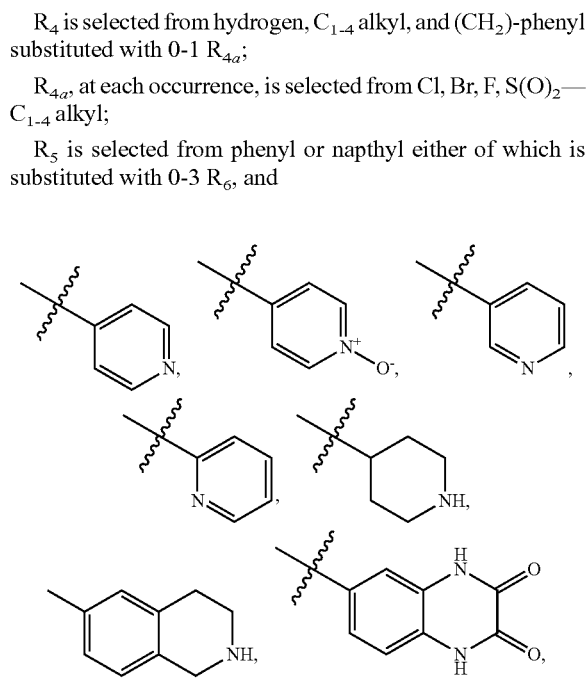

any of which is substituted with 0-3 $R_6$;

$R_6$ is selected from hydrogen, F, Cl, Br, $OCF_3$, $CF_3$, CN, $NO_2$, =O, OH, $OR_d$, $S(O)_pR_b$, $C(O)R_d$, $NR_aC(O)NR_aR_a$, $C(O)OR_d$, $S(O)_pNR_aR_a$, $NR_aS(O)_pR_b$, or $C_{1-4}$alkyl, and phenyl substituted with 0-1 $R_e$;

$R_7$ is Cl; and $R_8$ is Cl.

In another embodiment, the compound is of formula Ib

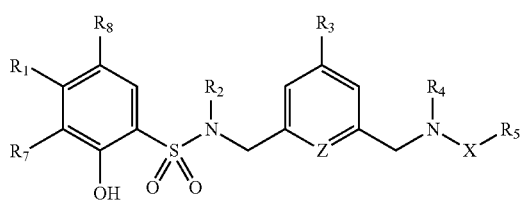

In another embodiment, the compound if of formula Ic

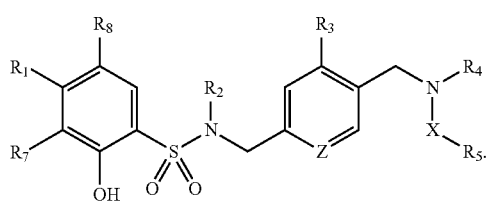

In another embodiment, X is —SO$_2$—, —CO—. In another embodiment, Y is —SO$_2$—.

In another embodiment, Z is CH. In another embodiment, Z is N or N-oxide.

In another embodiment, R$_1$ is selected from hydrogen, F, Br, Cl, C$_{1-6}$ alkyl, and —(CHR)$_r$-phenyl substituted with 0-2 R$_{1a}$. In an alternative embodiment, R$_1$ is selected from hydrogen, F, Br, Cl, and C$_{1-6}$ alkyl. In an alternative embodiment, R$_1$ is hydrogen.

In another embodiment, R$_{1a}$ is selected from H, C$_{1-6}$ alkyl, C$_{1-6}$ haloalkyl, Cl, Br, F, NO$_2$, CN, (CHR)$_r$OH, (CHR)$_r$SH, (CHR)$_r$OR$_b$, (CHR)$_r$S(O)$_p$R$_b$, (CHR)$_r$C(O)R$_d$, (CHR)$_r$N-R$_a$R$_a$, (CHR)$_r$C(O)NR$_a$R$_a$, (CHR)$_r$C(O)NR$_a$OR$_b$, (CHR)$_q$NR$_a$C(O)R$_d$, (CHR)$_r$NR$_a$C(O)OR$_b$, (CHR)$_r$OC(O)NR$_a$R$_a$, (CHR)$_r$C(O)OR$_d$, (CHR)$_r$S(O)$_p$NR$_a$R$_a$, (CHR)$_r$NR$_a$S(O)$_p$R$_b$, and a (CHR)$_r$—C$_{3-6}$ carbocyclic residue substituted with 0-5

In another embodiment, R$_2$ is selected from hydrogen, C$_{1-6}$ alkyl substituted with 0-3 R$_{2a}$, C$_{1-6}$ haloalkyl, —(CH$_2$)$_r$-aryl substituted with 0-5 R$_{2a}$, —(CH$_2$)$_r$-heterocycloalkyl substituted with 0-3 R$_{2a}$. In another embodiment, R$_2$ is selected from hydrogen, C$_{1-6}$ alkyl, —(CH$_2$)$_r$-aryl substituted with 0-5 R$_{2a}$. In another embodiment, R$_2$ is selected from hydrogen, C$_{1-6}$ alkyl, —(CH$_2$)$_r$-phenyl substituted with 0-5 R$_{2a}$. In another embodiment, R$_2$ is selected from hydrogen, C$_{1-6}$ alkyl, —(CH$_2$)$_r$-phenyl substituted with 0-3 R$_{2a}$.

In another embodiment, R$_{2a}$, at each occurrence is selected from C$_{1-6}$ alkyl, C$_{2-6}$ alkenyl, C$_{2-6}$ alkynyl, C$_{1-6}$ haloalkyl, (CH$_2$)$_r$C$_{3-6}$ cycloalkyl, Cl, Br, F, NO$_2$, CN, (CHR)$_r$OH, (CHR)$_r$SH, (CHR)$_r$OR$_b$, (CHR)$_r$S(O)$_p$R$_b$, (CHR)$_r$C(O)R$_d$, (CHR)$_r$NR$_a$R$_a$, (CHR)$_r$C(O)NR$_a$R$_a$, (CHR)$_r$C(O)NR$_a$OR$_b$, (CHR)$_r$NR$_a$C(O)R$_d$, (CHR)$_r$NR$_a$C(O)OR$_b$, (CHR)$_r$OC(O)NR$_a$R$_a$, (CHR)$_r$C(O)OR$_d$, (CHR)$_r$S(O)$_p$NR$_a$R$_a$, (CHR)$_r$N-R$_a$S(O)$_p$R$_b$, and a (CHR)$_r$—C$_{3-6}$ carbocyclic residue substituted with 0-5 R$_e$.

In another embodiment, R$_{2a}$, at each occurrence is selected from C$_{1-6}$ alkyl, C$_{1-6}$ haloalkyl, Cl, Br, F, NO$_2$, CN, (CH$_2$)$_r$OR$_d$, (CH$_2$)$_r$S(O)$_p$R$_b$, and a (CHR)$_r$—C$_{3-6}$ carbocyclic residue substituted with 0-2 R$_e$. In another embodiment, R$_{2a}$, at each occurrence is selected from C$_{1-4}$ alkyl, C$_{1-4}$ haloalkyl, Cl, Br, F, NO$_2$, CN, OH, SH, OR$_d$, S(O)$_p$R$_b$, and a (CH$_2$)$_r$-phenyl substituted with 0-1 R$_e$.

In another embodiment, R$_3$ is selected from hydrogen, F, Br, Cl, C$_{1-6}$ alkyl, (CHR)$_r$—C$_{3-6}$ cycloalkyl, (CHR)$_r$-aryl substituted with 0-3 R$_{3a}$, —O—C$_{1-6}$alkyl, —O—(CHR)$_r$-aryl substituted with 0-3 R$_{3a}$, and heterocycle substituted with 0-2 R$_{3a}$. In another embodiment, R$_3$ is selected from hydrogen, F, Br, Cl, C$_{1-6}$ alkyl, (CH$_2$)$_r$—C$_{3-6}$ cycloalkyl, (CH$_2$)$_r$-aryl substituted with 0-3 R$_{3a}$, —O—C$_{1-6}$alkyl, and —O(CH$_2$)$_r$-aryl substituted with 0-3 R$_{3a}$. In another embodiment, R$_3$ is selected from hydrogen, F, Br, Cl, C$_{1-6}$ alkyl, (CH$_2$)$_r$—C$_{3-6}$ cycloalkyl, (CH$_2$)$_r$-phenyl substituted with 0-3 R$_{3a}$, and —O(CH$_2$)$_r$-phenyl substituted with 0-3 R$_{3a}$. In another embodiment, R$_3$ is selected from hydrogen, F, Br, Cl, C$_{1-4}$ alkyl, cyclopropyl, (CH$_2$)$_r$-phenyl substituted with 0-1 R$_{3a}$, and —O(CH$_2$)$_r$-phenyl substituted with 0-1 R$_{3a}$.

In another embodiment, R$_4$ is selected from hydrogen, C$_{1-6}$ alkyl, (CHR)$_r$-aryl substituted with 0-2 R$_{4a}$, and (CHR)$_r$-heterocycle substituted with 0-2 R$_{4a}$. In another embodiment, R$_4$ is selected from hydrogen, C$_{1-6}$ alkyl, and (CH$_2$)$_r$-aryl substituted with 0-2 R$_{4a}$. In another embodiment, R$_4$ is selected from hydrogen, C$_{1-6}$ alkyl, and (CH$_2$)$_r$-phenyl substituted with 0-2 R$_{4a}$. In another embodiment, R$_4$ is selected from hydrogen, C$_{1-4}$ alkyl, and (CH$_2$)-phenyl substituted with 0-1 R$_{4a}$.

In another embodiment, R$_5$ is selected from aryl substituted with 0-5 R$_6$, and heterocyclyl substituted with 0-5 R$_6$.

In another embodiment, R$_5$ is selected from aryl substituted with 0-5 R$_6$, and

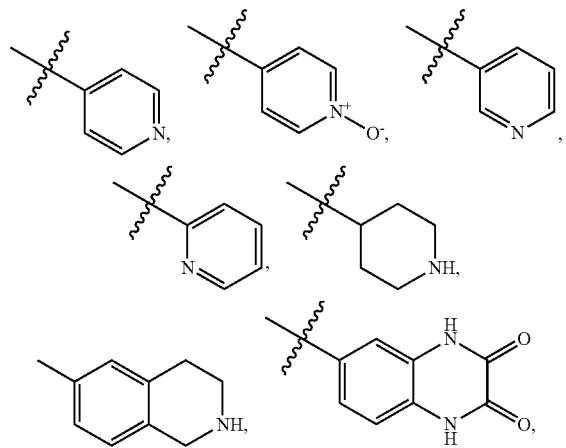

any of which is substituted with 0-5 R$_6$.

In another embodiment, R$_5$ is selected from phenyl or napthyl either of which is substituted with 0-3 R$_6$, and

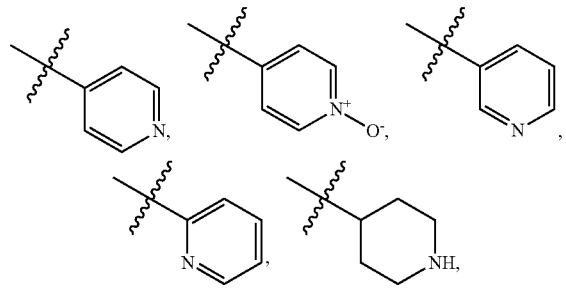

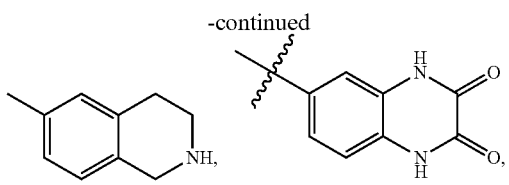

any of which is substituted with 0-3 $R_6$.

In another embodiment, $R_6$ is selected from hydrogen, H, F, Cl, Br, $OCF_3$, $CF_3$, CN, $NO_2$, =O, $(CHR)_rOH$, $(CHR)_rSH$, $(CHR)_rOR_b$, $(CHR)_rS(O)_pR_b$, $(CHR)_rC(O)R_d$, $(CHR)_rNR_aR_a$, $(CHR)_rC(O)NR_aR_a$, $(CHR)_rC(O)NR_aOR_b$, $(CHR)_rNR_aC(O)R_d$, $(CHR)_rNR_aC(O)OR_b$, $(CHR)_rOC(O)NR_aR_a$, $(CHR)_rNR_aC(O)NR_aR_a$, $(CHR)_rC(O)OR_d$, $(CHR)_rS(O)_pNR_aR_a$, $(CHR)_rNR_aS(O)_pR_b$, or $C_{1-6}$ alkyl substituted with 0-2 $R_e$, $C_{1-6}$ haloalkyl a $(CHR)_r$—$C_{3-6}$ carbocyclic residue substituted with 0-5 $R_e$, and a $(CHR)_r$-heterocyclyl substituted with 0-5 $R_e$. In another embodiment, $R_6$ is selected from hydrogen, H, F, Cl, Br, $OCF_3$, $CF_3$, CN, $NO_2$, =O, $(CH_2)_r$OH, $(CH_2)_r$SH, $(CH_2)_rOR_b$, $(CH_2)_rS(O)_pR_b$, $(CH_2)_rC(O)R_d$, $(CH_2)_rNR_aR_a$, $(CH_2)_rC(O)NR_aR_a$, $(CH_2)_rC(O)NR_aOR_b$, $(CH_2)_rNR_aC(O)R_d$, $(CH_2)_rNR_aC(O)OR_b$, $(CH_2)_r$ OC(O)N-$R_aR_a$, $(CH_2)_aNR_aC(O)NR_aR_a$, $(CH_2)_rC(O)OR_d$, $(CH_2)_rS(O)_pNR_aR_a$, $(CH_2)_rNR_aS(O)_pR_b$, or $C_{1-6}$ alkyl substituted with 0-2 $R_e$, $C_{1-6}$ haloalkyl a $(CHR)_r$—$C_{3-6}$ carbocyclic residue substituted with 0-5 $R_e$, and a $(CHR)_r$-heterocyclyl substituted with 0-5 $R_e$. In another embodiment, $R_6$ is selected from hydrogen, F, Cl, Br, $OCF_3$, $CF_3$, CN, $NO_2$, =O, $(CH_2)_r$OH, $(CH_2)_rOR_b$, $(CH_2)_rS(O)_pR_b$, $(CH_2)_rC(O)R_d$, $(CH_2)_rNR_aR_a$, $(CH_2)_rC(O)NR_aR_a$, $(CH_2)_rNR_aC(O)R_d$, $(CH_2)_rNR_aC(O)OR_b$, $(CH_2)_rOC(O)NR_aR_a$, $(CH_2)_rNR_aC(O)NR_aR_a$, $(CH_2)_rC(O)OR_d$, $(CH_2)_rS(O)_pNR_aR_a$, $(CH_2)_rNR_aS(O)_pR_b$, or $C_{1-6}$ alkyl substituted with 0-2 $R_e$, a $(CHR)_r$—$C_{3-6}$ carbocyclic residue substituted with 0-5 $R_e$. In another embodiment, $R_6$ is selected from hydrogen, F, Cl, Br, $OCF_3$, $CF_3$, CN, $NO_2$, =O, OH, $OR_b$, $S(O)_pR_b$, $C(O)R_d$, $NR_aC(O)$ $NR_aR_a$, $C(O)OR_d$, $S(O)_pNR_aR_a$, $NR_aS(O)_pR_b$, or $C_{1-4}$alkyl, and phenyl substituted with 0-1 $R_e$.

In another embodiment, $R_7$ is Cl; and $R_8$ is Cl.

In another embodiment, the compound is of formula (Ia)

Ia

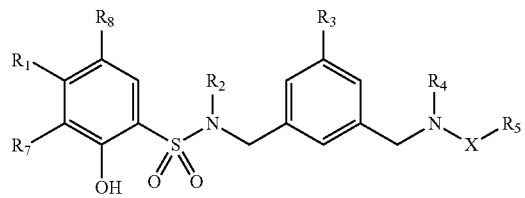

In another embodiment, r is 0. Alternatively, r is 1. Alternatively, r is 2.

In another embodiment, $R_a$, at each occurrence, is independently selected from H, $C_{1-6}$ alkyl substituted with 0-2 $R_e$, $C_{1-6}$ haloalkyl, and a $(CH_2)_r$—$C_{3-6}$ carbocyclic residue substituted with 0-5 $R_e$;

$R_b$, at each occurrence, is independently selected from $C_{1-6}$ alkyl substituted with 0-2 $R_e$, $C_{1-6}$ haloalkyl, a $(CH_2)_r$—$C_{3-6}$ carbocyclic residue substituted with 0-5 $R_e$;

$R_d$, at each occurrence, is independently selected from H, $C_{1-6}$ alkyl substituted with 0-2 $R_e$, $C_{1-6}$ haloalkyl, and a $(CH_2)_r$—$C_{3-6}$ carbocyclic residue substituted with 0-5 $R_e$;

$R_e$, at each occurrence, is independently selected from $C_{1-6}$ alkyl, $C_{2-6}$ alkenyl, $C_{2-6}$ alkynyl, $(CH_2)_rC_{3-6}$ cycloalkyl, Cl, F, Br, CN, $NO_2$, $CO_2H$, $(CF_2)_rCF_3$, $(CH_2)_rOC_{1-5}$ alkyl, OH, SH, $(CH_2)_rSC_{1-5}$ alkyl, $(CH_2)_rNR_fR_f$, and $(CH_2)_r$phenyl.

In another embodiment the present invention provides a pharmaceutical composition comprising a pharmaceutically acceptable carrier and at least one of the compounds of the present invention or a compound of formula I, Ia, Ib, or Ic or a stereoisomer, tautomer, pharmaceutically acceptable salt, solvate, or prodrug thereof.

In another embodiment, the present invention provides a pharmaceutical composition, comprising: a pharmaceutically acceptable carrier and a therapeutically effective amount of at least one of the compounds of the present invention or a compound of formula I, Ia, Ib, or Ic or a stereoisomer, tautomer, pharmaceutically acceptable salt, solvate or prodrug thereof.

In another embodiment, the present invention provides a novel method for treating cancers comprising: administering to a patient in need of such treatment a therapeutically effective amount of at least one of the compounds of the present invention or a compound of formula I, Ia, Ib, or Ic or a stereoisomer, tautomer, pharmaceutically acceptable salt, solvate or prodrug thereof.

In another embodiment, the present invention provides a novel method for treating cancer comprising: administering to a patient in need of such treatment a therapeutically effective amount of at least one of the compounds of the present invention or a compound of formula I, Ia, Ib, or Ic or a stereoisomer, tautomer, pharmaceutically acceptable salt, solvate or prodrug thereof, wherein the cancer is selected from mesothelioma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, ovarian cancer, cervical cancer, colon cancer, rectal cancer, cancer of the anal region, stomach cancer, gastrointestinal (gastric, colorectal, and duodenal), chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and biliary duct), primary or secondary central nervous system tumor, primary or secondary brain tumor, Hodgkin's disease, chronic or acute leukemia, chronic myeloid leukemia, lymphocytic lymphomas, lymphoblastic leukemia, follicular lymphoma, lymphoid malignancies of T-cell or B-cell origin, melanoma, multiple myeloma, oral cancer, small cell lung cancer, cancer of the kidney and ureter, renal cell carcinoma, carcinoma of the renal pelvis, neoplasms of the central nervous system, primary central nervous system lymphoma, non Hodgkin's lymphoma, spinal axis tumors, brain stem glioma, pituitary adenoma, adrenocortical cancer, gall bladder cancer, cancer of the spleen, cholangiocarcinoma, fibrosarcoma, neuroblastoma, retinoblastoma, or a combination thereof.

In another embodiment, the present invention provides a novel article of manufacture, comprising: (a) a first container; (b) a pharmaceutical composition located within the first container, wherein the composition, comprises: a first therapeutic agent, comprising: a compound of the present invention or a compound of formula I, Ia, Ib, or Ic; and (c) a package insert stating that the pharmaceutical composition can be used for the treatment of a cancer.

In another preferred embodiment, the present invention provides a novel article of manufacture, further comprising: (d) a second container; wherein components (a) and (b) are located within the second container and component (c) is located within or outside of the second container.

In another embodiment, the present invention provides a novel article of manufacture, comprising: (a) a first container; (b) a pharmaceutical composition located within the first container, wherein the composition, comprises: a first therapeutic agent, comprising: a compound of the present invention or a compound of formula I, Ia, Ib, or Ic; and (c) a package insert stating that the pharmaceutical composition can be used in combination with a second therapeutic agent to treat a cancer.

In another preferred embodiment, the present invention provides a novel article of manufacture, further comprising: (d) a second container; wherein components (a) and (b) are located within the second container and component (c) is located within or outside of the second container.

In another embodiment, the present invention provides a compound of the present invention for use in therapy.

In another embodiment, the present invention provides a compound of the present invention for use in therapy for treating a cancer.

In another embodiment, the present invention also provides the use of a compound of the present invention for the manufacture of a medicament for the treatment of a cancer.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

Definitions

The following are definitions of terms that may be used in the specification. The initial definition provided for a group or term herein applies to that group or term throughout the specification individually or as part of another group, unless otherwise indicated.

Compounds of this invention, may have one or more asymmetric centers. Unless otherwise indicated, all chiral (enantiomeric and diastereomeric) and racemic fowls of compounds of the present invention are included in the present invention. Many geometric isomers of olefins, C=N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric folios of a structure are intended, unless the specific stereochemistry or isomer form is specifically indicated. When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. All processes used to prepare compounds of the present invention and intermediates made therein are considered to be part of the present invention. When enantiomeric or diastereomeric products are prepared, they can be separated by conventional methods, for example, by chromatography or fractional crystallization. Compounds of the present invention, and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention. The inventive compounds may be in the free or hydrate form.

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

"Haloalkyl" is intended to include both branched and straight-chain saturated aliphatic hydrocarbon groups having the specified number of carbon atoms, substituted with 1 or more halogen. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

The term "halogen" or "halo" refers to fluorine, chlorine, bromine and iodine.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms, Preferred bridges are one or two carbon atoms. It is noted that a bridge always converts a monocyclic ring into a tricyclic ring. When a ring is bridged, the substituents recited for the ring may also be present on the bridge.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The terms "aryloxy", "arylamino", "arylalkylamino", "arylthio", "arylalkanoylamino", "arylsulfonyl", "arylalkoxy", "arylsulfinyl", "arylheteroaryl", "arylalkylthio", "arylcarbonyl", "arylalkenyl", or "arylalkylsulfonyl" refer to an aryl or substituted aryl bonded to an oxygen; an amino; an alkylamino; a thio; an alkanoylamino; a sulfonyl; an alkoxy; a sulfonyl; a heteroaryl or substituted heteroaryl; an alkylthio; a carbonyl; an alkenyl; or an alkylsulfonyl, respectively.

The term "aryloxy" refers to an aryl or a substituted aryl group bonded directly through an alkoxy group, such as methoxy or ethoxy (methoxy and ethoxy confusing —ArO—R.

The term "heteroaryl" refers to an optionally substituted, aromatic group for example, which is a 4 to 7 membered monocyclic, 7 to 11 membered bicyclic, or 10 to 15 membered tricyclic ring system, which has at least one heteroatom and at least one carbon atom-containing ring, for example, pyridine, tetrazole, indazole.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

An "alkylidene" group refers to an alkylene group consisting of at least two carbon atoms and at least one carbon-carbon double bond. Substituents on this group include those in the definition of "substituted alkyl".

The term "cycloalkyl" refers to an optionally substituted, saturated cyclic hydrocarbon ring systems, preferably containing 1 to 3 rings and 3 to 7 carbons per ring which may be further fused with an unsaturated $C_3$-$C_7$ carbocyclic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

As used herein, the term "heterocycle" or "heterocyclic group" is intended to mean a stable 5, 6, or 7-membered monocyclic or bicyclic or 7, 8, 9, 10, 11, 12, 13, or 14-membered bicyclic heterocyclic ring which is saturated, partially unsaturated or fully unsaturated, and which consists of carbon atoms and 1, 2, 3 or 4 heteroatoms independently selected from N, O and S; and including any bicyclic group in which any of the above-defined heterocyclic rings is fused to a benzene ring. The nitrogen and sulfur heteroatoms may optionally be oxidized (i.e., N→O and $S(O)_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azocinyl, benzimidazolyl, benzofuranyl, benzothiofuranyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,3,4-triazolyl, and xanthenyl. Also included are fused ring and Spiro compounds containing, for example, the above heterocycles.

Preferred 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5 to 6 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "aromatic heterocyclic group" or "heteroaryl" is intended to mean a stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, indolyl, pyrrolyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, benzodioxane, and the like. Heteroaryl groups can be substituted or unsubstituted. The nitrogen atom may be substituted or unsubstituted (i.e., N or NR wherein R is H or another substituent, if defined). The nitrogen and sulfur heteroatoms may optionally be oxidized (i.e., N→O and $S(O)_p$). It is to be noted that total number of S and O atoms in the aromatic heterocycle is not more than 1. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "carbocyclic ring" or "carbocyclyl" refers to stable, saturated, partially saturated or unsaturated, mono or bicyclic hydrocarbon rings that contain 3-12 atoms. Particularly, this includes a monocyclic ring containing 5 or 6 atoms or a bicyclic ring containing 9 or 10 atoms. Suitable values include cyclopropyl, cyclobutyl, cyclopentyl, cyclohexyl, cycloheptyl, dihydroindenyl and tetrahydronaphthyl. The term "optionally substituted" as it refers to "carbocyclic ring" or "carbocyclyl" herein indicates that the carbocyclic ring may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The term "heteroatoms" shall include oxygen, sulfur and nitrogen.

As referred to herein, the term "substituted" means that one or more hydrogen atoms is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

When any variable occurs more than one time in any constituent or formula for a compound, its definition at each occurrence is independent of its definition at every other occurrence. Thus, for example, if a group is shown to be substituted with 0-3 $R^{3a}$, then said group may optionally be substituted with up to three $R^{3a}$ groups and $R^{3a}$ at each occurrence is selected independently from the definition of $R^{3a}$. Also, combinations of substituents and/or variables are permissible only if such combinations result in stable compounds.

The compounds of formula I may exist in either a free, un-ionized from, or may form salts which are also within the scope of this invention. Pharmaceutically acceptable (i.e. non-toxic, physiologically acceptable) salts are on example, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for formula I may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, the disclosure of which is hereby incorporated by reference.

Compounds of the formula I may also have prodrug forms. Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

Various forms of prodrugs are well known in the art. For examples of such prodrug derivatives, see:

a) *Design of Prodrugs,* edited by H. Bundgaard, (Elsevier, 1985) and *Methods in Enzymology,* Vol. 112, pp. 309-396, edited by K. Widder, et al, (Academic Press, 1985);

b) *A Textbook of Drug Design and Development*, edited by Krosgaard-Larsen and H. Bundgaard, Chapter 5, "Design. and Application of Prodrugs," by H. Bundgaard, pp. 113-191 (1991); and c) H. Bundgaard, *Advanced Drug Delivery Reviews,* 8, pp. 1-38 (1992).

It should further be understood that solvates (e.g., hydrates) of the compounds of formula I are also with the scope of the invention. Methods of solvation are generally known in the art.

"Therapeutically effective amount" is intended to include an amount of a compound of the present invention that is effective when administered alone or in combination to inhibit Bcl-2 family antiapoptotic family proteins, such as Bcl-b, Mcl-1, Bcl-2, or BCl-Xl, or to treat the disorders listed herein. When applied to a combination, the term refers to combined amounts of the active ingredients that result in the therapeutic effect, whether administered in combination, serially or simultaneously.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

According to a further feature of the invention there is provided a method for producing an antiproliferative effect in a warm-blooded animal, such as a human being, in need of such treatment which comprises administering to said animal an effective amount of a compound of formula I or a pharmaceutically acceptable salt thereof as defined herein before.

The anti-proliferative treatment defined herein before may be applied as a sole therapy or may involve, in addition to a compound of the invention, one or more other substances and/or treatments. Such treatment may be achieved by way of the simultaneous, sequential or separate administration of the individual components of the treatment. The compounds of this invention may also be useful in combination with known anti-cancer and cytotoxic agents and treatments, including radiation. If formulated as a fixed dose, such combination products employ the compounds of this invention within the dosage range described below and the other pharmaceutically active agent within its approved dosage range. Compounds of formula I may be used sequentially with known anti-cancer or cytotoxic agents and treatment, including radiation when a combination formulation is inappropriate.

The term "anti-cancer" agent includes any known agent that is useful for the treatment of cancer including the following: 17α-ethinylestradiol, diethylstilbestrol, testosterone, prednisone, fluoxymesterone, dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, Zoladex; matrix metalloproteinase inhibitors; VEGF inhibitors, such as anti-VEGF antibodies (Avastin®) and small molecules such as ZD6474 and SU6668; Vatalanib, BAY-43-9006, SU11248, CP-547632, and CEP-7055; HER 1 and HER 2 inhibitors including anti-HER2 antibodies (Herceptin); EGFR inhibitors including gefitinib, erlotinib, ABX-EGF, EMD72000, 11F8, and cetuximab; Eg5 inhibitors, such as SB-715992, SB-743921, and MKT-833; pan Her inhibitors, such as cancertinib, EKB-569, CI-1033, AEE-788, XL-647, mAb 2C4, and GW-572016; Src inhibitors, e.g. dasatinib; Gleevec®; Casodex® (bicalutamide, Astra Zeneca), Tamoxifen; MEK-1 kinase inhibitors, MAPK kinase inhibitors, PI3 kinase inhibitors; PDGF inhibitors, such as imatinib; anti-angiogenic and antivascular agents which, by interrupting blood flow to solid tumors, render cancer cells quiescent by depriving them of nutrition; castration, which renders androgen dependent carcinomas non-proliferative; inhibitors of non-receptor and receptor tyrosine kinases; inhibitors of integrin signaling; tubulin acting agents such as vinblastine, vincristine, vinorelbine, vinflunine, paclitaxel, docetaxel, 7-O-methylthiomethylpaclitaxel, 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel, C-4 methyl carbonate paclitaxel, epothilone A, epothilone B, epothilone C, epothilone D, desoxyepothilone A, desoxyepothilone B, [1S-[1R*,3R*(E),7R*,10S*,11R*,12R*,16S*]]-7-11-dihydroxy-8,8,10,12,16-pentamethyl-3-[1-methyl-2-(2-methyl-4-thiazolyl)ethenyl]-4-aza-17 oxabicyclo[14.1.0] heptadecane-5,9-dione (ixabepilone), [1S-[1R*,3R*(E), 7R*,10S*,11R*,12R*,16S*]]-3-[2-[2-(aminomethyl)-4-thiazolyl]-1-methylethenyl]-7,11-dihydroxy-8,8,10,12,16-pentamethyl-4-17-dioxabicyclo[14.1.0]-heptadecane-5,9-dione, and derivatives thereof; CDK inhibitors, antiproliferative cell cycle inhibitors, epidophyllotoxin, etoposide, VM-26; antineoplastic enzymes, e.g., topoisomerase I inhibitors, camptothecin, topotecan, SN-38; procarbazine; mitoxantrone; platinum coordination complexes such as cisplatin, carboplatin and oxaliplatin; biological response modifiers; growth inhibitors; antihormonal therapeutic agents; leucovorin; tegafur; antimetabolites such as purine antagonists (e.g. 6-thioguanine and 6-mercaptopurine; glutamine antagonists, e.g. DON (AT-125; d-oxo-norleucine); ribonucleotide reductase inhibitors; mTOR inhibitors; and haematopoietic growth factors.

Additional cytotoxic agents include, cyclophosphamide, doxorubicin, daunorubicin, mitoxantrone, melphalan, hexamethyl melamine, thiotepa, cytarabin, idatrexate, trimetrexate, dacarbazine, L-asparaginase, bicalutamide, leuprolide, pyridobenzoindole derivatives, interferons, and interleukins.

In the field of medical oncology it is normal practice to use a combination of different forms of treatment to treat each patient with cancer. In medical oncology the other component(s) of such treatment in addition to the antiproliferative treatment defined herein before may be surgery, radiotherapy or chemotherapy. Such chemotherapy may cover three main categories of therapeutic agent:

(i) antiangiogenic agents that work by different mechanisms from those defined hereinbefore (for example, linomide, inhibitors of integrin $\alpha v \beta 3$ function, angiostatin, razoxane);

(ii) cytostatic agents such as antiestrogens (for example, tamoxifen, toremifene, raloxifene, droloxifene, iodoxifene), progestogens (for example, megestrol acetate), aromatase inhibitors (for example, anastrozole, letrozole, borazole, exemestane), antihormones, antiprogestogens, antiandrogens (for example, flutamide, nilutamide, bicalutamide, cyproterone acetate), LHRH agonists and antagonists (for example, gosereline acetate, leuprolide), inhibitors of testosterone $5\alpha$-dihydroreductase (for example, finasteride), farnesyltransferase inhibitors, anti-invasion agents (for example, metalloproteinase inhibitors such as marimastat and inhibitors of urokinase plasminogen activator receptor function) and inhibitors of growth factor function, (such growth factors include for example, EGF, FGF, platelet derived growth factor and hepatocyte growth factor, such inhibitors include growth factor antibodies, growth factor receptor antibodies such as Avastin® (bevacizumab) and Erbitux® (cetuximab); tyrosine kinase inhibitors and serine/threonine kinase inhibitors); and (iii) antiproliferative/antineoplastic drugs and combinations thereof, as used in medical oncology, such as antimetabolites (for example, antifolates such as methotrexate, fluoropyrimidines such as 5-fluorouracil, purine and adenosine analogues, cytosine arabinoside); Intercalating antitumour antibiotics (for example, anthracyclines such as doxorubicin, daunomycin, epirubicin and idarubicin, mitomycin-C, dactinomycin, mithramycin); platinum derivatives (for example, cisplatin, carboplatin); alkylating agents (for example, nitrogen mustard, melphalan, chlorombucil, busulphan, cyclophosphamide, ifosfamide nitrosoureas, thiotepa; antimitotic agents (for example, vinca alkaloids like vincristine, vinorelbine, vinblastine and vinflunine) and taxoids such as Taxol® (paclitaxel), Taxotere® (docetaxel) and newer microtubule agents such as epothilone analogs (ixabepilone), discodermolide analogs, and eleutherobin analogs; topoisomerase inhibitors (for example, epipodophyllotoxins such as etoposide and teniposide, amsacrine, topotecan, irinotecan); cell cycle inhibitors (for example, flavopyridols); biological response modifiers and proteasome inhibitors such as Velcade® (bortezomib).

As stated above, the formula I compounds of the invention are of interest for their antiproliferative effects. Such compounds of the invention are expected to be useful in a wide range of disease states including cancer, psoriasis, and rheumatoid arthritis.

Thus, the present invention provides methods for the treatment of a variety of cancers, including, but not limited to, the following:

carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma);

hematopoietic tumors of lymphoid lineage including leukemia, acute lymphocytic leukemia, acute lymphoblastic leukemia, B-cell lymphoma, T-cell lymphoma, Hodgkin's lymphoma, non-Hodgkin's lymphoma, hairy cell lymphoma, histiocytic lymphoma, and Burkett's lymphoma;

hematopoietic tumors of myeloid lineage including acute and chronic myelogenous leukemias, myelodysplastic syndrome, myeloid leukemia, and promyelocytic leukemia;

tumors of the central and peripheral nervous system including astrocytoma, neuroblastoma, glioma, and schwannomas;

tumors of mesenchymal origin including fibrosarcoma, rhabdomyosarcoma, and osteosarcoma; and other tumors including melanoma, xenoderma pigmentosum, keratoctanthoma, seminoma, thyroid follicular cancer, and teratocarcinoma.

The present invention provides methods for the treatment of a variety of non-cancerous proliferative diseases. The invention is useful to treat GIST, Breast cancer, pancreatic cancer, colon cancer, NSCLC, CML, and ALL, sarcoma, and various pediatric cancers.

The present invention provides methods for the treatment of a variety of proliferative diseases, including A method for treating mesothelioma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, ovarian cancer, cervical cancer, colon cancer, rectal cancer, cancer of the anal region, stomach cancer, gastrointestinal (gastric, colorectal, and duodenal), chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and biliary duct), primary or secondary central nervous system tumor, primary or secondary brain tumor, Hodgkin's disease, chronic or acute leukemia, chronic myeloid leukemia, lymphocytic lymphomas, lymphoblastic leukemia, follicular lymphoma, lymphoid malignancies of T-cell or B-cell origin, melanoma, multiple myeloma, oral cancer, small cell lung cancer, cancer of the kidney and ureter, renal cell carcinoma, carcinoma of the renal pelvis, neoplasms of the central nervous system, primary central nervous system lymphoma, non Hodgkin's lymphoma, spinal axis tumors, brain stem glioma, pituitary adenoma, adrenocortical cancer, gall bladder cancer, cancer of the spleen, cholangiocarcinoma, fibrosarcoma, neuroblastoma, retinoblastoma, or a combination thereof.

The pharmaceutical compositions of the invention containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets.

These excipients may be for example, inert diluents, such as calcium carbonate, sodium carbonate, lactose, calcium phosphate or sodium phosphate; granulating and disintegrating agents, for example, microcrystalline cellulose, sodium croscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropyl-cellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of oil-in-water emulsions. The oily phase may be a vegetable oil, for example olive oil or arachis oil, or a mineral oil, for example liquid paraffin or mixtures of these.

Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ Model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage will normally be determined by the prescribing physician with the dosage generally varying according to the age, weight, sex and response of the individual patient, as well as the severity of the patient's symptoms.

If formulated as a fixed dose, such combination products employ the compounds of this invention within the dosage range described above and the other pharmaceutically active agent or treatment within its approved dosage range. Compounds of formula I may also be administered sequentially with known anti-cancer or cytotoxic agents when a combination formulation is inappropriate. The invention is not limited in the sequence of administration; compounds of formula I may be administered either prior to or after administration of the known anti-cancer or cytotoxic agent(s).

The compounds may be administered in a dosage range of about 0.05 to 200 mg/kg/day, preferably less than 100 mg/kg/day, in a single dose or in 2 to 4 divided doses.

Biological Assays

Utility

In general, compounds of the present invention inhibit at least one of the following assays: BclB, Bcl2, Mcl1, BclX.

Compounds were profiled for their ability to disrupt in vitro binding interactions in fluorescence polarization assays (FPAs) using synthetic fluorochrome-labeled Bcl homology 3 (BH3) peptides derived from BIM [(FAM)-Ahx-DNRPEI-WIAQELRRIGDEFNAYYAR-NH$_2$ (SEQ ID NO: 1) (GenBank Accession No. O43521)] or BAK [Ac-GQVGRQLAI-IGE-LYS(FAM)-INR-NH$_2$ (SEQ ID NO:2) (GenBank Accession No. Q16611) amino acid sequences and four bacterial recombinant proteins [Bcl-b (GenBank Accession No. Q9HD36), Bcl-2 (GenBank Accession No. P10415), Bcl-Xl (GenBank Accession No. Q07817), Mcl-1 (GenBank Accession No. Q07820)] without their C-terminal transmembrane domain. Proteins were purified from bacterial lysates using their glutathione S-transferase (GST)-tag (Bcl-b, Bcl-2, Mcl-1) or His$_6$-tag (Bcl-Xl) and following one-step affinity chromatography procedures. Dissociation constants (Kd) for peptide binding protein were determined by fluorescence polarization in FPAs measuring BIM BH3 peptide binding Bcl-b, Mcl-1 or Bcl-2 protein or BAK BH3 peptide binding Bcl-Xl protein. The Kd values were generated by fitting the experimental data using a sigmoidal dose-response nonlinear regression model.

Compound inhibitory concentration values, IC$_{50}$ (50% reduction in fluorescence polarization), were determined using fluorochrome-labeled BH3 peptides and recombinant Bcl proteins in fluorescence polarization assays (FPAs). Compounds diluted in DMSO (0.5 ul) were transferred (in duplicate) to individual wells of a 384-well plate. The fluorochrome-labeled peptide was added followed by recombinant protein addition. Each binding FPA reaction (50 ul) contained BIM BH3 peptide (5 nM) or BAK BH3 peptide (1.5 nM) and Bcl-b (40 nM), Mcl-1 (28 nM), Bcl-2 (11 nM) or Bcl-Xl. (5 nM) protein suspended in assay buffer [20 mM sodium phosphate, pH 7.4, 1 mM EDTA, 50 mM NaCl., 0.05% Pluronic F68]. Reaction mixtures were incubated at ambient temperature for 60 minutes prior to measuring polarization (mP) using an Analyst (LJL, Molecular Devices, Sunnyvale, Calif.) programmed to detect an emission wavelength of 530 nm after excitation (excitation wavelength=485 nm).

Competitive compound inhibition constants (Ki) were calculated using FPA experimental data and a mathematical equation, $Ki=[I]_{50}/([L]_{50}/Kd+[P]_0/Kd+1)$, where $[I]_{50}$ denotes free inhibitor concentration at 50% inhibition, $[L]_{50}$ is free labeled ligand concentration at 50% inhibition, $[P]_0$ is free protein concentration at 0% inhibition, and Kd is the dissociation constant of the protein-ligand complex.

Examples 1 to 275 have a Ki of $\leq 10$ μM as measured in the Bclb/Bim assay described above.

The following compounds were found to have the Ki described in Table 1 when measured in the assays described above.

| Example No. | Bclb/Bim K$_i$ (μM) | Mcl-1/Bim K$_i$ (μM) | Bcl2/Bim K$_i$ (μM) |
|---|---|---|---|
| 2 | 0.05 | 0.02 | 0.02 |
| 4 | 0.28 | 0.06 | 0.06 |
| 8 | 0.10 | 0.04 | 0.01 |
| 13 | 0.09 | 0.03 | 0.02 |
| 15 | 0.08 | 0.01 | 0.01 |
| 39 | 0.289 | 0.207 | 0.153 |
| 49 | 0.138 | 0.204 | 0.347 |
| 56 | 0.103 | 0.187 | 0.148 |
| 61 | 0.133 | 1.023 | 0.500 |
| 64 | 0.074 | 0.169 | 0.096 |
| 71 | 0.247 | 0.970 | 0.469 |
| 72 | 0.182 | 1.151 | 0.349 |
| 73 | 0.144 | 0.384 | 0.319 |
| 77 | 0.077 | 0.194 | 0.133 |
| 91 | 0.033 | 0.052 | 0.042 |
| 92 | 0.012 | 0.060 | 0.046 |
| 94 | 0.04 | 0.06 | 0.06 |
| 95 | 0.06 | 0.07 | 0.12 |
| 96 | 0.06 | 0.01 | 0.11 |
| 97 | 0.07 | 0.10 | 0.11 |
| 98 | 0.16 | 0.28 | 0.23 |
| 106 | 0.04 | 0.04 | 0.04 |
| 107 | 0.21 | 0.52 | 0.48 |
| 130 | 0.44 | 2.06 | 0.84 |
| 135 | 0.28 | 0.49 | 0.61 |
| 137 | 0.22 | 0.48 | 0.25 |
| 138 | 0.45 | 1.76 | 0.82 |
| 140 | 0.50 | 1.73 | 0.66 |
| 143 | 0.17 | 0.45 | 0.37 |
| 147 | 0.45 | 1.73 | 0.96 |
| 150 | 0.20 | 0.46 | 0.44 |
| 175 | 0.06 | 0.03 | 0.04 |
| 176 | 0.18 | 0.48 | 0.44 |
| 190 | 0.15 | 0.55 | 0.18 |
| 191 | 0.18 | 0.53 | 0.11 |
| 211 | 0.16 | 0.53 | 0.48 |
| 213 | 0.47 | 2.70 | 1.22 |
| 214 | 0.61 | 1.64 | 1.80 |
| 219 | 0.12 | 0.04 | 0.17 |
| 222 | 0.03 | 0.03 | 0.17 |
| 226 | 0.50 | 2.28 | 3.73 |
| 232 | 0.09 | 0.05 | 0.09 |
| 235 | 0.06 | 0.04 | 0.08 |
| 240 | 0.11 | 0.47 | 0.12 |
| 256 | 0.14 | 2.12 | 0.13 |
| 266 | 0.30 | 1.68 | 0.72 |
| 274 | 0.45 | 1.57 | 0.52 |

Synthesis

In general, the compounds of Formula (I) can be prepared in accordance with Scheme I and the general knowledge of one skilled in the art. Accordingly, the compounds of the instant invention can be obtained by methods exemplified in the following Schemes.

Bis-sulfonamides or sulfonamide-carboxamides analogues with the substituents on the 3-methylamino group such as 6 and 8 were prepared as depicted in Scheme 1.

Reductive alkylation of tert-butyl 3-(aminomethyl)benzylcarbamate 1 with various aldehydes such as 4-fluorobenzaldehyde or biphenylbenzaldehyde in the presence of hydride reducing agent provides N-alkyl substituted tert-butyl 3-(aminomethyl)benzylcarbamates such as 2 (Scheme 1). Sulfonylation of the amine using various sulfonyl chlorides such as dichlorohydroxyphenylsulfonyl chloride 3 affords sulfonamide 4. Upon deprotection of the t-Boc group with acid followed by coupling with another sulfonyl chlorides such as 3 or various carboxylic acids provide bis-sulfonamide 6 and sulfonamide-carboxamide 8, respectively.

Analogues with 5-alkoxy substituents on the middle phenyl ring such as 13 were prepared starting from dimethyl 5-hydroxyisophthalate 9 (Scheme 2). Alkylation of dimethyl 5-hydroxyisophthalate with various alkyl halides such as benzyl bromide in the presence of suitable base provided dimethyl 5-(benzyloxy)isophthalate 10. Reduction of the ester using lithium aluminum hydride followed by mesylation provided bis-mesylated compound 11. Reaction of the bis-mesylated compound with sodium azide followed by reduction of the resulting azido groups afforded di-amine 12. Bis-sulfonylation of the amine 12 provided bis-sulfonamide 13.

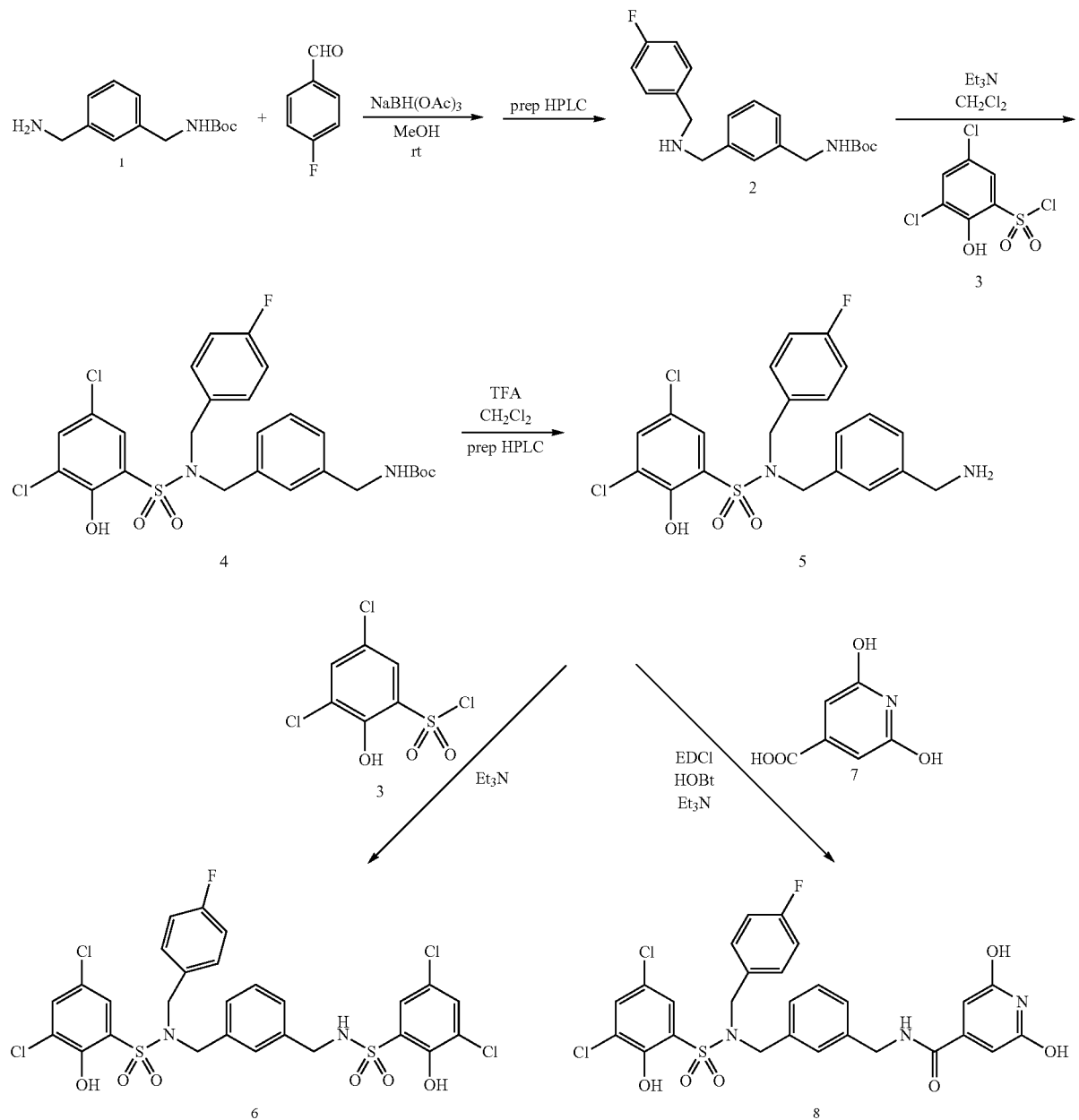

Scheme 1

Scheme 2

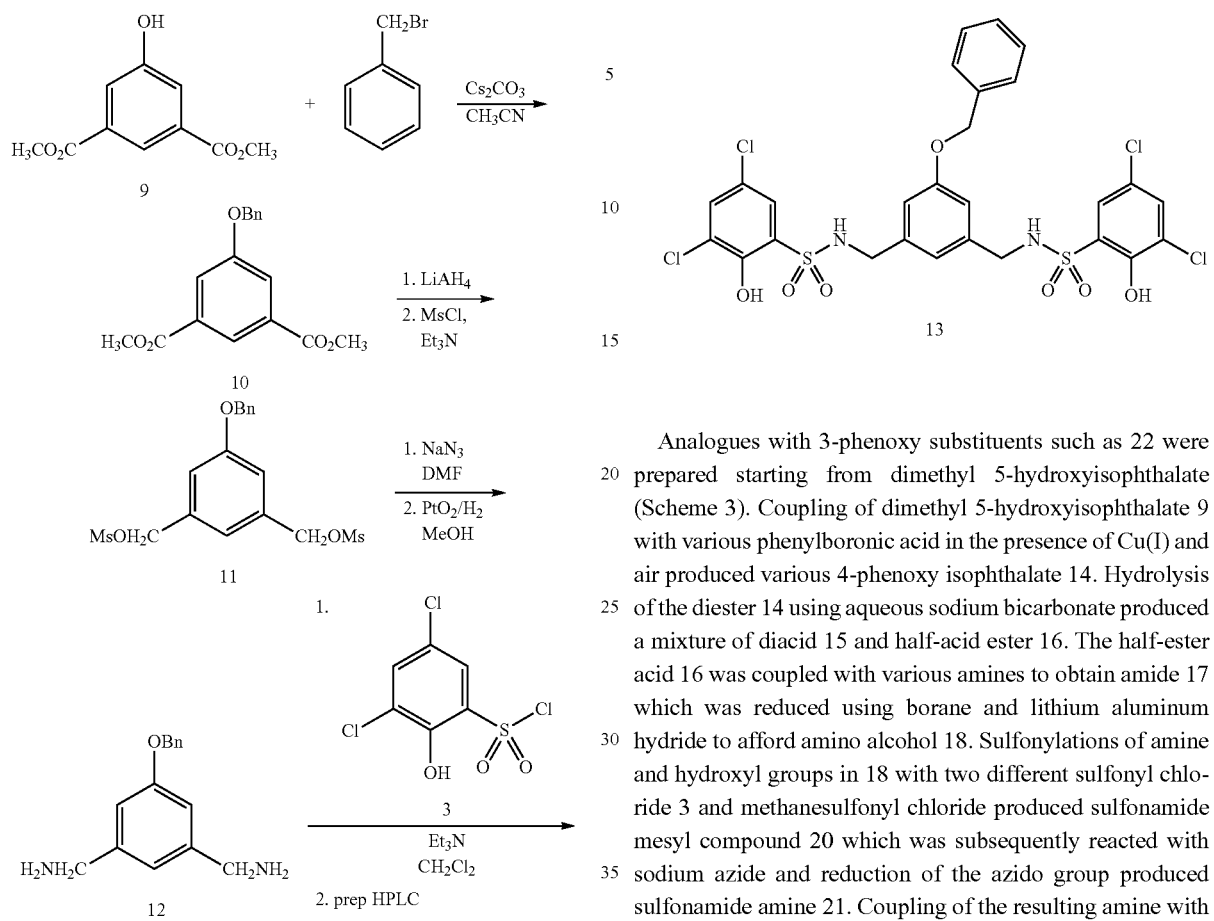

Analogues with 3-phenoxy substituents such as 22 were prepared starting from dimethyl 5-hydroxyisophthalate (Scheme 3). Coupling of dimethyl 5-hydroxyisophthalate 9 with various phenylboronic acid in the presence of Cu(I) and air produced various 4-phenoxy isophthalate 14. Hydrolysis of the diester 14 using aqueous sodium bicarbonate produced a mixture of diacid 15 and half-acid ester 16. The half-ester acid 16 was coupled with various amines to obtain amide 17 which was reduced using borane and lithium aluminum hydride to afford amino alcohol 18. Sulfonylations of amine and hydroxyl groups in 18 with two different sulfonyl chloride 3 and methanesulfonyl chloride produced sulfonamide mesyl compound 20 which was subsequently reacted with sodium azide and reduction of the azido group produced sulfonamide amine 21. Coupling of the resulting amine with sulfonyl chloride 3 afforded bis-sulfonamide 22.

Scheme 3

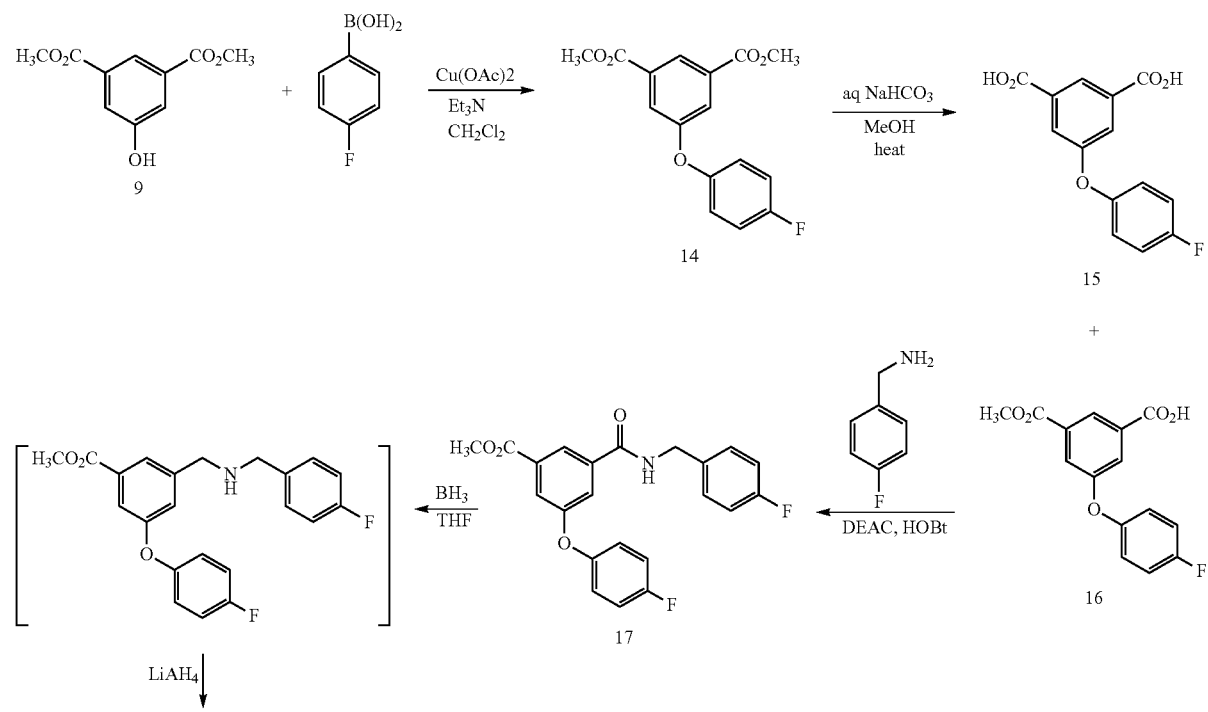

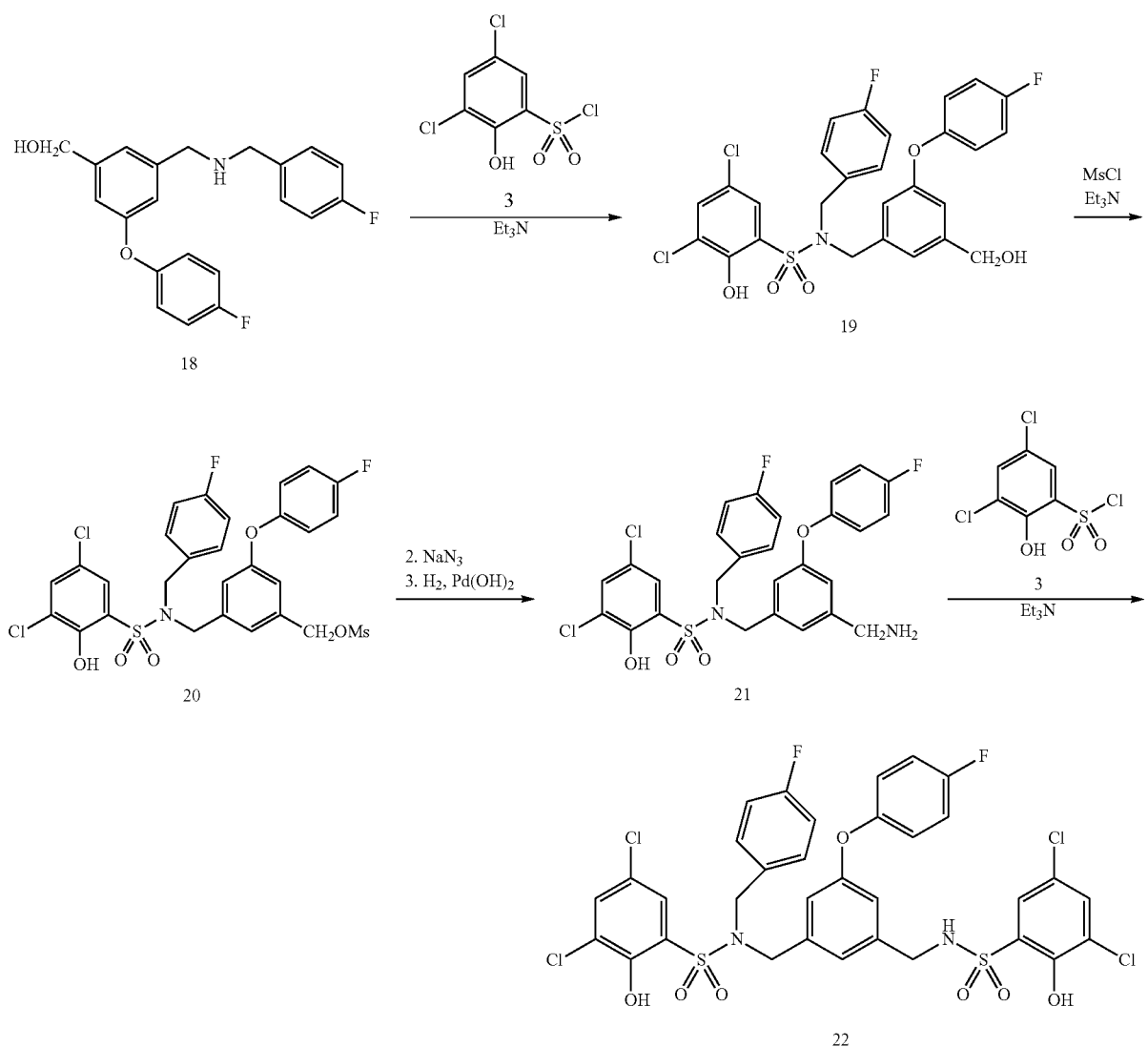

Biphenyl bis-sulfonamide analogue was prepared starting from dimethyl 4'-fluorobiphenyl-3,5-dicarboxylate 23 which was prepared via Suzuki coupling reaction of dimethyl 5-bromoisophthalate with 4-fluorophenylboronic acid (Scheme 4). Following the similar procedures as described in Scheme 3 yielded biphenyl bis-sulfonamides such as 3,5-dichloro-N-((4'-fluoro-5-((N-(4-fluorobenzyl)-4-methylphenylsulfonamido)methyl)biphenyl-3-yl)methyl)-2-hydroxybenzenesulfonamide 31.

Scheme 4

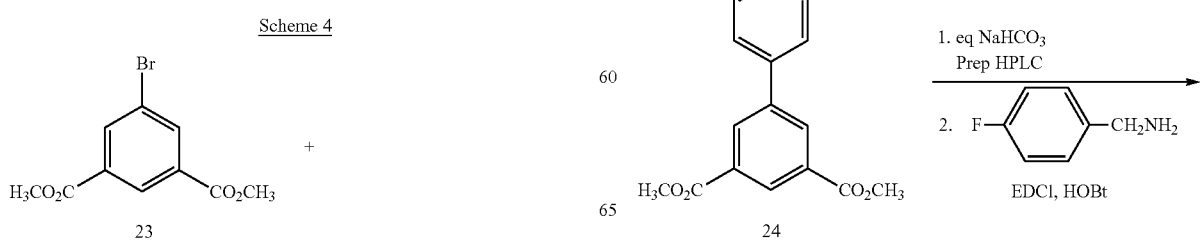

35
-continued

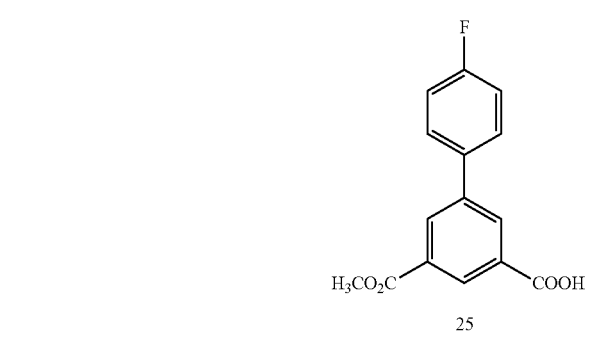

25

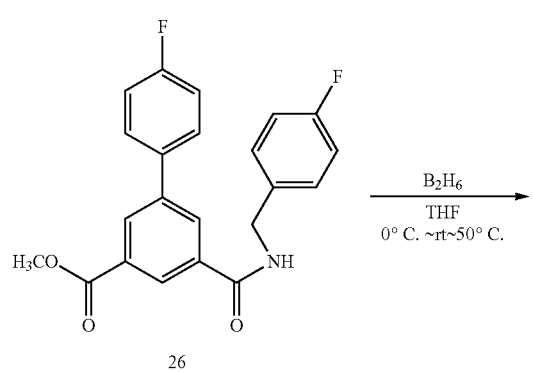

26

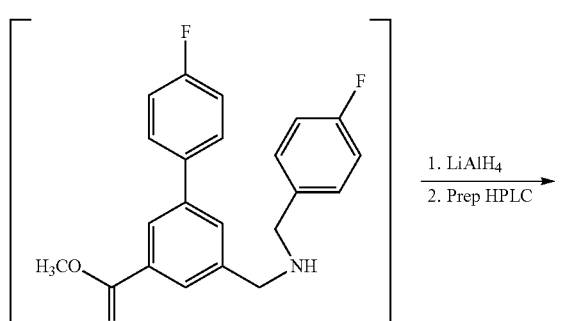

27

36
-continued

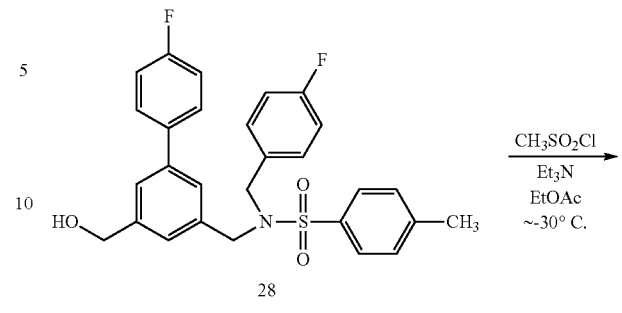

28

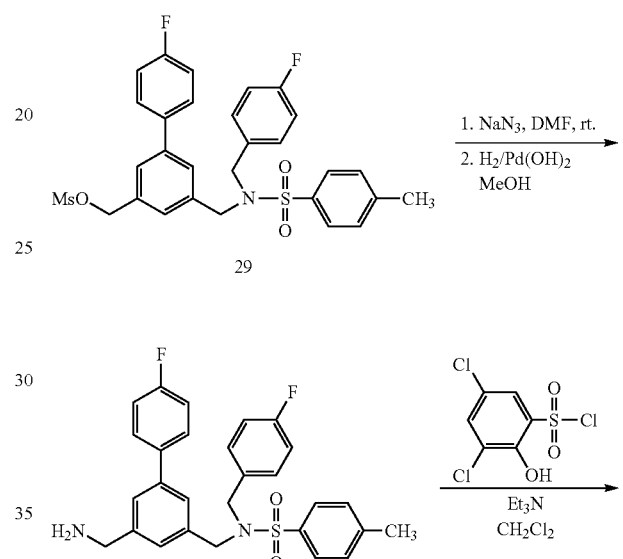

29

30

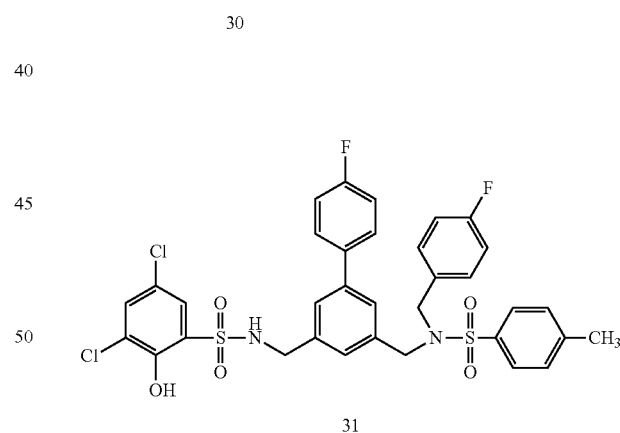

31

Analogues substituted halogen on the middle phenyl ring such as 35 and 36 were prepared starting from 5-chloroisophthalic acid 32 following the similar procedures as described in Schemes 3 and 4 (Scheme 5).

Phenylsulfamoyl compound 43 was prepared from amine 38 and 3-cyano-benzenesulfonyl chloride 39 (Scheme 6). Coupling of 38 with 39 in the presence of Et₃N provided sulfonamide 40, which was reduced to 41 using borane. Following the similar procedure as above afforded phenylsulfamoyl compound 43.

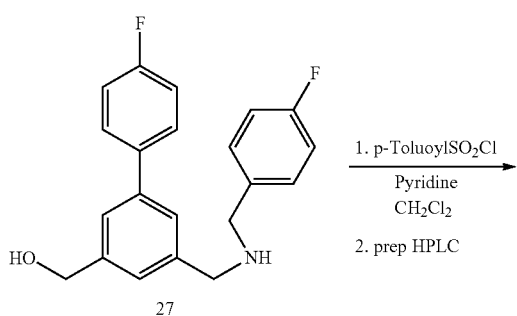

Scheme 5
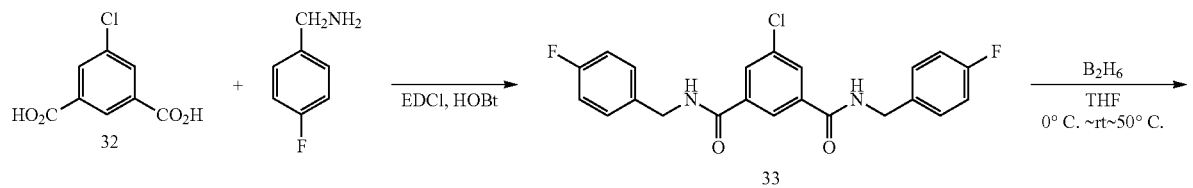
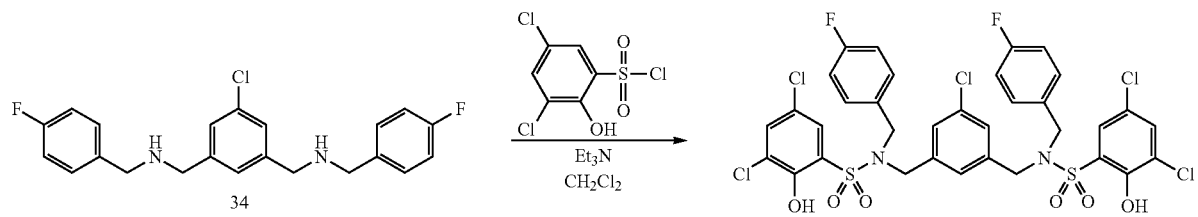
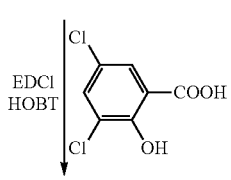
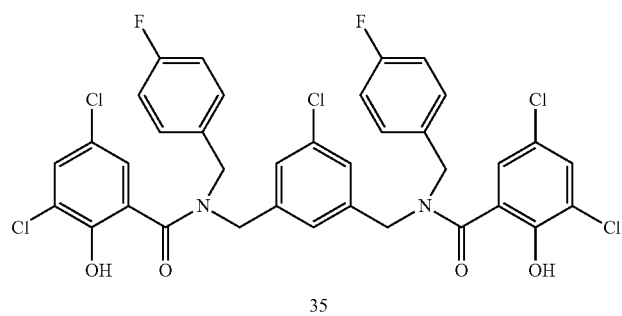
Scheme 6
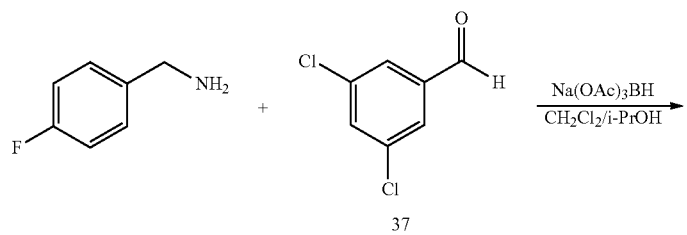
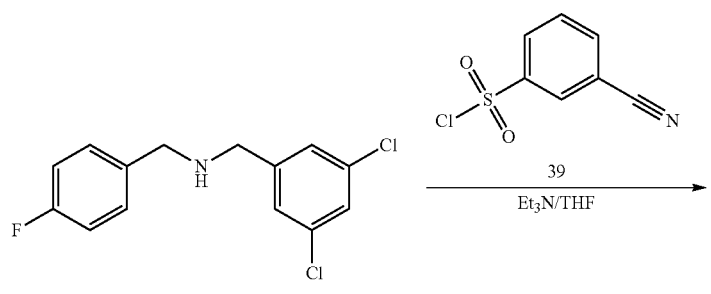

-continued
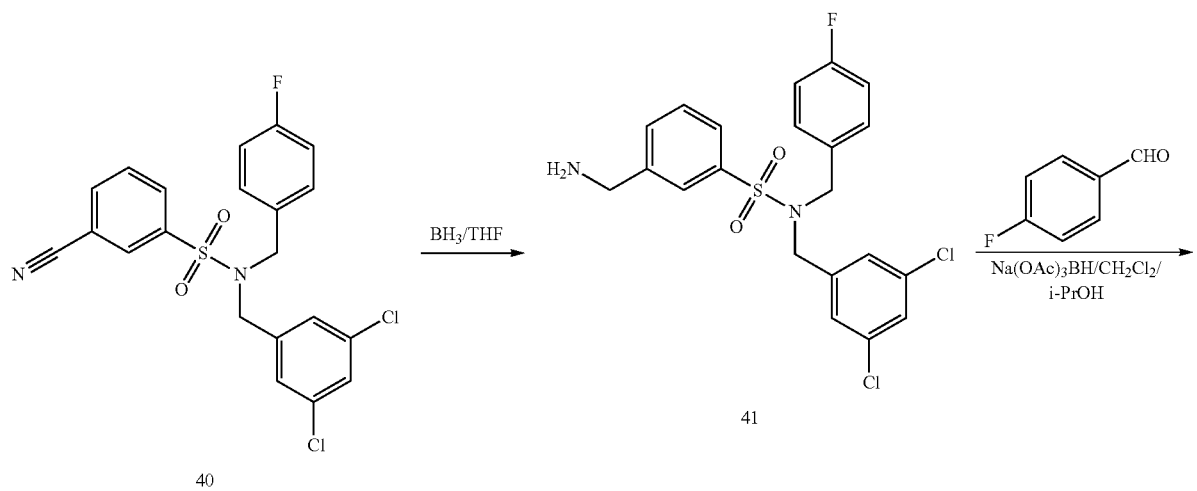
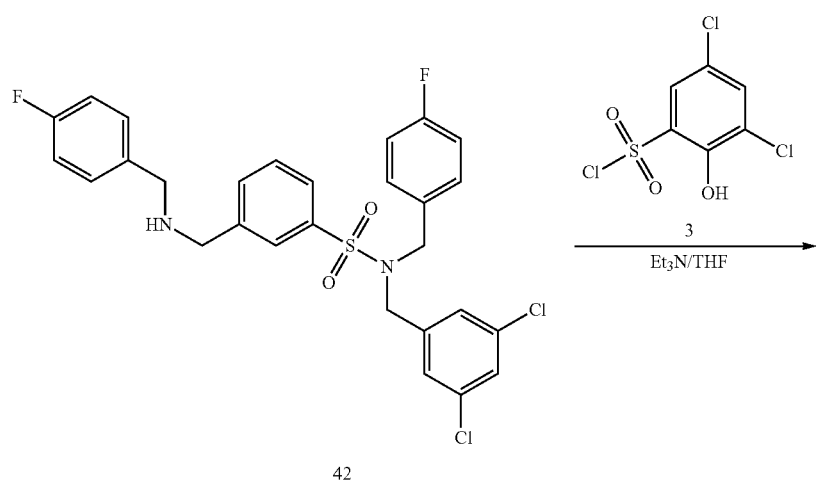
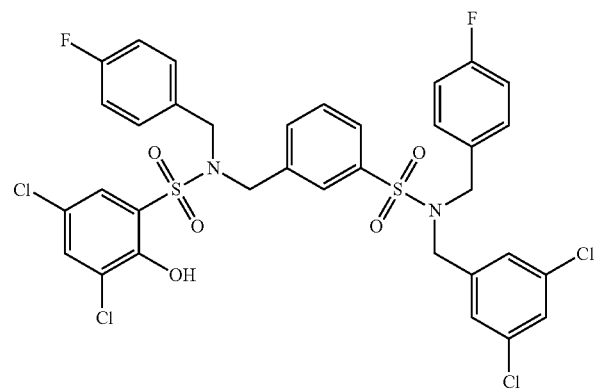
Benzamide compound 48 was prepared following the similar procedure as shown above using the starting material of benzoic acid derivative 44 (Scheme 7).

Scheme 7
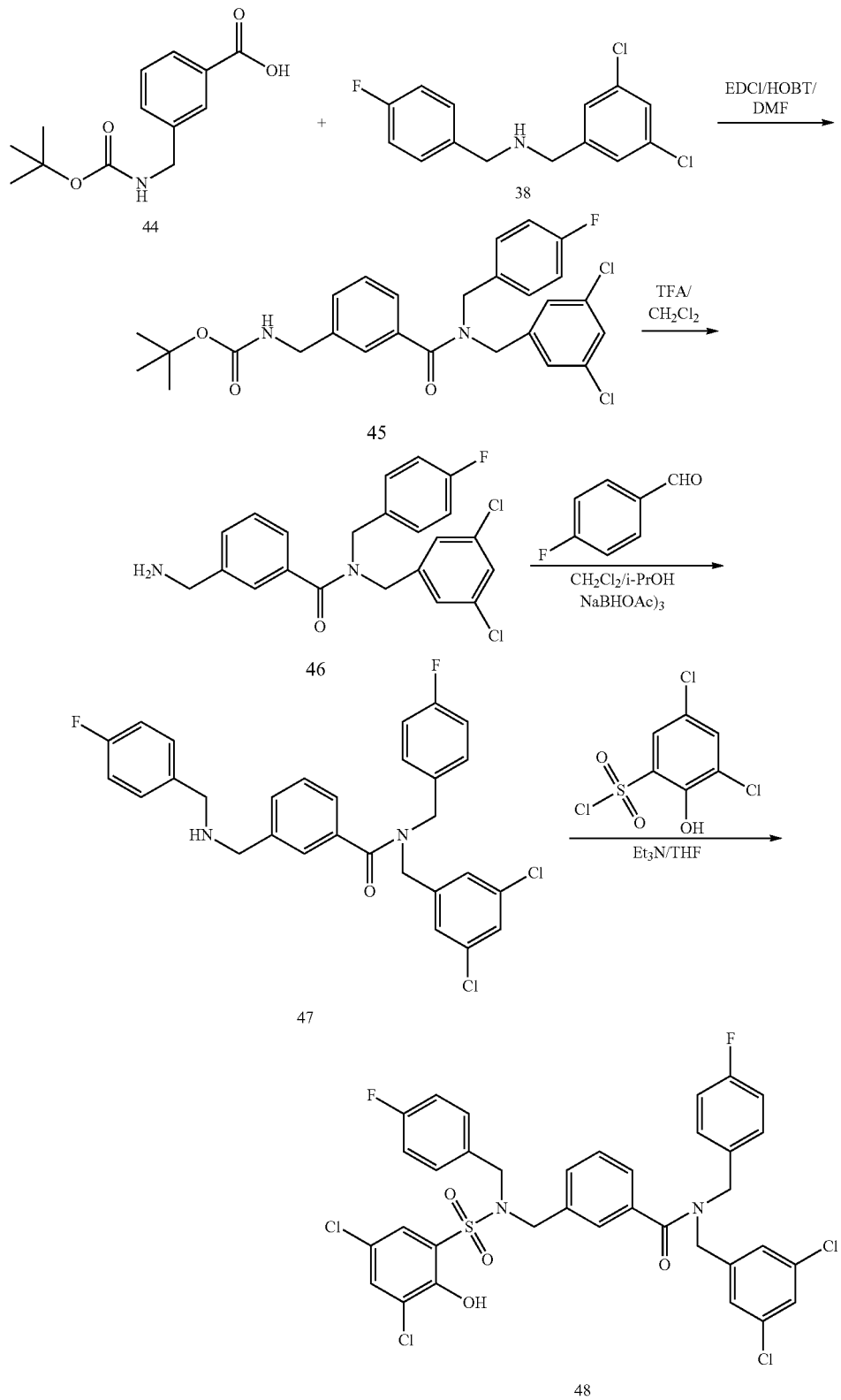
Bis-sulfonamides 50 and 54 were prepared following the similar procedures by use of the starting material, 1,4-phenylenedimethanamine and tert-butyl 4-(aminomethyl)benzylcarbamate, respectively (Schemes 8 and 9).

Scheme 8
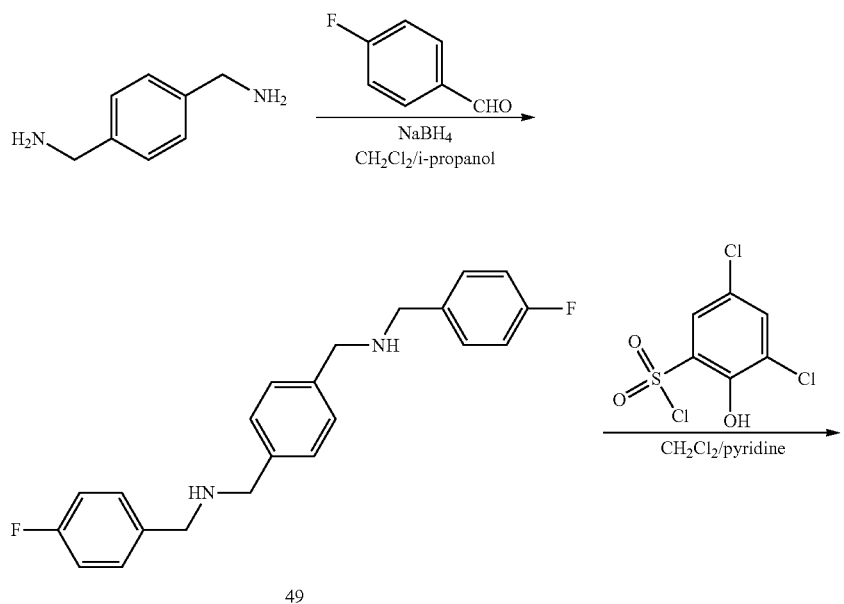
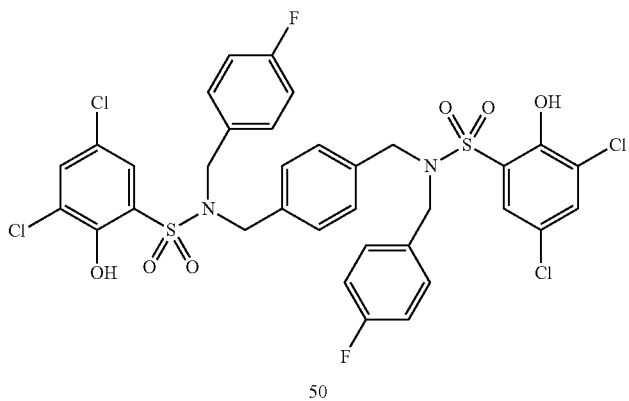
Scheme 9
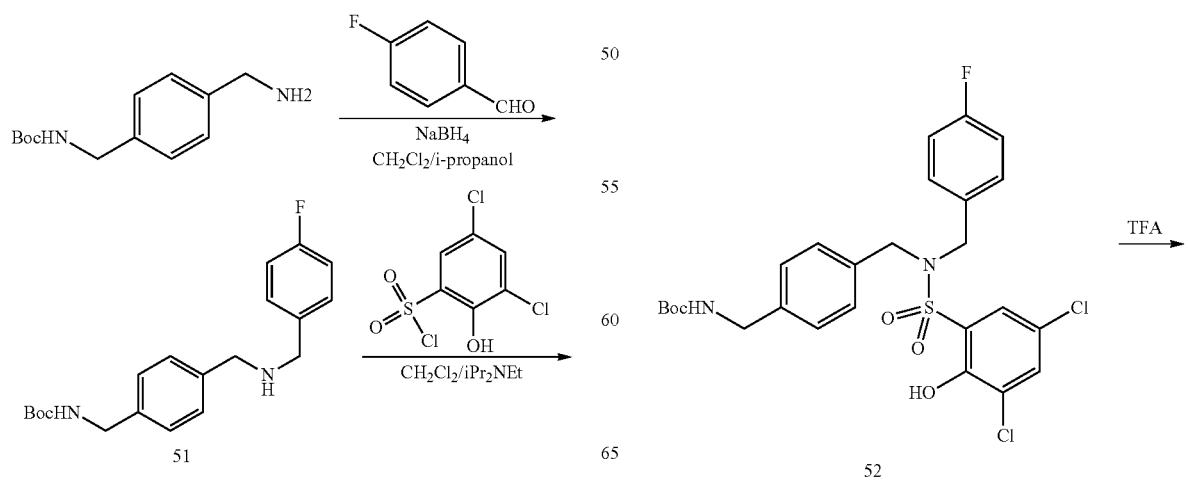

45
-continued
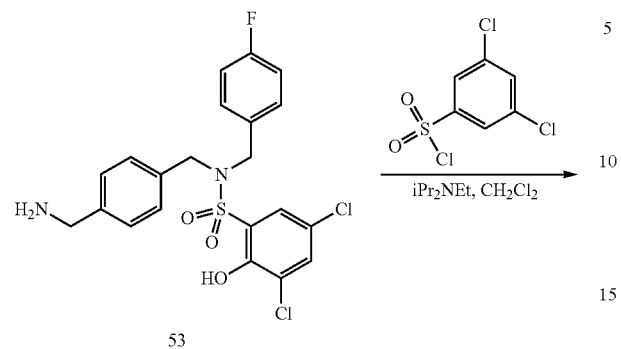
53
46
-continued
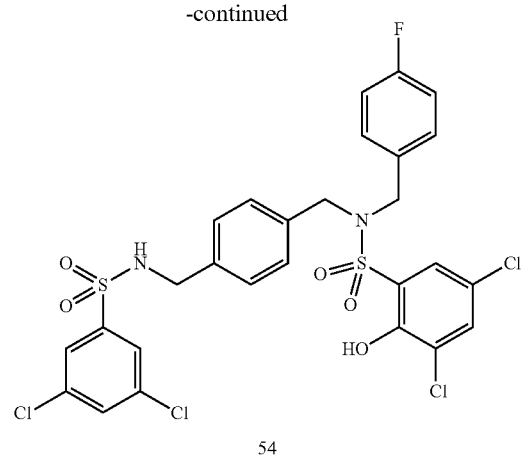
54
Scheme 10
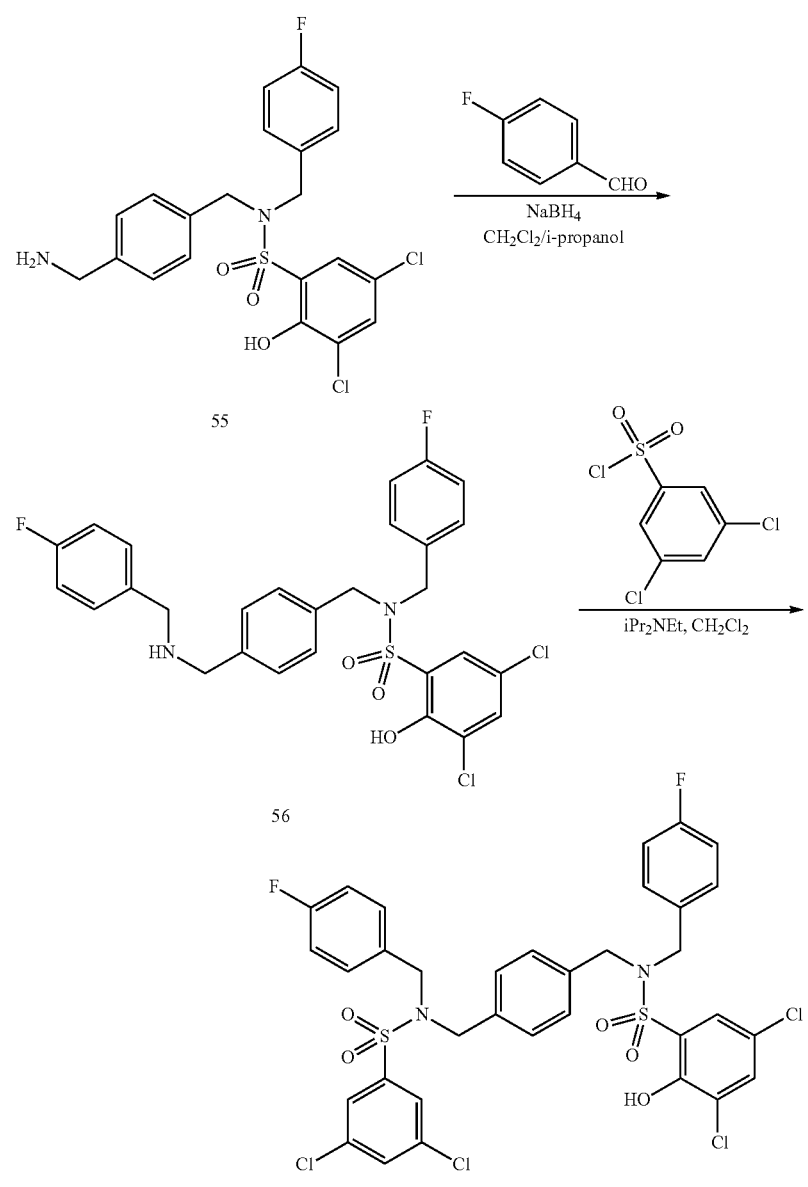
55
56
57

Amide analogues 63 were prepared using the synthetic route outlined in Scheme 11. Reductive alkylation of amine 58 with aldehyde 59 occurred in the presence of triethylamine and sodium triacetoxyborohydride to afford the secondary amine 60. Sulfonylation of compound 60 with phenylsulfonyl chloride derivative 3 provided sulfonamide 61. Hydrolysis of the ester moiety of 61 under basic conditions provided acid 62, which was subsequently coupled to various amines under standard conditions (HATU=O-(7-azabenzotriazol-1-yl)-N,N,N'N'-tetramethyluronium hexafluorophosphate) in the presence of Hunig's base to afford the amide analogues 63.

Scheme 11

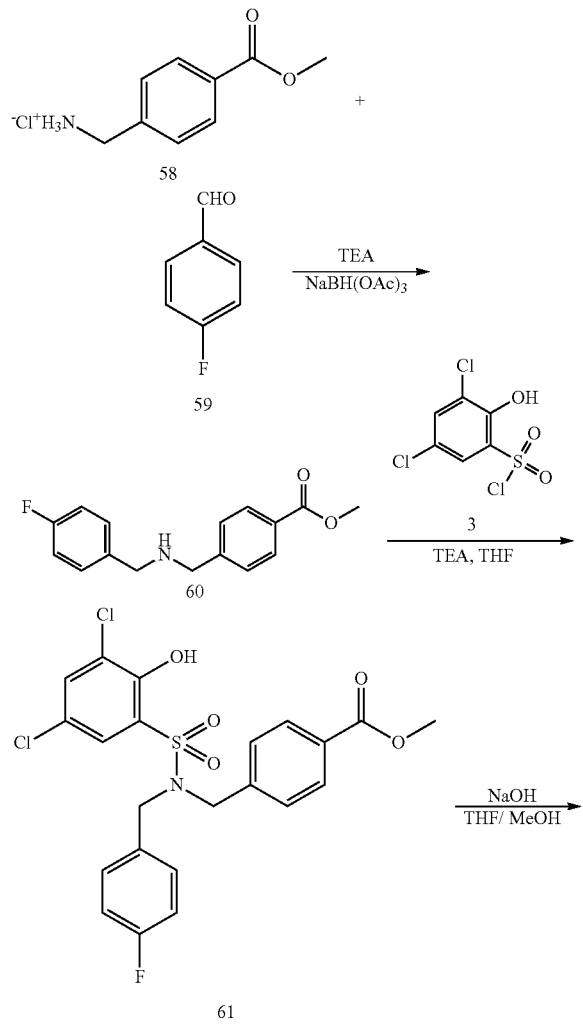

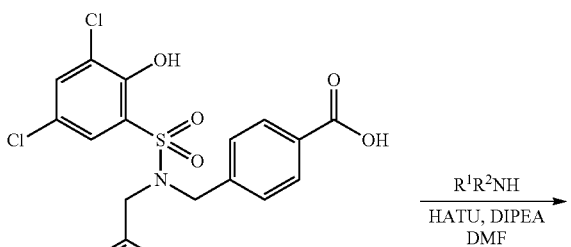

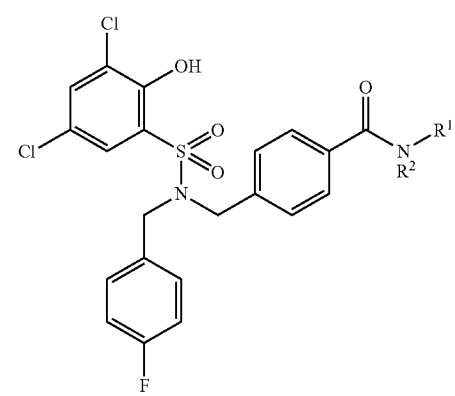

Similarly, analogues with a substituent on the benzamide were obtained using chemistry detailed in Scheme 12. Benzyl bromide derivative 64 was coupled with the 4-fluorophenyl-methanamine (65) and triethylamine to afford the secondary amine 66. Sulfonylation of compound 66 with the sulfonyl chloride derivative 3, followed by base-promoted hydrolysis gave acid 67. The coupling of 67 with various amines afforded amide analogues 68.

Scheme 12

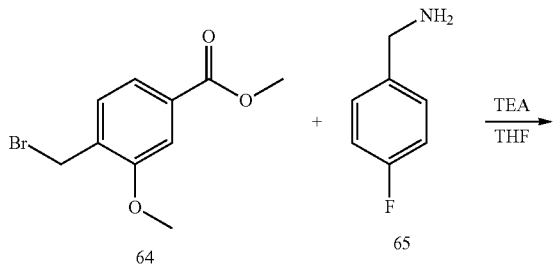

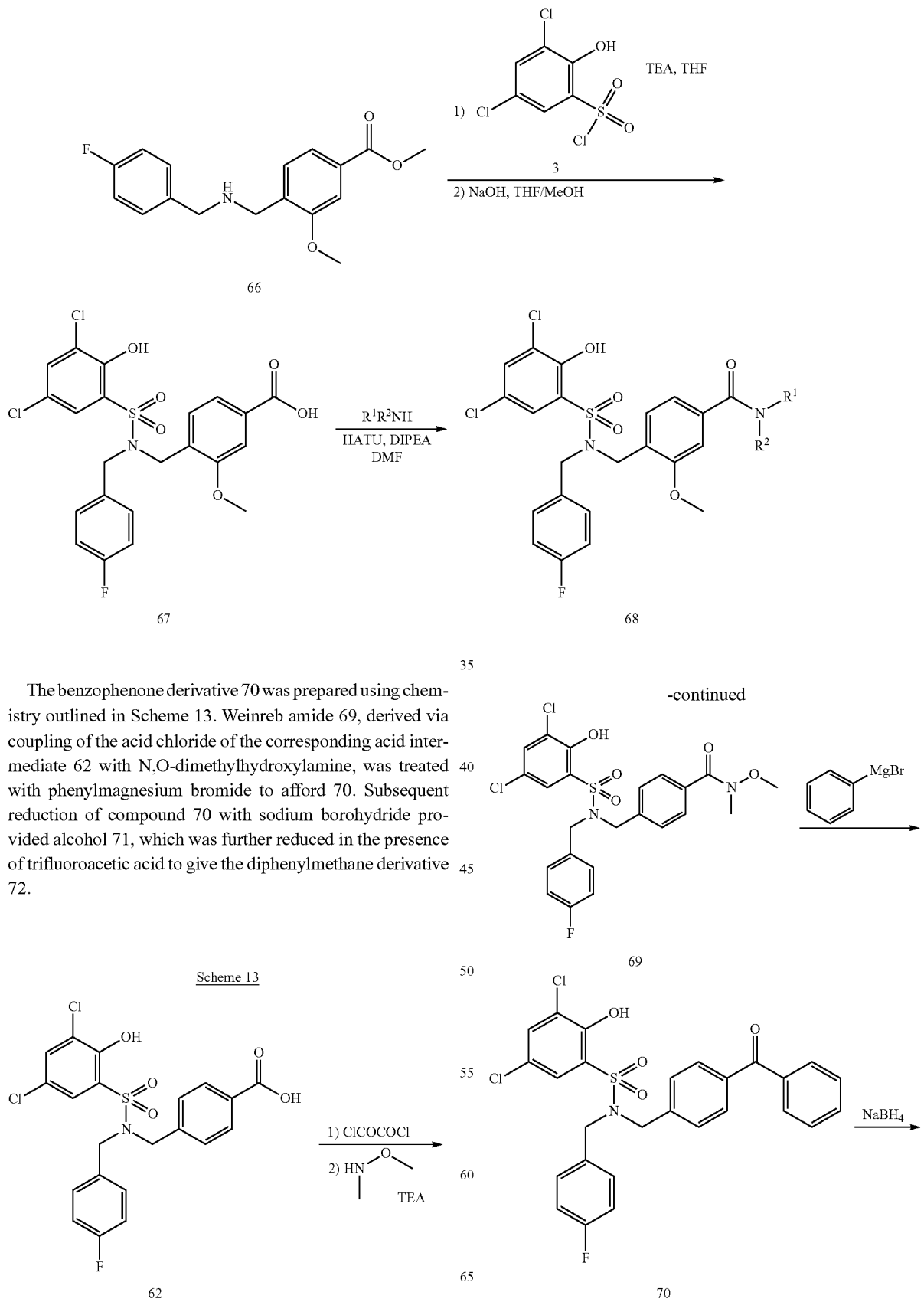

The benzophenone derivative 70 was prepared using chemistry outlined in Scheme 13. Weinreb amide 69, derived via coupling of the acid chloride of the corresponding acid intermediate 62 with N,O-dimethylhydroxylamine, was treated with phenylmagnesium bromide to afford 70. Subsequent reduction of compound 70 with sodium borohydride provided alcohol 71, which was further reduced in the presence of trifluoroacetic acid to give the diphenylmethane derivative 72.

Scheme 13

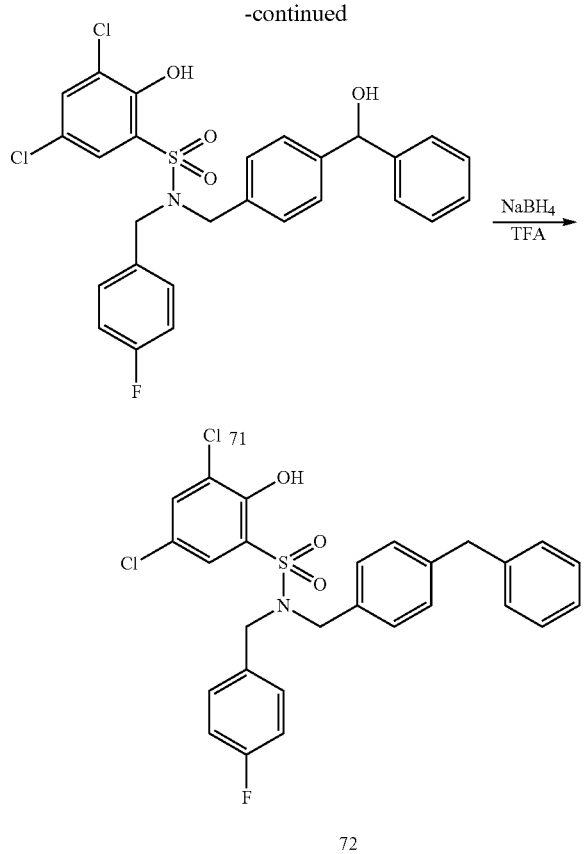

The amide and urea analogs 80 and 81 were prepared using the synthetic routes outlined in Scheme 14. Reductive amination of 4'-fluorobiphenyl-4-carbaldehyde (73, Zhang, T. Y. and Allen, M. J. *Tetrahedron Lett.* 1999, 40, 5813) with the benzylamine intermediate I afforded the secondary amine 74. Sulfonylation of 74 using conditions described previously gave compound 75. Removal of the Boc protecting of 75 under acidic conditions furnished the benzylamine derivative 76, which underwent smooth reductive alkylation with isobutyraldehyde to provide 77. Treatment of amine 77 with carboxylic acids 78 in the presence of EDCI (N-(3-dimethylaminopropyl)-N'-ethylcarbodiimide hydrochloride) and HOBT (1-hydroxybenzotriazole) gave the corresponding amides 80. Alternatively, coupling of compound 77 with isocyanates 79 provided the corresponding ureas 81.

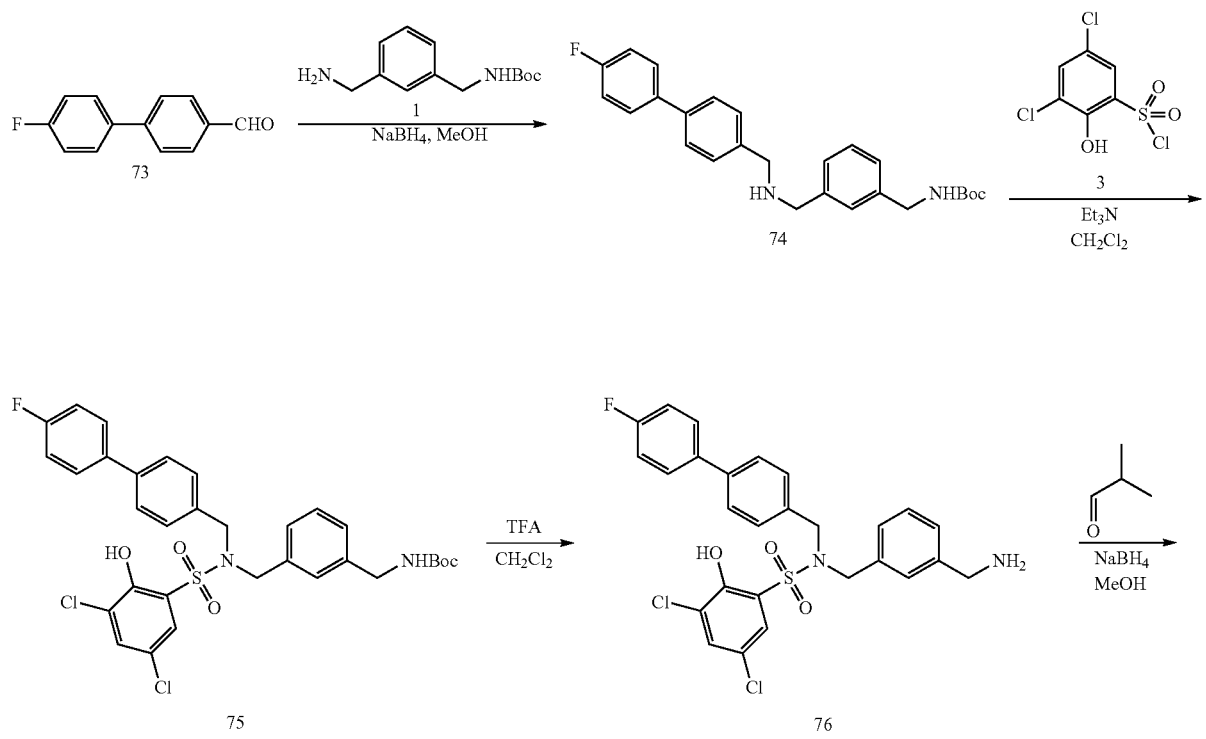

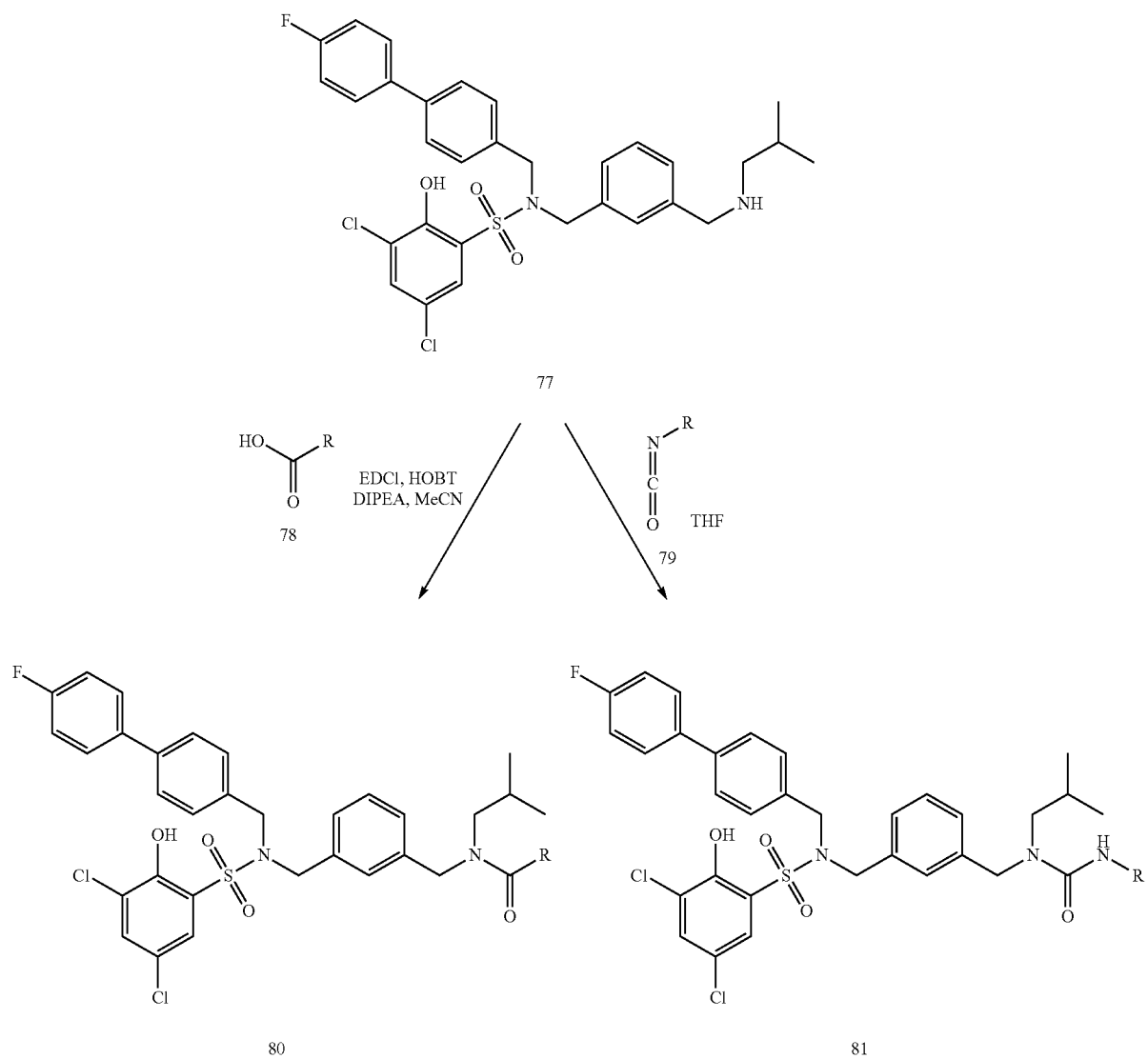

The bis-sulfonamide analogues 87 were prepared using chemistry detailed in Scheme 15. Treatment of phthaloyl dichloride (82) with excess 4-fluorophenylmethanamine (65) provided the diamide 83. Exhaustive reduction of 83 with borondimethylsulfide gave diamine 84. Sulfonylation of compound 84 with 3,5-dichlorobenzene-1-sulfonyl chloride (85) gave 86, which was further sulfonylated with compound 3 to afford 87.

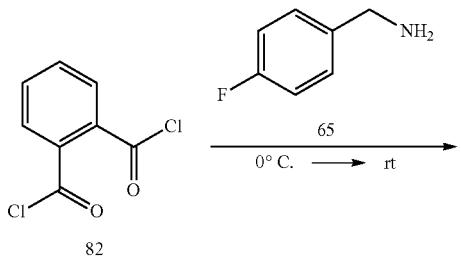

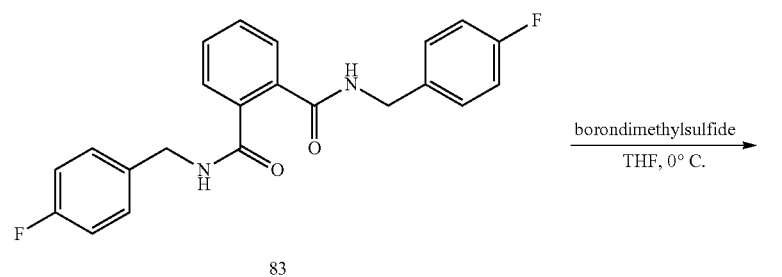

83

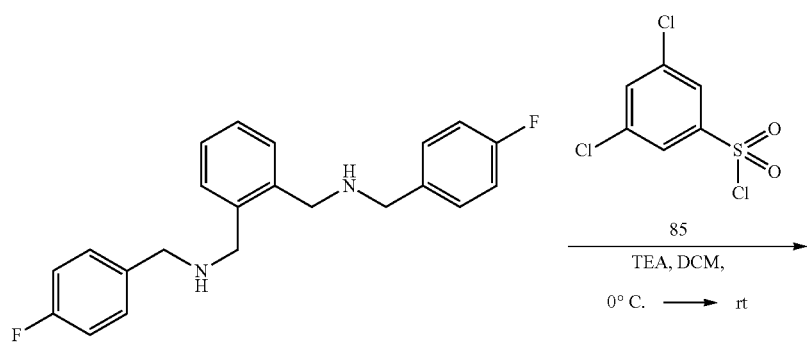

84

85

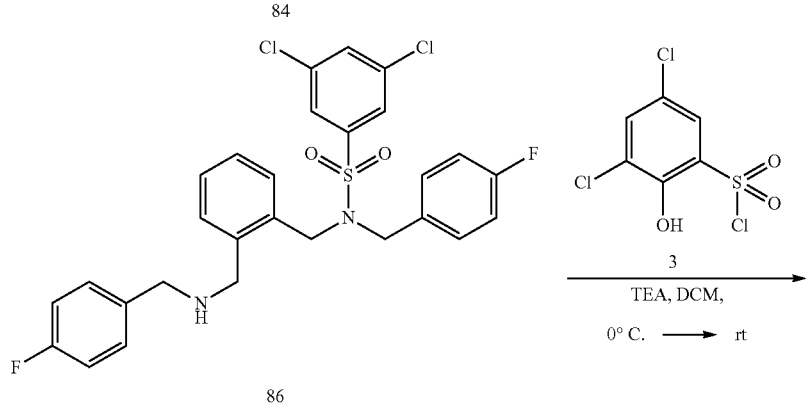

86

3

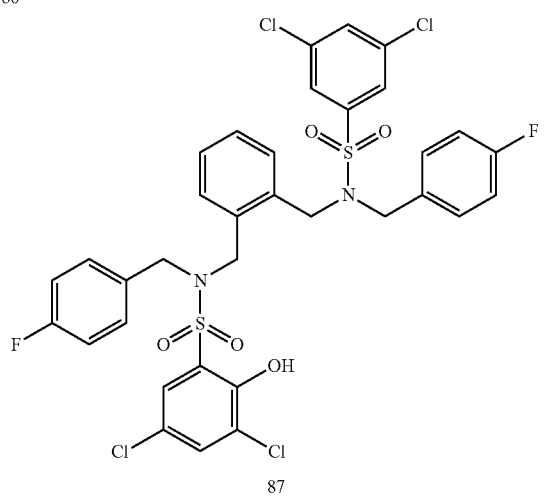

87

The chlorobiphenyl derivative 92 was prepared using the chemistry outlined in Scheme 16. Reductive amination of aldehyde 88 with 4-fluorophenylmethanamine (65) provided the secondary amine 89. Sulfonylation of intermediate 89 with the sulfonyl chloride derivative 90 and triethylamine provided the benzoic acid derivative 91. Coupling of the acid chloride derived from compound 91 with benzylamine afforded amide 92.

Scheme 16

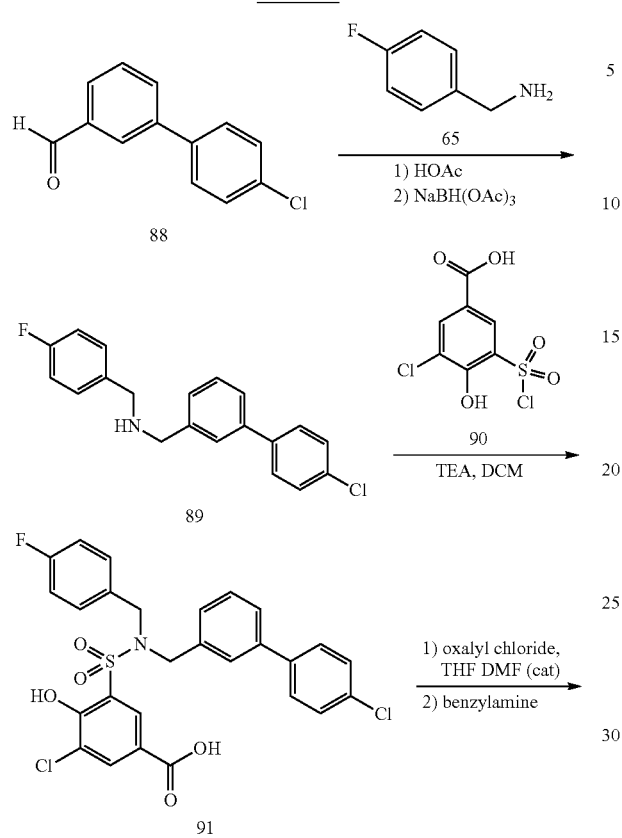

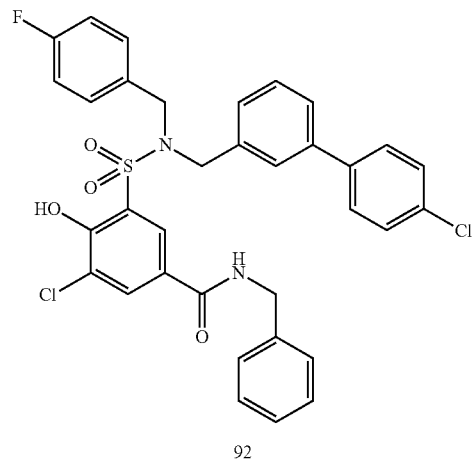

Similarly, the biaryl ether analogue 99 was prepared using the chemistry outlined in Scheme 17. Treatment of 4-fluorobenzaldehyde (93) with 4-(trifluoromethyl)phenol (94) in the presence of potassium carbonate and DMF at elevated temperature gave the biaryl ether 95. Reductive amination of the benzaldehyde intermediate 95 with 4-fluorophenylmethanamine (65) provided the secondary amine 96. Sulfonylation of intermediate 96 with the sulfonyl chloride derivative 97 in the presence of triethylamine provided the benzoic acid derivative 98. Coupling of the acid chloride derived from 98 with aniline gave amide 99.

Scheme 17

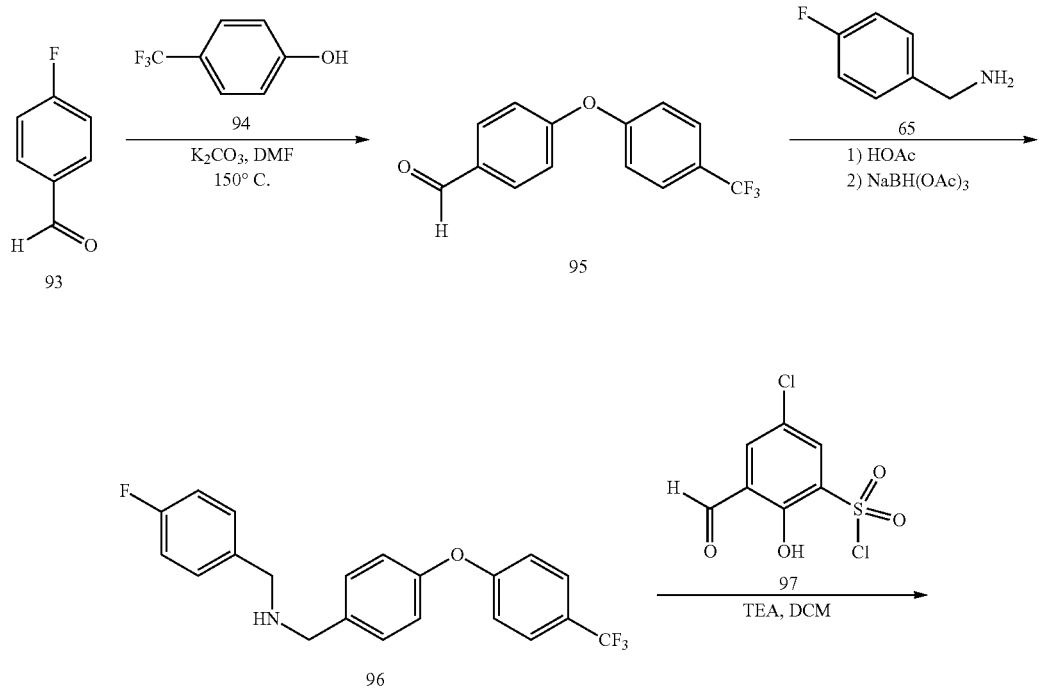

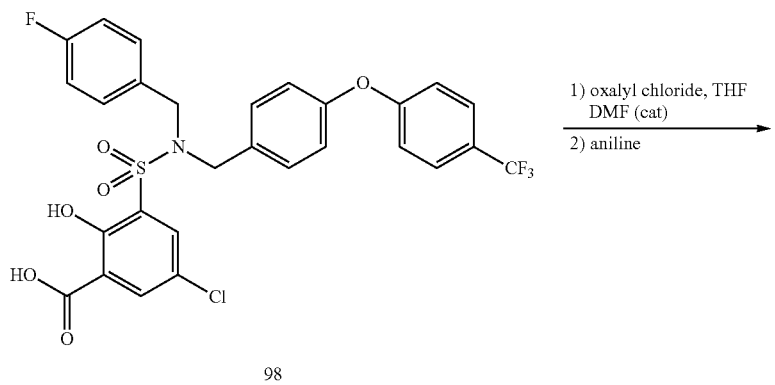

98

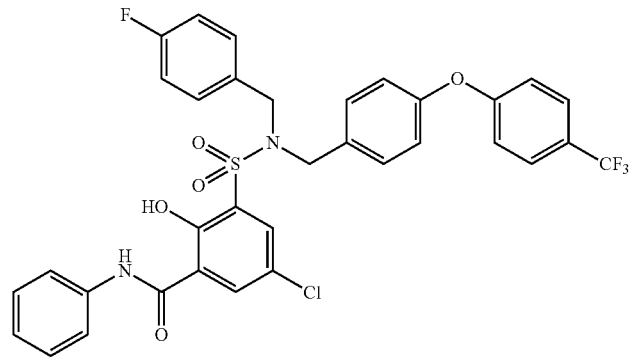

99

The substituted biphenyl analogues 104 and 106 were prepared using the chemistry outlined in Scheme 18. Treatment of 3-bromobenzaldehyde (100) with the boronic acid derivatives 101 in the presence of palladium(II) acetate and sodium carbonate gave the biphenyl compounds 102. Reductive amination of the benzaldehyde intermediates 102 with 4-fluo-rophenylmethanamine (65) provided the secondary amine 103. Sulfonylation of intermediate 103 with the sulfonyl chloride derivative 3 provided phenol 104. Alternatively, sulfonylation of compound 103 with the sulfonyl chloride 105 afforded phenol analogue 106.

Scheme 18

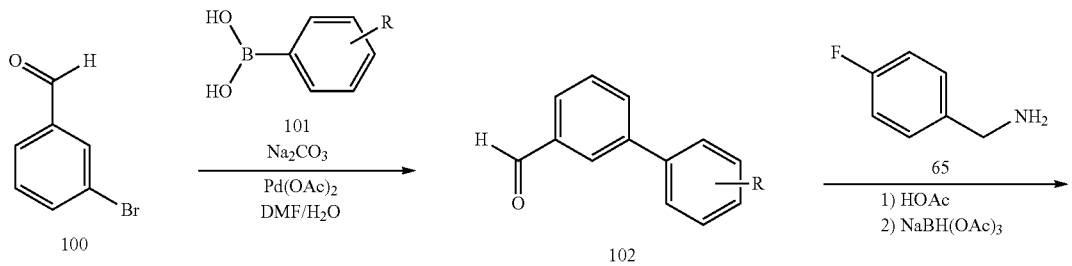

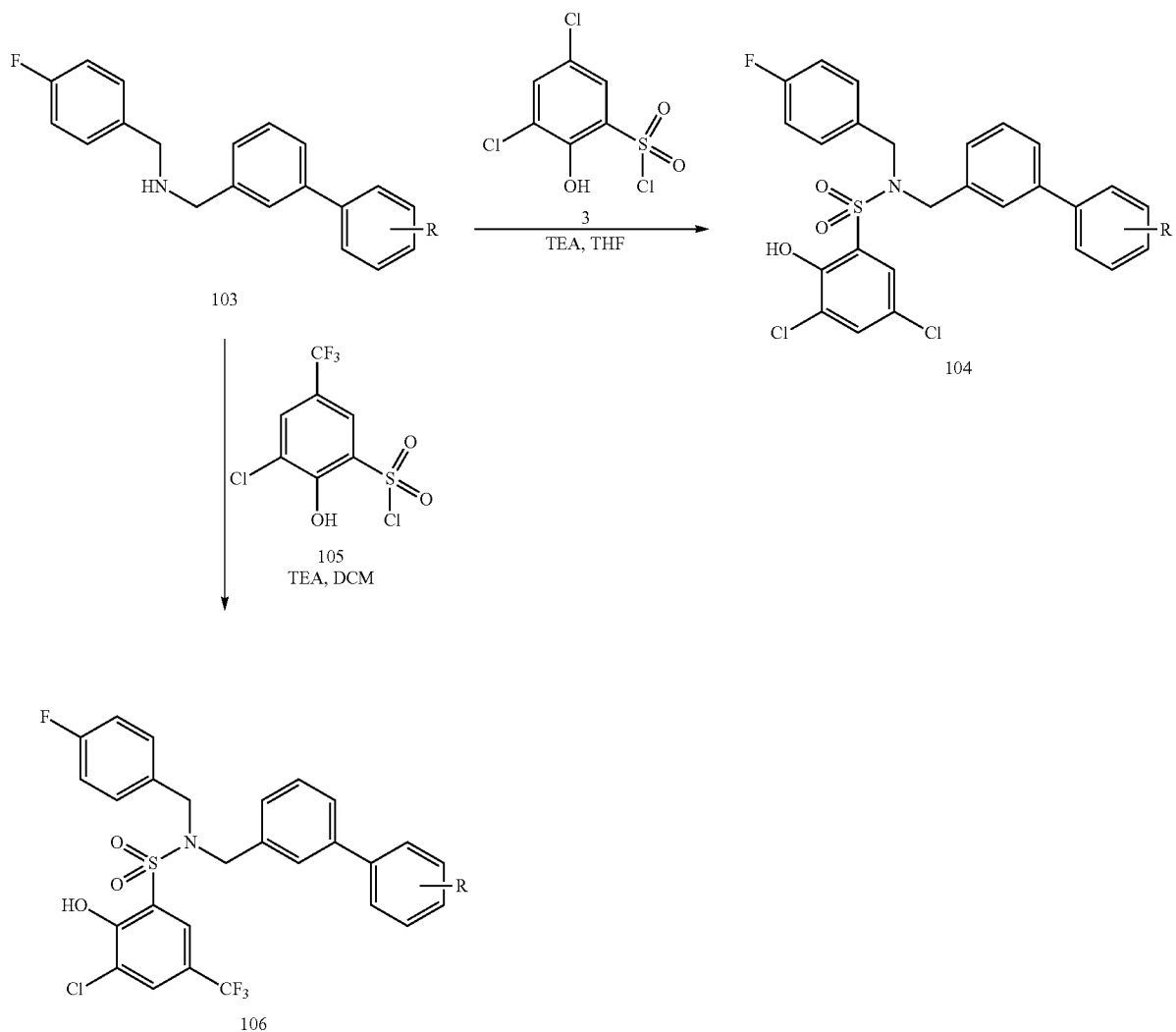

Similarly, the substituted biphenyl analogue 113 was prepared using the chemistry outlined in Scheme 19. Coupling of methyl 3-bromo-2-methoxybenzoate (107) with 4-chlorophenylboronic acid (108) in the presence of palladium(II) acetate and potassium carbonate gave the biphenyl compound 109. Reduction of the ester moiety of 109 with lithium aluminum hydride at low temperature, followed by oxidation of the intermediate benzylalcohol 110 with pyridinium chlorochromate furnished aldehyde 111. Reductive amination of the benzaldehyde intermediate 111 with 4-fluorophenylmethanamine (65) provided the secondary amine 112. Sulfonylation of intermediate 112 with the sulfonyl chloride 3, using previously described conditions, provided phenol 113.

Scheme 19

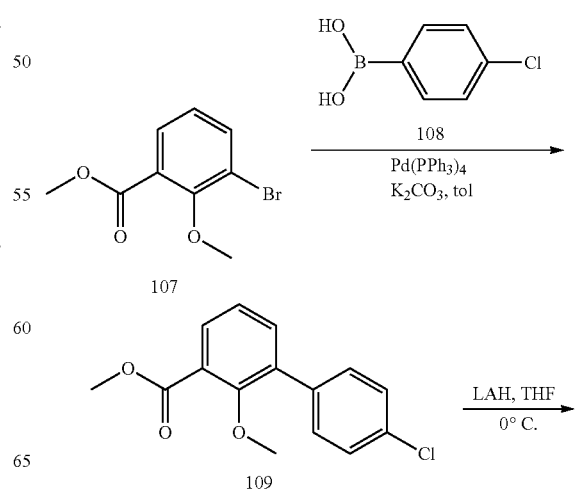

-continued

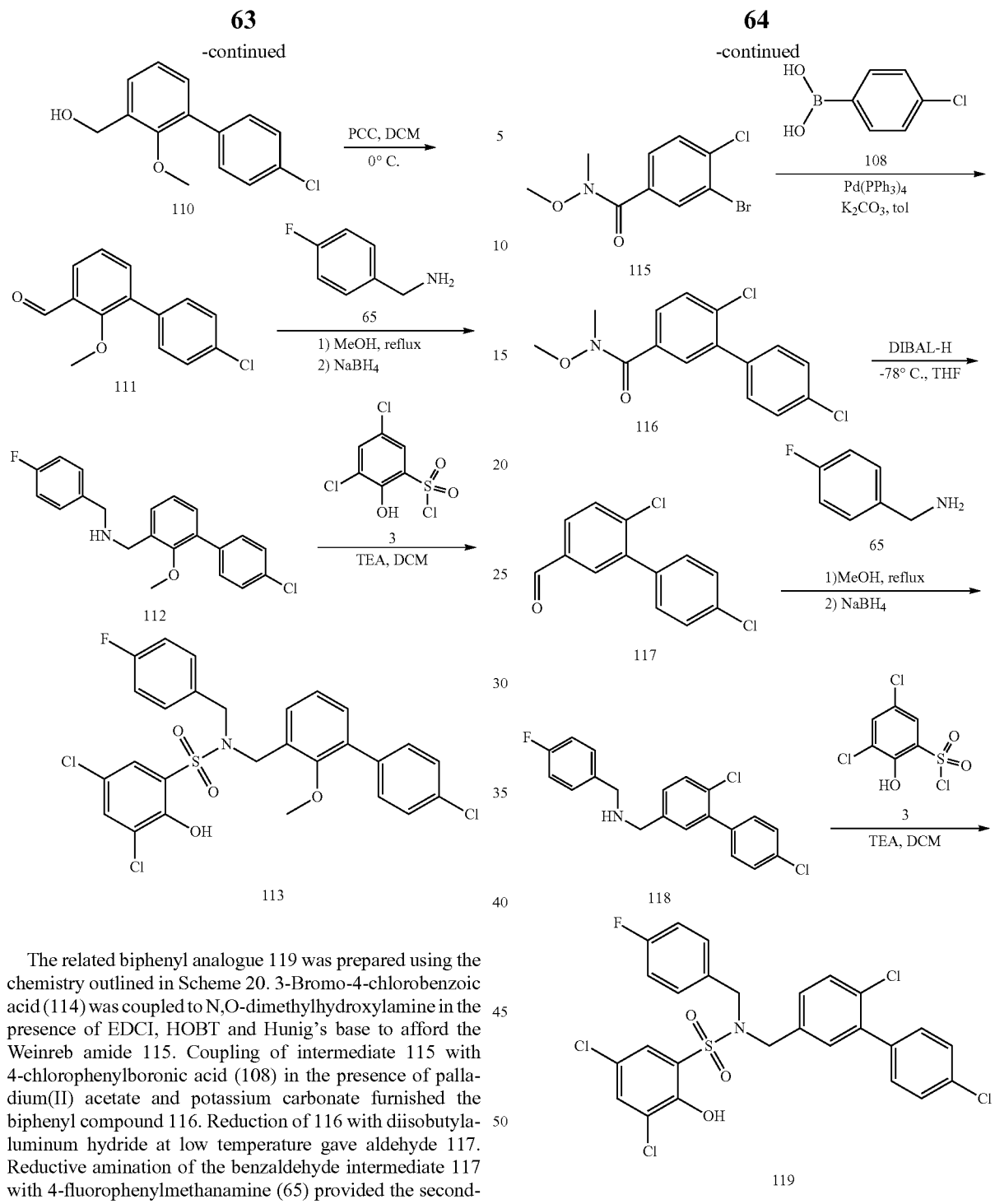

The related biphenyl analogue 119 was prepared using the chemistry outlined in Scheme 20. 3-Bromo-4-chlorobenzoic acid (114) was coupled to N,O-dimethylhydroxylamine in the presence of EDCI, HOBT and Hunig's base to afford the Weinreb amide 115. Coupling of intermediate 115 with 4-chlorophenylboronic acid (108) in the presence of palladium(II) acetate and potassium carbonate furnished the biphenyl compound 116. Reduction of 116 with diisobutylaluminum hydride at low temperature gave aldehyde 117. Reductive amination of the benzaldehyde intermediate 117 with 4-fluorophenylmethanamine (65) provided the secondary amine 118, which was sulfonylated with 3 to give phenol 119.

Scheme 20

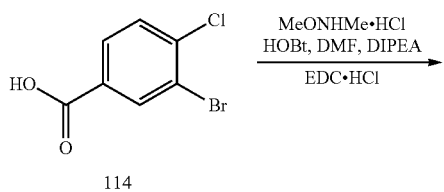

The sulfide analogue 127 was prepared using the synthetic route outlined in Scheme 21. Methyl 3-(bromomethyl)benzoate (120) was coupled to 2-phenylethanethiol (121) in the presence of cesium carbonate and DMF to give the thioether 122. Hydrolysis of the ester moiety of 122 under basic conditions furnished the acid 123, which was directly coupled to 2-(4-fluorophenyl)ethanamine (124). Reduction of the resulting intermediate 125 with borane provided the secondary amine 126, which was sulfonylated with 3, using conditions previously described.

Scheme 21
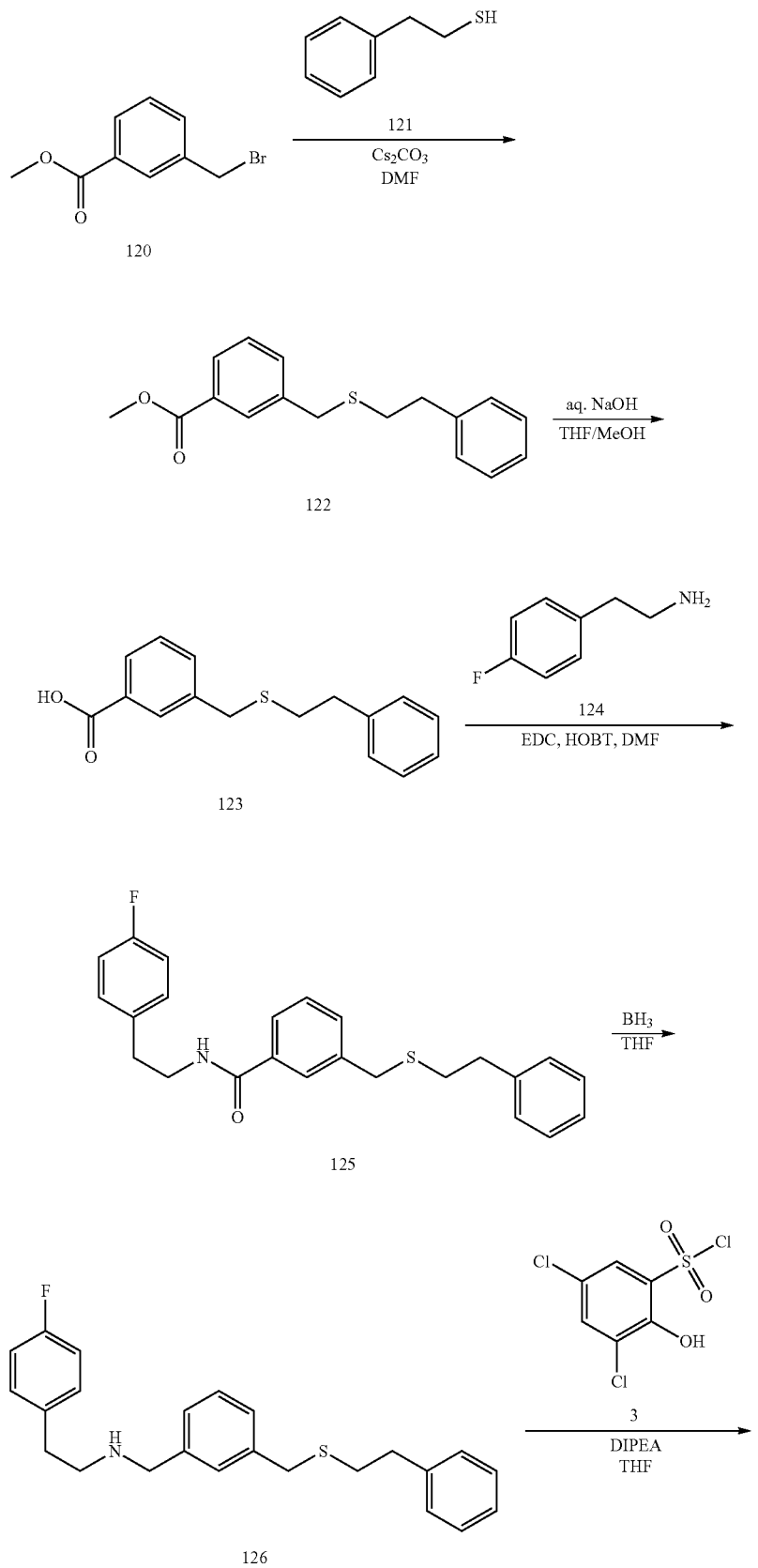

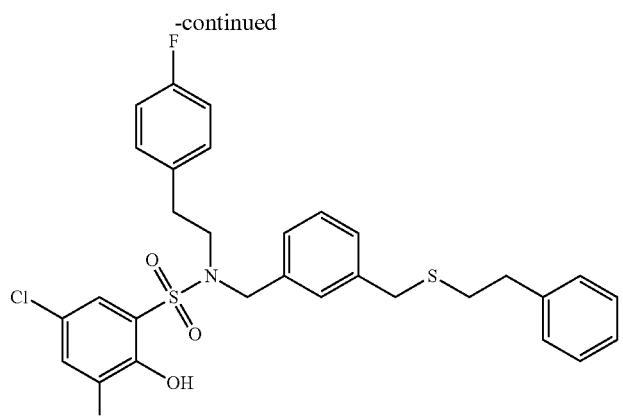

127

The biaryl ether analogues 135 were prepared using the synthetic routes outlined in Scheme 22. 3-Hydroxybenzaldehyde (128) was coupled to 1-bromo-4-fluorobenzene (129) in the presence of copper powder and pyridine at elevated temperature to give ether 130. Formation of the oxime 131 with hydroxylamine in methanol followed by hydrogenation with Raney nickel in aqueous ammonia/ethanol afforded the benzylamine derivative 132. Reductive alkylation of 132 with various aldehydes 133 gave the secondary amines 134, which were sulfonylated with 3, using conditions previously described.

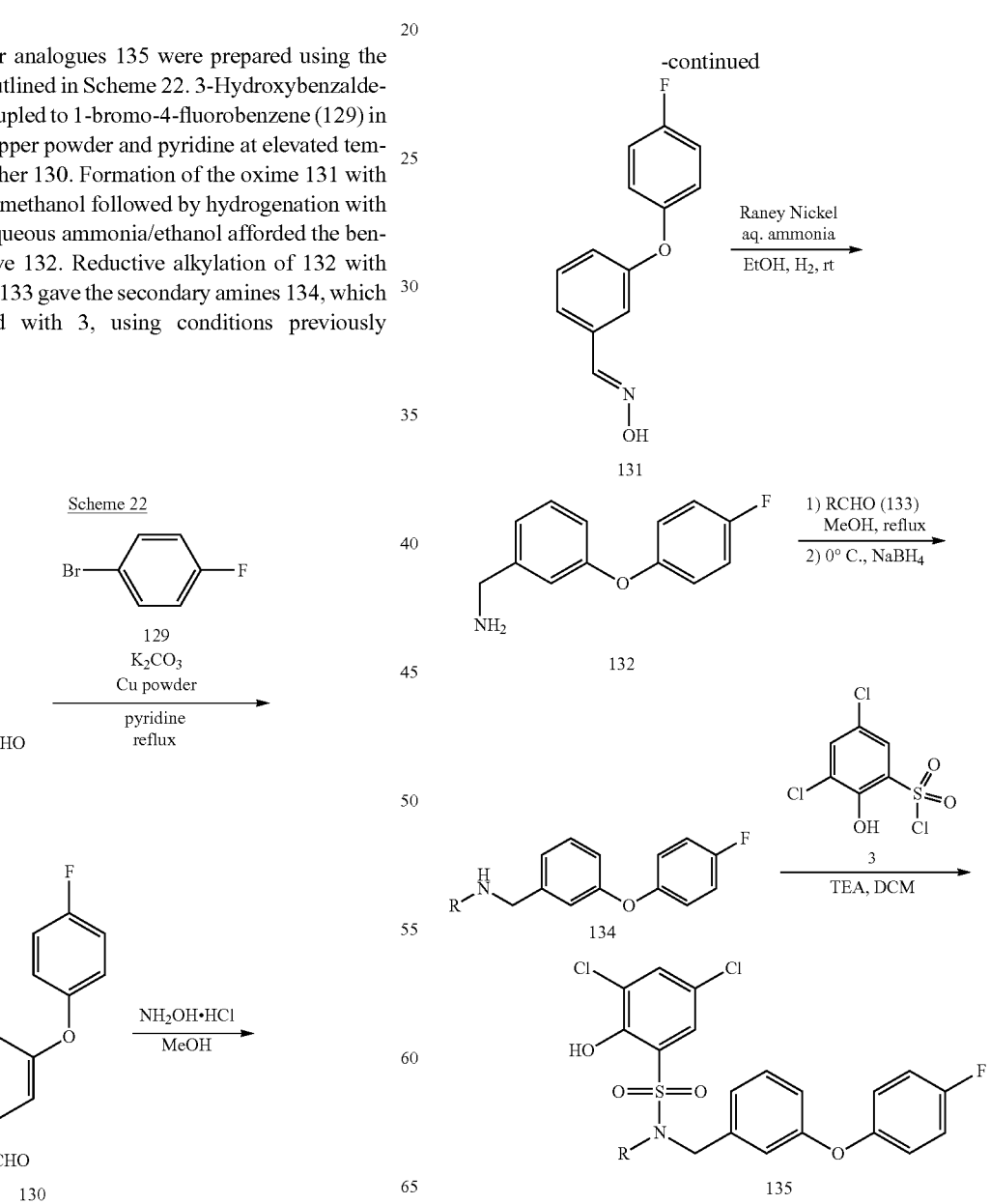

The pyridyl-based analogue 141 was prepared using the synthetic route outlined in Scheme 23. The mesylate 137, derived from methyl 6-(hydroxymethyl)picolinate (136, Breschi, M. C. et al. *J. Med. Chem.* 2006, 49, 2628) was treated with 4-fluorophenylmethanamine (65) in the presence of cesium carbonate and acetonitrile to afford amine 138. Sulfonylation of intermediate 138 with compound 3 and triethylamine furnished phenol 139. Hydrolysis of the ester moiety of 139 under basic conditions provided the carboxylic acid 140, which was coupled to the secondary amine 38 under standard conditions to give the desired amide 141.

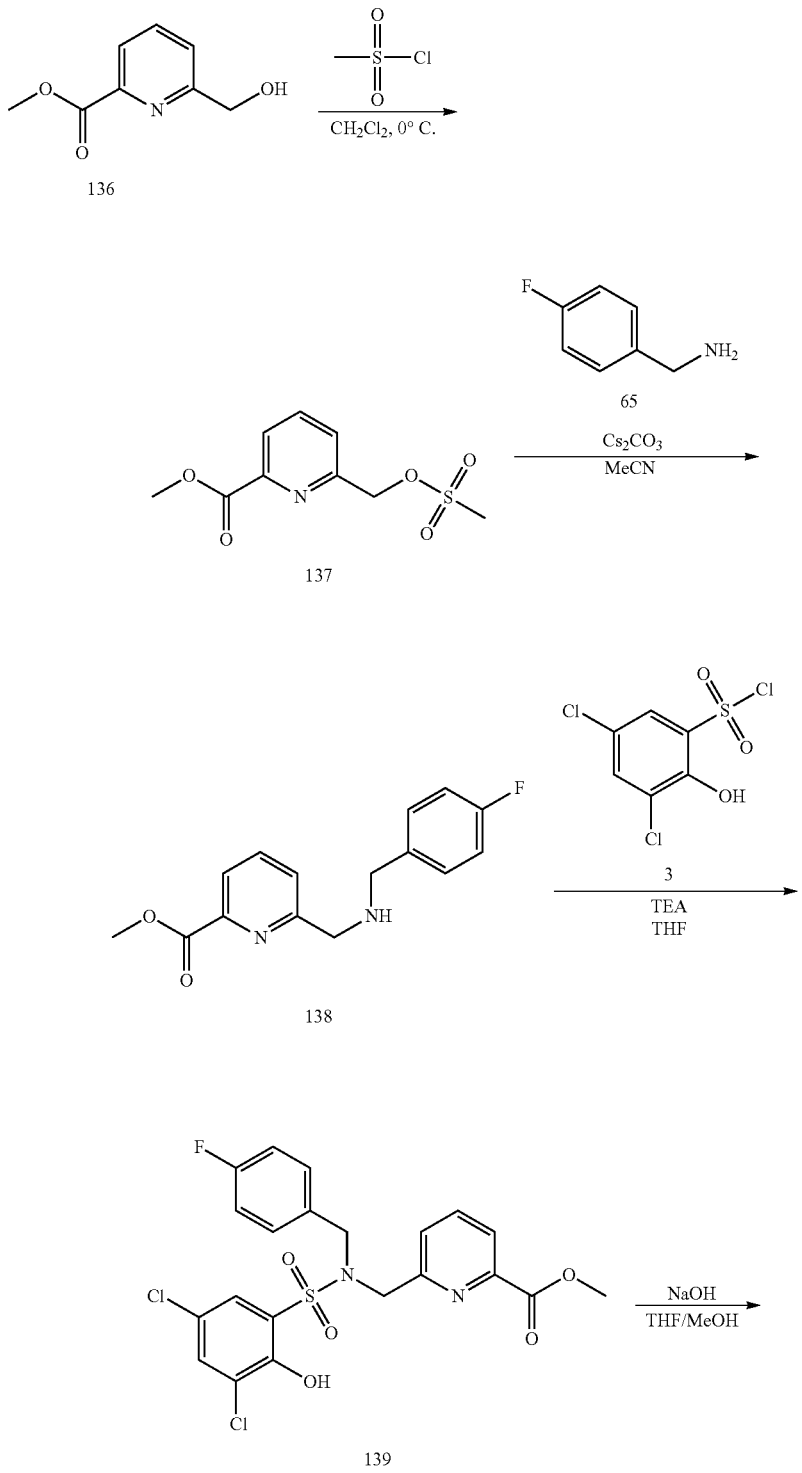

Scheme 23

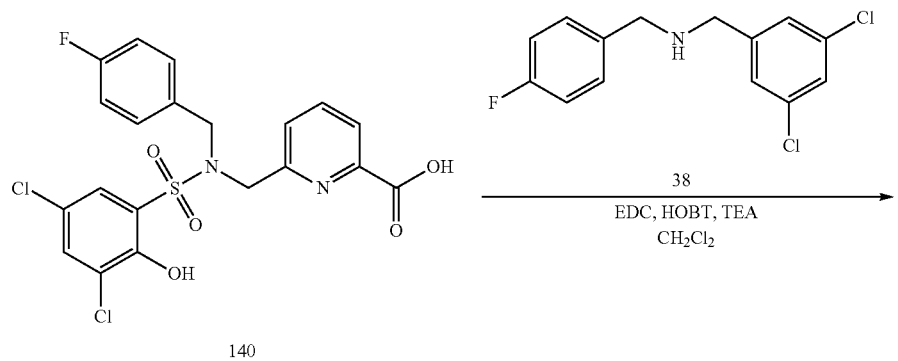

140

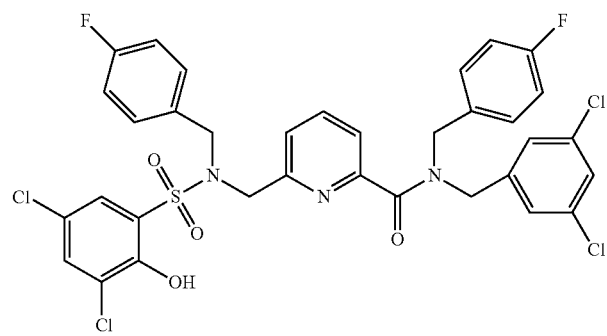

141

EXAMPLES

General Experimental

Flash column chromatography was carried out on E. Merck Kieselgel 60 silica gel (230-400 mesh) using the TELEDYNE ISCO machine. Preparative HPLC was run on YMC OD S-10 50×500 mm column eluting with a mixture of solvent A and B (starting from 10% of solvent B to 100% solvent B over a 30 minute gradient time; Solvent A: 10% MeOH-90% $H_2O$-0.1% TFA; Solvent B: 90% MeOH-10% $H_2O$-0.1% TFA; flow rate 84 mL/min; ITV 220 nm). $^1H$ and $^{13}C$ NMR spectra were obtained on a JOEL 500 MHz Eclipse NMR spectrometer operating at 500.16 MHz and 125.77 MHz, respectively. Chemical shifts are reported as ppm downfield from an internal tetramethylsilane standard. The abbreviations of br s, d, t and in in $^1H$ NMR refer to broad singlet, doublet, triplet and multiplet, respectively. Unless otherwise noted, LCMS data were obtained using a Chromolith S5 ODS 4.6×50 mm column eluting with a mixture of solvent A and B (starting from 0% Solvent B to 100% Solvent B over a 4 minute gradient time, and then 100% Solvent B for 1 minute; Solvent A: 10% MeOH-90% $H_2O$-0.1% TFA and Solvent B: 90% MeOH-10% $H_2O$-0.1% TFA; UV detection at 220 nm) and the MS data were recorded as $(M+H)^+$.

Example 1

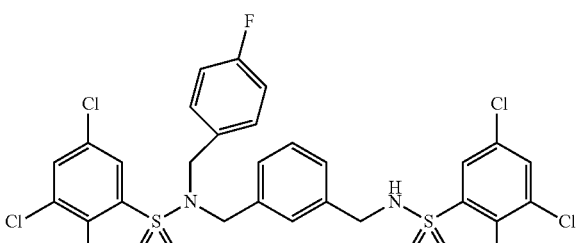

3,5-Dichloro-N-(3-((3,5-dichloro-2-hydroxyphenyl-sulfonamido)methyl)benzyl)-N-(4-fluorobenzyl)-2-hydroxybenzenesulfonamide

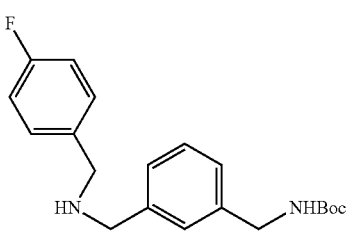 [SMILES: CC(C)(C)OC(=O)NCc1cccc(CNCc2ccc(F)cc2)c1]

A) tert-Butyl 3-((benzylamino)methyl)benzylcarbamate

To a solution of tert-butyl 3-(aminomethyl)benzylcarbamate (500 mg, 2.12 mmol) in MeOH (7 mL) at rt was added 4-fluorobenzaldehyde (263 mg, 2.12 mmol). In 5 minutes a solid of sodium triacetoxyborohydride (390 mg) was added to the above mixture and stirred for 4 h. Additional triacetoxyborohydride (200 mg) was added to the reaction mixture and stirred for 1 h. It was mostly concentrated and the residue was purified by prep HPLC to obtain the product as a glassy material of TFA salt (650 mg, 67%). $^1$H NMR (CDCl$_3$): δ 9.71 (s, 1H), 7.29~7.18 (m, 6H), 6.95 (t, J=8.5 Hz, 2H), 4.19 (s, 2H), 3.83 (s, 2H), 3.80 (s, 2H), 1.42 (s, 9H).

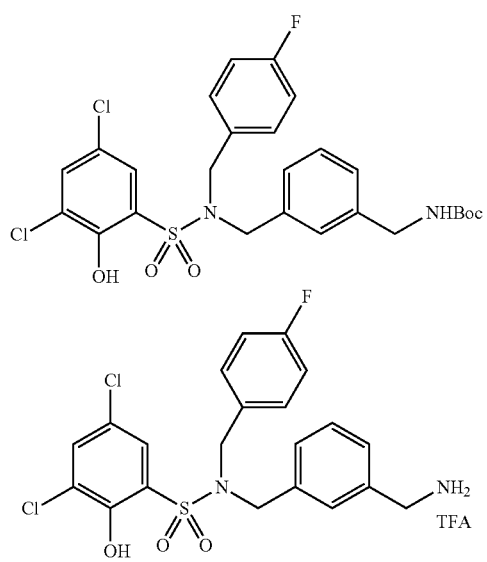

B) tert-Butyl 3-((3,5-dichloro-N-(4-fluorobenzyl)-2-hydroxyphenylsulfonamido)methyl)benzylcarbamate and N-(3-(Aminomethyl)benzyl)-3,5-dichloro-N-(4-fluorobenzyl)-2-hydroxybenzenesulfonamide To a solution of 3,5-dichloro-2-hydroxybenzene-1-sulfonyl chloride 3 (186 mg, 0.71 mmol) in CH$_2$Cl$_2$ (6 mL) at rt was added a solution of tert-butyl 3-((benzylamino)methyl)benzylcarbamate TFA salt (325 mg, 0.71 mmol) in CH$_2$Cl$_2$ (5 mL) with stirring. After 1.5 h aq NaHCO$_3$ solution and CH$_2$Cl$_2$ were added to the reaction mixture, the organic layer was separated, dried over MgSO$_4$ and concentrated to obtain the crude product (440 mg) as a viscous material which was used directly for the next step without any further purification. $^1$H NMR (CDCl$_3$): δ 7.54 (s, 1H), 7.30 (s, 1H), 7.29~7.00 (m, 6H), 6.77 (t, J=8.6 Hz, 2H), 4.37 (s, 2H), 4.36 (s, 2H), 3.69 (d, J=5.5 Hz, 2H), 1.39 (s, 9H).

The crude coupling product obtained above was dissolved in CH$_2$Cl$_2$ (6 mL) and here was added TFA (1.0 mL) at rt. It was stirred for 2.5 h, concentrated in vacuo, and the residue was purified by prep HPLC to obtain the product as a glassy material of TFA salt (210 mg, overall 51%). $^1$H NMR (CD$_3$OD): δ 7.56 (s, 1H), 7.30 (s, 1H), 7.29~7.10 (m, 6H), 6.89 (t, J=8.8 Hz, 2H), 4.52 (s, 2H), 4.44 (s, 2H), 4.02 (s, 2H); MS (ESI): (M+H)$^+$=469.33.

C) 3,5-Dichloro-N-(3-((3,5-dichloro-2-hydroxyphenylsulfonamido)methyl)benzyl)-N-(4-fluorobenzyl)-2-hydroxybenzenesulfonamide To a solution of N-(3-(aminomethyl)benzyl)-3,5-dichloro-N-(4-fluorobenzyl)-2-hydroxybenzenesulfonamide (50 mg, 0.11 mmol) in THF (3 mL) and DMF (1 ml) was added TEA (0.03 mL, 0.21 mmol), followed by 3,5-dichloro-2-hydroxybenzene-1-sulfonyl chloride 3 (29 mg, 0.11 mmol) at 0° C. under nitrogen. The reaction mixture was stirred at 0° C. for 4 h. The mixture was concentrated and the residue was purified by preparative HPLC. Fractions containing the desired product were combined, concentrated, and lyophilized to give 6 white solid (13 mg, 18%). $^1$H NMR (CD$_3$OD): δ 7.57 (d, J=2.4 Hz, 1H), 7.52 (d, J=2.8 Hz, 1H), 7.37 (m, 2H), 7.05 (d, J=8.8 Hz, 2H), 6.98 (m, 2H), 6.83 (m, 3H), 6.71 (s, 1H), 4.33 (s, 2H), 4.23 (s, 2H), 3.97 (s, 2H); MS (ESI), (M−H)$^-$=693.1.

Example 2

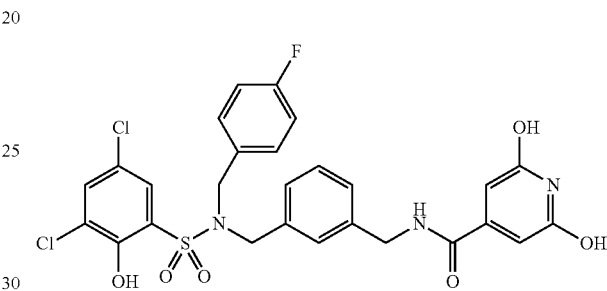

N-(3-((3,5-Dichloro-N-(4-fluorobenzyl)-2-hydroxyphenylsulfonamido)methyl)benzyl)-2,6-dihydroxyisonicotinamide To a solution of citrazinic acid (60 mg, 0.39 mmol) in DMF (4 mL) at rt was added 1-(3-(dimethylamino)propyl)-3-ethylcarbodiimide hydrochloride (EDCI.HCl, 90 mg, 0.46 mmol) followed by HOBt.H$_2$O (52 mg) at rt. After 5 min. the free base of sulfonamide 5 (180 mg, 0.38 mmol) and DMAP (50 mg) were added to the mixture, and the reaction mixture was stirred overnight. The next morning it was mostly concentrated in vacuo, and the residue was purified by preparative HPLC to obtain the product 8 as a light brown solid (60 mg, 25%).

$^1$H NMR (CD$_3$OD): δ 7.57 (s, 1H), 7.52 (s, 1H), 7.10~6.99 (m, 6H), 6.81 (t, J=8.8 Hz, 2H), 4.35 (s, 2H), 4.34 (s, 2H), 4.32 (s, 2H); MS (ESI): (M+H)$^+$=606.38

Example 3

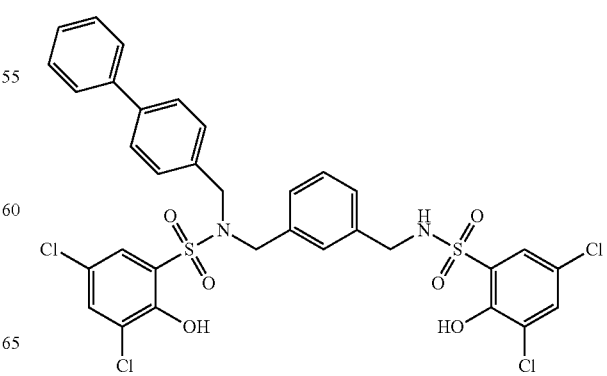

N-(Biphenyl-4-ylmethyl)-3,5-dichloro-N-(3-((3,5-dichloro-2-hydroxyphenylsulfonamido)methyl)benzyl)-2-hydroxybenzenesulfonamide

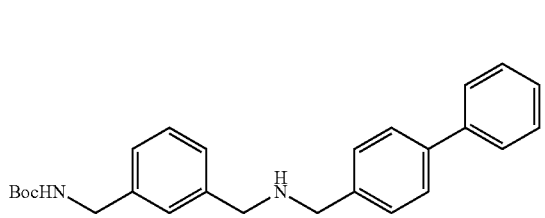 [SMILES: CC(C)(C)OC(=O)NCc1cccc(CNCc2ccc(-c3ccccc3)cc2)c1]

A) tert-Butyl 3-((biphenyl-4-ylmethylamino)methyl) benzylcarbamate

A solution of tort-butyl 3-(aminomethyl)benzylcarbamate (3.0 g, 12.7 mmol) and biphenyl-4-carbaldehyde (2.2 g, 12.1 mmol) in CH$_2$Cl$_2$ (20.0 mL) and DMF (10.0 mL) was stirred at it for 40 min and treated with sodium triacetoxyborohydride (5.12 g, 24.2 mmol). The resulting reaction mixture was stirred at rt for 3 h, and then concentrated. The residue was partitioned between saturated aq NaHCO$_3$ and ethyl acetate. The EtOAc layer was separated, washed with brine, dried over MgSO$_4$, and concentrated in vacuo. The residue was purified by silica gel flash chromatography eluting with CH$_2$Cl$_2$ and 20% of ethyl acetate in CH$_2$Cl$_2$ to obtain the desired product as a white solid (2.6 g, 53%). $^1$H NMR (MeOH-d$_4$): δ 7.71 (d, J=8.0 Hz, 2H), 7.65 (d, J=8.4 Hz, 2H), 7.56 (d, J=8.0 Hz, 2H), 7.48-7.36 (m, 7H), 4.27 (s, 2H), 4.18 (s, 2H), 4.16 (s, 2H), 1.47 (s, 9H).

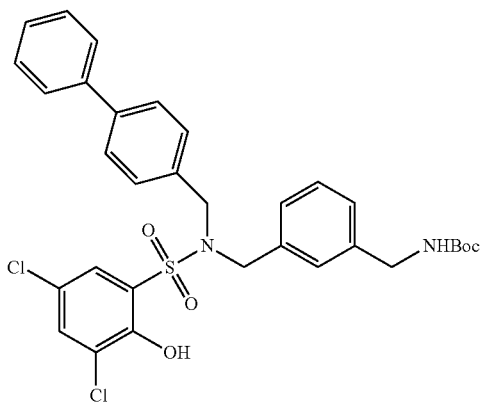 [SMILES: CC(C)(C)OC(=O)NCc1cccc(CN(Cc2ccc(-c3ccccc3)cc2)S(=O)(=O)c2cc(Cl)cc(Cl)c2O)c1]

B) tert-Butyl 3-((N-(biphenyl-4-ylmethyl)-3,5-dichloro-2-hydroxyphenylsulfonamido)methyl)benzylcarbamate To a solution of tert-butyl 3-((biphenyl-4-ylmethylamino) methyl)benzylcarbamate (2.42 g, 6.01 mmol) in CH$_2$Cl$_2$ (30.0 mL) was added a solution of 3,5-dichloro-2-hydroxybenzene-1-sulfonyl chloride (1.65 g, 6.31 mmol) in CH$_2$Cl$_2$ (8.0 mL) at ice bath temperature followed by Et$_3$N (2.5 mL, 18.0 mmol). The reaction mixture was stirred at ice bath temperature for 1.5 h and concentrated in vacuo. The residue was purified by flash chromatography on SiO$_2$ eluting with CH$_2$Cl$_2$ to 8% of ethyl acetate in CH$_2$Cl$_2$ to give the product as a white glassy solid (2.78 g, 72.5%). $^1$H NMR (CDCl$_3$): δ 9.18 (bs, 1H), 7.59-7.38 (m, 9H), 7.28-7.21 (m, 4H), 7.06 (m, 2H), 4.48 (s, 2H), 4.43 (s, 2H), 4.25 (s, 2H), 1.49 (s, 9H).

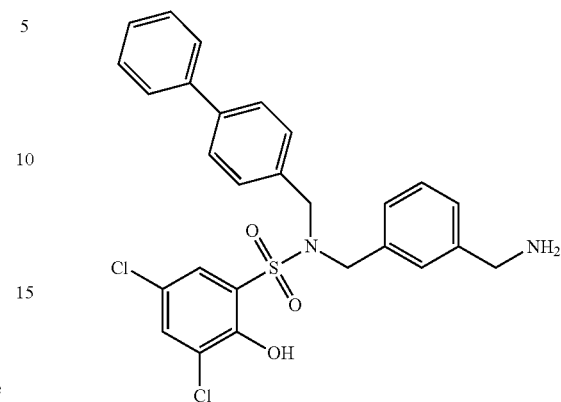

C) N-(3-(Aminomethyl)benzyl)-N-(biphenyl-4-ylmethyl)-3,5-dichloro-2-hydroxybenzenesulfonamide To a solution of tert-butyl 3-((N-(biphenyl-4-ylmethyl)-3,5-dichloro-2-hydroxyphenylsulfonamido)methyl)benzylcarbamate (2.77 g, 4.41 mmol) in CH$_2$Cl$_2$ (15 mL) at rt was added TFA (6.8 mL, 88.0 mmol). The reaction mixture was stirred at rt for 4 h. It was concentrated and the residue was diluted with ethyl acetate and saturated aq NaHCO$_3$ solution. The EtOAc layer was separated, washed with brine, dried over MgSO$_4$ and concentrated in vacuo to give the product as a white solid (2.3 g, 96%). $^1$H NMR (DMSO-d$_6$): δ 8.30 (bs, 1H), 7.61 (d, J=7.6 Hz, 2H), 7.59 (s, 1H), 7.51 (d, J=8.0 Hz, 2H), 7.45 (t, J=7.6 Hz, 2H), 7.32 (m, 2H), 7.29-7.18 (m, 5H), 7.10 (m, 1H), 4.43 (s, 4H), 3.93 (s, 2H), 3.32 (s, 2H).

D) N-(Biphenyl-4-ylmethyl)-3,5-dichloro-N-(3-((3,5-dichloro-2-hydroxyphenylsulfonamido)methyl) benzyl)-2-hydroxybenzenesulfonamide The titled compound was prepared in a similar procedure as shown in Example 1.

$^1$H NMR (CD$_3$OD): δ 7.58 (d, J=3.6 Hz, 1H), 7.48 (m, 3H), 7.41-7.16 (m, 6H), 7.23 (t, J=7.3 Hz, 1H), 7.10 (d, J=8.0 Hz, 2H), 6.99 (m, 2H), 6.88 (m, 1H), 6.74 (s, 1H), 4.37 (s, 2H), 4.31 (s, 2H), 3.96 (s, 2H).

Example 4

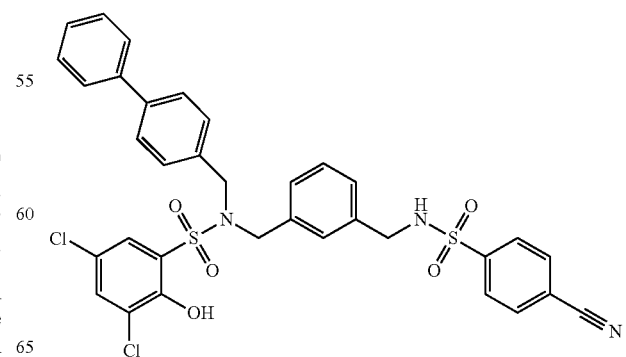

N-(Biphenyl-4-ylmethyl)-3,5-dichloro-N-(3-((4-cyanophenylsulfonamido)methyl)benzyl)-2-hydroxybenzenesulfonamide To a solution of 4-cyanobenzene-1-sulfonyl chloride (26 mg, 0.13 mmol) in CH$_2$Cl$_2$ (3 ml) was added Et$_3$N (0.07 ml, 0.49 mmol) followed by N-(3-(aminomethyl)benzyl)-N-(biphenyl-4-ylmethyl)-3,5-dichloro-2-hydroxybenzenesulfonamide (65 mg, 0.12 mmol) at rt under nitrogen. The reaction mixture was stirred at 25° C. for 2 h. It was concentrated and the residue was purified by preparative HPLC. Fractions containing the desired product were combined, concentrated, and lyophilized to give the product as a white solid (50 mg, 56%).

$^1$H NMR (CD$_3$OD): δ 7.78 (d, J=8.4 Hz, 2H), 7.72 (d, J=8.4 Hz, 2H), 7.57 (d, J=2.4 Hz, 1H), 7.47 (m, 2H), 7.45 (s, 1H), 7.33 (m, 4H), 7.23 (t, J=7.2 Hz, 1H), 7.06 (d, J=8.4 Hz, 2H), 7.02 (d, J=7.6 Hz, 1H), 6.95 (t, J=8.0 Hz, 2H), 6.84 (s, 1H), 4.35 (s, 2H), 4.34 (s, 2H), 3.91 (s, 2H).

Example 5

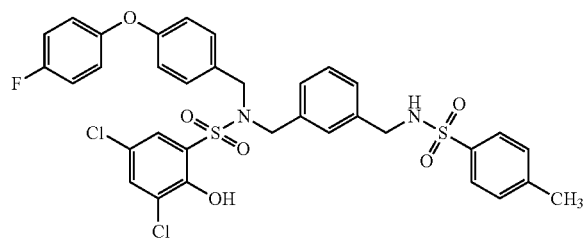 [SMILES: Cc1ccc(S(=O)(=O)NCc2cccc(CN(Cc3ccc(Oc4ccc(F)cc4)cc3)S(=O)(=O)c3cc(Cl)cc(Cl)c3O)c2)cc1]

3,5-Dichloro-N-(4-(4-fluorophenoxy)benzyl)-2-hydroxy-N-(3-((4-methylphenylsulfonamido)methyl)benzyl)benzenesulfonamide

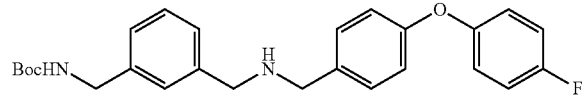 [SMILES: CC(C)(C)OC(=O)NCc1cccc(CNCc2ccc(Oc3ccc(F)cc3)cc2)c1]

A) tert-Butyl 3-((4-(4-fluorophenoxy)benzylamino)methyl)benzylcarbamate

A solution of tert-butyl 3-(aminomethyl)benzylcarbamate (0.70 g, 2.94 mmol) and 4-(4-fluorophenoxy)benzaldehyde (0.6 g, 2.78 mmol) in CH$_2$Cl$_2$ (15 mL) was stirred at rt under nitrogen for 40 min, and then treated with sodium triacetoxyhydroborate (1.24 g, 5.83 mmol). The resulting mixture was stirred at rt. for 3 h. The reaction mixture was concentrated and the residue was partitioned between saturated NaHCO$_3$ solution and ethyl acetate. The organic layer (clear solution) was washed with brine, dried over MgSO$_4$. The filtrate was concentrated and the residue was dissolved in CH$_2$Cl$_2$ and ethyl acetate. The solution was loaded into solid sample cartridge, vacuum dried. The sample was purified by silica gel flash chromatography. Elution with 0-30% of ethyl acetate in CH$_2$Cl$_2$ gave the desired product as viscous oil (0.73 g, 59%). $^1$H NMR (DMSO-d$_6$): δ 7.33-7.28 (m, 2H), 7.24-7.19 (m, 5H), 7.13 (m, 1H), 7.08-7.02 (m, 2H), 6.95 (m, 2H), 4.12 (m, 2H), 3.76 (s, 4H), 1.39 (s, 9H); MS (ESI): (M+H)$^+$=437.3.

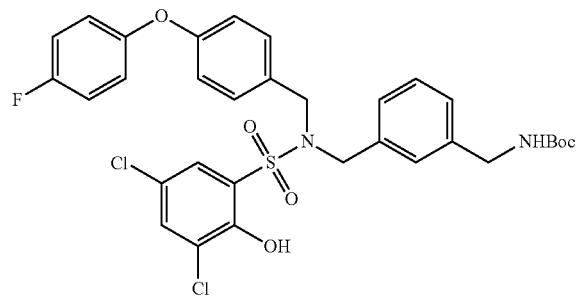 [SMILES: CC(C)(C)OC(=O)NCc1cccc(CN(Cc2ccc(Oc3ccc(F)cc3)cc2)S(=O)(=O)c2cc(Cl)cc(Cl)c2O)c1]

B) tert-Butyl 3-((3,5-dichloro-N-(4-(4-fluorophenoxy)benzyl)-2-hydroxyphenylsulfonamido)methyl)benzylcarbamate To a solution of tert-butyl 3-((4-(4-fluorophenoxy)benzylamino)methyl)benzylcarbamate (0.72 g, 1.64 mmol) in CH$_2$Cl$_2$ (15 mL) added 3,5-dichloro-2-hydroxybenzene-1-sulfonyl chloride (0.45 g, 1.72 mmol) and Et$_3$N (0.68 ml, 4.91 mmol). The reaction mixture was stirred at 0° C. under nitrogen for 1.5 h. The reaction mixture was concentrated and the residue was extracted with ethyl acetate and saturated NaHCO$_3$ solution. The organic layer was washed successively with brine, 1 N HCl, brine, and concentrated after drying over MgSO$_4$ to give viscous solid (0.99 g, 82%). $^1$H NMR (CDCl$_3$): δ 9.10 (bs, 1H), 7.52 (d, J=2.8 Hz, 1H), 7.40 (d, J=2.8 Hz, 1H), 7.28-7.17 (m, 1H), 7.14-6.90 (m, 9H), 6.85 (d, J=8.3 Hz, 2H), 4.36 (m, 4H), 4.23 (m, 2H), 1.46 (s, 9H); MS (ESI): (M+H)$^+$=605.2.

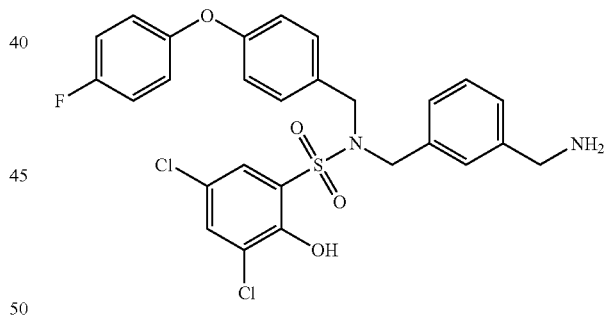

C) N-(3-(Aminomethyl)benzyl)-3,5-dichloro-N-(4-(4-fluorophenoxy)benzyl)-2-hydroxybenzenesulfonamide To a solution of tert-butyl 3-((3,5-dichloro-N-(4-(4-fluorophenoxy)benzyl)-2-hydroxyphenylsulfonamido)methyl)benzylcarbamate (0.98 g, 1.48 mmol) in CH$_2$Cl$_2$ (15 mL) was added TFA (2.28 mL, 29.6 mmol). The reaction mixture was stirred at rt for 3 h. The mixture was concentrated and the residue was partitioned between ethyl acetate and saturated NaHCO$_3$ solution. The organic layer (clear solution) was washed with brine, dried over MgSO$_4$ and concentrated to give white solid (0.65 g, 70%). $^1$H NMR (DMSO-d$_6$): δ 8.50 (bs, 1H), 7.52 (s, 1H), 7.34 (d, J=2.8 Hz, 1H), 7.2.9 (d, J=2.8 Hz, 1H), 7.26-7.21 (m, 4H), 7.12-7.08 (m, 3H), 6.97-6.94 (m, 2H), 6.80 (d, J=6.8 Hz, 2H), 4.41 (s, 2H), 4.32 (s, 2H), 3.94 (s, 2H); MS (ESI): (M+H)⁺=561.1.

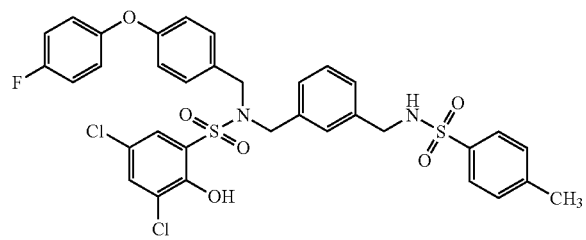 [SMILES: Cc1ccc(S(=O)(=O)NCc2cccc(CN(Cc3ccc(Oc4ccc(F)cc4)cc3)S(=O)(=O)c3cc(Cl)cc(Cl)c3O)c2)cc1]

D) 3,5-Dichloro-N-(4-(4-fluorophenoxy)benzyl)-2-hydroxy-N-(3-((4-methylphenylsulfonamido)methyl)benzyl)benzenesulfonamide To a suspension of 4-methylbenzene-1-sulfonyl chloride (25 mg, 0.13 mmol) in CH$_2$Cl$_2$ (3 mL) were added Et$_3$N (0.10 ml, 075 mmol) and N-(3-(aminomethyl)benzyl)-3,5-dichloro-N-(4-(4-fluorophenoxy)benzyl)-2-hydroxybenzenesulfonamide (70 mg, 0.13 mmol). The reaction mixture was stirred at rt. under nitrogen for 2 h. The mixture was concentrated and dissolved in MeOH, purified by preparative HPLC. The fractions containing the desired product were combined, concentrated and lyophilized to give white solid (52 mg, 58%).

¹H NMR (MeOH-d$_4$): δ 7.59-7.56 (m, 3H), 7.51 (d, J=2.6 Hz, 1H), 7.22 (d, J=8.0 Hz, 2H), 7.05-6.80 (m, 10H), 6.90 (d, J=6.6 Hz, 2H), 4.31 (s, 2H), 4.28 (s, 2H), 3.85 (s, 2H), 2.30 (s, 3H); MS (ESI): (M−H)⁻=712.9.

Example 6

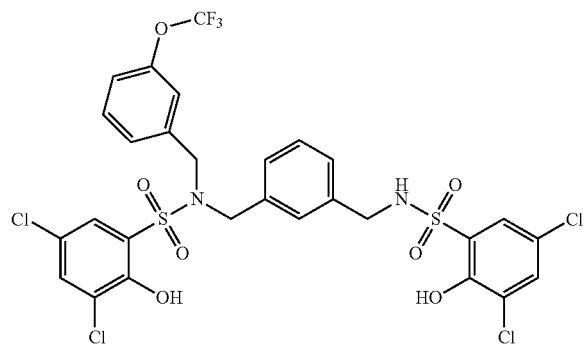 [SMILES: O=S(=O)(NCc1cccc(CN(Cc2cccc(OC(F)(F)F)c2)S(=O)(=O)c2cc(Cl)cc(Cl)c2O)c1)c1cc(Cl)cc(Cl)c1O]

3,5-Dichloro-N-(3-((3,5-dichloro-2-hydroxyphenylsulfonamido)methyl)benzyl)-2-hydroxy-N-(3-(trifluoromethoxy)benzyl)benzenesulfonamide ¹H NMR (CD$_3$OD): δ 7.65 (d, J=2.4 Hz, 1H), 7.58 (d, J=2.4 Hz, 1H), 7.41 (m, 2H), 7.29 (t, J=7.3 Hz, 1H), 7.15-6.97 (m, 5H), 6.85 (m, 1H), 6.75 (s, 1H), 4.46 (s, 2H), 4.29 (s, 2H), 4.00 (s, 2H); MS (ESI): M−H)⁻=778.1.

Example 7

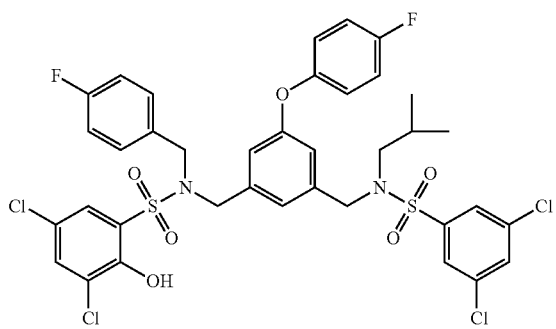 [SMILES: CC(C)CN(Cc1cc(CN(Cc2ccc(F)cc2)S(=O)(=O)c2cc(Cl)cc(Cl)c2O)cc(Oc2ccc(F)cc2)c1)S(=O)(=O)c1cc(Cl)cc(Cl)c1]

3,5-Dichloro-N-(3-((3,5-dichloro-N-isobutylphenylsulfonamido)methyl)-5-(4-fluorophenoxy)benzyl)-N-(4-fluorobenzyl)-2-hydroxybenzenesulfonamide

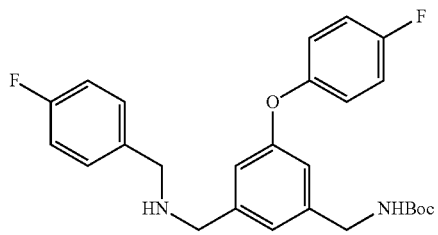 [SMILES: CC(C)(C)OC(=O)NCc1cc(CNCc2ccc(F)cc2)cc(Oc2ccc(F)cc2)c1]

A) tert-Butyl 3-((4-fluorobenzylamino)methyl)-5-(4-fluorophenoxy)benzylcarbamate To a solution of tert-butyl 3-(aminomethyl)-5-(4-fluorophenoxy)benzylcarbamate (1.37 g, 3.96 mmol) in CH$_2$Cl$_2$ (15 mL) and 2-propanol (15 mL) was added 4-fluorobenzaldehyde (0.42 mL, 3.96 mmol). The reaction mixture was stirred at rt. under nitrogen for 40 min, and then treated with sodium triacetoxyhydroborate (1.76 g, 8.31 mmol). The resulting mixture was stirred at rt for 2 h. The reaction mixture was concentrated and the residue was partitioned between saturated NaHCO$_3$ solution and ethyl acetate. The organic layer (clear solution) was washed with brine and dried over MgSO$_4$. The filtrate was concentrated. The sample was purified by flash chromatography. Elution with 0-35% of ethyl acetate in CH$_2$Cl$_2$ gave the product as viscous oil (1.2 g, 67%). ¹H NMR (CD$_3$OD): δ 7.35-7.32 (m, 2H), 7.13-6.99 (m, 7H), 6.87 (s, 1H), 6.80 (s, 1H), 4.20 (s, 2H), 3.70 (s, 2H), 1.44 (s, 9H); MS (ESI): (M−H)⁻=513.1.

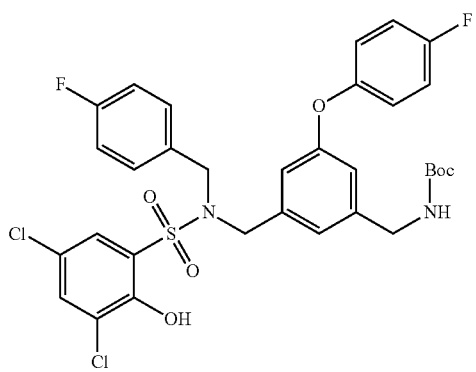 [SMILES: CC(C)(C)OC(=O)NCc1cc(CN(Cc2ccc(F)cc2)S(=O)(=O)c2cc(Cl)cc(Cl)c2O)cc(Oc2ccc(F)cc2)c1]

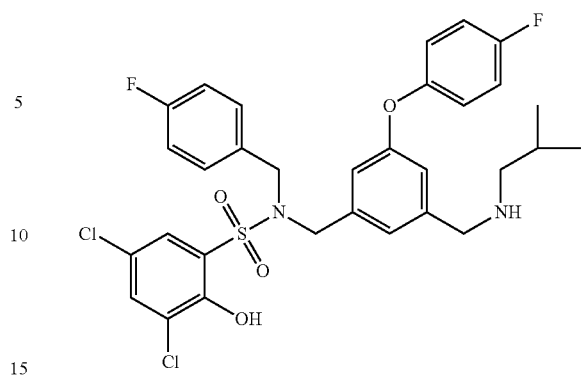

B) tert-Butyl 3-((3,5-dichloro-N-(4-fluorobenzyl)-2-hydroxyphenylsulfonamido)methyl)-5-(4-fluorophenoxy)benzylcarbamate To a solution of tert-butyl 3-((4-fluorobenzylamino)methyl)-5-(4-fluorophenoxy)benzylcarbamate (0.72 g, 1.58 mmol) in THF (15 mL) were added 3,5-dichloro-2-hydroxybenzenesulfonyl chloride (0.41 g, 1.58 mmol) and Et$_3$N (0.66 mL, 4.75 mmol). The reaction mixture was stirred at rt for 1.5 h. The mixture was concentrated. The sample was purified by flash chromatography. Elution with 0 to 35% of ethyl acetate in dichloromethane gave the product as a white solid (0.65 g, 61%). $^1$H NMR (CDCl$_3$): δ 9.01 (s, 1H), 7.55 (d, J=2.0 Hz, 1H), 7.45 (s, 1H), 7.15-7.06 (m, 4H), 7.01-6.92 (m, 4H), 6.76 (s, 2H), 6.54 (s, 1H), 4.41 (s, 2H), 4.32 (s, 2H), 4.21 (d, J=5.6 Hz, 2H), 1.49 (s, 9H); MS (ESI): (M−H)$^-$=677.1.

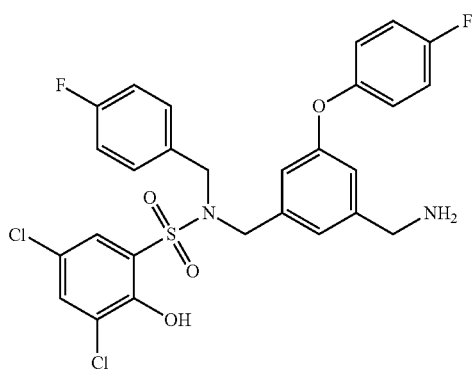 [SMILES: NCc1cc(CN(Cc2ccc(F)cc2)S(=O)(=O)c2cc(Cl)cc(Cl)c2O)cc(Oc2ccc(F)cc2)c1]

C) N-(3-(Aminomethyl)-5-(4-fluorophenoxy)benzyl)-3,5-dichloro-N-(4-fluorobenzyl)-2-hydroxybenzenesulfonamide To a solution of tert-butyl 3-((3,5-dichloro-N-(4-fluorobenzyl)-2-hydroxyphenylsulfonamido)methyl)-5-(4-fluorophenoxy)benzylcarbamate (0.65 g, 0.96 mmol) in CH$_2$Cl$_2$ (8 mL) was added TFA (1.10 mL, 14.4 mmol). The reaction mixture was stirred at rt. for 3 h. The reaction mixture was concentrated and to the residue was added saturated NaHCO$_3$ solution and ethyl acetate. The organic layer was washed with brine twice, dried over MgSO$_4$, and concentrated in vacuo to give white solid (0.53 g, 96%). $^1$H NMR (CD$_3$OD): δ 7.49 (d, J=2.8 Hz, 1H), 7.35 (d, J=2.8 Hz, 1H), 7.21-7.09 (m, 4H), 6.99-6.90 (m, 5H), 6.85 (s, 1H), 6.64 (s, 1H), 4.48 (s, 2H), 4.40 (s, 2H), 3.93 (s, 2H); MS (ESI): (M+H)$^+$=579.0.

D) 3,5-Dichloro-N-(4-fluorobenzyl)-N-(3-(4-fluorophenoxy)-5-((isobutylamine)methyl)benzyl)-2-hydroxybenzenesulfonamide To a suspension of N-(3-(aminomethyl)-5-(4-fluorophenoxy)benzyl)-3,5-dichloro-N-(4-fluorobenzyl)-2-hydroxybenzenesulfonamide (0.53 g, 0.92 mmol) in CH$_2$Cl$_2$ (7 mL) and 2-propanol (7 mL) was added iso-butyraldehyde (0.09 mL, 1.0 mmol) and the reaction mixture was stirred at rt under nitrogen for 40 min. The reaction mixture turned into a clear solution after the addition of aldehyde. To the mixture was added sodium triacetoxyhydroborate (0.41 g, 1.92 mmol). The resulting mixture was stirred at rt. for 4 h. The reaction mixture was concentrated and the residue was partitioned between saturated NaHCO$_3$ solution and ethyl acetate. The organic layer (clear solution) was washed with brine, and dried over MgSO$_4$. The filtrate was concentrated to give light yellow solid (0.5 g, 69%). The analytical pure sample was obtained by preparation HPLC purification. $^1$H NMR (CD$_3$OD): δ 7.57 (dd, J=11.6, 2.4 Hz, 2H), 7.07-7.02 (m, 4H), 6.98 (s, 1H), 6.90-6.80 (m, 5H), 6.69 (d, J=1.6 Hz, 1H), 4.42 (s, 2H), 4.36 (s, 2H), 4.00 (s, 2H), 2.73 (d, J=7.2 Hz, 2H), 1.90 (m, 1H), 0.92 (d, J=6.8 Hz, 6H); MS (ESI): (M+H)$^+$=635.0.

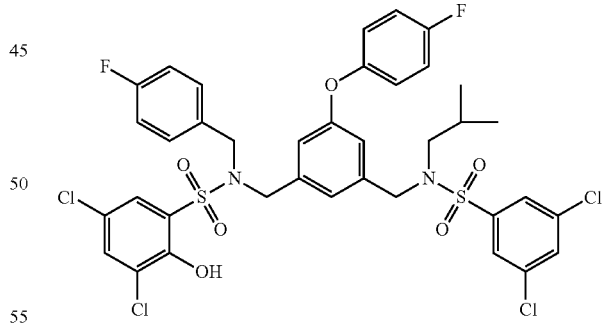

E) 3,5-Dichloro-N-(3-((3,5-dichloro-N-isobutylphenylsulfonamido)methyl)-5-(4-fluorophenoxy)benzyl)-N-(4-fluorobenzyl)-2-hydroxybenzenesulfonamide To a solution of 3,5-dichlorobenzenesulfonyl chloride (27.0 mg, 0.11 mmol) in CH$_2$Cl$_2$ (3 mL) was added 3,5-dichloro-N-(4-fluorobenzyl)-N-(3-(4-fluorophenoxy)-5-((isobutylamino)methyl)benzyl)-2-hydroxybenzenesulfonamide (70 mg, 0.11 mmol, 80% purity), followed by the addition of Et₃N (0.09 mL, 0.66 mmol). The reaction mixture was stirred at rt for 1 h. The reaction mixture was diluted with CH₂Cl₂ and saturated NaHCO₃ solution. The organic layer was concentrated. To the residue was added 1 N NaOH/MeOH/THF. The resulting mixture was left for 2 h. The mixture was concentrated and the residue was diluted with CH₂Cl₂ and water. The organic layer was concentrated. The residue was dissolved in MODEL and purified by preparative HPLC. Fractions containing the desired product were combined, concentrated, and lyophilized to give a white solid (35 mg, 38%). ¹H NMR (CD₃OD): δ 7.67-7.63 (m, 4H), 7.57 (d, J=2.8 Hz, 1H), 7.14-7.04 (m, 4H), 6.91 (t, J=8.8 Hz, 2H), 6.87-6.83 (m, 2H), 6.70 (s, 1H), 6.63 (s, 1H), 6.56 (s, 1H), 4.40 (s, 2H), 4.32 (s, 2H), 4.21 (s, 2H), 2.91 (d, J=7.6 Hz, 2H), 1.65 (m, 1H), 0.74 (d, J=6.4 Hz, 6H); MS (ESI): (M−H)⁻=843.0.

Example 8

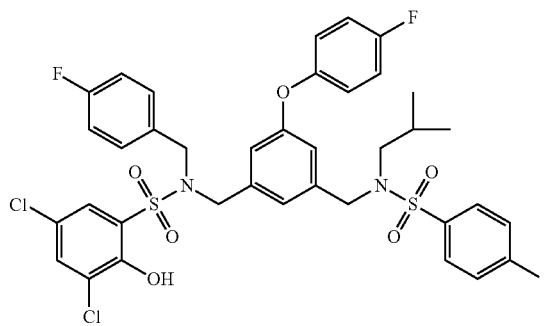 [SMILES: Cc1ccc(S(=O)(=O)N(Cc2cc(CN(Cc3ccc(F)cc3)S(=O)(=O)c3cc(Cl)cc(Cl)c3O)cc(Oc3ccc(F)cc3)c2)CC(C)C)cc1]

3,5-Dichloro-N-(4-fluorobenzyl)-N-(3-(4-fluorophenoxy)-5-((N-isobutyl-4-methylphenylsulfonamido)methyl)benzyl)-2-hydroxybenzenesulfonamide ¹H NMR (MeOD-d₄): δ 7.65-7.63 (m, 3H), 7.55 (d, J=2.4 Hz, 1H), 7.34 (d, J=8.0 Hz, 2H), 7.13-7.04 (m, 4H), 6.93-6.83 (m, 4H), 6.67 (s, 2H), 6.52 (s, 1H), 4.40 (s, 2H), 4.30 (s, 2H), 4.12 (s, 2H), 2.80 (d, J=7.6 Hz, 2H), 2.38 (s, 3H), 1.56 (m, 1H), 0.70 (d, J=6.8 Hz, 6H); MS (ESI): (M−H)⁻=787.2.

Example 9

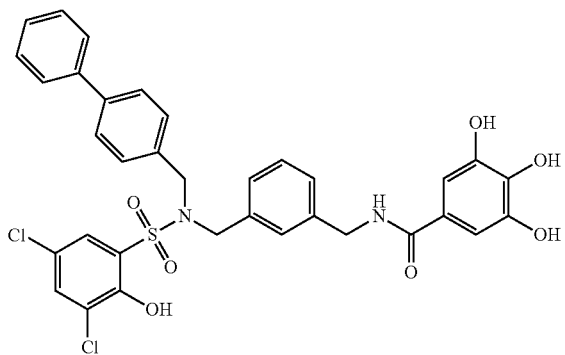 [SMILES: O=C(NCc1cccc(CN(Cc2ccc(-c3ccccc3)cc2)S(=O)(=O)c2cc(Cl)cc(Cl)c2O)c1)c1cc(O)c(O)c(O)c1]

N-(3-((N-Biphenyl-4-ylmethyl)-3,5-dichloro-2-hydroxyphenylsulfonamido)methyl)benzyl)-3,4,5-trihydroxybenzamide To a solution 3,4,5-trihydroxybenzoic acid (23 mg, 0.14 mmol) in DMF (3 mL) were added EDCI.HCl (31 mg, 0.16 mmol) and HOBt.H₂O (19 mg, 0.12 mmol). The reaction mixture was stirred at rt for 30 min, and then treated with N,N-diisopropylethylamine (0.1 mL) and N-(3-(aminomethyl)benzyl)-N-(biphenyl-4-ylmethyl)-3,5-dichloro-2-hydroxybenzenesulfonamide (65 mg, 0.12 mmol). The resulting mixture was stirred at rt for 18 h. It was concentrated in vacuo, and the residue was purified by preparative HPLC. The fractions containing the desired product were combined, concentrated and lyophilized to afford the product as a white solid (35 mg, 41%). ¹H NMR (MeOH-d₄): δ 7.60 (d, J=2.4 Hz, 1H), 7.50 (d, J=2.4 Hz, 1H), 7.41 (d, J=8.4 Hz, 2H), 7.36-7.16 (m, 5H), 7.14-6.97 (m, 5H), 6.90 (d, J=5.6 Hz, 1H), 6.84 (s, 2H), 4.38 (s, 4H), 4.36 (s, 2H).

Example 10

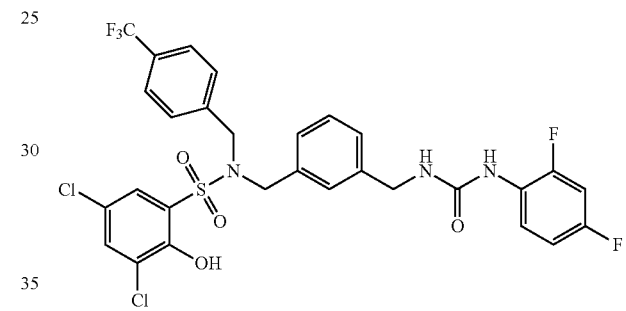

3,5-Dichloro-N-(3-((3-(2,4-difluorophenyl)ureido)methyl)benzyl)-2-hydroxy-N-(4-(trifluoromethyl)benzyl)benzenesulfonamide

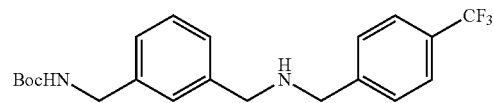 [SMILES: CC(C)(C)OC(=O)NCc1cccc(CNCc2ccc(C(F)(F)F)cc2)c1]

A) tert-Butyl 3-((4-(trifluoromethyl)benzylamino)methyl)benzylcarbamate

To a solution of tert-butyl 3-(aminomethyl)benzylcarbamate (0.80 g, 3.39 mmol) in methanol (0.11 g, 3.39 mmol) was added 4-(trifluoromethyl)benzaldehyde (0.45 mL, 3.39 mmol) under nitrogen. The reaction mixture was stirred for 10 min, followed by the addition of sodium triacetoxyborohydride (1.08 g, 5.08 mmol). The resulting mixture was stirred at rt. for 20 h. To the reaction mixture was added 1 N HCl solution and the mixture was concentrated. The residue was extracted with ethyl acetate and saturated sodium bicarbonate solution. The organic layer was washed with brine, dried over MgSO₄, and concentrated to give an oil. The sample was purified by silica gel flash chromatography. Elution with dichloromethane to 30% of ethyl acetate in dichloromethane gave a colorless oil (0.64 g, 47%). ¹H NMR (CDCl₃): δ 7.61 (d, J=8.4 Hz, 2H), 7.51 (d, J=8.0 Hz, 2H), 7.33-7.22 (m, 4H), 4.34 (m, 2H), 3.89 (s, 2H), 3.82 (s, 2H), 1.48 (s, 9H); MS (ESI): (M+H)⁺=395.4.

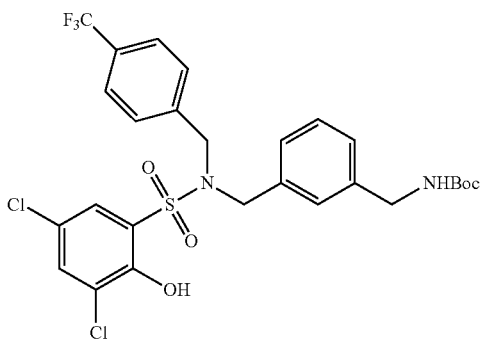 [SMILES: CC(C)(C)OC(=O)NCc1cccc(CN(Cc2ccc(C(F)(F)F)cc2)S(=O)(=O)c2cc(Cl)cc(Cl)c2O)c1]

B) tert-Butyl 3-((3,5-dichloro-2-hydroxy-N-(4-(trifluoromethyl)benzyl)phenylsulfonamido)methyl)benzylcarbamate To a solution of rent-butyl 3-((4-(trifluoromethyl)benzylamino)methyl)benzylcarbamate (0.19 g, 0.48 mmol) in CH₂Cl₂ (5 mL) were added triethylamine (0.20 mL, 1.45 mmol) and 3,5-dichloro-2-hydroxybenzene-1-sulfonyl chloride (0.13 g, 0.48 mmol) solution in CH₂Cl₂ (2 mL). The reaction mixture was stirred at 0° C. for 1 h. To the reaction mixture was added saturated NaHCO₃ and CH₂Cl₂. The organic layer was washed with brine, dried over magnesium sulfate, and concentrated in vacuo. The residue was dissolved in CH₂Cl₂ and loaded onto the solid sample cartridge. The sample was purified by silica gel flash chromatography. Elution with dichloromethane to 15% of ethyl acetate in dichloromethane gave a colorless gummy solid (0.17 g, 56%). ¹H NMR (CDCl₃): δ 8.98 (bs, 1H), 7.55 (m, 3H), 7.49 (d, J=2.4 Hz, 1H), 7.27 (d, J=6.4 Hz, 2H), 7.21-7.15 (m, 2H), 6.97 (m, 2H), 4.48 (s, 2H), 4.38 (s, 2H), 4.21 (m, 2H), 1.49 (s, 9H); MS (ESI): (M+H)⁺=563.07.

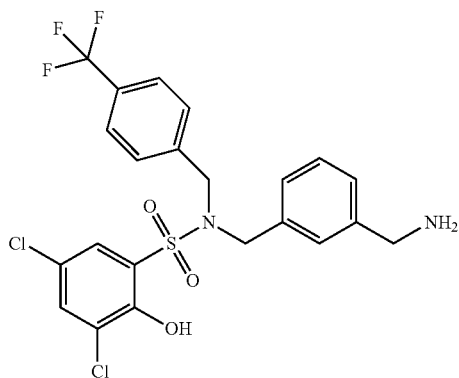 [SMILES: NCc1cccc(CN(Cc2ccc(C(F)(F)F)cc2)S(=O)(=O)c2cc(Cl)cc(Cl)c2O)c1]

C) N-(3-(Aminomethyl)benzyl)-3,5-dichloro-2-hydroxy-N-(4-(trifluoromethyl)benzyl)benzenesulfonamide To a solution of tert-butyl 3-((3,5-dichloro-2-hydroxy-N-(4-(trifluoromethyl)benzyl)phenylsulfonamido)methyl)benzylcarbamate (0.4 g, 0.65 mmol) in CH₂Cl₂ (10 mL) was added TFA (1.49 mL, 19.4 mmol). The resulting mixture was stirred at rt for 16 h. The mixture was concentrated, and the residue was partitioned between saturated NaHCO₃ and ethyl acetate. The organic layer was washed with brine twice, dried over MgSO₄, and concentrated in vacuo to give a light yellow solid (0.32 g, 86%). ¹H NMR (DMF-d₇): δ 7.52 (m, 2H), 7.50 (m, 4H), 7.48 (m, 2H), 7.2-7.0 (m, 2H), 4.75 (s, 2H), 4.51 (s, 2H), 4.25 (m, 2H); MS (ESI): (M+H)⁺=519.11.

3,5-Dichloro-N-(3-((3-(2,4-difluorophenyl)ureido)methyl)benzyl)-2-hydroxy-N-(4-(trifluoromethyl)benzyl)benzenesulfonamide To a solution of N-(3-(aminomethyl)benzyl)-3,5-dichloro-2-hydroxy-N-(4-(trifluoromethyl)benzyl)benzenesulfonamide (40 mg, 0.08 mmol) in DMF (2 mL) was added 2,4-difluorophenyl isocyanate (10.0 μL, 0.09 mmol). The resulting mixture was stirred at rt for 3 h under nitrogen. The mixture was concentrated and purified by preparative HPLC. Fractions containing the desired product were combined, concentrated and lyophilized to give a white solid (30 mg, 57%). ¹H NMR (CD₃OD): δ 7.59 (d, J=2.8 Hz, 1H), 7.52 (d, J=2.2 Hz, 1H), 7.48 (d, J=7.7 Hz, 2H), 7.44 (d, J=8.8 Hz, 2H), 7.39-7.37 (m, 4H), 7.31 (t, 7.7 Hz, 2H), 7.24 (d, J=7.7 Hz, 2H), 7.19 (t, J=7.1 Hz, 2H), 7.09 (m, 2H), 7.02 (s, 1H), 6.89 (d, J=6.6 Hz, 1H), 4.48 (s, 2H), 4.40 (s, 2H), 4.23 (s, 2H); MS (ESI): (M+H)⁺=714.2.

Example 11

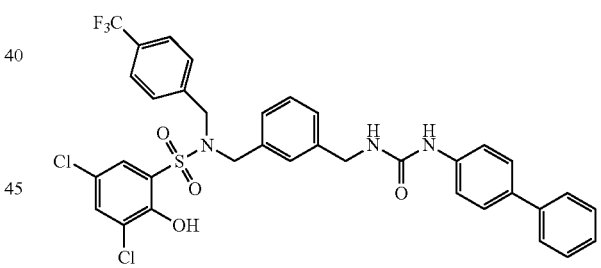

N-(3-((3-Biphenyl-4-ylureido)methyl)benzyl)-3,5-dichloro-2-hydroxy-N-(4-(trifluoromethyl)benzyl)benzenesulfonamide To a solution of N-(3-(aminomethyl)benzyl)-3,5-dichloro-2-hydroxy-N-(4-(trifluoromethyl)benzyl)benzenesulfonamide (60 mg, 0.12 mmol) in DMF (3 mL) was added 4-biphenyl isocyanate (23.7 mg, 0.12 mmol). The resulting mixture was stirred at rt. for 2 h under nitrogen. The mixture was concentrated and dissolved in MeOH, purified by preparative HPLC. The fractions containing the desired product were combined, concentrated and lyophilized to give white solid (50 mg, 60%).

¹H NMR (CD₃OD): δ 7.85 (m, 1H), 7.58 (d, J=2.8 Hz, 1H), 7.52 (d, 2.4 Hz, 1H), 7.37 (d, 8.0 Hz, 2H), 7.23 (d, J=8.0 Hz,

2H), 7.07 (d, J=6.0 Hz, 2H), 6.99 (s, 1H), 6.90-6.80 (m, 2H), 6.79-6.77 (m, 1H), 4.47 (s, 2H), 4.38 (s, 2H), 4.20 (s, 2H); MS (ESI): (M+H)$^+$=674.14.

Example 12

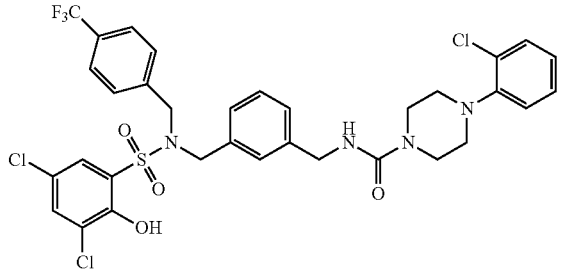 [SMILES: O=C(NCc1cccc(CN(Cc2ccc(C(F)(F)F)cc2)S(=O)(=O)c2cc(Cl)cc(Cl)c2O)c1)N1CCN(c2ccccc2Cl)CC1]

4-(2-Chlorophenyl)-N-(3-((3,5-dichloro-2-hydroxy-N-(4-(trifluoromethyl)benzyl)phenylsulfonamido)methyl)benzyl)piperazine-1-carboxamide To a solution of N-(3-(aminomethyl)benzyl)-3,5-dichloro-2-hydroxy-N-(4-(trifluoromethyl)benzyl)benzenesulfonamide (60 mg, 0.12 mmol) in DMF (2 mL) were added N,N-diisopropylethylamine (0.08 mL, 0.46 mmol) and 1,1'-carbonyldiimidazole (20.6 mg, 0.13 mmol). The resulting mixture was stirred at it for 1 h under nitrogen, then 1-(2-chlorophenyl)piperazine monohydrochloride (29.6 mg, 0.13 mmol) was added. The mixture was stirred overnight. The mixture was concentrated and purified by preparative HPLC. Fractions containing the desired product were combined, concentrated and lyophilized to give white solid (54 mg, 62%). $^1$H NMR (MeOD-d$_4$): δ 7.57 (d, J=2.8 Hz, 1H), 7.52 (d, J=2.8 Hz, 1H), 7.40 (d, J=8.3 Hz, 2H), 7.28 (m, 1H), 7.21 (d, J=8.3 Hz, 2H), 7.15 (m, 1H), 7.06 (m, 4H), 6.92 (m, 1H), 6.88 (m, 1H), 4.45 (s, 2H), 4.41 (s, 2H), 4.21 (s, 2H), 3.50 (t, J=5.0 Hz, 4H), 2.93 (t, J=5.0 Hz, 4H); MS (ESI): (M+H)$^+$=743.2.

Example 13

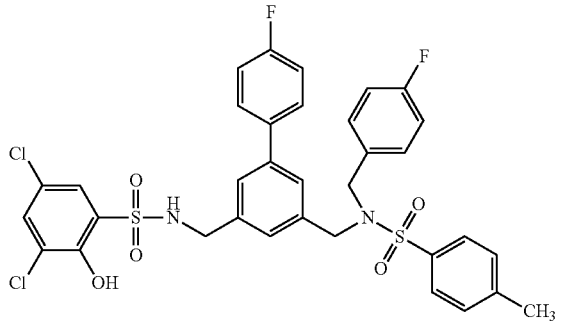 [SMILES: Cc1ccc(S(=O)(=O)N(Cc2ccc(F)cc2)Cc2cc(CNS(=O)(=O)c3cc(Cl)cc(Cl)c3O)cc(-c3ccc(F)cc3)c2)cc1]

3,5-Dichloro-N-((4'-fluoro-5-((N-(4-fluorobenzyl)-4-methylphenylsulfonamido)methyl)biphenyl-3-yl)methyl)-2-hydroxybenzenesulfonamide

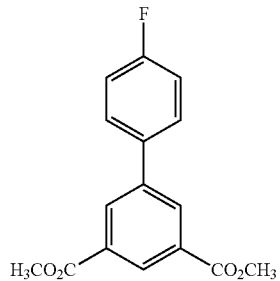 [SMILES: COC(=O)c1cc(C(=O)OC)cc(-c2ccc(F)cc2)c1]

A) Dimethyl 4'-fluorobiphenyl-3,5-dicarboxylate

A mixture of dimethyl 5-bromoisophthalate (5.47 g, 20.03 mmol), 4-fluorophenylboronic acid (4.20 g, 30.0 mmol) and cesium carbonate (9 g, 27.6 mmol) in dioxane (60 mL) was purged with Ar gas for a few minutes, to the mixture was added Pd(PPh$_3$)$_4$ (1 g, 0.865 mmol). The reaction mixture was heated at 90° C. overnight. The next morning additional Pd-catalyst (~300 mg) was added, and the reaction mixture was heated at 90° C. for an additional 7 h. To the reaction mixture was added EtOAc and water, and the insoluble material was filtered. The EtOAc layer was separated, dried over MgSO$_4$, concentrated in vacuo and the residual solid was mixed with ether. The insoluble solid was filtered and the filtrate was concentrated. To the residue was added ether, the insoluble solid was filtered (this solid was mostly boronic acid) and the filtrate solution was concentrated. The residue was purified by flash column chromatography on SiO$_2$ which provided a mixture of desired product and dimethyl 5-bromoisophthalate (3.4 g). This mixture was carried on into the same coupling reaction again repeating the same procedure except it was heated at 77° C. for 16 h. The solid was filtered, washed with EtOAc, and the filtrate solution was washed with water, dried, concentrated, and the residue was passed through a flash column on SiO$_2$ eluting with 3:1/Hex:EtOAc, which provided the desired product (3.0 g, 10.41 mmol, 52%) as a white solid. $^1$H NMR (CDCl$_3$): δ 8.62 (d, J=1.7 Hz, 1H), 8.39 (d, J=1.7 Hz, 2H), 7.61 (dd, J=8.8, 5.5 Hz, 2H), 7.15 (t, J=8.8 Hz, 2H), 3.96 (s, 6H).

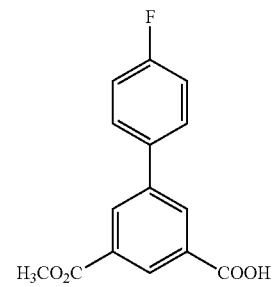 [SMILES: COC(=O)c1cc(C(=O)O)cc(-c2ccc(F)cc2)c1]

B) 4'-Fluoro-5-(methoxycarbonyl)biphenyl-3-carboxylic acid

A mixture of dimethyl 4'-fluorobiphenyl-3,5-dicarboxylate (1.0 g, 3.47 mmol) and NaHCO$_3$ (480 mg, 5.71 mmol) in THF (10 ml), MeOH (10.00 mL) and water (5 mL) was heated at reflux temperature for 6 h. An additional 400 mg of NaHCO₃ was added to the reaction mixture and it was heated at reflux temp overnight (16 h). The reaction mixture was concentrated in vacuo, and the residue was acidified using 1N aq HCl, concentrated and purified by prep HPLC to obtain diacid (310 mg) and mono acid (300 mg) as white solids.

Mono Acid ¹H NMR (CDCl₃): δ 8.70 (s, 1H), 8.44 (s, 2H), 7.61 (dd, J=8.8, 5.5 Hz, 2H), 7.15 (t, J=8.24 Hz, 2H), 3.97 (s, 3H).

to the reaction mixture at rt and stirred for 2 h. To the reaction mixture was added EtOAc slowly, stirred for 10 minutes, and were added MeOH and TFA slowly. After stirring for 30 minutes, the mixture was concentrated and the residue was purified by prep HPLC to obtain the product as a white solid of the TFA salt (470 mg, 68%). ¹H NMR (CD₃OD): δ 7.66~7.16 (m, 11H), 4.71 (s, 2H), 4.30 (s, 2H), 4.27 (s, 2H); MS (ESI): (M+H)⁺340.26.

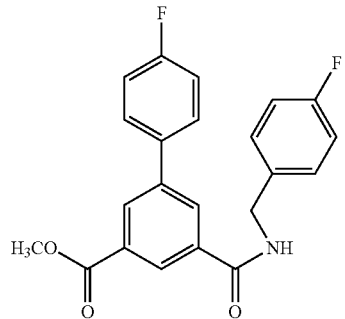 [SMILES: COC(=O)c1cc(C(=O)NCc2ccc(F)cc2)cc(-c2ccc(F)cc2)c1]

C) Methyl 4'-fluoro-5-(4-fluorobenzylcarbamoyl) biphenyl-3-carboxylate

To a solution of 4'-fluoro-5-(methoxycarbonyl)biphenyl-3-carboxylic acid (400 mg, 1.459 mmol) in DMF/CH₂Cl₂ at rt was added EDCI.HCl (363 mg, 1.896 mmol) followed by HOBt.H₂O (197 mg, 1.459 mmol). After one minute, (4-fluorophenyl)methanamine (183 mg, 1.459 mmol) was added to the mixture and the reaction mixture was stirred at rt for 4 h. To the reaction mixture were added EtOAc and aq. NaHCO₃. The EtOAc layer was separated, washed with water, dried over MgSO₄ and concentrated in vacuo to obtain a crude product as a light yellow solid (585 mg, >100% yield), MS: M+H=382.21. The crude product was used directly in the next step without further purification. ¹H NMR (CDCl₃): δ 8.39 (s, 1H), 8.32 (s, 1H), 7.58~7.02 (m, 9H), 4.63 (d, J=6.0 Hz, 2H), 3.95 (s, 3H).

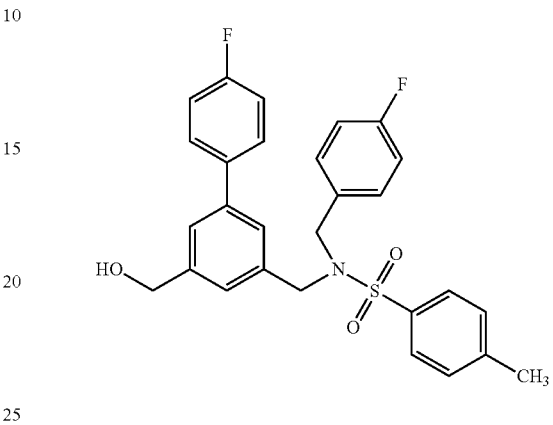

E) N-((4'-Fluoro-5-(hydroxymethyl)biphenyl-3-yl) methyl)-N-(4-fluorobenzyl)-4-methylbenzene-sulfonamide and N-((4'-fluoro-5-(methoxymethyl) biphenyl-3-yl)methyl)-N-(4-fluorobenzyl)-4-methylbenzenesulfonamide To a solution of (4'-fluoro-5-((4-fluorobenzylamino)methyl)biphenyl-3-yl)methanol TEA salt (260 mg, 0.573 mmol) and Et₃N (200 mg, 1.976 mmol) in CH₂Cl₂ (6 mL) at 0° C. was added p-toluenesulfonyl chloride (220 mg, 1.154 mmol). The mixture was stirred for 1 h at ~5° C. and concentrated. The resulting residue was purified by prep HPLC to obtain the desired product (110 mg, 39%). ¹H NMR (CD₃OD): δ 7.76 (d, J=7.7 Hz, 2H), 7.43~6.87 (m, 13H), 4.53 (s, 2H), 4.37 (s, 2H), 4.33 (s, 2H), 2.41 (s, 3H); MS (ESI): (M+H)⁺494.

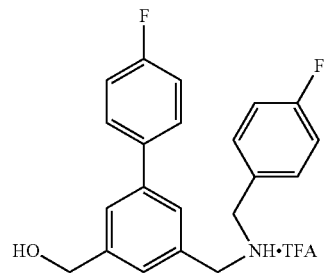

D) 4'Fluoro-5-((4-fluorobenzylamino)methyl)biphenyl-3-yl)methanol TFA salt

To a solution of methyl 4'-fluoro-5-(4-fluorobenzylcarbamoyl)biphenyl-3-carboxylate (585 mg, 1.534 mmol) in THF (6 mL) at ice bath temperature was added borane (10 mL of 1 M solution in THF) slowly. After 30 min the mixture was warmed to rt, stirred for 1.5 h and heated at 55° C. for 13 h. An additional 5 mL of 1M solution of LiAlH₄ in THF was added

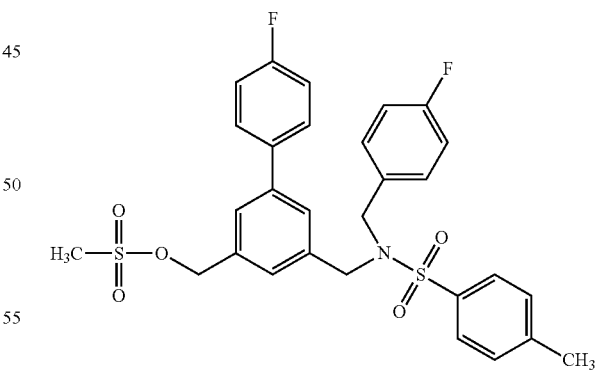

F) (4'-Fluoro-5-((N-(4-fluorobenzyl)-4-methylphenylsulfonamido)methyl)biphenyl-3-yl)methyl methanesulfonate To a solution of N-((4'-fluoro-5-(hydroxymethyl)biphenyl-3-yl)methyl)-N-(4-fluorobenzyl)-4-methylbenzenesulfonamide (100 mg, 0.203 mmol) and Et₃N (0.15 mL) in EtOAc (5 mL) at −30° C. was added methanesulfonyl chloride (25 mg, 0.218 mmol) in EtOAc (10 mL) slowly with stirring. After 1 h, a small amount of 1N aq HCl and EtOAc were added to the reaction mixture. The EtOAc layer was separated, dried over MgSO$_4$ and concentrated in vacuo to obtain the product as a viscous material. It was enough pure to use for next step without any further purification. MS (ESI): (M+H)$^+$=572.18.

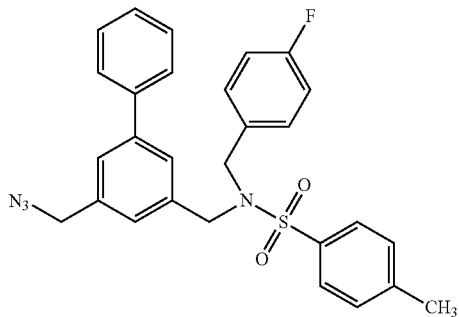 [SMILES: Cc1ccc(S(=O)(=O)N(Cc2ccc(F)cc2)Cc2cc(CN=[N+]=[N-])cc(-c3ccccc3)c2)cc1]

G) N-((5-(azidomethyl)biphenyl-3-yl)methyl)-N-(4-fluorobenzyl)-4-methylbenzenesulfonamide The crude product obtained above was mixed with DMF (4 mL) and sodium azide (25 mg, 0.385 mmol), and stirred at rt over the weekend. To the mixture were added EtOAc and water. The EtOAc layer was separated, dried over MgSO$_4$ and concentrated in vacuo. The residue was purified by prep HPLC to obtain the azido product (47 mg) as a glassy solid material. $^1$H NMR (CD$_3$OD): δ 7.69 (d, J=8.2 Hz, 2H), 7.36~6.77 (m, 13H), 4.30 (s, 2H), 4.25 (s, 2H), 4.20 (s, 2H), 2.34 (s, 3H); MS (ESI): (M+H)$^+$-N$_2$=491.15.

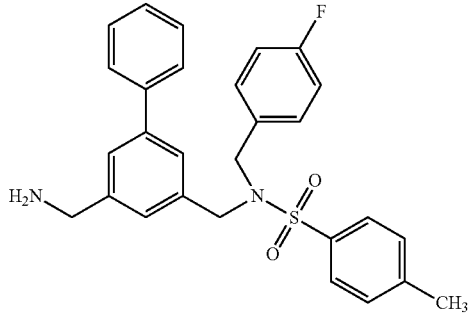 [SMILES: Cc1ccc(S(=O)(=O)N(Cc2ccc(F)cc2)Cc2cc(CN)cc(-c3ccccc3)c2)cc1]

H) N-((5-(Aminomethyl)biphenyl-3-yl)methyl)-N-(4-fluorobenzyl)-4-methylbenzenesulfonamide A mixture of azide (47 mg) and 20% of Pd (OH)$_2$ on carbon (20 mg) in EtOAc (4 mL) and MeOH (2 mL) was stirred under 1 atm of H$_2$ gas. The reaction was complete in 1 h. A small amount of toluene was added and the mixture was stirred for 10 minutes. The reaction mixture was filtered and the filtrate was concentrated in vacuo to obtain ~45 mg of viscous amino product. This material was used directly in the next step. MS (ESI): (M+H)$^+$=493.

I) 3,5-Dichloro-N-((4'-fluoro-5-((N-4-fluorobenzyl)-4-methylphenylsulfonamido)methyl)biphenyl-3-yl)methyl)-2-hydroxybenzenesulfonamide To a solution of N-((5-(aminomethyl)-4'-fluorobiphenyl-3-yl)methyl)-N-(4-fluorobenzyl)-4-methylbenzenesulfonamide (40 mg, 0.081 mmol) and Et$_3$N (40 mg, 0.395 mmol) in CH$_2$Cl$_2$ (4 mL) at rt was added solid 3,5-dichloro-2-hydroxybenzene-1-sulfonyl chloride (21.24 mg, 0.081 mmol) with stirring. The reaction was complete within an hour. The mixture was concentrated and the residue was purified by prep HPLC to provide the desired product as a white solid (30 mg). $^1$H NMR (CDCl$_3$): δ 7.72 (d, J=8.2 Hz, 2H), 7.51 (d, J=2.2 Hz, 1H), 7.34-6.83 (m, 14H), 5.32 (t, J=6.0 Hz, 1H), 4.25 (s, 2H), 4.245 (s, 2H), 4.12 (d, J=6.0 Hz, 2H), 2.43 (s, 3H); MS (ESI): (M+H)$^+$=717.

Example 14

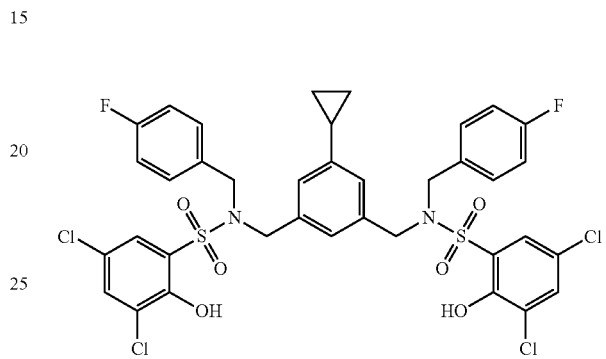

N,N'-(5-Cyclopropyl-1,3-phenylene)bis(methylene)bis(3,5-dichloro-N-(4-fluorobenzyl)-2-hydroxybenzenesulfonamide

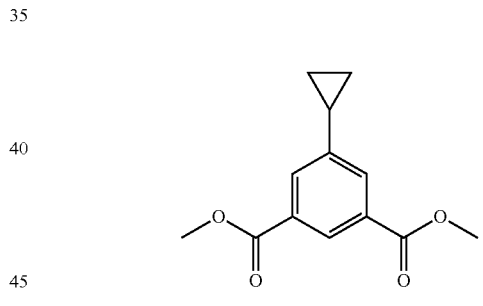

A) Dimethyl 5-cyclopropylisophthalate

A suspension of dimethyl 5-cyclopropylisophthalate (2.0 g, 7.32 mmol), cyclopropylboronic acid (1.0 g, 11.7 mmol) and potassium phosphate (4.66 g, 21.97 mmol) in toluene (45 mL) was purged with argon, and treated with Pd(OAc)$_2$ (0.49 g, 2.2 mmol) followed by tricyclohexylphosphine solution (2.2 mL of 1M solution, 2.2 mmol) and water (1.0 mL). The resulting reaction mixture was heated at 100° C. for 3 h, cooled to rt and filtered through a Celite® pad. The filtrate solution was diluted with ethyl acetate and water. The organic layer was separated, washed with brine, dried over MgSO$_4$ and concentrated. The residue was purified by silica gel column chromatography eluting with hexane to 10% of ethyl acetate in hexane to obtain the desired product as a light yellow solid (1.36 g, 74%). $^1$H NMR (CDCl$_3$): δ 8.47 (t, J=1.6 Hz, 1H), 7.94 (d, J=1.6 Hz, 2H), 3.96 (s, 6H), 2.07 (m, 1H), 1.07 (m, 2H), 0.81 (m, 2H).

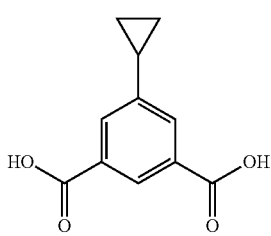 [SMILES: O=C(O)c1cc(C(=O)O)cc(C2CC2)c1]

B) 5-Cyclopropylisophthalic acid

To a solution of dimethyl 5-cyclopropylisophthalate (0.8 g, 3.42 mmol) in MeOH (10 mL) and THF (10 mL) was added potassium hydroxide (0.23 g, 4.1 mmol) with stirring. The reaction mixture was heated at 78° C. for 7 h. It was cooled to rt and concentrated in vacuo. To the residue was added a small amount of acetic acid. The mixture was purified by preparative HPLC. The fractions containing the desired product were combined, concentrated and lyophilized to afford 5-cyclopropylisophthalic acid as a white solid (89 mg, 12%) and 3-cyclopropyl-5-(methoxycarbonyl)benzoic acid as a white solid (0.43 g, 56%). $^1$H NMR (DMSO-d$_6$): δ 13.21 (s, 2H), 8.25 (t, J=1.2 Hz, 1H), 7.85 (d, J=1.2 Hz, 2H), 2.13 (m, 1H), 1.03 (m, 2H), 0.76 (m, 2H).

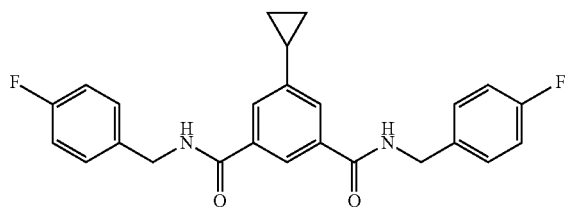 [SMILES: O=C(NCc1ccc(F)cc1)c1cc(C(=O)NCc2ccc(F)cc2)cc(C2CC2)c1]

C) 5-Cyclopropyl-N1,N3-bis(4-fluorobenzyl)isophthalamide

To a solution of 5-cyclopropylisophthalic acid (100 mg, 0.485 mmol) in DMF (4 mL) were added EDCI.HCl (0.23 g, 1.21 mmol) and HOBt.H$_2$O (0.89 g, 0.58 mmol). The reaction mixture was stirred at rt for 30 minutes and then treated with N,N-diisopropylethylamine (0.33 mL, 1.94 mmol) and (4-fluorophenyl)methanamine (0.14 mL, 1.2 mmol). The resulting mixture was stirred at rt for 4 h and it was poured into a mixture of water and ethyl acetate. The organic layer was separated, washed with brine, dried over MgSO$_4$ and concentrated. The residue was purified by preparative HPLC. The fractions containing the desired product were combined, concentrated and lyophilized to afford the product as a white solid (94 mg, 45%).

$^1$H NMR (CDCl$_3$): δ 8.42 (t, J=1.6 Hz, 1H), 7.53 (d, J=1.6 Hz, 2H), 7.24 (m, 4H), 6.95 (m, 4H), 6.51 (m, 2H), 4.51 (d, 5.6 Hz, 4H), 1.86 (m, 1H), 0.94 (m, 2H), 0.68 (m, 2H).

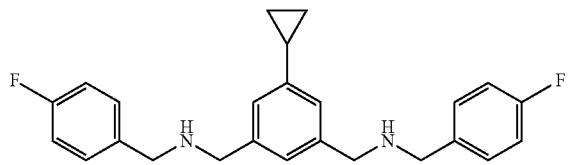 [SMILES: Fc1ccc(CNCc2cc(CNCc3ccc(F)cc3)cc(C3CC3)c2)cc1]

D) {3-Cyclopropyl-5-[(4-fluoro-benzylamino)-methyl]-benzyl}-(4-fluoro-benzyl)-amine To a solution of 5-cyclopropyl-N1,N3-bis(4-fluorobenzyl)isophthalamide (94 mg, 0.22 mmol) in THF (7.0 mL) was added borane (1.4 mL of 1M solution in THF, 1.4 mmol). The reaction mixture was heated at 70° C. for 5 h, cooled to 0° C. and treated with trifluoroacetic acid and MeOH. The resulting mixture was stirred at rt for 45 min, concentrated in vacuo and the residue was purified by preparative HPLC. The fractions containing the desired product were combined, concentrated and lyophilized to afford the product as a white solid of TFA salt (96 mg, 68%). $^1$H NMR (CD$_3$OD): δ 7.43 (m, 4H), 7.26-7.05 (m, 7H), 4.15 (s, 4H), 4.12 (s, 4H), 1.86 (m, 1H), 0.95 (m, 2H), 0.68 (m, 2H).

E) N,N'-(5-Cyclopropyl-1,3-phenylene)bis(methylene)bis(3,5-dichloro-N-(4-fluorobenzyl)-2-hydroxybenzenesulfonamide To a solution of N,N'-(5-cyclopropyl-1,3-phenylene)bis(methylene)bis(1-(4-fluorophenyl)methanamine) (90 mg, 0.15 mmol) in CH$_2$Cl$_2$ (3.0 mL) were added Et$_3$N (0.16 mL, 1.16 mmol) and 3,5-dichloro-2-hydroxybenzene-1-sulfonyl chloride (80 mg, 0.31 mmol). The reaction mixture was stirred at rt. for 2 h. The mixture was concentrated and the residue was purified by preparative HPLC. The fractions containing the desired product were combined, concentrated and lyophilized to afford the product as a white solid (25 mg, 21%). $^1$H NMR (CD$_3$OD): δ 7.58 (dd, J=16.8, 2.4 Hz, 4H), 7.13 (m, 4H), 6.92 (m, 4H), 6.54 (s, 1H), 6.51 (s, 2H), 4.40 (s, 4H), 4.23 (s, 4H), 1.63 (m, 1H), 0.85 (m, 2H), 0.40 (m, 2H).

Example 15

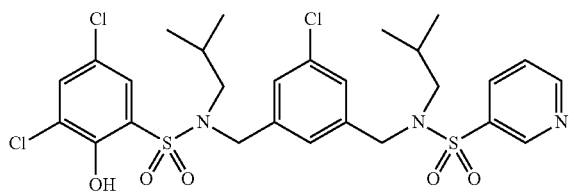 [SMILES: CC(C)CN(Cc1cc(Cl)cc(CN(CC(C)C)S(=O)(=O)c2cc(Cl)cc(Cl)c2O)c1)S(=O)(=O)c1cccnc1]

tert-Butyl 3-chloro-5-((3,5-dichloro-2-hydroxy-N-isobutylphenylsulfonamido)methyl)benzyl(isobutyl) carbamate

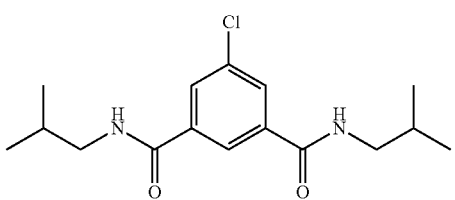 [SMILES: CC(C)CNC(=O)c1cc(Cl)cc(C(=O)NCC(C)C)c1]

A) 5-Chloro-N1,N3-diisobutylisophthalamide

To a solution of 5-chloroisophthalic acid (7.0 g, 34.9 mmol) in DMF (30 mL) were added N1-((ethylimino)methylene)-N3,N3-dimethylpropane-1,3-diamine hydrochloride (16.73 g, 87.0 mmol) and HOBt.H$_2$O (10.69 g, 69.8 mmol) at 0° C., followed by the addition of 10 mL of isobutylamine (8.67 mL, 87.0 mmol). The resulting mixture was stirred at rt for 3 h. The mixture was diluted with 1 N HCl solution and ethyl acetate. The organic layer was washed with brine, 1N NaOH solution, brine, dried over MgSO₄ and concentrated to give a white solid (8.14 g, 72%). ¹H NMR (CDCl₃): δ 8.01 (d, J=1.6 Hz, 1H), 7.85 (d, T=1.6 Hz, 2H), 6.32 (m, 2H), 3.29 (dd, J=6.8, 6.4 Hz, 4H), 1.91 (m, 2H), 0.98 (d, J=6.8 Hz, 12H).

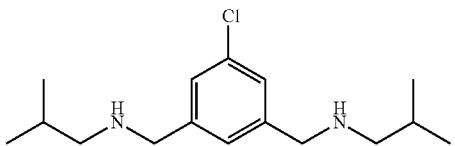 [SMILES: CC(C)CNCc1cc(Cl)cc(CNCC(C)C)c1]

B) [3-Chloro-5-(isobutylamino-methyl)-benzyl]-isobutyl-amine

To 5-chloro-N1,N3-diisobutylisophthalamide (8.1 g, 26.1 mmol) was added borane (1 M solution in THF, 130.0 mL, 130.0 mmol). The reaction mixture was stirred at rt under nitrogen for 32 h. The starting material was still remaining. Additional borane (50 mL of 1 M solution in THF) was added and the reaction mixture was heated at 60° C. for another 6 h, then cooled to rt. To the mixture were added 100 mL of MeOH and HCl solution (100 mL of 4 N HCL) were added and the mixture was stirred for 2 h. The resulting mixture was concentrated in vacuo. The residue was diluted with ethyl acetate and water. The pH of the aqueous layer was adjusted ro pH 9 using act NaOH. It was mixed with ethyl acetate. The organic layer was washed with brine, dried over MgSO₄ and concentrated to give the product as a colorless oil (6.0 g, 72%). ¹H NMR (CD₃OD): δ 7.31 (s, 2H), 7.26 (s, 1H), 3.76 (s, 4H), 2.39 (d, J=6.8 Hz, 4H), 1.80 (m, 2H), 0.94 (d, J=6.8 Hz, 12H); MS (ESI): (M+H)⁺=283.4.

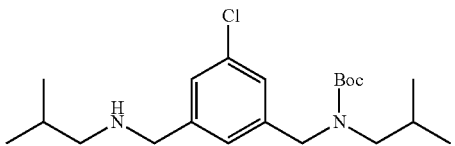 [SMILES: CC(C)CNCc1cc(Cl)cc(CN(CC(C)C)C(=O)OC(C)(C)C)c1]

C) tert-Butyl 3-chloro-5-((isobutylamino)methyl)benzyl)isobutyl)carbamate

To a solution of [3-chloro-5-(isobutylamino-methyl)-benzyl]-isobutyl-amine (0.60 g, 2.12 mmol) in acetonitrile (4 mL) was added a solution di-tert-butyl dicarbonate (0.45 mL, 2.12 mmol) in acetonitrile (2.0 mL) dropwise at 0° C. The reaction mixture was stirred at it for 2 h. HPLC showed a mixture of the starting diamine, mono-Boc product and bis-Boc products. The reaction mixture was concentrated and the residue was purified by ISCO silica gel column chromatography. The column was eluted with dichloromethane to 25% of ethyl acetate in dichloromethane. Fractions containing the desired product were combined and concentrated to give colorless oil (0.27 g, 33%). ¹H NMR (CD₃OD): δ 7.28 (s, 1H), 7.13 (s, 2H), 4.43 (s, 2H), 3.72 (s, 2H), 3.03 (m, 2H), 2.35 (d, J=6.6 Hz, 2H), 1.95 (m, 1H), 1.76 (m, 1H), 1.49-1.39 (m, 9H), 0.90 (d, J=6.6 Hz, 6H), 0.86 (m, 6H); MS (ESI): (M+H)⁺=383.4.

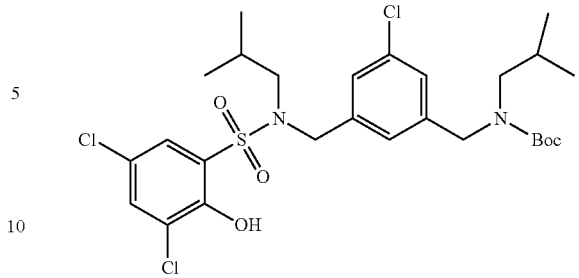

D) tert-Butyl 3-chloro-5-((3,5-dichloro-2-hydroxy-N-isobutylphenylsulfonamido)methyl)benzyl(isobutyl)carbamate To a solution of tert-butyl 3-chloro-5-((isobutylamino)methyl)benzyl(isobutyl)carbamate (2.4 g, 6.27 mmol) in CH₂Cl₂ (30 mL) was added Et₃N (1.3 mL, 9.40 mmol), followed by the addition of 3,5-dichloro-2-hydroxybenzenesulfonyl chloride (1.80 g, 6.89 mmol). The reaction mixture was stirred at rt for 2 h. The mixture was diluted with CH₂Cl₂ and water. The organic layer was washed with saturated NaHCO₃ solution, NH₄Cl solution, brine solution, and dried over MgSO₄. The filtrate was concentrated and the residue was purified by silica gel flash chromatography. The column was eluted with hexane to 80% dichloromethane in hexane. The fractions containing the desired product were combined and concentrated to give colorless viscous solid (2.8 g, 72%).
¹H NMR (CDCl₃): δ 9.12 (s, 1H), 7.55 (s, 1H), 7.50 (s, 1H), 7.14 (s, 1H), 7.06 (m, 1H), 7.02 (m, 1H), 4.38 (m, 4H), 3.00 (m, 4H), 1.91 (m, 1H), 1.76 (m, 1H), 1.43 (m, 9H), 0.89 (d, J=6.0 Hz, 6H), 0.83 (d, J=6.8 Hz, 6H); MS (ESI): (M−H)⁻=607.2.

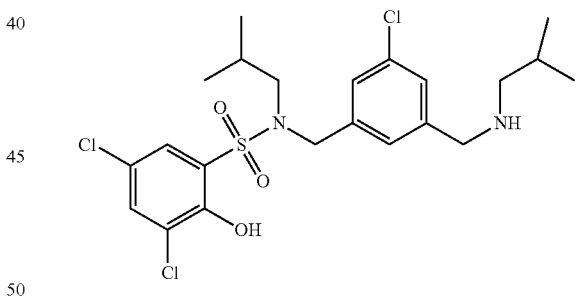

E) 3,5-Dichloro-N-(3-chloro-5-((isobutylamino)methyl)benzyl)-2-hydroxy-N-isobutylbenzenesulfonamide To a solution of tert-butyl 3-chloro-5-((3,5-dichloro-2-hydroxy-N-isobutylphenylsulfonamido)methyl)benzyl(isobutyl)carbamate (0.23 g, 0.38 mmol) in methylene chloride (5 mL) was added TFA (0.87 mL, 11.3 mmol). The reaction mixture was stirred at rt for 2 h., concentrated and the residue was partitioned between saturated NaHCO₃ solution and ethyl acetate. The organic layer was washed with brine, dried over MgSO₄ and concentrated to give the desired product as white solid (0.18 g, 92%). ¹H NMR (CD₃OD): δ 7.45 (d, J=2.8 Hz, 2H), 7.40 (s, 2H), 7.37 (s, 1H), 7.31 (d, J=2.8 Hz, 1H), 4.57 (s, 2H), 4.07 (s, 2H), 3.04 (d, J=7.2 Hz, 2H), 2.80 (d, J=7.2 Hz, 2H), 2.00 (m, 1H), 1.68 (m, 1H), 1.00 (d, J=6.6 Hz, 6H), 0.76 (d, J=6.6 Hz, 6H); MS (ESI): (M+H)+=507.22, 509.21.

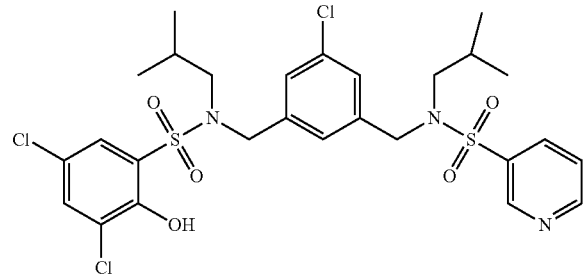 [SMILES: CC(C)CN(Cc1cc(Cl)cc(CN(CC(C)C)S(=O)(=O)c2cc(Cl)cc(Cl)c2O)c1)S(=O)(=O)c1cccnc1]

F) N-(3-chloro-5-((3,5-dichloro-2-hydroxy-N-isobutylphenylsulfonamido)methyl)benzyl)-N-isobutylpyridine-3-sulfonamide To a solution of pyridine-3-sulfonyl chloride (70 mg, 0.40 mmol) in THF (4 mL) were added 3,5-dichloro-N-(3-chloro-5-((isobutylamino)methyl)benzyl)-2-hydroxy-N-isobutylbenzenesulfonamide (100 mg, 0.20 mmol) and Et$_3$N (0.14 mL, 0.98 mmol). The reaction mixture was stirred at rt for 3 h. The mixture was concentrated. To the residue was added 1 N NaOH/THF/MeOH. After 4 h, the mixture was concentrated and the residue was purified by preparative HPLC. Fractions containing the desired product were combined, concentrated, and lyophilized to give the desired product as a white solid (60 mg, 40%).
$^1$H NMR (CD$_3$OD): δ 8.91 (d, J=1.6 Hz, 1H), 8.75 (m, 1H), 8.21 (m, 1H), 7.62 (m, 3H), 7.18 (s, 1H), 7.14 (s, 1H), 7.09 (s, 1H), 4.42 (s, 2H), 4.30 (s, 2H), 3.05 (d, J=7.6 Hz, 2H), 2.96 (d, J=7.6 Hz, 2H), 1.66 (m, 2H), 0.73 (m, 12H); MS (ESI): (M+H)+=648.1.

Example 16

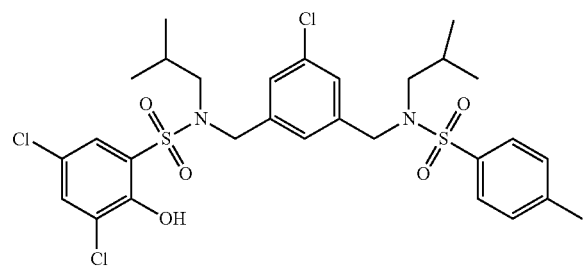 [SMILES: Cc1ccc(S(=O)(=O)N(Cc2cc(Cl)cc(CN(CC(C)C)S(=O)(=O)c3cc(Cl)cc(Cl)c3O)c2)CC(C)C)cc1]

3,5-Dichloro-N-(3-chloro-5-((N-isobutyl-4-methylphenylsulfonamido)methyl)benzyl)-2-hydroxy-N-isobutylbenzenesulfonamide $^1$H NMR (CD$_3$OD): δ 7.67 (d, J=8.0 Hz, 2H), 7.63 (d, J=2.8 Hz, 1H), 7.58 (d, J=2.4 Hz, 1H), 7.37 (d, J=8.0 Hz, 2H), 7.11 (d, J=9.6 Hz, 2H), 7.00 (s, 1H), 4.39 (s, 2H), 4.20 (s, 2H), 3.05 (d, J=7.6 Hz, 2H), 2.84 (d, J=7.6 Hz, 2H), 2.41 (s, 3H), 1.69-1.56 (m, 2H), 0.73 (d, J=6.4 Hz, 6H), 0.71 (d, J=6.8 Hz, 6H); MS (ESI): (M–H)−=661.0.

Example 17

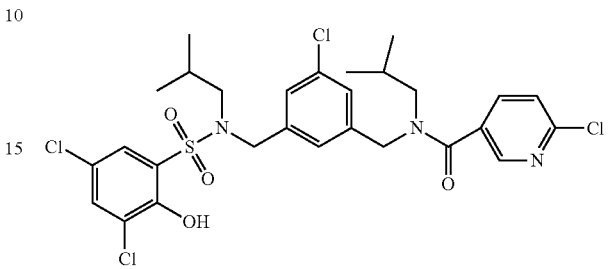

6-Chloro-N-(3-chloro-5-((3,5-dichloro-2-hydroxy-N-isobutylphenylsulfonamido)methyl)benzyl)-N-isobutylnicotinamide To a solution of 6-chloronicotinic acid (34.1 mg, 0.22 mmol) in DMF (4 mL) were added N1-((ethylimino)methylene)-N3,N3-dimethylpropane-1,3-diamine hydrochloride (60 mg, 032 mmol), HOBt.H$_2$O (30 mg, 0.20 mmol) and 3,5-dichloro-N-(3-chloro-5-((isobutylamino)methyl)benzyl)-2-hydroxy-N-isobutylbenzenesulfonamide (100 mg, 0.20 mmol). The resulting reaction mixture was stirred at rt. for 18 h. The mixture was diluted with saturated NaHCO$_3$ solution and ethyl acetate. The organic layer was concentrated. The residue was dissolved in 1 N NaOH solution and THF for 2 h. The mixture was concentrated and dissolved in MeOH, purified by preparative HPLC. Fractions containing the desired product were combined, concentrated, and lyophilized to give the desired product as white solid (62 mg, 40%). $^1$H NMR (CD$_3$OD): δ 8.50-8.35 (m 1H), 8.0-7.8 (m, 1H), 7.70-7.49 (m, 3H), 7.34 (m, 1H), 7.16 (m, 1H), 7.10 (m, 1H), 4.72-4.45 (m, 4H), 3.30-3.03 (m, 4H), 2.1-1.6 (m, 2H), 0.96-0.71 (m, 12H); MS (ESI): (M–H)−=646.0.

Example 18

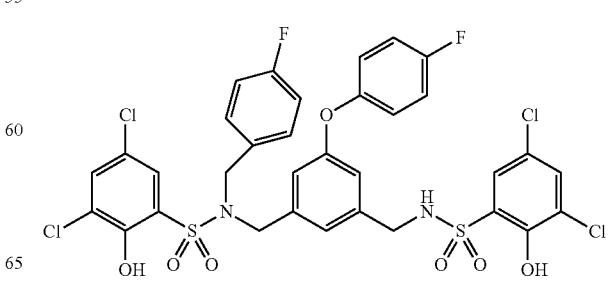

3,5-Dichloro-N-(3-((3,5-dichloro-2-hydroxyphenyl-sulfonamido)methyl)-5-(4-fluorophenoxy)benzyl)-N-(4-fluorobenzyl)-2-hydroxybenzenesulfonamide

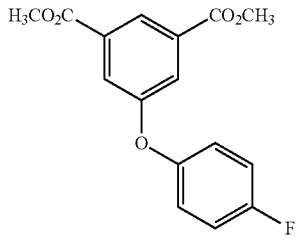 [SMILES: COC(=O)c1cc(Oc2ccc(F)cc2)cc(C(=O)OC)c1]

A) Dimethyl 5-(4-fluorophenoxy)isophthalate

A mixture of dimethyl 5-hydroxyisophthalate (3.1 g, 14.75 mmol), 4-fluorophenylboronic acid (4.13 g, 29.5 mmol), copper(II) acetate (2.68 g, 14.75 mmol) and triethylamine (4.48 g, 44.2 mmol) in $CH_2Cl_2$ (65 mL) was stirred at rt in the open air for 38 h. An additional 1 g of fluorophenylboronic acid was added and the reaction mixture was continued to stir at rt in the open air. After 24 h, an additional 1 g of fluorophenylboronic acid and 300 mg of copper acetate were added to the reaction mixture and it was continued to stir for 6 h in the open air. The mixture was mixed with $CHCl_3$ and aq HCl, the organic layer was separated, washed with aq HCl, aq $NaHCO_3$, dried over $MgSO_4$, concentrated, and the residue was purified by flash column chromatography on $SiO_2$ eluting with Hexane:EtOAc:MeOH/800:200:40 to obtain the desired product (3.8 g, 12.49 mmol, 85% yield) as a white solid. $^1$H NMR ($CDCl_3$): δ 8.36 (s, 1H), 7.75 (s, 2H), 7.06~6.96 (m, 4H), 3.89 (s, 6H).

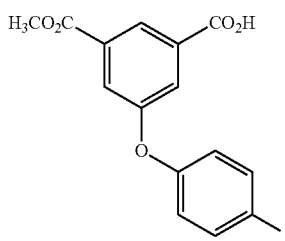

B) 3-(4-Fluorophenoxy)-5-(methoxycarbonyl)benzoic acid

A mixture of dimethyl 5-(4-fluorophenoxy)isophthalate (3.8 g, 12.49 mmol) and sodium bicarbonate (1.2 g, 14.28 mmol) in MeOH (100 mL) and water (15 mL) was heated at 80° C. overnight. An additional 500 mg of sodium bicarbonate was added to the reaction mixture and continued to heat at 100° C. for 6 h. HPLC showed a mixture of monoacid (major), diacid (minor) and a small amount of starting material. Prep HPLC provided diacid, 5-(4-fluorophenoxy)isophthalic acid (0.4 g, 1.448 mmol, 11.60% yield) and monoacid, 3-(4-fluorophenoxy)-5-(methoxycarbonyl)benzoic acid (2.2 g, 7.58 mmol, 60.7% yield) as a white solid.

$^1$H NMR ($CDCl_3$): δ 8.44 (s, 1H), 7.82 (s, 2H), 7.10-6.986 (m, 4H), 3.92 (s, 3H)

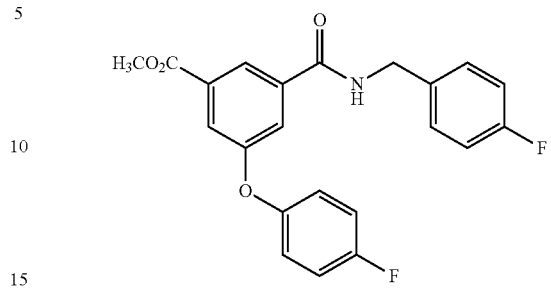

C) Methyl 3-(4-fluorobenzylcarbamoyl)-5-(4-fluorophenoxy)benzoate

To a solution of 3-(4-fluorophenoxy)-5-(methoxycarbonyl)benzoic acid (2.2 g, 7.58 mmol) in DMF/$CH_2Cl_2$ at rt was added EDCI.HCl (1.889 g, 9.85 mmol) followed by HOBt.$H_2O$ (1.024 g, 7.58 mmol) with stirring. After one minute (4-fluorophenyl)methanamine (0.949 g, 7.58 mmol) was added to the mixture and it was stirred at rt for 4 h. EtOAc and aq $NaHCO_3$ were added to the mixture. The EtOAc layer was separated, washed with water, dried over $MgSO_4$ and concentrated in vacuo to obtain a crude product (2.7 g, 6.79 mmol, 90% yield) as a light yellow solid. The crude product was used in the next step without further purification. MS (ESI): (M+H)$^+$=382.21.

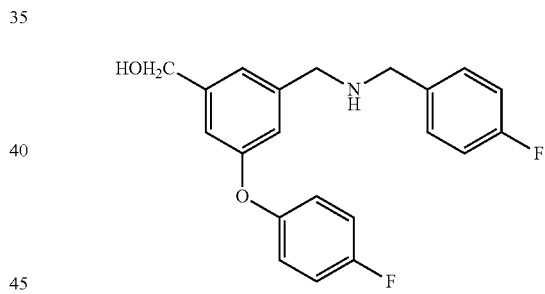

D) (3-((4-Fluorobenzylamino)methy)-5-(4-fluorophenoxy)phenyl)methanol

To a solution of methyl 3-(4-fluorobenzylcarbamoyl)-5-(4-fluorophenoxy)benzoate (2.7 g, 6.79 mmol) in 10 mL of THF at ice bath temp was added borane (40 mL of 1 M solution in THF) slowly. After 10 min, the mixture was warmed to rt, stirred for 30 min and heated at 50° C. for 10 h. The mixture was cooled to rt and treated with 10 mL of 1M solution of LiAlH$_4$ in THF. The mixture was stirred for 2 h and treated with EtOAc. The resulting mixture was treated with MeOH and TFA slowly, stirred for a while, mostly concentrated. Water and MeOH were added to the residue and the insoluble material was filtered. The filtrate was concentrated. Purification of the residue using prep HPLC provided the desired product as a white solid of TFA salt (1.74 g, 54.6%). $^1$H NMR (CD$_3$OD): δ 7.49~6.97 (m, 11H), 4.56 (s, 2H), 4.19 (s, 2H), 4.16 (s, 2H); MS (ESI): (M+H)$^+$=356.24.

101

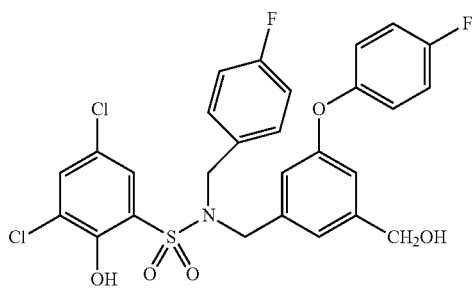

E) 3,5-Dichloro-N-(4-fluorobenzyl)-N-(3-(4-fluorophenoxy)-5-(hydroxymethyl)benzyl)-2-hydroxybenzenesulfonamide To a mixture of (3-((4-fluorobenzylamino)methyl)-5-(4-fluorophenoxy)phenyl)methanol TFA salt (1.74 g, 3.71 mmol) and Et$_3$N (1.2 g, 11.86 mmol) in CH$_2$Cl$_2$ (20 ml) at 0° C. was added 3,5-didichloro-2-hydrixybezene-1-sulfonyl chloride (0.97 g, 3.71 mmol). The mixture was stirred for 1.5 h, warmed to rt, stirred for 30 min, and concentrated. The residue was mixed with aq 1N aq HCl and EtOAc. The EtOAc layer was separated, dried over MgSO$_4$ and concentrated in vacuo. The residue was purified by prep HPLC to obtain the desired product (1.5 g, 2.58 mmol, 69.7% yield) as a white solid. $^1$H NMR (CDCl$_3$): δ 7.44 (d, J=11.0 Hz, 2H), 7.06~6.77 (m, 10H), 6.50 (s, 1H), 4.51 (s, 2H), 4.33 (s, 2H), 4.27 (s, 2H).

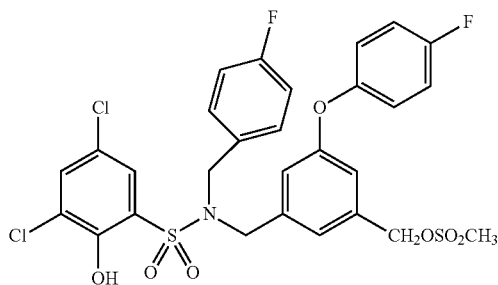

F) 3-((3,5-Dichloro-N-(4-fluorobenzyl)-2-hydroxyphenylsulfonamido)methyl)-5-(4-fluorophenoxy)benzyl methanesulfonate To a solution of 3,5-dichloro-N-(4-fluorobenzyl)-N-(3-(4-fluorophenoxy)-5-(hydroxymethyl)benzyl)-2-hydroxybenzenesulfonamide (1.1 g, 1.895 mmol) and methanesulfonyl chloride (0.147 mL, 1.895 mmol) in EtOAc at −30° C. was added Et$_3$N (0.4 mL, 2.87 mmol) under Ar atm. The mixture was stirred for 1 h, but only a small amount of product was produced. Thus, additional methanesulfonyl chloride (0.25 mL) and Et$_3$N (0.6 mL) were added at −30° C. The mixture was slowly warmed to rt, stirred at rt for 2 h and treated with 1N aq HCl and EtOAc. The EtOAc layer was separated, washed with water, dried over MgSO$_4$ and concentrated in vacuo to obtain the desired product as a viscous material (~1.4 g). This material was used directly for the next step without further purification. $^1$H NMR (CDCl$_3$): δ 7.61 (d, J=2.8 Hz, 1H), 7.57 (d, J=2.2 Hz, 1H), 7.07-6.89 (m, 8H), 6.82 (d, J=1.6 Hz, 2H), 6.63 (s, 1H), 5.06 (s, 2H), 4.37 (s, 2H), 4.34 (s, 2H), 2.97 (s, 3H; MS: (M−H)$^-$=656.1.

102

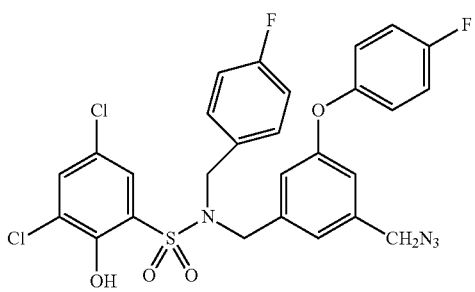

G) N-(3-(Azidomethyl)-5-(4-fluorophenoxy)benzyl)-3,5-dichloro-N-(4-fluorobenzyl)-2-hydroxybenzenesulfonamide The crude mesylated product (1.4 g) was mixed with DMF (10 mL) and NaN$_3$ (220 mg), and stirred at rt overnight. The mixture was diluted with water and EtOAc. The EtOAc layer was separated, washed with dilute aq HCl and water, dried over MgSO$_4$ and concentrated in vacuo to obtain the desired product as a viscous material (1.0 g, 1.652 mmol, 87% yield). This material was used directly in the next step without further purification. $^1$H NMR (CDCl$_3$): δ 7.5 (d, J=2.2 Hz, 1H), 7.45 (s, 1H), 7.11~6.73 (m, 10H), 6.61 (s, 1H), 4.38 (s, 2H), 4.33 (s, 2H), 4.22 (s, 2H); MS: (M−H)$^-$=603.

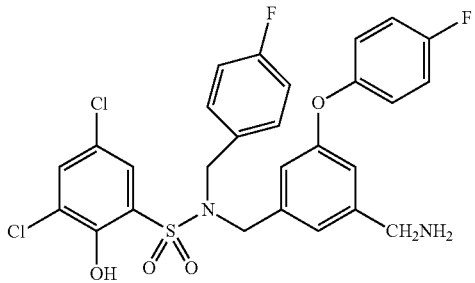

H) N-(3-(Aminomethyl)-5-(4-fluorophenoxy)benzyl)-3,5-dichloro-N-(4-fluorobenzyl)-2-hydroxybenzenesulfonamide A mixture of N-(3-(azidomethyl)-5-(4-fluorophenoxy)benzyl)-3,5-dichloro-N-(4-fluorobenzyl)-2-hydroxybenzenesulfonamide (1.0 g, 1.652 mmol) and 100 mg of 20% of Pd(OH)$_2$ on carbon in EtOAc (15 mL) and MeOH (15 mL) was stirred at rt under 1 atm of H$_2$ gas for 3 h. To the mixture was added toluene. The resulting mixture was stirred for a while, and the solid was filtered, washed with methanol. The filtrate was concentrated in vacuo to obtain the desired product (0.88 g, 1.519 mmol, 92% yield) as a white solid. $^1$H NMR (CD$_3$OD): δ 7.49 (d, J=2.8 Hz, 1H), 7.35 (d, J=2.8 Hz, 1H), 7.21-7.09 (m, 4H), 6.99-6.90 (m, 5H), 6.85 (s, 1H), 6.64 (s, 1H), 4.48 (s, 2H), 4.40 (s, 2H), 3.93 (s, 2H); MS (ESI): (M+H)$^+$=579.0.

I) 3,5-Dichloro-N-(3-((3,5-dichloro-2-hydroxyphenylsulfonamido)methyl)-5-(4-fluorophenoxy)benzyl)-N-(4-fluorobenzyl)-2-hydroxybenzenesulfonamide To a solution of 3,5-dichloro-2-hydroxybenzene-1-sulfonyl chloride (27.1 mg, 0.104 mmol) in 4 mL of $CH_2Cl_2$ was added solid N-(3-(aminomethyl)-5-(4-fluorophenoxy)benzyl)-3,5-dichloro-N-(4-fluorobenzyl)-2-hydroxybenzenesulfonamide (60 mg, 0.104 mmol) followed by $Et_3N$ (110 μL) at rt. The mixture was stirred at rt for 45 min. Direct purification of the reaction mixture by prep HPLC provided the desired product (71 mg, 85%). $^1H$ NMR ($CD_3OD$): δ 7.68 (s, 1H), 7.60 (s, 1H), 7.49 (s, 2H), 7.13~6.90 (m, 8H), 6.67 (s, 1H), 6.61 (s, 1H), 6.45 (s, 1H), 4.44 (s, 2H), 4.30 (s, 2H), 4.08 (s, 2H); MS (ESI): $(M+H)^+$=805.

Example 19

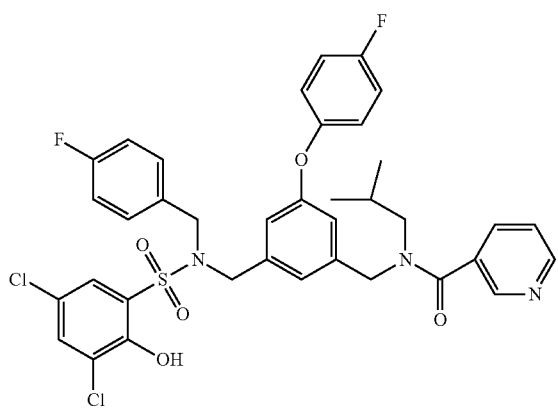 [SMILES: CC(C)CN(Cc1cc(CN(Cc2ccc(F)cc2)S(=O)(=O)c2cc(Cl)cc(Cl)c2O)cc(Oc2ccc(F)cc2)c1)C(=O)c1cccnc1]

N-(3-((3,5-Dichloro-N-(4-fluorobenzyl)-2-hydroxyphenylsulfonamido)methyl)-5-(4-fluorophenoxy)benzyl)-N-isobutylnicotinamide To a solution of nicotinic acid (20.34 mg, 0.165 mmol) in DMF (4 mL) were added EDCI.HCl (36.0 mg, 0.19 mmol), HOBt.H$_2$O (16.9 mg, 0.11 mmol) and 3,5-dichloro-N-(4-fluorobenzyl)-N-(3-(4-fluorophenoxy)-5-((isobutylamino)methyl)benzyl)-2-hydroxybenzenesulfonamide (70 mg, 0.11 mmol). The resulting reaction mixture was stirred at rt for 18 h. The mixture was diluted with saturated NaHCO$_3$ solution and ethyl acetate. The organic layer was separated and concentrated. The residue was dissolved in a mixture of 1 N NaOH, MeOH and THF. After 4 h, the mixture was concentrated. The residue was diluted with water and ethyl acetate. The organic layer was concentrated, dissolved in MeOH, and purified by preparative HPLC to give the desired product TFA salt as a white solid (27 mg, 28%).

$^1H$ NMR ($CD_3OD$): δ 8.61-8.52 (m, 2H), 7.94 (m, 1H), 7.62-7.52 (m, 3H), 7.03 (m, 4H), 6.92-6.63 (m, 5H), 4.60-4.32 (m, 6H), 3.19 (m, 1H), 2.96 (d, J=7.2 Hz, 1H), 2.05-1.85 (m, 1H), 0.90 (d, J=6.4 Hz, 3H), 0.66 (d, J=6.4 Hz, 3H); MS (ESI): $(M+H)^+$=740.

Example 20

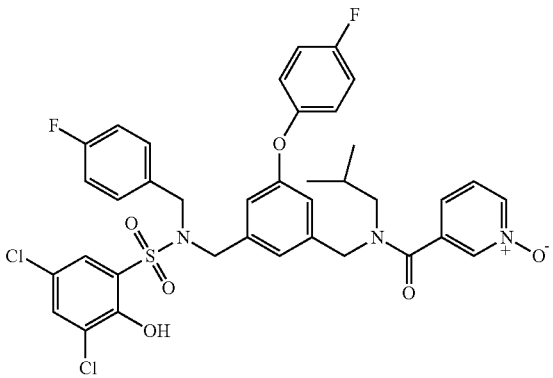 [SMILES: CC(C)CN(Cc1cc(CN(Cc2ccc(F)cc2)S(=O)(=O)c2cc(Cl)cc(Cl)c2O)cc(Oc2ccc(F)cc2)c1)C(=O)c1ccc[n+](O)c1]

3-((3-((3,5-N-chloro-N-(4-fluorobenzyl)-2-hydroxyphenylsulfonamido)methyl)-5-(4-fluorophenoxy)benzyl)(isobutyl)carbamoyl)pyridine 1-oxide $^1H$ NMR ($CD_3OD$): δ 8.32-8.18 (m, 2H), 7.63-7.52 (m, 4H), 7.06-7.01 (m, 4H), 6.89-6.42 (m, 7H), 4.57-4.33 (m, 6H), 3.16 (m, 1H), 2.95 (d, J=7.2 Hz, 1H), 2.05-1.80 (m, 1H), 0.88 (d, J=6.4 Hz, 3H), 0.69 (d, J=6.4 Hz, 3H); MS (ESI): $(M-H)^-$=754.1.

Example 21

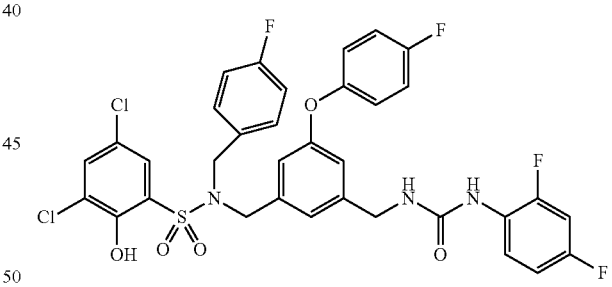

3,5-Dichloro-N-(3-((3-(2,4-difluorophenyl)ureido)methyl)-5-(4-fluorophenoxy)benzyl)-N-(4-fluorobenzyl)-2-hydroxybenzenesulfonamide To a solution of N-(3-(aminomethyl)-5-(4-fluorophenoxy)benzyl)-3,5-dichloro-N-(4-fluorobenzyl)-2-hydroxybenzenesulfonamide (62 mg, 0.107 mmol) in DMF (2.5 mL) was added isocyanate (40 μL). The reaction was complete within an hour. Purification by prep HPLC provided the desired product (30 mg, 38%).

$^1H$ NMR ($CD_3OD$): δ 7.88 (m, 1H), 7.69 (d, J=2.4 Hz, 1H), 7.61 (d, J=2.4 Hz, 1H), 7.18~6.78 (m, 12H), 6.54 (s, 1H), 4.47 (s, 2H), 4.41 (s, 2H), 4.29 (s, 2H); MS (ESI): $(M+H)^+$=734.

Example 22

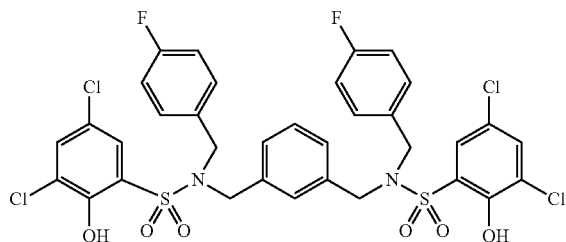 [SMILES: O=S(=O)(c1cc(Cl)cc(Cl)c1O)N(Cc1ccc(F)cc1)Cc1cccc(CN(Cc2ccc(F)cc2)S(=O)(=O)c2cc(Cl)cc(Cl)c2O)c1]

N-(4-Fluoro-benzyl)-N-(3-{[(4-fluoro-benzyl)-(3,5-dichloro-2-hydroxybenzene)sulfonyl-amino]-methyl}-benzyl)-3,5-dichloro-2-hydroxybenzene-sulfonamide

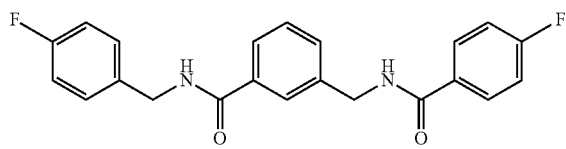 [SMILES: O=C(NCc1cccc(C(=O)NCc2ccc(F)cc2)c1)c1ccc(F)cc1]

A) N1,N3-Bis(4-fluorobenzyl)isophthalamide

To a heterogeneous mixture of isophthalic acid (4.98 g, 30.0 mmol) and (4-fluorophenyl)methanamine (7.50 g, 60.0 mmol) in DMF (80 mL) was added EDCI.HCl (12 g, 62.6 mmol) followed by HOBt.H$_2$O (1 g, 6.53 mmol) at rt with stirring. The reaction mixture soon became a homogeneous solution. After 4 h to the mixture water and EtOAc were added, the EtOAc layer was separated and washed with 1N HCl followed by 0.5 N NaOH. EtOAc layer was taken, and during this process white solid precipitation occurred. The solid was filtered, washed with EtOAc. The filtrate solution was mostly concentrated, the residue was triturated with Et$_2$O, the solid was filtered, washed with Et$_2$O and the combined solid was dried to obtain the desired product (10 g, 88%) as a white solid. $^1$H NMR (CD$_3$OD): δ 8.31 (s, 1H), 7.99, (dd, J=7.7, 1.7 Hz, 2H), 7.56 (t, J=8.0 Hz, 1H), 7.39~7.02 (m, 8H), 4.5 (s, 4H); MS (ESI): (M+H)$^+$=381.

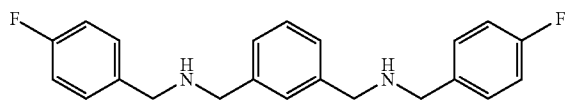 [SMILES: Fc1ccc(CNCc2cccc(CNCc3ccc(F)cc3)c2)cc1]

B) (4-Fluoro-benzyl)-{3-[(4-fluoro-benzylamino)-methyl]-benzyl}-amine

To a partially heterogeneous mixture of N1,N3-bis(4-fluorobenzyl)isophthalamide (5.1 g, 13.41 mmol) in THF (70 mL) at ice bath temp was added a cold solution of borane (100 mL of 1 M solution in THF) slowly. It was stirred at ice bath tem for 1 h. It was warmed to rt and stirred for 30 h at rt. The mixture was warmed to ~60° C. and stirred for 2 h. To the mixture was added 5 mL of HOAc, stirred for 1 h and it was mostly concentrated. To the residue was slowly added 150 mL of MeOH and 150 mL of 1N HCl with stirring, stirred for 2 h at rt, heated at 65° C. for 30 min and it was mostly concentrated. The mixture was mixed with EtOAc and aq NaHCO$_3$, the EtOAc layer was separated, washed with water, dried over MgSO$_4$ and concentrated in vacuo to obtain the desired product (4.5 g, 95%) as a viscous material of crude product. This crude product was used directly for the next step without any further purification.

$^1$H NMR (CDCl$_3$): δ 7.35~6.97 (m, 12H), 3.80 (d, J=8.2 Hz, 8H); MS (ESI): (M+H)$^+$=353.

C) N-(4-Fluoro-benzyl)-N-(3-{[(4-fluoro-benzyl)-(3,5-dichloro-2-hydroxybenzene)sulfonyl-amino]-methyl}-benzyl)-3,5-dichloro-2-hydroxybenzene-sulfonamide To a solution of (4-fluoro-benzyl)-{3-[(4-fluoro-benzylamino)-methyl]-benzyl}-amine (300 mg, 0.851 mmol) and Et$_3$N (1.2 mL) in CH$_2$Cl$_2$ at ice bath temp was added a solid of 3,4-dichloro-2-hydroxybenzene-1-sulfonyl chloride (445 mg, 1.703 mmol) with stirring. After 30 min it was warmed to rt, stirred at rt for 5 h. To the mixture were added CH$_2$Cl$_2$ (50 mL) and 1N aq HCl, the organic layer was separated, dried over MgSO$_4$, concentrated and the residue was purified by prep HPLC to obtain the desired product (240 mg, 35%) as a white solid. $^1$H NMR (CD$_3$OD): δ 7.57 (d, J=2.7 Hz, 2H), 7.55 (d, J=2.7 Hz, 2H), 7.49-6.74 (m, 12H), 4.29 (s, 4H), 4.24 (s, 4H); MS (ESI): (M+H)$^+$=803.

Example 23

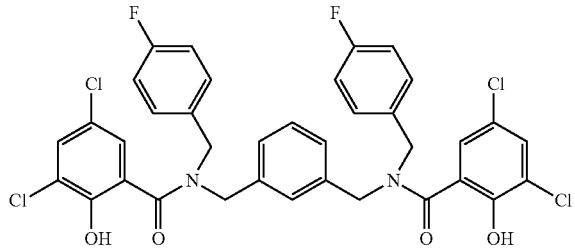 [SMILES: O=C(c1cc(Cl)cc(Cl)c1O)N(Cc1ccc(F)cc1)Cc1cccc(CN(Cc2ccc(F)cc2)C(=O)c2cc(Cl)cc(Cl)c2O)c1]

N-(4-Fluoro-benzyl)-N-(4-{[(4-fluoro-benzyl)-(3,5-dichloro-2-hydroxybenzene)carbamoyl]-methyl}-benzyl)-3,5-dichloro-2-hydroxybenzamide To a solution of 3,5-dichloro-2-hydroxybenzoic acid (300 mg, 1.449 mmol) in DMF (5 mL) at rt was added EDCI.HCl (300 mg, 1.565 mmol) followed by N,N'-(1,3-phenylenebis(methylene))bis(1-(4-fluorophenyl)methanamine) (365 mg, 1.036 mmol) in 2 mL of DMF and hydrated HOBt.H$_2$O (200 mg), and the reaction mixture was stirred at rt overnight. The mixture was directly purified by prep HPLC to provide a monoacylated product 3,5-dichloro-N-(4-fluorobenzyl)-N-(3-((4-fluorobenzylamino)methyl)benzyl)-2-hydroxybenzamide (0.12 g, 21.4%) and a diacylated product, N,N'-(1,3-phenylenebis(methylene))bis(3,5-dichloro-N-(4-fluorobenzyl)-2-hydroxybenzamide) (0.245 g, 32.4%). $^1$H NMR (CD$_3$OD): δ 7.34~6.80 (m, 16H), 4.59 (s, 4H), 4.24 (s, 4H); MS (ESI): (M+H)$^+$=731.

Example 24

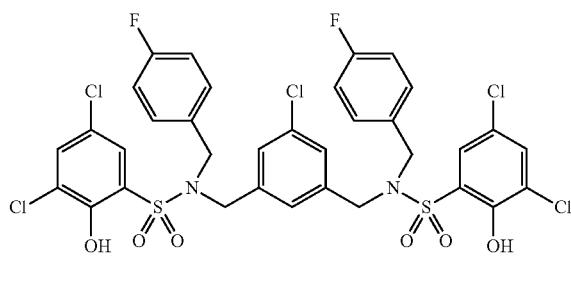 [SMILES: O=S(=O)(c1cc(Cl)cc(Cl)c1O)N(Cc1ccc(F)cc1)Cc1cc(Cl)cc(CN(Cc2ccc(F)cc2)S(=O)(=O)c2cc(Cl)cc(Cl)c2O)c1]

N-(4-Fluoro-benzyl)-N-(3-chloro-5-{[(4-fluoro-benzyl)-(3,5-dichloro-2-hydroxybenzene)sulfonylamino]-methyl}-benzyl)-3,5-dichloro-2-hydroxybenzenesulfonamide To a solution of N,N'-(5-chloro-1,3-phenylene)bis(methylene)bis(1-(4-fluorophenyl)methanamine) (600 mg, 1.551 mmol) and Et$_3$N (1.6 mL) in CH$_2$Cl$_2$ at ice bath temp was added a solid of 3,5-dichloro-2-hydroxybenzene-1-sulfonyl chloride (542 mg, 2.073 mmol) with stirring. After 30 min it was warmed to rt and stirred at rt overnight. The mixture was concentrated in vacuo, and prep HPLC purification afforded the desired product (0.32 g, 25%) as a white solid.

$^1$H NMR (CD$_3$OD): δ 7.57 (d, J=2.2 Hz, 2H), 7.52 (d, J=2.2 Hz, 2H), 7.07~6.79 (m, 10H), 6.71 (s, 1H), 4.33 (s, 4H), 4.24 (s, 4H); MS (ESI): (M+H)$^+$=837.

Example 25

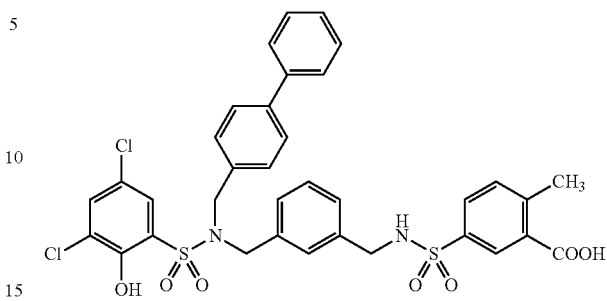

5-(N-(3-((N-(Biphenyl-4-ylmethyl)-3,5-dichloro-2-hydroxyphenylsulfonamido)methyl)benzyl)sulfamoyl)-2-methylbenzoic acid To a solution of N-(3-(aminomethyl)benzyl)-N-(biphenyl-4-ylmethyl)-3,5-dichloro-2-hydroxybenzenesulfonamide (50 mg, 0.095 mmol) and Et$_3$N (0.13 mL) in CH$_2$Cl$_2$ (4 mL) was added a solid of 5-(chlorosulfonyl)-2-methylbenzoic acid (22.24 mg, 0.095 mmol) at rt and it was stirred at it for 70 min. Direct purification of the mixture after concentration by prep HPLC provided the desired product (40 mg, 58.1%) as a white solid after lyophilization. $^1$H NMR (CD$_3$OD): δ 8.17 (d, J=2.0 Hz, 1H), 7.93 (dd, J=8.3, 2.2 Hz, 1H), 7.56~6.90 (m, 15H), 6.76 (s, 1H), 4.34 (s, 2H), 4.31 (s, 2H), 3.87 (s, 2H), 2.52 (s, 3H); MS (ESI): (M+H)$^+$=725.

Examples 26 to 93

The following examples were prepared using the procedures described above:

| Ex. No. | Structure | Name | HPLC tR (minute) | LCMS (M + H) |
|---|---|---|---|---|
| 26 | 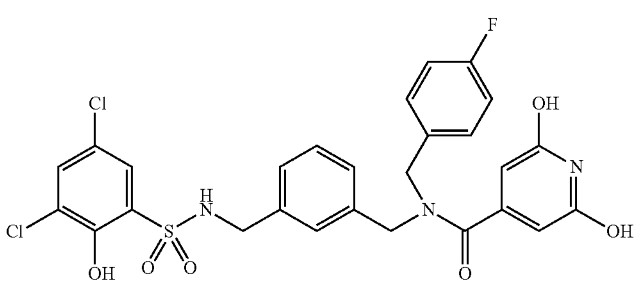 [SMILES: O=C(c1cc(O)nc(O)c1)N(Cc1ccc(F)cc1)Cc1cccc(CNS(=O)(=O)c2cc(Cl)cc(Cl)c2O)c1] | N-(3-((3,5-dichloro-2-hydroxyphenylsulfonamido)methyl)benzyl)-N-(4-fluorobenzyl)-2,6-dihydroxyisonicotinamide | 3.5 | 606.14 |
| 27 | 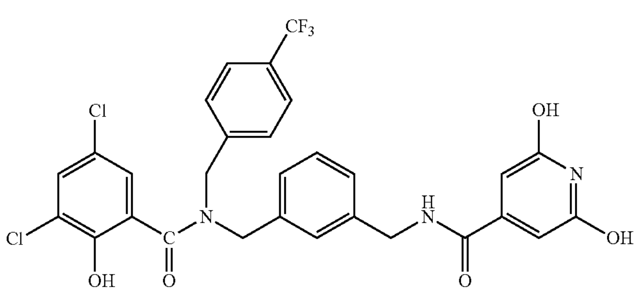 [SMILES: O=C(NCc1cccc(CN(Cc2ccc(C(F)(F)F)cc2)C(=O)c2cc(Cl)cc(Cl)c2O)c1)c1cc(O)nc(O)c1] | N-(3-((3,5-dichloro-2-hydroxy-N-(4-(trifluoromethyl)benzyl)benzamide)methyl)benzyl)-2,6-dihydroxyisonicotinamide | 3.47 | 620.2 |

-continued

| Ex. No. | Structure | Name | HPLC tR (minute) | LCMS (M + H) |
|---|---|---|---|---|
| 28 | 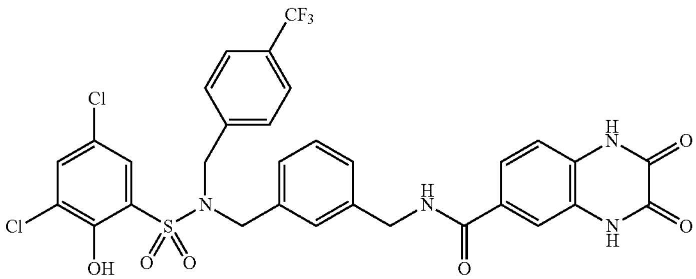 [SMILES: O=C(NCc1cccc(CN(Cc2ccc(C(F)(F)F)cc2)S(=O)(=O)c2cc(Cl)cc(Cl)c2O)c1)c1ccc2[nH]c(=O)c(=O)[nH]c2c1] | N-(3-((3,5-dichloro-2-hydroxy-N-(4-(trifluoromethyl)ben-zyl)phenylsulfon-amido)methyl)benzyl)-2,3-dioxo-1,2,3,4-tetrahydroquinoxaline-6-carboxamide | 3.86 | 707.1 |
| 29 | 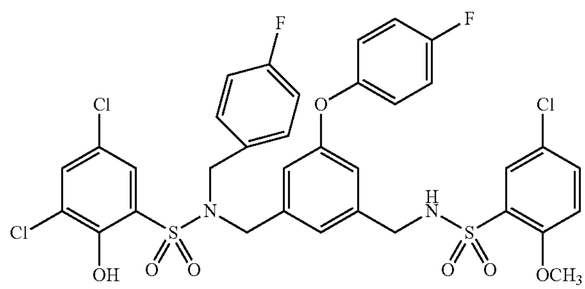 [SMILES: COc1ccc(Cl)cc1S(=O)(=O)NCc1cc(CN(Cc2ccc(F)cc2)S(=O)(=O)c2cc(Cl)cc(Cl)c2O)cc(Oc2ccc(F)cc2)c1] | 3,5-dichloro-N-(3-((5-chloro-2-methoxyphenyl-sulfonamido)methyl-5-(4-fluorophenoxy)benzyl)-N-(4-fluorobenzyl)-2-hydroxybenzenesulfonamide | 4.28 | 785.14 |
| 30 | 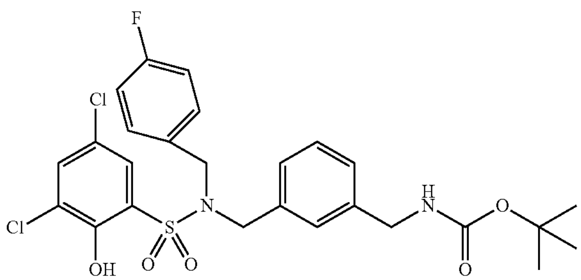 [SMILES: CC(C)(C)OC(=O)NCc1cccc(CN(Cc2ccc(F)cc2)S(=O)(=O)c2cc(Cl)cc(Cl)c2O)c1] | tert-butyl 3-((3,5-dichloro-N-(4-fluorobenzyl)-2-hydroxyphenyl-sulfonamido)methyl)benzylcarbamate | 4.27 | 570.7 |
| 31 | 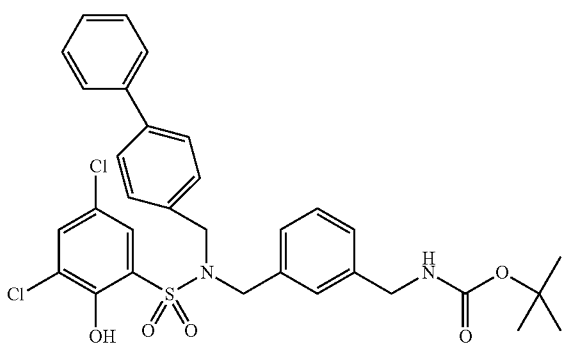 [SMILES: CC(C)(C)OC(=O)NCc1cccc(CN(Cc2ccc(-c3ccccc3)cc2)S(=O)(=O)c2cc(Cl)cc(Cl)c2O)c1] | tert-butyl 3-((N-(biphenyl-4-ylmethyl)-3,5-dichloro-2-hydroxyphenyl-sulfonamido)methyl)benzylcarbamate | 4.41 | |
| 32 | 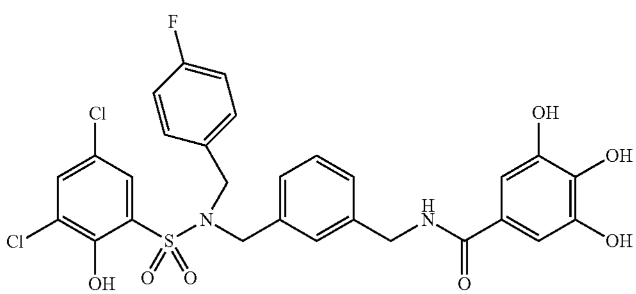 [SMILES: O=C(NCc1cccc(CN(Cc2ccc(F)cc2)S(=O)(=O)c2cc(Cl)cc(Cl)c2O)c1)c1cc(O)c(O)c(O)c1] | N-(3-((3,5-dichloro-N-(4-fluorobenzyl)-2-hydroxyphenyl-sulfonamido)methyl)benzyl)-3,4,5-trihydroxybenzamide | 3.59 | 621.1 |

| Ex. No. | Structure | Name | HPLC tR (minute) | LCMS (M + H) |
|---|---|---|---|---|
| 33 | 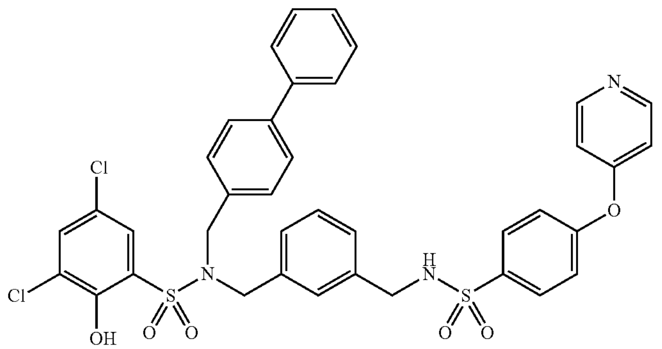 [SMILES: O=S(=O)(NCc1cccc(CN(Cc2ccc(-c3ccccc3)cc2)S(=O)(=O)c2cc(Cl)cc(Cl)c2O)c1)c1ccc(Oc2ccncc2)cc1] | N-(biphenyl-4-ylmethyl)-3,5-dichloro-2-hydroxy-N-(3-((4-(pyridin-4-yloxy)phenylsulfonamido)methyl)benzyl)benzenesulfonamide | 3.73 | 760.6 |
| 34 | 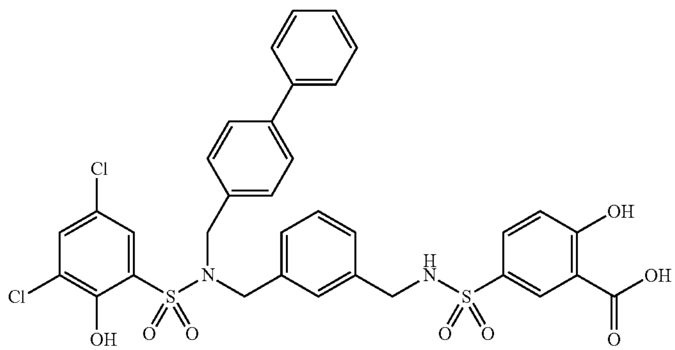 [SMILES: O=C(O)c1cc(S(=O)(=O)NCc2cccc(CN(Cc3ccc(-c4ccccc4)cc3)S(=O)(=O)c3cc(Cl)cc(Cl)c3O)c2)ccc1O] | 5-(N-(3-((N-(biphenyl-4-ylmethyl)-3,5-dichloro-2-hydroxyphenylsulfonamido)methyl)benzyl)sulfamoyl)-2-hydroxybenzoic acid | 4.22 | |
| 35 | 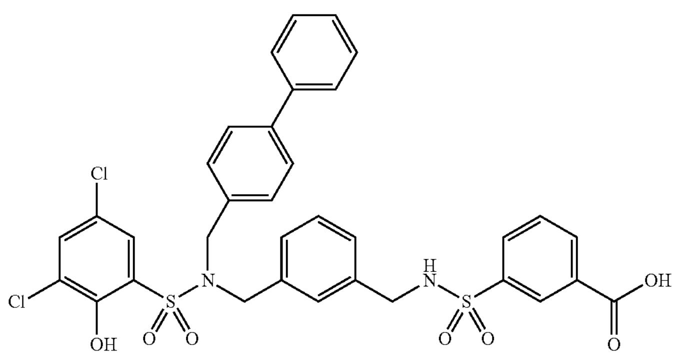 [SMILES: O=C(O)c1cccc(S(=O)(=O)NCc2cccc(CN(Cc3ccc(-c4ccccc4)cc3)S(=O)(=O)c3cc(Cl)cc(Cl)c3O)c2)c1] | 3-(N-(3-((N-(biphenyl-4-ylmethyl)-3,5-dichloro-2-hydroxyphenylsulfonamido)methyl)benzyl)sulfamoyl)benzoic acid | 4.15 | 711.2 |
| 36 | 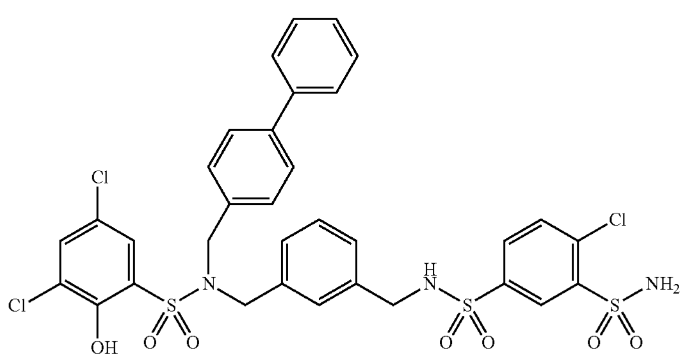 [SMILES: NS(=O)(=O)c1cc(S(=O)(=O)NCc2cccc(CN(Cc3ccc(-c4ccccc4)cc3)S(=O)(=O)c3cc(Cl)cc(Cl)c3O)c2)ccc1Cl] | N1-(3-((N-(biphenyl-4-ylmethyl)-3,5-dichloro-2-hydroxyphenylsulfonamido)methyl)benzyl)-4-chlorobenzene-1,3-disulfonamide | 4.08 | |

| Ex. No. | Structure | Name | HPLC tR (minute) | LCMS (M + H) |
|---|---|---|---|---|
| 37 | 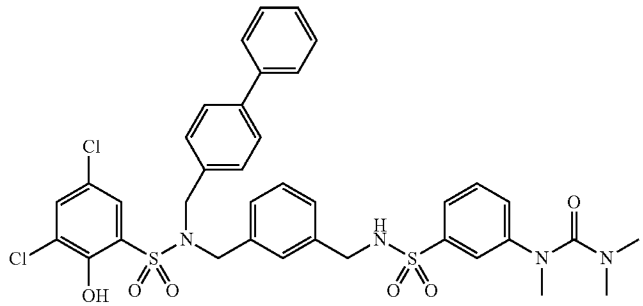 [SMILES: CN(C)C(=O)N(C)c1cccc(S(=O)(=O)NCc2cccc(CN(Cc3ccc(-c4ccccc4)cc3)S(=O)(=O)c3cc(Cl)cc(Cl)c3O)c2)c1] | N-(biphenyl-4-ylmethyl)-3,5-dichloro-2-hydroxy-N-(3-((3-(1,3,3-trimethylureido)phenyl-sulfonamido)methyl)benzyl)benzenesulfonamide | 4.17 | |
| 38 | 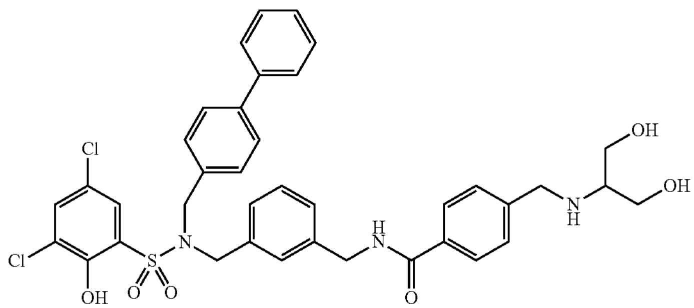 [SMILES: O=C(NCc1cccc(CN(Cc2ccc(-c3ccccc3)cc2)S(=O)(=O)c2cc(Cl)cc(Cl)c2O)c1)c1ccc(CNC(CO)CO)cc1] | N-(3-((N-(biphenyl-4-ylmethyl)-3,5-dichloro-2-hydroxyphenyl-sulfonamido)methyl)benzyl)-4-((1,3-dihydroxypropan-2-ylamino)methyl)benzamide | 3.62 | 734.6 |
| 39 | 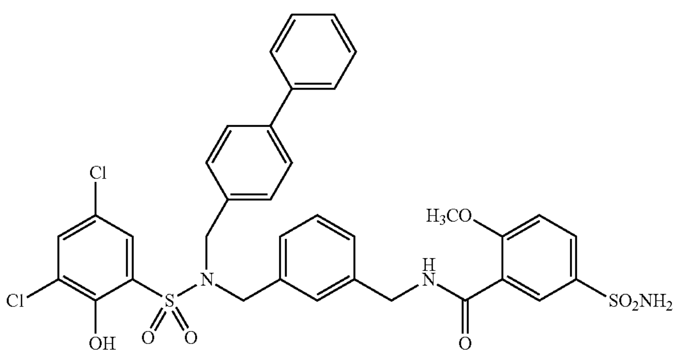 [SMILES: COc1ccc(S(N)(=O)=O)cc1C(=O)NCc1cccc(CN(Cc2ccc(-c3ccccc3)cc2)S(=O)(=O)c2cc(Cl)cc(Cl)c2O)c1] | N-(3-((N-(biphenyl-4-ylmethyl)-3,5-dichloro-2-hydroxyphenyl-sulfonamido)methyl)benzyl)-2-methoxy-5-sulfamoylbenzamide | 4.01 | 740 |
| 40 | 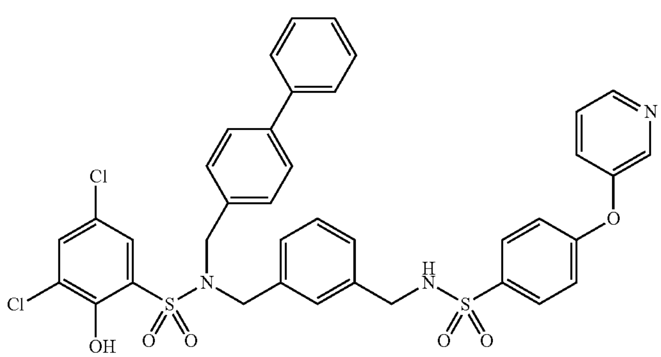 [SMILES: O=S(=O)(NCc1cccc(CN(Cc2ccc(-c3ccccc3)cc2)S(=O)(=O)c2cc(Cl)cc(Cl)c2O)c1)c1ccc(Oc2cccnc2)cc1] | N-(biphenyl-4-ylmethyl)-3,5-dichloro-2-hydroxy-N-(3-((4-(pyridin-3-yloxy)phenylsulfon-amido)methyl)benzyl)benzenesulfonamide | 4.22 | 760.6 |

| Ex. No. | Structure | Name | HPLC tR (minute) | LCMS (M + H) |
|---|---|---|---|---|
| 41 | 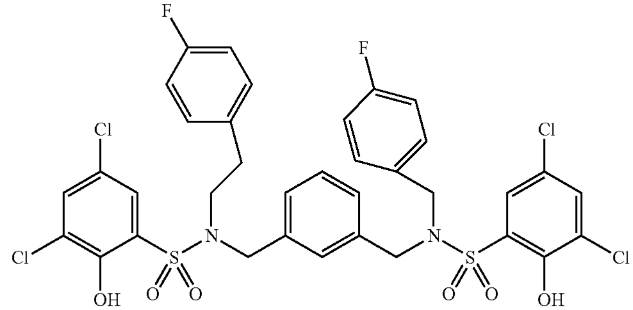 [SMILES: O=S(=O)(c1cc(Cl)cc(Cl)c1O)N(CCc1ccc(F)cc1)Cc1cccc(CN(Cc2ccc(F)cc2)S(=O)(=O)c2cc(Cl)cc(Cl)c2O)c1] | 3,5-dichloro-N-(3-((3,5-dichloro-N-(4-fluorobenzyl)-2-hydroxyphenyl-sulfonamido)methyl)benzyl)-N-(4-fluorophenethyl)-2-hydroxybenzenesulfonamide | 4.68 | 817.52 |
| 42 | 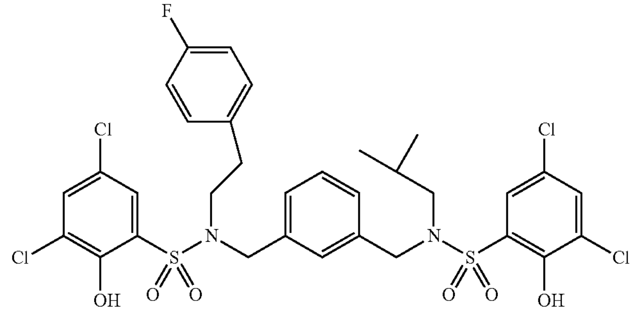 [SMILES: CC(C)CN(Cc1cccc(CN(CCc2ccc(F)cc2)S(=O)(=O)c2cc(Cl)cc(Cl)c2O)c1)S(=O)(=O)c1cc(Cl)cc(Cl)c1O] | 3,5-dichloro-N-(3-((3,5-dichloro-2-hydroxy-N-isobutylphenyl-sulfonamido)methyl)benzyl)-N-(4-fluorophenethyl)-2-hydroxybenzenesulfonamide | 4.61 | 765.56 |
| 43 | 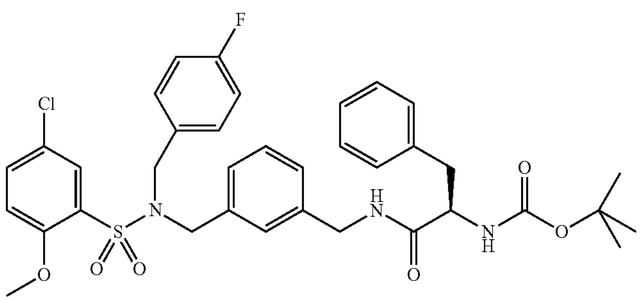 [SMILES: COc1ccc(Cl)cc1S(=O)(=O)N(Cc1ccc(F)cc1)Cc1cccc(CNC(=O)[C@@H](Cc2ccccc2)NC(=O)OC(C)(C)C)c1] | (R)-tert-butyl 1-(3-((5-chloro-N-(4-fluorobenzyl)-2-methoxyphenyl-sulfonamido)methyl)benzylamino)-1-oxo-3-phenylpropan-2-ylcarbamate | 4.12 | 696.6 |
| 44 | 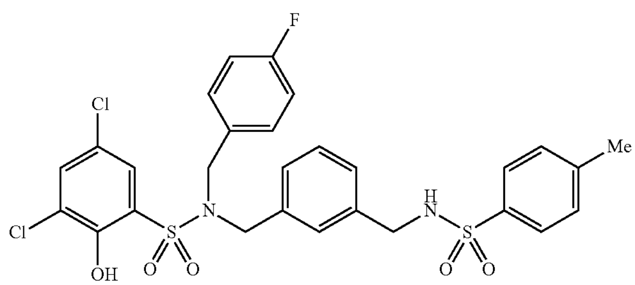 [SMILES: Cc1ccc(S(=O)(=O)NCc2cccc(CN(Cc3ccc(F)cc3)S(=O)(=O)c3cc(Cl)cc(Cl)c3O)c2)cc1] | 3,5-dichloro-N-(4-fluorobenzyl)-2-hydroxy-N-(3-((4-methylphenyl-sulfonamido)methyl)benzyl)benzenesulfonamide | 4.03 | |
| 45 | 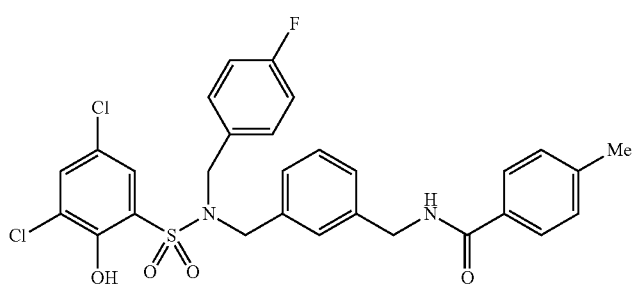 [SMILES: Cc1ccc(C(=O)NCc2cccc(CN(Cc3ccc(F)cc3)S(=O)(=O)c3cc(Cl)cc(Cl)c3O)c2)cc1] | N-(3-((3,5-dichloro-N-(4-fluorobenzyl)-2-hydroxyphenyl-sulfonamido)methyl)benzyl)-4-methylbenzamide | 4.05 | 587.5 |

| Ex. No. | Structure | Name | HPLC tR (minute) | LCMS (M + H) |
|---|---|---|---|---|
| 46 | 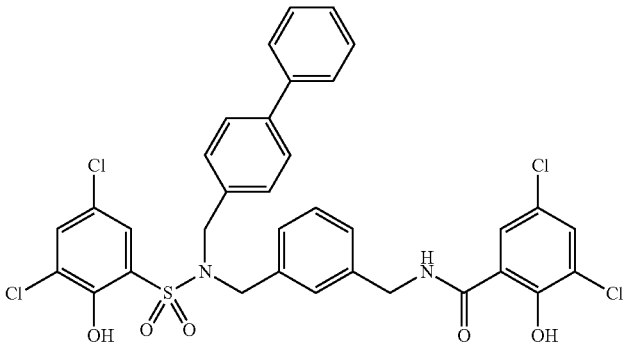 [SMILES: O=C(NCc1cccc(CN(Cc2ccc(-c3ccccc3)cc2)S(=O)(=O)c2cc(Cl)cc(Cl)c2O)c1)c1cc(Cl)cc(Cl)c1O] | N-(3-((N-(biphenyl-4-ylmethyl)-3,5-dichloro-2-hydroxyphenyl-sulfonamido)methyl)benzyl)-3,5-dichloro-2-hydroxybenzamide | 4.91 | 717.3 |
| 47 | 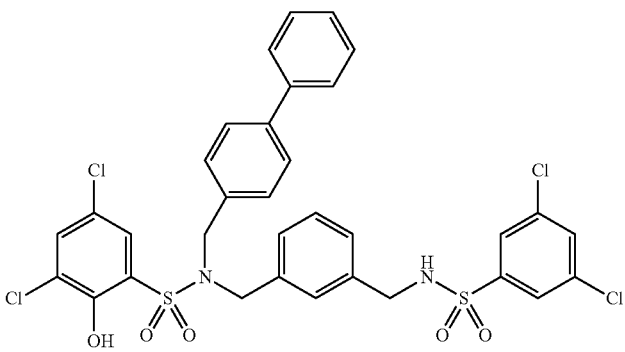 [SMILES: O=S(=O)(NCc1cccc(CN(Cc2ccc(-c3ccccc3)cc2)S(=O)(=O)c2cc(Cl)cc(Cl)c2O)c1)c1cc(Cl)cc(Cl)c1] | N-(biphenyl-4-ylmethyl)-3,5-dichloro-N-(3-((3,5-dichlorophenyl-sulfonamido)methyl)benzyl)-2-hydroxybenzenesulfonamide | 4.6 | 737.3 |
| 48 | 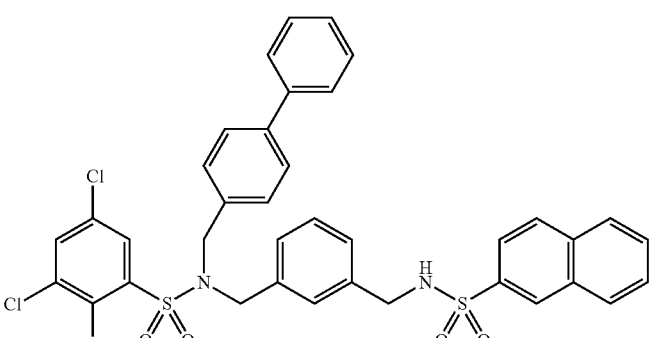 | N-(3-((N-(biphenyl-4-ylmethyl)-3,5-dichloro-2-hydroxyphenyl-sulfonamido)methyl)benzyl)naphthalene-2-sulfonamide | 4.41 | |
| 49 | 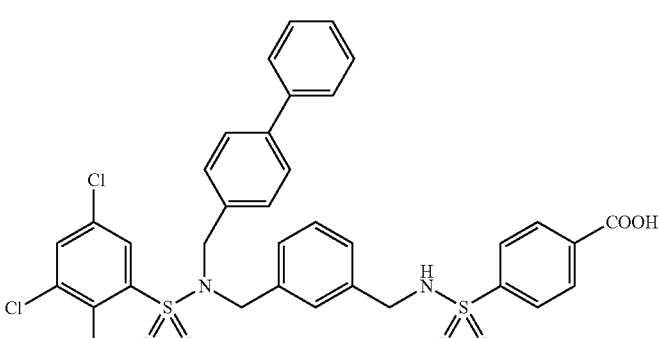 | 4-(N-(3-((N-(biphenyl-4-ylmethyl)-3,5-dichloro-2-hydroxyphenyl-sulfonamido)methyl)benzyl)sulfamoyl)benzoic acid | 4.13 | 711.1 |

-continued

| Ex. No. | Structure | Name | HPLC tR (minute) | LCMS (M + H) |
|---|---|---|---|---|
| 50 | 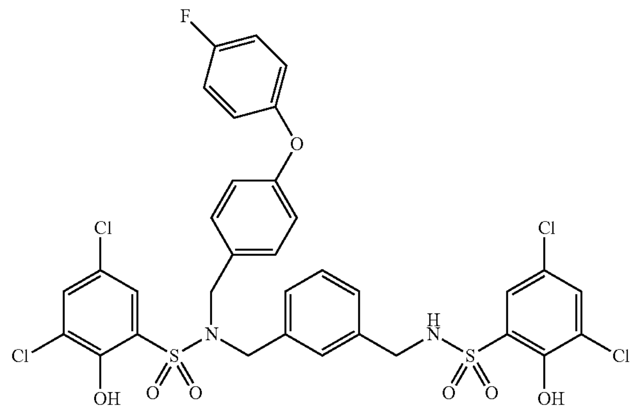 [SMILES: O=S(=O)(NCc1cccc(CN(Cc2ccc(Oc3ccc(F)cc3)cc2)S(=O)(=O)c2cc(Cl)cc(Cl)c2O)c1)c1cc(Cl)cc(Cl)c1O] | 3,5-dichloro-N-(3-((3,5-dichloro-2-hydroxyphenyl-sulfonamido)methyl)benzyl)-N-(4-(4-fluorophenoxy)benzyl)-2-hydroxybenzenesulfonamide | 4.47 | |
| 51 | 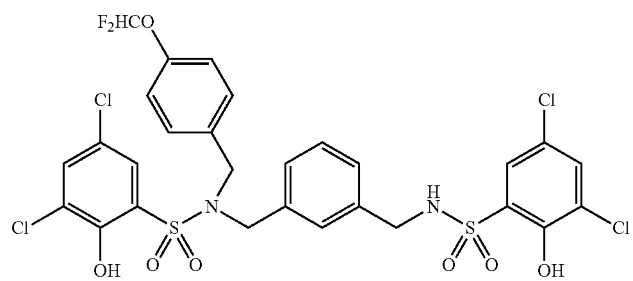 [SMILES: O=S(=O)(NCc1cccc(CN(Cc2ccc(OC(F)F)cc2)S(=O)(=O)c2cc(Cl)cc(Cl)c2O)c1)c1cc(Cl)cc(Cl)c1O] | 3,5-dichloro-N-(3-((3,5-dichloro-2-hydroxyphenylsulfonamido)methyl)benzyl)-N-(4-(difluoromethoxy)benzyl)-2-hydroxy-benzenesulfonamide | 4.16 | |
| 52 | 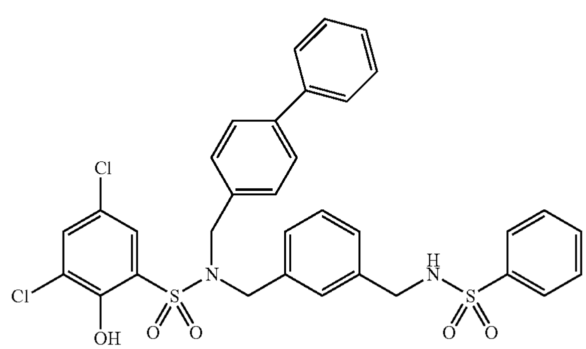 [SMILES: O=S(=O)(NCc1cccc(CN(Cc2ccc(-c3ccccc3)cc2)S(=O)(=O)c2cc(Cl)cc(Cl)c2O)c1)c1ccccc1] | N-(biphenyl-4-ylmethyl)-3,5-dichloro-2-hydroxy-N-(3-(phenylsulfonamido-methyl)benzyl)benzenesulfonamide | 4.33 | |
| 53 | 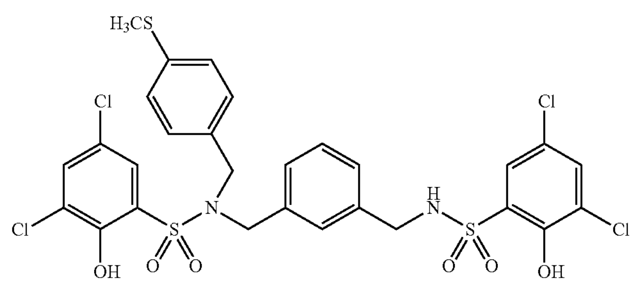 | 3,5-dichloro-N-(3-((3,5-dichloro-2-hydroxyphenyl-sulfonamido)methyl)benzyl)-2-hydroxy-N-(4-(methylthio)benzyl)benzenesulfonamide | 4.31 | |

-continued

| Ex. No. | Structure | Name | HPLC tR (minute) | LCMS (M + H) |
|---|---|---|---|---|
| 54 | 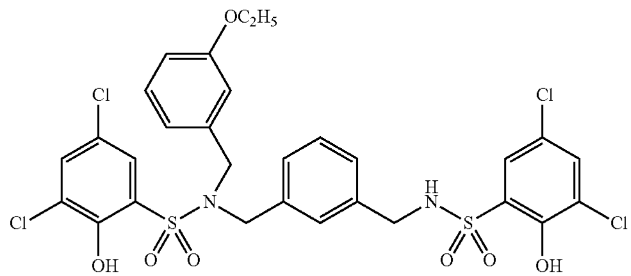 | 3,5-dichloro-N-(3-((3,5-dichloro-2-hydroxyphenyl-sulfonamido)methyl)benzyl)-N-(3-ethoxybenzyl)-2-hydroxybenzenesulfonamide | 4.29 | |
| 55 | 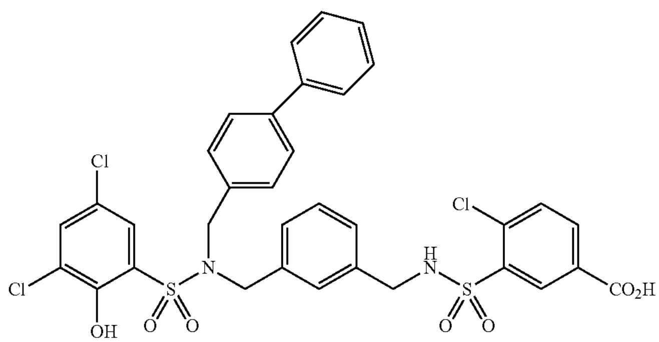 [SMILES: O=C(O)c1ccc(Cl)c(S(=O)(=O)NCc2cccc(CN(Cc3ccc(-c4ccccc4)cc3)S(=O)(=O)c3cc(Cl)cc(Cl)c3O)c2)c1] | 3-(N-(3-((N-(biphenyl-4-ylmethyl)-3,5-dichloro-2-hydroxyphenyl-sulfonamido)methyl)benzyl)sulfamoyl)-4-chlorobenzoic acid | 4.15 | 747.15 |
| 56 | 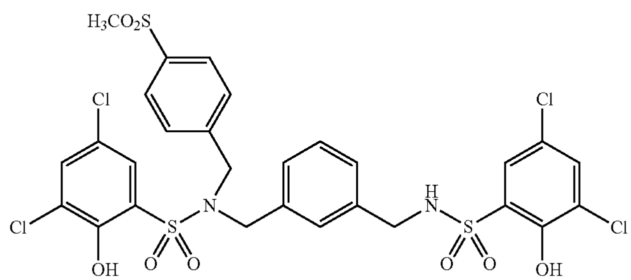 | 3,5-dichloro-N-(3-((3,5-dichloro-2-hydroxyphenyl-sulfonamido)methyl)benzyl)-2-hydroxy-N-(4-(methylsulfonyl)benzyl)benzenesulfonamide | 3.87 | |
| 57 | 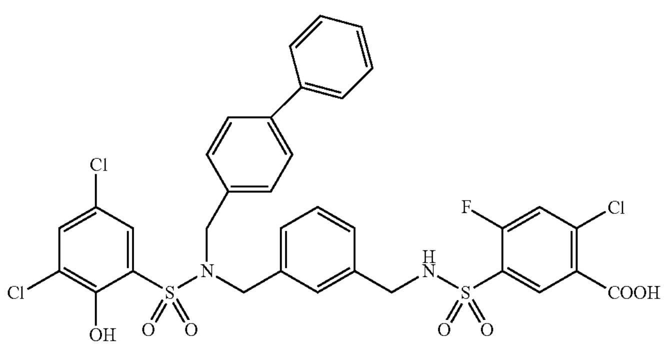 [SMILES: O=C(O)c1cc(S(=O)(=O)NCc2cccc(CN(Cc3ccc(-c4ccccc4)cc3)S(=O)(=O)c3cc(Cl)cc(Cl)c3O)c2)c(F)cc1Cl] | 5-(N-(3-((N-(biphenyl-4-ylmethyl)-3,5-dichloro-2-hydroxyphenyl-sulfonamido)methyl)benzyl)sulfamoyl)-2-chloro-4-fluorobenzoic acid | 4.16 | 765.02 |
| 58 | 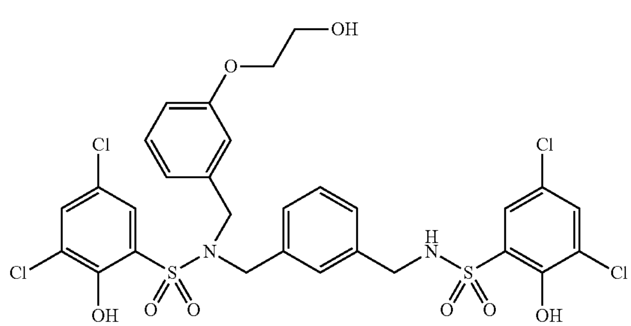 [SMILES: O=S(=O)(NCc1cccc(CN(Cc2cccc(OCCO)c2)S(=O)(=O)c2cc(Cl)cc(Cl)c2O)c1)c1cc(Cl)cc(Cl)c1O] | 3,5-dichloro-N-(3-((3,5-dichloro-2-hydroxyphenylsulfonamido)methyl)benzyl)-2-hydroxy-N-(3-(2-hydroxyethoxy)benzyl)benzenesulfonamide | 3.97 | 737 |

| Ex. No. | Structure | Name | HPLC tR (minute) | LCMS (M + H) |
|---|---|---|---|---|
| 59 | 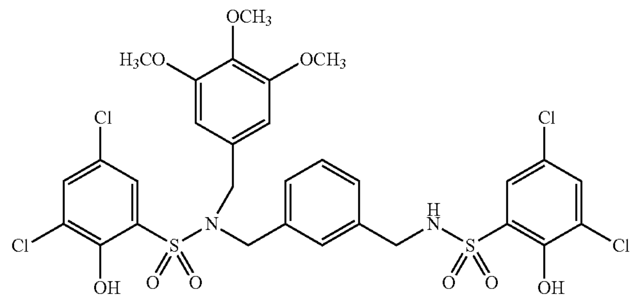 [SMILES: COc1cc(CN(Cc2cccc(CNS(=O)(=O)c3cc(Cl)cc(Cl)c3O)c2)S(=O)(=O)c2cc(Cl)cc(Cl)c2O)cc(OC)c1OC] | 3,5-dichloro-N-(3-((3,5-dichloro-2-hydroxyphenylsulfonamido)methyl)benzyl)-2-hydroxy-N-(3,4,5-trimethoxybenzyl)benzenesulfonamide | 4.06 | |
| 60 | 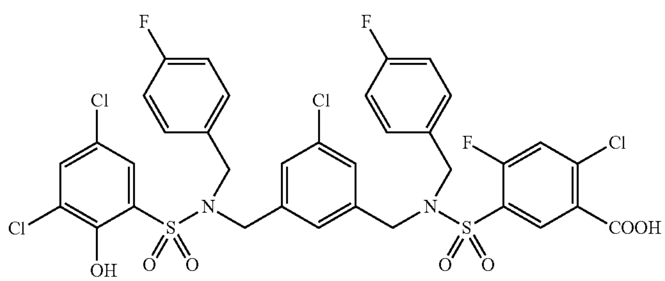 [SMILES: O=C(O)c1cc(S(=O)(=O)N(Cc2ccc(F)cc2)Cc2cc(Cl)cc(CN(Cc3ccc(F)cc3)S(=O)(=O)c3cc(Cl)cc(Cl)c3O)c2)c(F)cc1Cl] | 2-chloro-5-(N-(3-chloro-5-((3,5-dichloro-N-(4-fluorobenzyl)-2-hydroxyphenylsulfonamido)methyl)benzyl)-N-(4-fluorobenzyl)sulfamoyl)-4-fluorobenzoic acid | 4.56 | 849.33 |
| 61 | 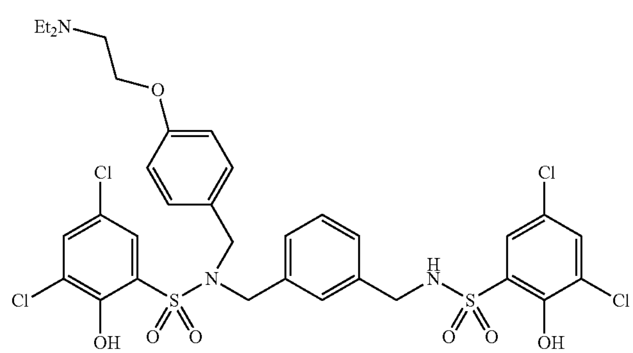 | 3,5-dichloro-N-(3-((3,5-dichloro-2-hydroxyphenylsulfonamido)methyl)benzyl)-N-(4-(2-(diethylamino)ethoxy)benzyl)-2-hydroxybenzenesulfonamide | 3.43 | 792.3 |
| 62 | 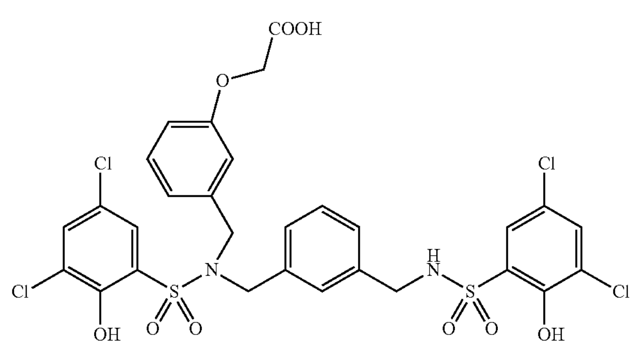 [SMILES: O=C(O)COc1cccc(CN(Cc2cccc(CNS(=O)(=O)c3cc(Cl)cc(Cl)c3O)c2)S(=O)(=O)c2cc(Cl)cc(Cl)c2O)c1] | 2-(3-((3,5-dichloro-N-(3-((3,5-dichloro-2-hydroxyphenylsulfonamido)methyl)benzyl)-2-hydroxyphenylsulfonamido)methyl)phenoxy)acetic acid | 3.96 | |

-continued

| Ex. No. | Structure | Name | HPLC tR (minute) | LCMS (M + H) |
|---|---|---|---|---|
| 63 | 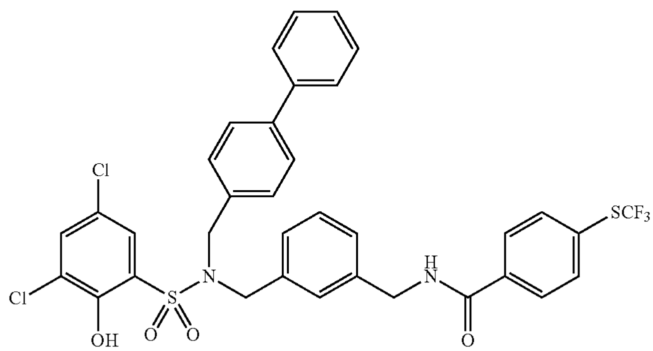 | N-(3-((N-(biphenyl-4-ylmethyl-3,5-dichloro-2-hydroxyphenylsulfonamido)methyl)benzyl)-4-(trifluoromethylthio)benzamide | 4.62 | 731.39 |
| 64 | 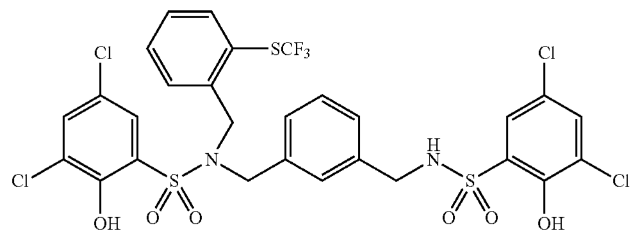 | 3,5-dichloro-N-3-((3,5-dichloro-2-hydroxyphenylsulfonamido)methyl)benzyl)-2-hydroxy-N-(2-(trifluoromethylthio)benzyl)benzenesulfonamide | 4.31 | 777.01 |
| 65 | 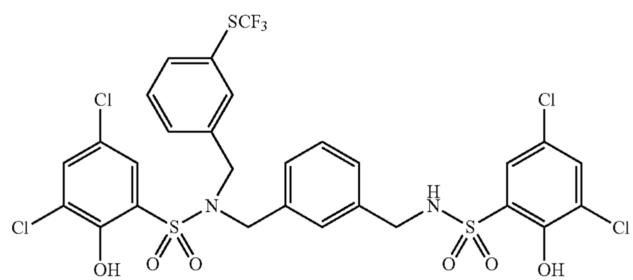 | 3,5-dichloro-N-3-((3,5-dichloro-2-hydroxyphenylsulfonamido)methyl)benzyl)-2-hydroxy-N-(3-(trifluoromethylthio)benzyl)benzenesulfonamide | 4.38 | 777.03 |
| 66 | 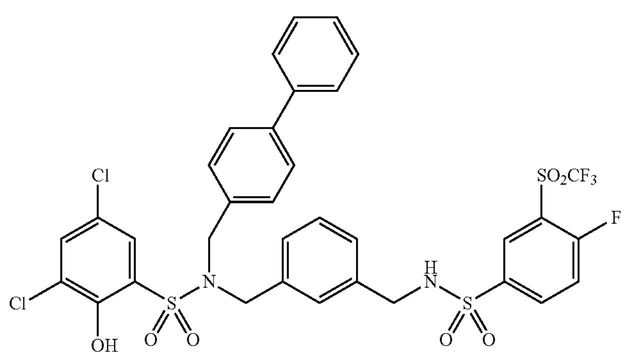 | N-(biphenyl-4-ylmethyl)-3,5-dichloro-N-(3-((4-fluoro-3-(trifluoromethylsulfonyl)phenylsulfonamido)methyl)benzyl)-2-hydroxybenzenesulfonamide | 4.37 | |
| 67 | 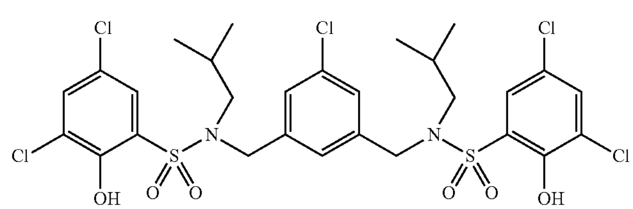 [SMILES: CC(C)CN(Cc1cc(Cl)cc(CN(CC(C)C)S(=O)(=O)c2cc(Cl)cc(Cl)c2O)c1)S(=O)(=O)c1cc(Cl)cc(Cl)c1O] | N,N'-(5-chloro-1,3-phenylene)bis(methylene)bis(3,5-dichloro-2-hydroxy-N-isobutylbenzenesulfonamide) | 4.56 | 733.07 |

| Ex. No. | Structure | Name | HPLC tR (minute) | LCMS (M + H) |
|---|---|---|---|---|
| 68 | 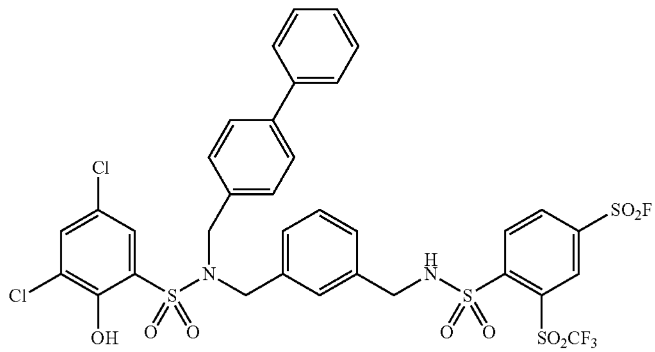 | 4-(N-(3-((N-(biphenyl-4-ylmethyl)-3,5-dichloro-2-hydroxyphenylsulfonamido)methyl)benzyl)sulfamoyl)-3-(trifluoromethylsulfonyl)benzene-1-sulfonyl fluoride | 4.67 | |
| 69 | 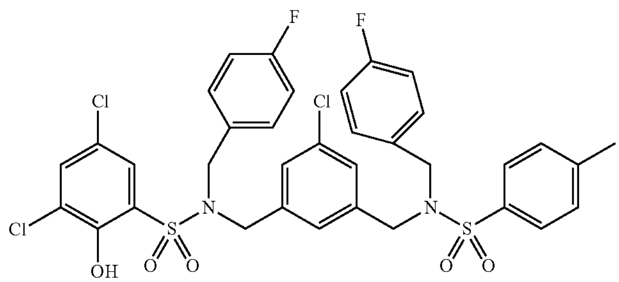 [SMILES: Cc1ccc(S(=O)(=O)N(Cc2ccc(F)cc2)Cc2cc(Cl)cc(CN(Cc3ccc(F)cc3)S(=O)(=O)c3cc(Cl)cc(Cl)c3O)c2)cc1] | 3,5-dichloro-N-(3-chloro-5-((N-(4-fluorobenzyl)-4-methylphenylsulfonamido)methyl)benzyl)-N-(4-fluorobenzyl)-2-hydroxybenzenesulfonamide | 3.7 | 767.24 |
| 70 | 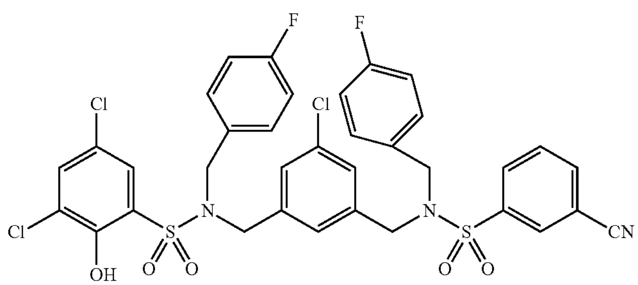 [SMILES: N#Cc1cccc(S(=O)(=O)N(Cc2ccc(F)cc2)Cc2cc(Cl)cc(CN(Cc3ccc(F)cc3)S(=O)(=O)c3cc(Cl)cc(Cl)c3O)c2)c1] | 3,5-dichloro-N-(3-chloro-5-((3-cyano-N-(4-fluorobenzyl)phenylsulfonamido)methyl)benzyl)-N-(4-fluorobenzyl)-2-hydroxybenzenesulfonamide | 4.35 | 778.24 |
| 71 | 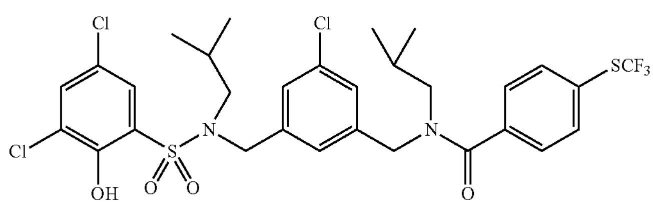 | N-(3-chloro-5-((3,5-dichloro-2-hydroxy-N-isobutylphenylsulfonamido)methyl)benzyl)-N-isobutyl-4-(trifluoromethylthio)benzamide | 4.58 | 713.2 |
| 72 | 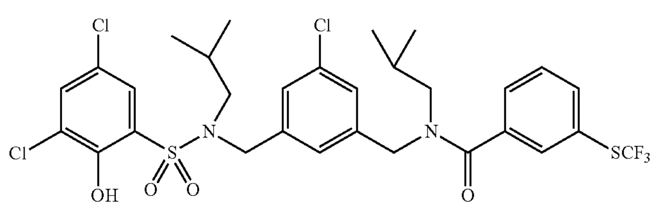 | N-(3-chloro-5-((3,5-dichloro-2-hydroxy-N-isobutylphenylsulfonamido)methyl)benzyl)-N-isobutyl-3-(trifluoromethylthio)benzamide | 4.53 | 713.1 |
| 73 | 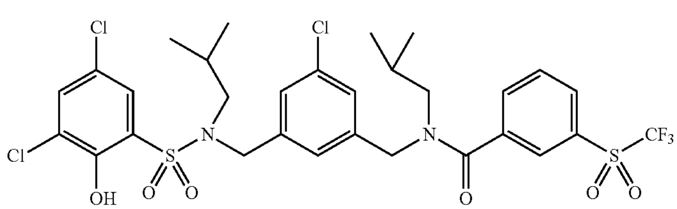 [SMILES: CC(C)CN(Cc1cc(Cl)cc(CN(CC(C)C)S(=O)(=O)c2cc(Cl)cc(Cl)c2O)c1)C(=O)c1cccc(S(=O)(=O)C(F)(F)F)c1] | N-(3-chloro-5-((3,5-dichloro-2-hydroxy-N-isobutylphenylsulfonamido)methyl)benzyl)-N-isobutyl-3-(trifluoromethylsulfonyl)benzamide | 4.36 | 745.2 |

-continued

| Ex. No. | Structure | Name | HPLC tR (minute) | LCMS (M + H) |
|---|---|---|---|---|
| 74 | 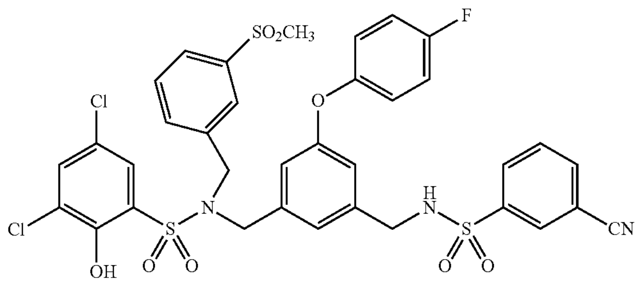 [SMILES: CS(=O)(=O)c1cccc(CN(Cc2cc(CNS(=O)(=O)c3cccc(C#N)c3)cc(Oc3ccc(F)cc3)c2)S(=O)(=O)c2cc(Cl)cc(Cl)c2O)c1] | 3,5-dichloro-N-(3-((3-cyanophenylsulfonamido)methyl)-5-(4-fluorophenoxy)benzyl)-2-hydroxy-N-(3-(methylsulfonyl)benzyl)benzenesulfonamide | 3.62 | 802.3 |
| 75 | 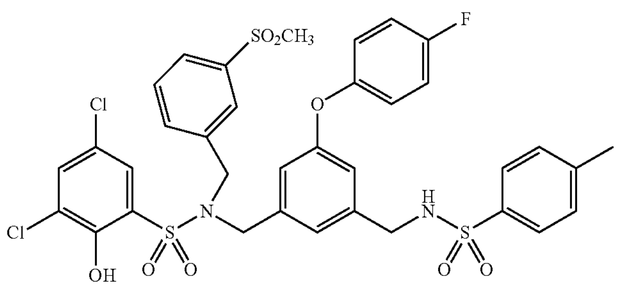 [SMILES: Cc1ccc(S(=O)(=O)NCc2cc(CN(Cc3cccc(S(C)(=O)=O)c3)S(=O)(=O)c3cc(Cl)cc(Cl)c3O)cc(Oc3ccc(F)cc3)c2)cc1] | 3,5-dichloro-N-(3-(4-fluorophenoxy)-5-((4-methylphenylsulfonamido)methyl)benzyl)-2-hydroxy-N-(3-(methylsulfonyl)benzyl)benzenesulfonamide | 3.75 | 793.3 |
| 76 | 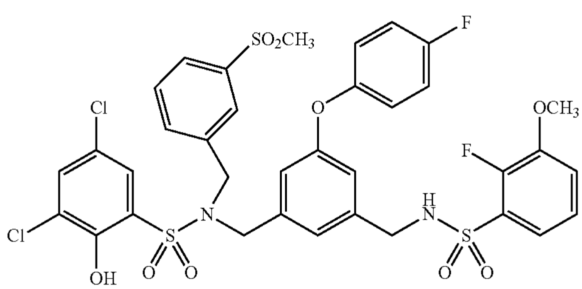 [SMILES: COc1cccc(S(=O)(=O)NCc2cc(CN(Cc3cccc(S(C)(=O)=O)c3)S(=O)(=O)c3cc(Cl)cc(Cl)c3O)cc(Oc3ccc(F)cc3)c2)c1F] | N-(3-((3,5-dichloro-2-hydroxy-N-(3-(methylsulfonyl)benzyl)phenylsulfonamido)methyl)-5-(4-fluorophenoxy)benzyl)-2-fluoro-3-methoxybenzamide | 3.55 | 791.3 |
| 77 | 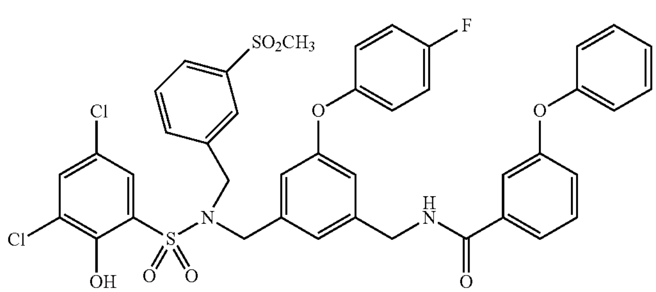 [SMILES: CS(=O)(=O)c1cccc(CN(Cc2cc(CNC(=O)c3cccc(Oc4ccccc4)c3)cc(Oc3ccc(F)cc3)c2)S(=O)(=O)c2cc(Cl)cc(Cl)c2O)c1] | N-(3-((3,5-dichloro-2-hydroxy-N-(3-(methylsulfonyl)benzyl)phenylsulfonamido)methyl)-5-(4-fluorophenoxy)benzyl)-3-phenoxybenzamide | 3.93 | 835.3 |
| 78 | 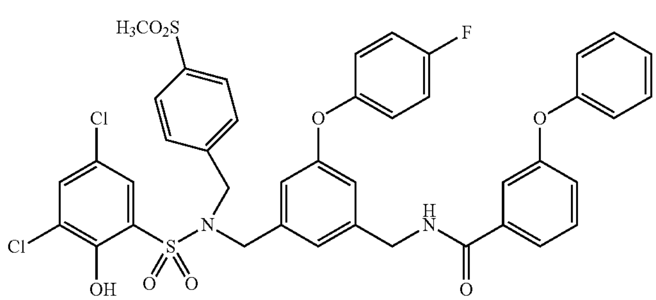 | N-(3-((3,5-dichloro-2-hydroxy-N-(4-(methylsulfonyl)benzyl)phenylsulfonamido)methyl)-5-(4-fluorophenoxy)benzyl)-3-phenoxybenzamide | 4.15 | 835.3 |

-continued

| Ex. No. | Structure | Name | HPLC tR (minute) | LCMS (M + H) |
|---|---|---|---|---|
| 79 | 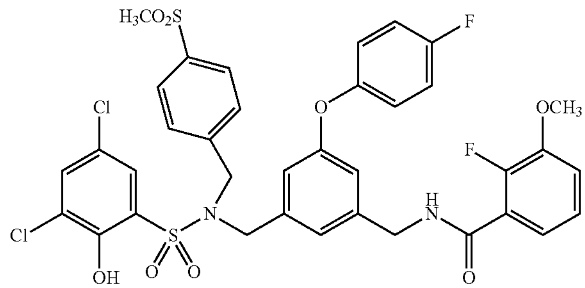 | N-(3-((3,5-dichloro-2-hydroxy-N-(4-(methylsulfonyl)benzyl)phenylsulfonamido)methyl)-5-(4-fluorophenoxy)benzyl)-2-fluoro-3-methoxybenzamide | 3.84 | 791.2 |
| 80 | 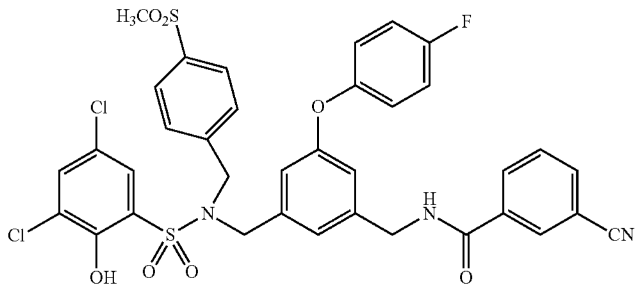 | 3,5-dichloro-N-(3-((3-cyanophenylsulfonamido)methyl)-5-(4-fluorophenoxy)benzyl)-2-hydroxy-N-(4-(methylsulfonyl)benzyl)benzenesulfonamide | 3.77 | |
| 81 | 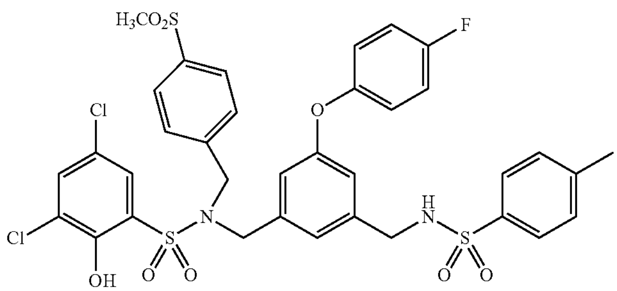 | 3,5-dichloro-N-(3-(4-fluorophenoxy)-5-((4-methylphenylsulfonamido)methyl)benzyl)-2-hydroxy-N-(4-(methylsulfonyl)benzyl)benzenesulfonamide | 3.94 | |
| 82 | 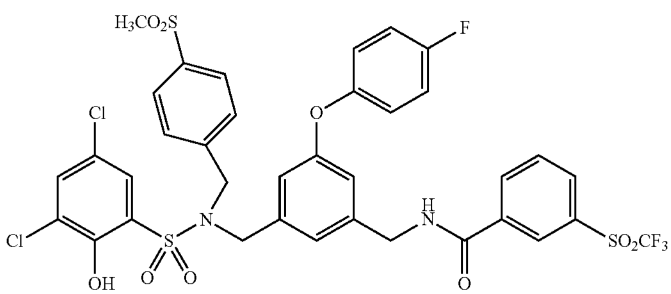 | N-(3-((3,5-dichloro-2-hydroxy-N-(4-(methylsulfonyl)benzyl)phenylsulfonamido)methyl)-5-(4-fluorophenoxy)benzyl)-3-(trifluoromethylsulfonyl)benzamide | 4.02 | |
| 83 | 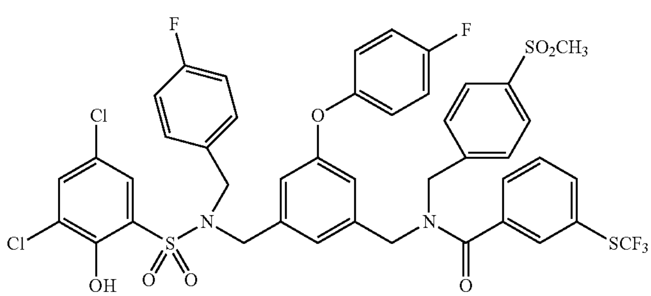 | N-(3-((3,5-dichloro-N-(4-fluorobenzyl)-2-hydroxyphenylsulfonamido)methyl)-5-(4-fluorophenoxy)benzyl)-N-(4-(methylsulfonyl)benzyl)-3-(trifluoromethylthio)benzamide | 4.33 | |

-continued

| Ex. No. | Structure | Name | HPLC tR (minute) | LCMS (M + H) |
|---|---|---|---|---|
| 84 | 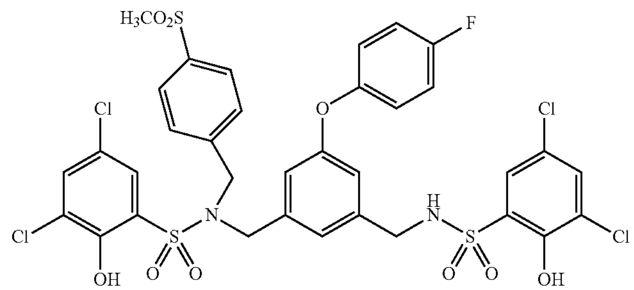 | 3,5-dichloro-N-(3-((3,5-dichloro-2-hydroxyphenyl-sulfonamido)methyl)-5-(4-fluorophenoxy)benzyl)-2-hydroxy-N-(4-(methylsulfonyl)benzyl)benzenesulfonamide | 4.09 | |
| 85 | 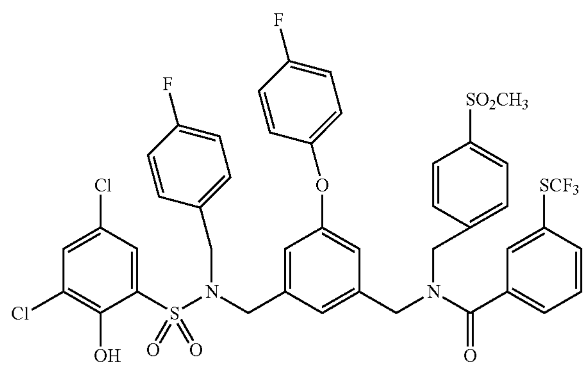 | N-(3-((3,5-dichloro-N-(4-fluorobenzyl)-2-hydroxyphenyl-sulfonamido)methyl)-5-(4-fluorophenoxy)benzyl)-N-(4-(methylsulfonyl)benzyl)-3-(trifluoromethylthio)benzamide | 4.05 | |
| 86 | 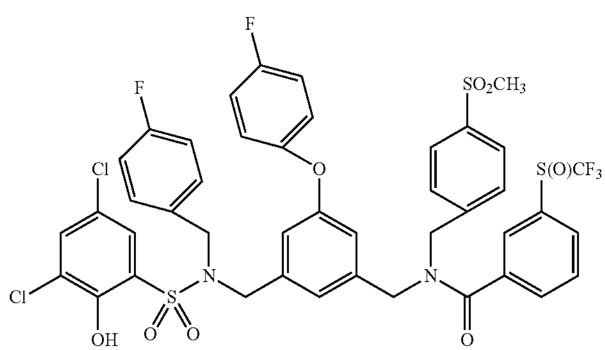 | N-(3-((3,5-dichloro-N-(4-fluorobenzyl)-2-hydroxyphenyl-sulfonamido)methyl)-5-(4-fluorophenoxy)benzyl)-N-(4-(methylsulfonyl)benzyl)-3-(trifluoromethyl-sulfinyl)benzamide | 4.11 | |
| 87 | 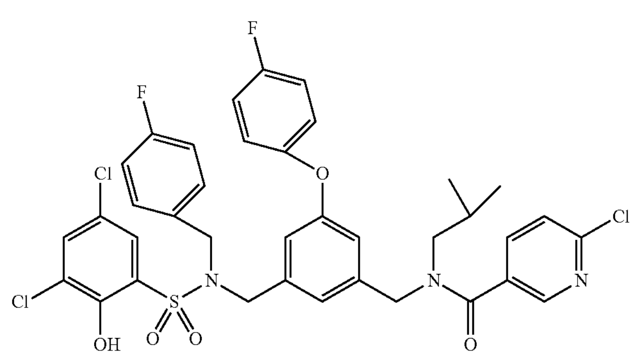 [SMILES: CC(C)CN(Cc1cc(CN(Cc2ccc(F)cc2)S(=O)(=O)c2cc(Cl)cc(Cl)c2O)cc(Oc2ccc(F)cc2)c1)C(=O)c1ccc(Cl)nc1] | 6-chloro-N-(3-((3,5-dichloro-N-(4-fluorobenzyl)-2-hydroxyphenyl-sulfonamido)methyl)-5-(4-fluorophenoxy)benzyl)-N-isobutylnicotinamide | 4.36 | 776.1 |

-continued

| Ex. No. | Structure | Name | HPLC tR (minute) | LCMS (M + H) |
|---|---|---|---|---|
| 88 | 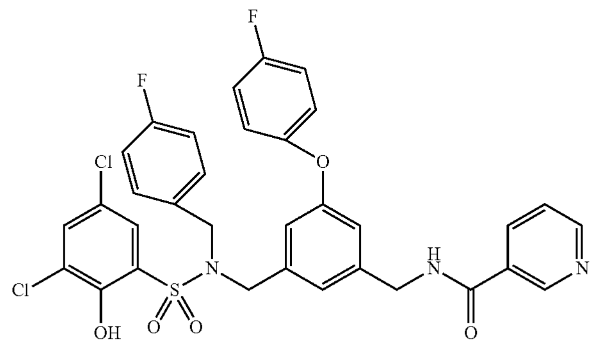 [SMILES: O=C(NCc1cc(CN(Cc2ccc(F)cc2)S(=O)(=O)c2cc(Cl)cc(Cl)c2O)cc(Oc2ccc(F)cc2)c1)c1cccnc1] | N-(3-((3,5-dichloro-N-(4-fluorobenzyl)-2-hydroxyphenyl-sulfonamido)methyl)-5-(4-fluorophenoxy)benzyl) nicotinamide | 3.81 | 684.1 |
| 89 | 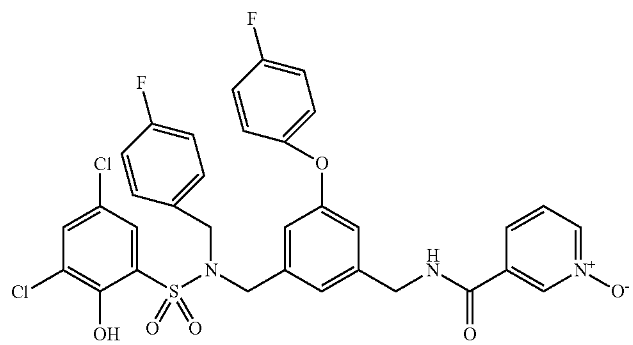 [SMILES: O=C(NCc1cc(CN(Cc2ccc(F)cc2)S(=O)(=O)c2cc(Cl)cc(Cl)c2O)cc(Oc2ccc(F)cc2)c1)c1ccc[n+]([O-])c1] | 3-(3-((3,5-dichloro-N-(4-fluorobenzyl)-2-hydroxyphenyl-sulfonamido)methyl)-5-(4-fluorophenoxy) benzylcarbamoyl)pyridine 1-oxide | 3.94 | 700.1 |
| 90 | 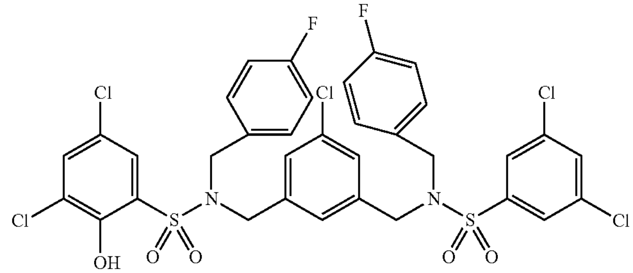 [SMILES: O=S(=O)(c1cc(Cl)cc(Cl)c1)N(Cc1ccc(F)cc1)Cc1cc(Cl)cc(CN(Cc2ccc(F)cc2)S(=O)(=O)c2cc(Cl)cc(Cl)c2O)c1] | 3,5-dichloro-N-(3-chloro-5-((3,5-dichloro-N-(4-fluorobenzyl) phenylsulfon-amido)methyl)benzyl)-N-(4-fluorobenzyl)-2-hydroxybenzenesulfonamide | 4.7 | 820.6 |
| 91 | 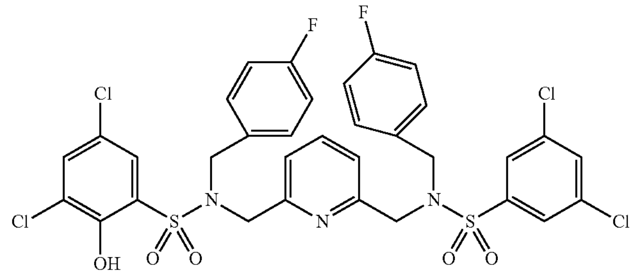 [SMILES: O=S(=O)(c1cc(Cl)cc(Cl)c1)N(Cc1ccc(F)cc1)Cc1cccc(CN(Cc2ccc(F)cc2)S(=O)(=O)c2cc(Cl)cc(Cl)c2O)n1] | 3,5-dichloro-N-((6-((3,5-dichloro-N-(4-fluorobenzyl)phenylsulfonamido) methyl)pyridin-2-yl)methyl)-N-(4-fluorobenzyl)-2-hydroxybenzenesulfonamide | 4.44 | 787.9 |
| 92 | 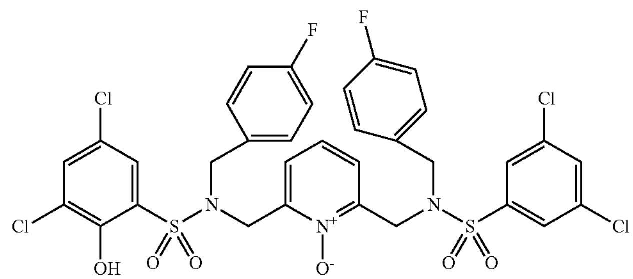 [SMILES: O=S(=O)(c1cc(Cl)cc(Cl)c1)N(Cc1ccc(F)cc1)Cc1cccc(CN(Cc2ccc(F)cc2)S(=O)(=O)c2cc(Cl)cc(Cl)c2O)[n+]1[O-]] | 2-((3,5-dichloro-N-(4-fluorobenzyl)-2-hydroxyphenylsulfonamido) methyl)-6-((3,5-dichloro-N-(4-fluorobenzyl)phenylsulfonamido) methyl)pyridine 1-oxide | 4.14 | 804 |

| Ex. No. | Structure | Name | HPLC tR (minute) | LCMS (M + H) |
|---|---|---|---|---|
| 93 | 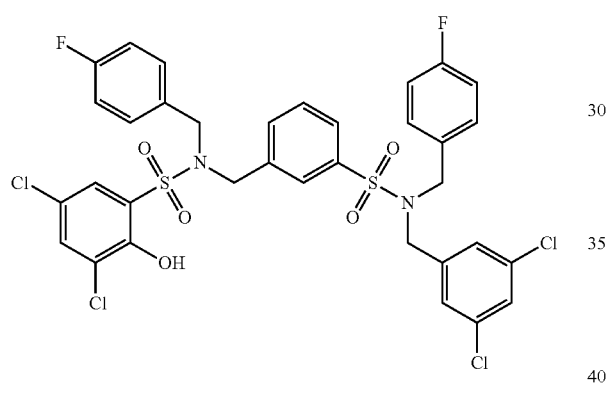 | 3,5-dichloro-N-(3-((3,5-dichloro-N-isobutylphenyl-sulfonamido)methyl)benzyl)-N-((4'-fluorobiphenyl-4-yl)methyl)-2-hydroxybenzenesulfonamide | 5.11 | |

Example 94

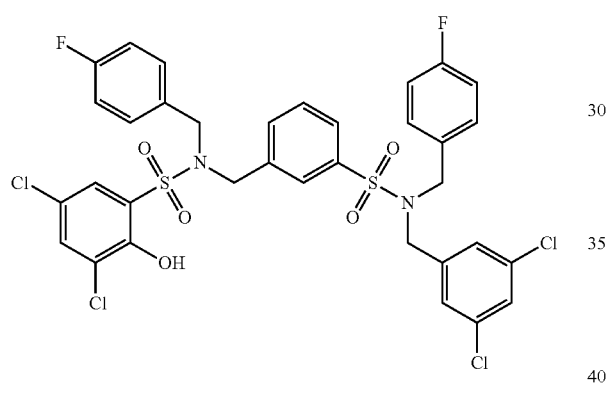

3,5-Dichloro-N-(3-(N-(3,5-dichlorobenzyl)-N-(4-fluorobenzyl)sulfamoyl)benzyl)-N-(4-fluorobenzyl)-2-hydroxybenzenesulfonamide

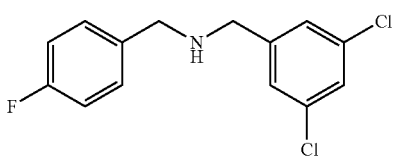 [SMILES: Fc1ccc(CNCc2cc(Cl)cc(Cl)c2)cc1]

A) N-(3,5-Dichlorobenzyl)-1-(4-fluorophenyl)methanamine

To a solution of 3,5-dichlorobenzaldehyde (3.9 g, 22.3 mmol) in 2-propanol (20 mL) and CH₂Cl₂ (20 mL) was added 4-fluorobenzylamine (2.93 mL, 25.6 mmol). The resulting mixture was stirred at rt for 1 h. The mixture was cooled to ice bath temperature and was treated with sodium triacetoxyborohydride (7.56 g, 35.7 mmol) under N₂ atmosphere. The resulting mixture was stirred at rt for 22 h. To the reaction mixture was added saturated aq NaHCO₃ solution and it was stirred for 0.2 h, and concentrated in vacuo. The residue was mixed with ethyl acetate and saturated aq NaHCO₃ solution. The organic layer was separated, washed with brine, dried over MgSO₄ and concentrated. The residue was purified by flash silica gel column chromatography on silica gel to obtain (ISCO. Condition: 40 g column. Eluents: 0-6% of B, gradient, solvent A: CH₂Cl₂, solvent B: ethyl acetate (5% 2 M ammonia in MeOH). 35 min run. The desired product peak came from 5 min to 15 min) the desired product as a colorless oil (5.6 g, 80%). $^1$H NMR (CDCl₃): δ 7.34-7.27 (m, 5H), 7.08-7.03 (m, 2H), 3.78 (s, 2H), 3.77 (s, 2H), 1.85 (bs, 1H); MS (ESI): [M+H]$^+$=284.0.

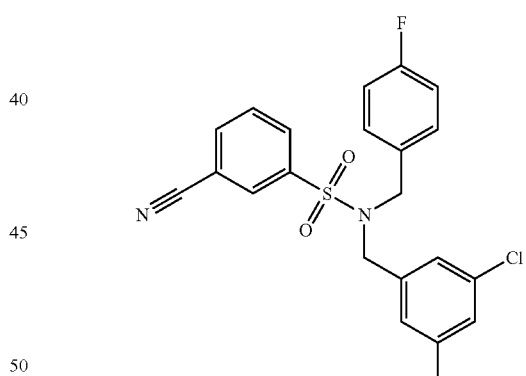

B) 3-Cyano-N-(3,5-dichlorobenzyl)-N-(4-fluorobenzyl)benzenesulfonamide

To a solution of N-(3,5-dichlorobenzyl)-1-(4-fluorophenyl)methanamine (1.40 g, 4.91 mmol) in THF (15 mL) was added 3-cyanobenzene-1-sulfonyl chloride (0.9 g, 4.46 mmol) and Et₃N (1.22 mL, 8.93 mmol) at rt for 2 h. Additional sulfonyl chloride (0.35 g) and Et₃N (0.5 mL) were added. The reaction mixture was stirred at rt for 15 h. The mixture was concentrated and the residue was diluted with ethyl acetate and 1 N HCl solution. The organic layer was separated, washed with brine, saturated aq NaHCO₃ solution, dried over MgSO₄, and concentrated to give a glassy material which was purified by flash silica gel column chromatography on silica gel (ISCO. Column: 24 g. Eluent: A: hexane. B: ethyl acetate. Condition: A to 25% of B (50 min gradient) to obtain the desired product as a white solid (1.8 g, 81%). $^1$H NMR (CDCl$_3$): δ 8.08-8.02 (m, 2H), 7.93-7.90 (m, 1H), 7.70 (t, J=8.0 Hz, 1H), 7.25-7.24 (m, 1H), 7.13-7.09 (m, 2H), 6.98 (t, J=8.0 Hz, 2H), 6.90 (d, J=4.0 Hz, 2H), 4.38 (s, 2H), 4.30 (s, 2H); MS (ESI): [M−H]$^−$=506.9.

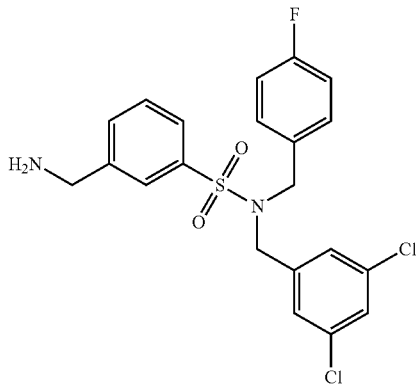 [SMILES: NCc1cccc(S(=O)(=O)N(Cc2ccc(F)cc2)Cc2cc(Cl)cc(Cl)c2)c1]

C) 3-(Aminomethyl)-N-(3,5-dichlorobenzyl)-N-(4-fluorobenzyl)benzenesulfonamide

To a solution of 3-cyano-N-(3,5-dichlorobenzyl)-N-(4-fluorobenzyl)benzenesulfonamide (0.9 g, 2.00 mmol) in THF (10 mL) at rt was added dropwise a solution of borane (1 M solution in THF) (16 mL, 16.02 mmol) under nitrogen atmosphere. The reaction mixture was stirred at rt. for 3 h, acidified by dropwise addition of TEA and it was stirred for 30 min. The solvents were removed and the residue was diluted with ethyl acetate and saturated aq NaHCO$_3$ solution. The organic layer was separated, washed with brine, dried over MgSO$_4$, and the crude product was purified by flash silica gel column chromatography on silica gel (ISCO. Column: 24 g. Eluent: A: CH$_2$Cl$_2$. B: 10% of 2 M ammonia in MeOH of ethyl acetate. Condition: A to 40% of B (45 min gradient) to obtain the desired product as a white solid (0.29 g, 32%). $^1$H NMR (CDCl$_3$): δ 7.82 (s, 1H), 7.75 (d, J=8.0 Hz, 1H), 7.63 (d, J=8.0 Hz, 1H), 7.54 (t, J=8.0 Hz, 1H), 7.20-7.19 (m, 1H), 7.11-7.08 (m, 2H), 6.97-6.92 (m, 2H), 6.86-6.85 (m, 2H), 4.32 (s, 2H), 4.26 (s, 2H), 4.00 (s, 2H), 1.58 (bs, 2H); MS (ESI): [M+H]$^+$=452.9.

D) N-(3,5-Dichlorobenzyl)-N-(4-fluorobenzyl)-3-((4-fluorobenzylamino)methyl)benzenesulfonamide To a solution of 3-(aminomethyl)-N-(3,5-dichlorobenzyl)-N-(4-fluorobenzyl)benzenesulfonamide (290 mg, 0.64 mmol) in CH$_2$Cl$_2$ (6 mL) was added 4-fluorobenzaldehyde (0.07 mL, 0.64 mmol). The resulting mixture was stirred at rt. for 1 h. To the mixture was added sodium triacetoxyborohydride (217 mg, 1.02 mmol) under N$_2$ atmosphere. The resulting mixture was stirred at rt for 20 h. To the reaction mixture was added saturated aq NaHCO$_3$ solution and the mixture was stirred for 20 minutes. The mixture was concentrated. The residue was diluted with ethyl acetate and saturated aq NaHCO$_3$ solution. The organic layer was washed with brine and dried over MgSO$_4$. The filtrate was concentrated and the residue was purified by flash chromatography on silica gel eluting with 100% CH$_2$Cl$_2$ to 25% ethyl acetate in CH$_2$Cl$_2$ to obtain the desired product as a colorless oil (0.16 g, 45%). $^1$H NMR (CDCl$_3$): δ 7.86 (s, 1H), 7.76 (d, J=8.0 Hz, 1H), 7.65 (d, J=8.0 Hz, 1H), 7.53 (t, J=8.0 Hz, 1H), 7.33-7.29 (m, 2H), 7.16-7.15 (m, 1H), 7.09-6.99 (m, 4H), 6.94-6.89 (m, 2H), 6.85-6.84 (m, 2H), 4.32 (s, 2H), 4.25 (s, 2H), 3.89 (s, 2H), 3.78 (s, 2H), 1.77 (bs, 1H); MS (ESI): [M+H]$^+$=561.0.

E) 3,5-Dichloro-N-(3-(N-(3,5-dichlorobenzyl)-N-(4-fluorobenzyl)sulfamoyl)benzyl)-N-(4-fluorobenzyl)-2-hydroxybenzenesulfonamide To a solution of N-(3,5-dichlorobenzyl)-N-(4-fluorobenzyl)-3-((4-fluorobenzylamino)methyl)benzenesulfonamide (75 mg, 0.13 mmol) in THF (4 mL) at rt was added 3,5-dichloro-2-hydroxybenzene-1-sulfonyl chloride (38 mg, 0.15 mmol) and Et$_3$N (0.06 mL, 0.40 mmol) and it was stirred at rt for 1.5 h. Additional sulfonyl chloride (15 mg) and Et$_3$N (0.05 mL) were added to the reaction mixture, and it was continued to stir for 2 h. The mixture was concentrated and the residue was purified by preparative HPLC (Condition: solvent A: 10% MeOH-90% H$_2$O-0.1% TFA; Solvent B: 90% MeOH-10% H$_2$O-0.1% TFA. Column 3: YMC S5 ODS 20×100 mm; 45% B to final 100% B, gradient time: 10 minutes, flow rate: 20 ml/min) to give the desired product as a white solid (56 mg, 53%). $^1$H NMR (CD$_3$OD): δ 7.72 (d, J=7.2 Hz, 1H), 7.70 (d, J=2.8 Hz, 1H), 7.64 (s, 1H), 7.58 (d, J=2.8 Hz, 1H), 7.50-7.46 (m, 2H), 7.20-7.10 (m, 5H), 6.93-6.90 (m, 6H), 4.61 (s, 2H), 4.46 (s, 2H), 4.26 (s, 2H), 4.21 (s, 21-1); MS (ESI): [M−H]$^−$=784.9.

Example 95

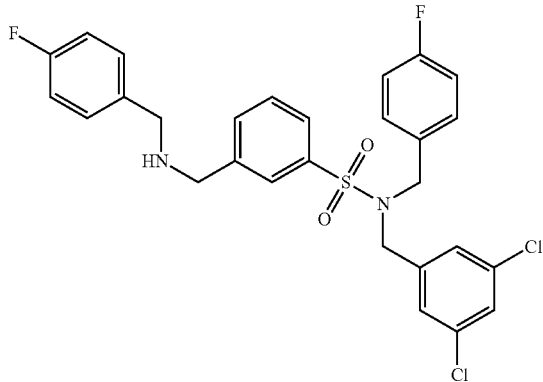 [SMILES: O=S(=O)(c1cccc(CNCc2ccc(F)cc2)c1)N(Cc1ccc(F)cc1)Cc1cc(Cl)cc(Cl)c1]

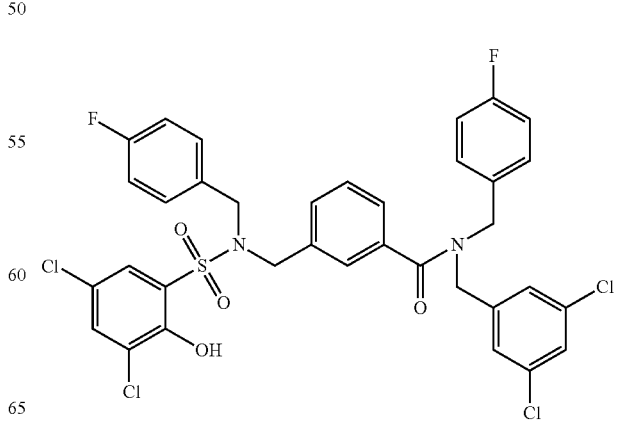

3-((3,5-Dichloro-N-(4-fluorobenzyl)-2-hydroxyphenylsulfonamido)methyl)-N-(3,5-dichlorobenzyl)-N-(4-fluorobenzyl)benzamide

A) tert-Butyl 3-((3,5-dichlorobenzyl)(4-fluorobenzyl)carbamoyl)benzylcarbamate

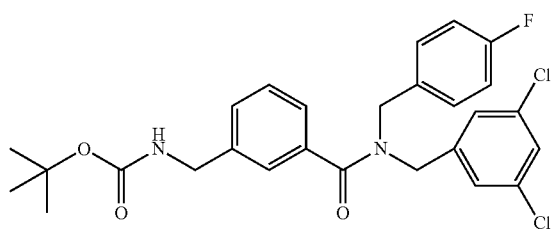 [SMILES: CC(C)(C)OC(=O)NCc1cccc(C(=O)N(Cc2ccc(F)cc2)Cc2cc(Cl)cc(Cl)c2)c1]

A solution of N-(3,5-dichlorobenzyl)-1-(4-fluorophenyl)methanamine (0.5 g, 1.76 mmol), EDCI.HCl (0.47 g, 2.46 mmol), 3-(Boc-aminomethyl)benzoic acid (0.53 g, 2.11 mmol) and HOBT.H$_2$O (0.16 g, 1.06 mmol) in DMF (8 mL) was stirred at rt for 20 h. The residue was diluted with ethyl acetate and 1 N HCl solution. The organic layer was separated, washed with 1N NaOH solution, brine, dried over MgSO$_4$, concentrated and the residue was purified by flash chromatography on silica gel (Eluent: A: CH$_2$Cl$_2$, B: ethyl acetate; condition: 100% A to 15% B. (35 min gradient) to obtain the desired product as a white solid (0.81 g, 89%). $^1$H NMR (CDCl$_3$): δ 7.42-7.32 (m, 5H), 7.17-6.99 (m, 6H), 4.88-4.63 (m, 2H), 4.42-4.35 (m, 4H), 1.47 (s, 9H).

B) 3-(Aminomethyl)-N-(3,5-dichlorobenzyl)-N-(4-fluorobenzyl)benzamide

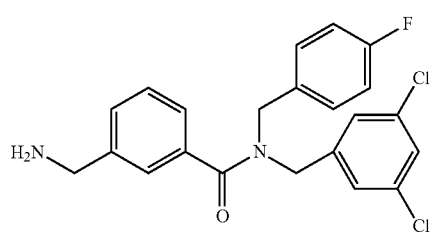 [SMILES: NCc1cccc(C(=O)N(Cc2ccc(F)cc2)Cc2cc(Cl)cc(Cl)c2)c1]

To a solution of tert-butyl 3-((3,5-dichlorobenzyl)(4-fluorobenzyl)carbamoyl)benzylcarbamate (0.8 g, 1.55 mmol) in CH$_2$Cl$_2$ (8 mL) was added TFA (1.19 mL, 15.5 mmol). The reaction mixture was stirred at rt. for 4 h, concentrated and the residue was diluted with ethyl acetate and saturated aq NaHCO$_3$ solution. The organic layer was separated, washed with brine, dried over MgSO$_4$, and concentrated to give the product as a white solid (0.61 g, 95%). $^1$H NMR (DMSO-d$_6$): δ 7.52-7.06 (m, 11H), 4.65-4.40 (m, 4H), 3.72 (s, 2H); MS (ESI): [M+H]$^+$=416.9.

C) N-(3,5-Dichlorobenzyl)-N-(4-fluorobenzyl)-3-((4-fluorobenzylamino)methyl)benzamide

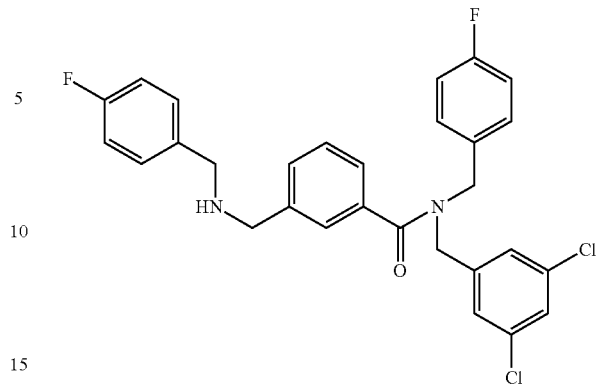

To a solution of 3-(aminomethyl)-N-(3,5-dichlorobenzyl)-N-(4-fluorobenzyl)benzamide (0.6 g, 1.44 mmol) in CH$_2$Cl$_2$ (6.0 mL) and 2-propanol (6.0 mL) was added 4-fluorobenzaldehyde (0.16 mL, 1.44 mmol). The resulting mixture was stirred at rt for 1.5 h. The reaction mixture was cooled to ice bath temperature and was added sodium triacetoxyborohydride (0.49 g, 2.30 mmol) under N$_2$ atmosphere. The resulting mixture was stirred at rt for 20 h. To the reaction mixture was added saturated aq NaHCO$_3$ solution and the mixture was stirred for 20 minutes. The mixture was concentrated, and the residue was diluted with ethyl acetate and saturated aq NaHCO$_3$ solution. The organic layer was separated, washed with brine, dried over MgSO$_4$ and concentrated. The residue was purified by flash chromatography on silica gel (ISCO. condition: 24 g column; eluents: 0-25% of ethyl acetate in CH$_2$Cl$_2$, gradient over 40 minutes) to obtain the desired product as colorless oil (0.47, 63%). $^1$H NMR (CDCl$_3$): δ 7.55-7.29 (m, 7H), 7.17-7.00 (m, 8H), 4.70-4.63 (m, 2H), 4.43-4.36 (m, 2H), 3.82 (s, 2H), 3.77 (s, 2H); MS (ESI): [M+H]$^+$=524.9.

D) 3-((3,5-Dichloro-N-(4-fluorobenzyl)-2-hydroxyphenylsulfonamido)methyl)-N-(3,5-dichlorobenzyl)-N-(4-fluorobenzyl)benzamide To a solution of N-(3,5-dichlorobenzyl)-N-(4-fluorobenzyl)-3-((4-fluorobenzylamino)methyl)benzamide (70 mg, 0.13 mmol) in THF (3 mL) were added 3,5-dichloro-2-hydroxybenzenesulfonyl chloride (42 mg, 0.16 mmol) and Et$_3$N (0.02 mL, 0.13 mmol). The resulting mixture was stirred at rt for 2 h, concentrated and the residue was dissolved in MeOH and purified by preparative HPLC to give the desired product as a white solid (51 mg, 51%). $^1$H NMR (CD$_3$OD): δ 7.71 (s, 7.66 (d, J=4.0 Hz, 1H), 7.34-7.07 (m, 13H), 6.81 (t, J=8.0 Hz, 2H), 4.75-4.65 (m, 2H), 4.54 (s, 2H), 4.43-4.40 (m, 4H); MS (ESI): [M+H]$^+$=751.0.

Example 96

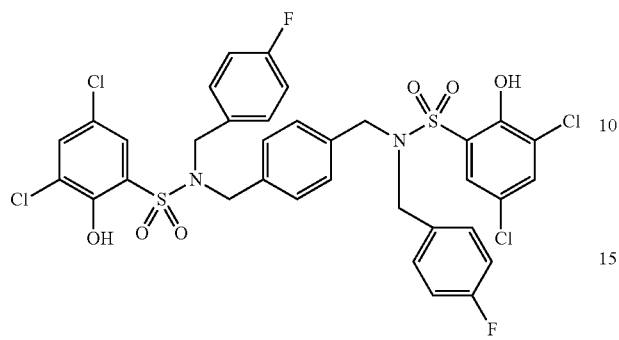

N-(4-Fluoro-benzyl)-N-(4-{[(4-fluoro-benzyl)-(3,5-dichloro-2-hydroxybenzene)sulfonyl-amino]-methyl}-benzyl)-3,5-dichloro-2-hydroxybenzene-sulfonamide

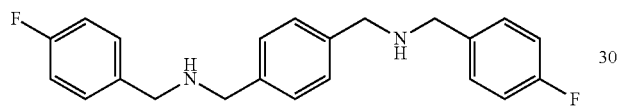

A) (4-Fluoro-benzyl)-{4-[(4-fluoro-benzylamino)-methyl]-benzyl}-amine

To a solution of 4-fluorobenzaldehyde (2.482 g, 20.00 mmol) in a mixed solvent (20 mL of methylene chloride nd 10 mL of i-propanol) at rt, was added 1,4-phenylenedimethanamine (1.362 g, 10 mmol, Aldrich). The reaction mixture was stirred at rt for 5 h. To this mixture, sodium borohydride (0.567 g, 15.0 mmol, 1.5 eq) was added, and it was stirred at rt overnight. The reaction mixture was quenched by adding 10 mL of MeOH and 10 mL of aq. NaHCO$_3$. The reaction mixture was extracted with EtOAc (3×50 mL). The combined organic extracts were dried, concentrated and purified by ISCO system, eluting with CH$_2$Cl$_2$/EtOAc to give the title compound (2.45 g, 66%) as a viscous material, MS (ESI): 353.1 (M+H)$^+$.

B) N-(4-Fluoro-benzyl)-N-(4-{[(4-fluoro-benzyl)-(3,5-dichloro-2-hydroxybenzene)sulfonyl-amino]-methyl}-benzyl)-3,5-dichloro-2-hydroxybenzene-sulfonamide To a solution of (4-fluoro-benzyl)-{4-[(4-fluoro-benzylamino)-methyl]-benzyl}-amine (50 mg, 0.142 mmol) in CH$_2$Cl$_2$ (2 mL) at rt was added 3,5-dichloro-2-hydroxybenzene-1-sulfonyl chloride (74.2 mg, 0.284 mmol) followed by diisopropylethylamine (0.2 mL, 1.42 mmol). The reaction mixture was stirred at rt overnight, concentrated and purified by prep HPLC to obtain the desired product as a white solid (67 mg, 56%). $^1$H NMR (CD$_3$OD) δ 8.99 (br s, 2H), 7.55 (d, 2H, J=2.5 Hz), 7.41 (d, 2H, J=2.5 Hz), 7.07 (m, 4H), 7.01 (s, 4H), 6.96 (t, 4H, J=8.6 Hz), 4.34 (s, 4H), 4.32 (s, 4H); MS (ESI): 800.9 (M−H)$^−$.

Example 97

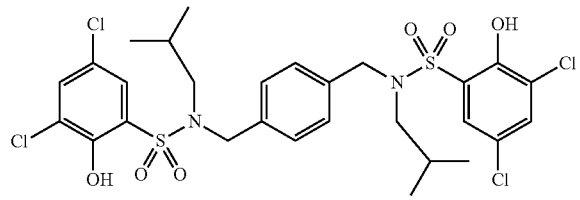 [SMILES: CC(C)CN(Cc1ccc(CN(CC(C)C)S(=O)(=O)c2cc(Cl)cc(Cl)c2O)cc1)S(=O)(=O)c1cc(Cl)cc(Cl)c1O]

N-Isobutyl-N-{4-[(isobutyl-(3,5-dichloro-2-hydroxybenzene)sulfonyl-amino)-methyl]-benzyl}-(3,5-dichloro-2-hydroxybenzene)sulfonamide Same procedure as for Example 96 using the iso-butyraldehyde. $^1$H NMR (DMSO-d6) δ 11.06 (br s, 2H), 7.83 (d, 3.1 Hz), 7.64 (d, 2H, J=3.1 Hz), 7.20 (s, 4H), 4.40 (s, 4H), 2.98 (d, 4H, J=8.1 Hz), 1.54 (m, 2H), 0.65 (d, 12H, J=8.1 Hz); MS (ESI): 698.6 (M+H)$^+$.

Example 98

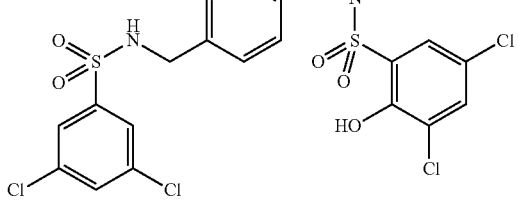

3,5-Dichloro-N-(4-((3,5-dichlorophenylsulfonamido)methyl)benzyl)-N-(4-fluorobenzyl)-2-hydroxybenzenesulfonamide

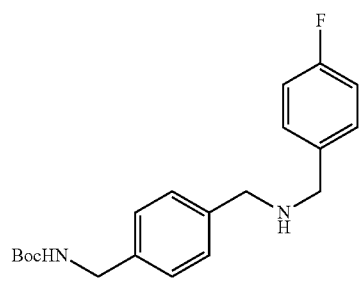 [SMILES: CC(C)(C)OC(=O)NCc1ccc(CNCc2ccc(F)cc2)cc1]

A) tert-Butyl 4-((4-fluorobenzylamino)methyl)benzylcarbamate

To a solution of 4-fluorobenzaldehyde (496 mg, 4.00 mmol) in a mixed solvent of CH$_2$Cl$_2$ (10 mL) and 2-propanol (2 mL) at rt was added tert-butyl 4-(aminomethyl)benzylcarbamate (945 mg, 4.00 mmol, Aldrich). The reaction mixture was stirred at rt overnight. The next morning, sodium borohydride (296 mg, 8.0 mmol) was added, and the mixture was stirred at rt for 2 h. The reaction mixture was quenched by adding 3 mL of MeOH and 3 mL of saturated aq NaHCO$_3$. The mixture was extracted with EtOAc (3×50 mL). The combined organic extracts were dried, concentrated and purified by flash column chromatography on silica gel eluting with CH$_2$Cl$_2$/EtOAc to give the title compound (0.69 g, 48%) as a viscous material. MS (ESI): 345.1 (M+H)$^+$.

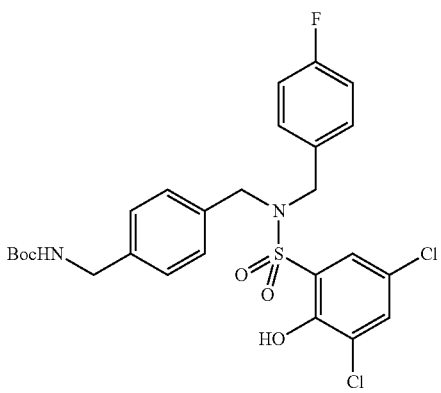 [SMILES: CC(C)(C)OC(=O)NCc1ccc(CN(Cc2ccc(F)cc2)S(=O)(=O)c2cc(Cl)cc(Cl)c2O)cc1]

B) tert-Butyl 4-((3,5-dichloro-N-(4-fluorobenzyl)-2-hydroxyphenylsulfonamido)methyl)benzylcarbamate To a solution of tert-butyl 4-((4-fluorobenzylamino)methyl)benzylcarbamate (654 mg, 1.90 mmol, Aldrich) in CH$_2$Cl$_2$ (5 mL) were added 3,5-dichloro-2-hydroxybenzene-1-sulfonyl chloride (497 mg, 0.50 mmol, Aldrich) and diisopropylethylamine (1.34 mL, 9.50 mmol). The reaction mixture was stirred at rt overnight. The mixture was diluted with methylene chloride (100 mL) and washed with saturated aq sodium bicarbonate solution and brine, dried over MgSO$_4$, concentrated and purified by flash column chromatography on silica gel eluting with CH$_2$Cl$_2$/EtOAc to give the title compound (604 mg, 53%) as a white solid. MS (ESI): m/z 566.9.

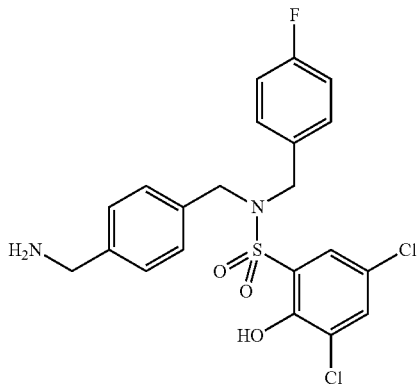 [SMILES: NCc1ccc(CN(Cc2ccc(F)cc2)S(=O)(=O)c2cc(Cl)cc(Cl)c2O)cc1]

C) N-(4-(Aminomethyl)benzyl)-3,5-dichloro-N-(4-fluorobenzyl)-2-hydroxybenzenesulfonamide To a solution of tert-butyl 4-((3,5-dichloro-N-(4-fluorobenzyl)-2-hydroxyphenylsulfonamido)methyl)benzylcarbamate (569 mg, 1.00 mmol) in methylene chloride (9 mL) was added TFA (3 mL). The reaction mixture was stirred at rt for 2 h, and then concentrated. The residue was dissolved in with methylene chloride (100 mL) and washed with saturated aq sodium bicarbonate solution, brine, dried over MgSO$_4$, and concentrated to give the title compound (446 mg, 95%) as a tan solid. MS (ESI): m/z 468.9 (M+H)$^+$.

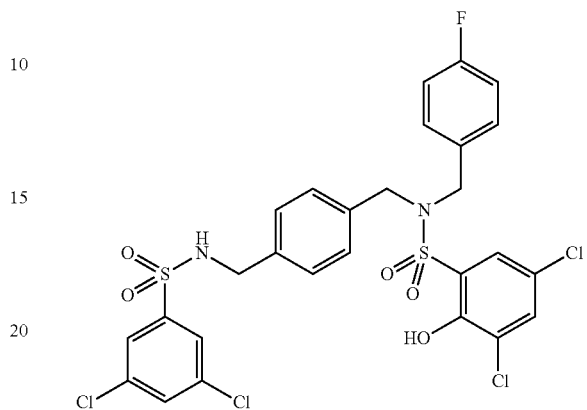

D) 3,5-Dichloro-N-(4-((3,5-dichlorophenylsulfonamido)methyl)benzyl)-N-(4-fluorobenzyl)-2-hydroxybenzenesulfonamide To a solution of N-(4-(aminomethyl)benzyl)-3,5-dichloro-N-(4-fluorobenzyl)-2-hydroxybenzenesulfonamide (47 mg, 0.10 mmol) in CH$_2$Cl$_2$ (1 mL) were added 3,5-dichlorobenzene-1-sulfonyl chloride (25 mg, 0.10 mmol) and diisopropylethylamine (0.17 mL, 1.00 mmol). The reaction mixture was stirred at rt for 2 h and then concentrated. The residue was dissolved in methanol and purified by prep HPLC to give the title compound (19 mg, 27%) as a white solid. $^1$H NMR (DMSO-d6) δ 11.14 (br s, 1H), 8.41 (t, 1H, J=5.1 Hz), 7.84 (d, 1H, J=2.1 Hz), 7.80 (s, 1H), 7.64 (d, 2H, J=2.5 Hz), 7.52 (d, 1H, J=2.1 Hz), 7.11-6.98 (m, 7H), 4.39 (s, 2H), 4.34 (s, 2H), 4.03 (d, 2H, J=3.1 Hz); MS (ESI): 678.7 (M+H)$^+$.

Example 99

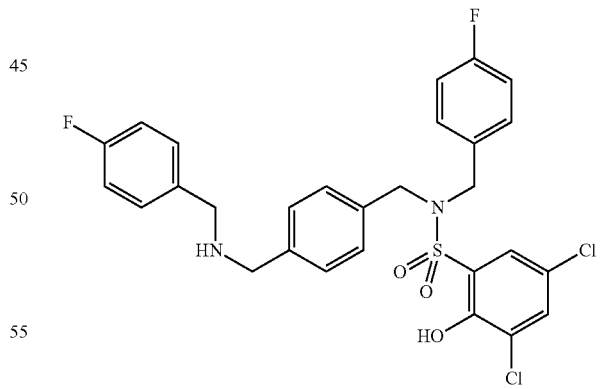

3,5-Dichloro-N-(4-((3,5-dichloro-N-(4-fluorobenzyl)phenylsulfonamido)methyl)benzyl)-N-(4-fluorobenzyl-2-hydroxybenzenesulfonamide

A) 3,5-Dichloro-N-(4-fluorobenzyl)-N-(4-((4-fluorobenzylamino)methyl)benzyl)-2-hydroxybenzenesulfonamide To a solution of N-(4-(aminomethyl)benzyl)-3,5-dichloro-N-(4-fluorobenzyl)-2-hydroxybenzenesulfonamide (235 mg, 0.50 mmol) in a mixed solvent (10 mL of CH$_2$Cl$_2$ and 2 mL of i-propanol) at rt was added 4-fluorobenzaldehyde (62 mg, 0.50 mmol). The reaction mixture was stirred at rt overnight. The next morning, sodium borohydride (37 mg, 1.00 mmol) was added, and the mixture was stirred at rt for 2 h. The reaction mixture was quenched by adding 3 mL of MeOH and 3 ml of saturated aq NaHCO$_3$. The reaction mixture was extracted with EtOAc (3×50 mL). The combined organic extracts were dried, concentrated and purified by prep HPLC to give the title compound (164 mg, 57%) as a white solid. MS (ESI): 577.0 (M+H)$^+$.

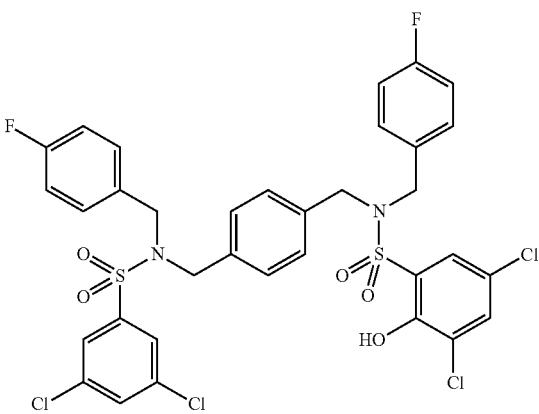 [SMILES: O=S(=O)(c1cc(Cl)cc(Cl)c1)N(Cc1ccc(F)cc1)Cc1ccc(CN(Cc2ccc(F)cc2)S(=O)(=O)c2cc(Cl)cc(Cl)c2O)cc1]

B) 3,5-Dichloro-N-(4-((3,5-dichloro-N-(4-fluorobenzyl)phenylsulfonamido)methyl)benzyl)-N-(4-fluorobenzyl)-2-hydroxybenzenesulfonamide To a solution of 3,5-dichloro-N-(4-fluorobenzyl)-N-(4-((4-fluorobenzylamino)methyl)benzyl)-2-hydroxybenzenesulfonamide (47 mg, 0.10 mmol) in CH$_2$Cl$_2$ (1 mL) were added 3,5-dichlorobenzene-1-sulfonyl chloride (25 mg, 0.10 mmol) and diisopropylethylamine (0.042 mL, 0.30 mmol). The reaction mixture was stirred at rt for 2 h, and concentrated. The residue was dissolved in methanol and purified by prep HPLC to give the title compound (9.9 mg, 12%) as a white solid. $^1$H NMR (DMSO-d6) δ 11.17 (br s, 1H), 7.96 (t, 1H, J=5.1 Hz), 7.84 (d, 1H, J=2.1 Hz), 7.76 (d, 2H, J=2.5 Hz), 7.57 (d, 1H, J=2.1 Hz), 7.18-6.97 (m, 12H), 4.40 (s, 2H), 4.37 (s, 2H), 4.35 (s, 2H), 4.34 (s, 2H); MS (ESI) 786.8 (M+H)$^+$.

Example 100

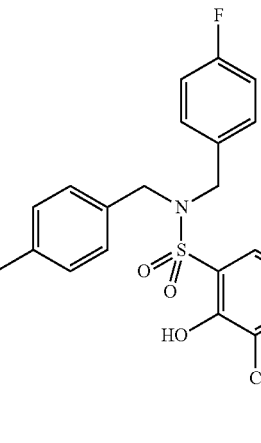

N-(4-((3,5-Dichloro-N-(4-fluorobenzyl)-2-hydroxyphenylsulfonamido)methyl)benzyl)-N-(4-fluorobenzyl)-6-(trifluoromethyl)pyridine-3-sulfonamide To a solution of 3,5-dichloro-N-(4-fluorobenzyl)-N-(4-((4-fluorobenzylamino)methyl)benzyl)-2-hydroxybenzenesulfonamide (47 mg, 0.10 mmol) in CH$_2$Cl$_2$ (1 mL) were added 6-(trifluoromethyl)pyridine-3-sulfonyl chloride (25 mg, 0.10 mmol, Aldrich) and diisopropylethylamine (0.042 mL, 0.30 mmol). The reaction mixture was stirred at rt for 2 h, and then concentrated. The residue was dissolved in methanol and purified by prep HPLC to give the title compound (24.0 mg, 57%) as a white solid. $^1$H NMR (DMSO-d6) δ 11.17 (br s, 1H), 9.15 (s, 1H), 8.50 (d, 1H, J=8.1 Hz), 8.11 (d, 1H, J=8.1 Hz), 7.83 (d, 2H, J=2.3 Hz), 7.56 (d, 1H, J=2.3 Hz), 7.17-6.97 (m, 12H), 4.40 (s, 2H), 4.39 (s, 2H), 4.37 (s, 2H), 4.34 (s, 2H); MS (ESI): 786.1 (M+H)$^+$.

Examples 101-102

The following examples were prepared using similar procedures to those noted above:

| Ex. No. | Structure | Name | HPLC t$_R$ (minute)* | LCMS |
|---|---|---|---|---|
| 101 | 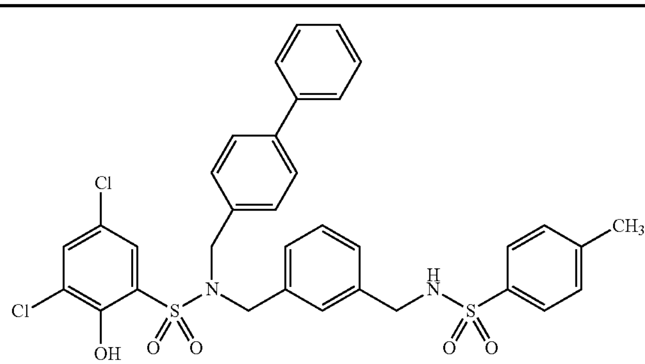 | N-(Biphenyl-4-ylmethyl)-3,5-dichloro-2-hydroxy-N-(3-((4-methylphenylsulfonamido)methyl)benzyl)benzenesulfonamide | 4.22 | (M − H)$^-$ 679.1 |

| Ex. No. | Structure | Name | HPLC $t_R$ (minute)* | LCMS |
|---|---|---|---|---|
| 102 | 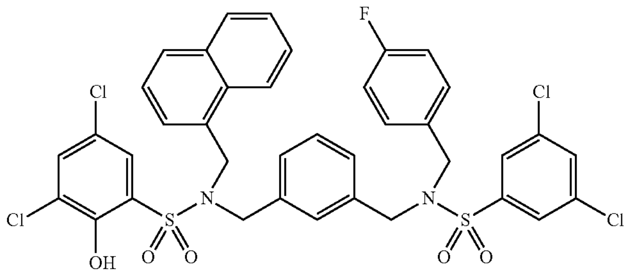 [SMILES: O=S(=O)(c1cc(Cl)cc(Cl)c1)N(Cc1ccc(F)cc1)Cc1cccc(CN(Cc2cccc3ccccc23)S(=O)(=O)c2cc(Cl)cc(Cl)c2O)c1] | 3,5-Dichloro-N-(3-((3,5-dichloro-N-(4-fluorobenzyl)phenylsulfonamido)methyl)benzyl)-2-hydroxy-N-(naphthalen-1-ylmethyl)-benzenesulfonamide | 4.84 | (M − H)⁻ 817 |

Example 105

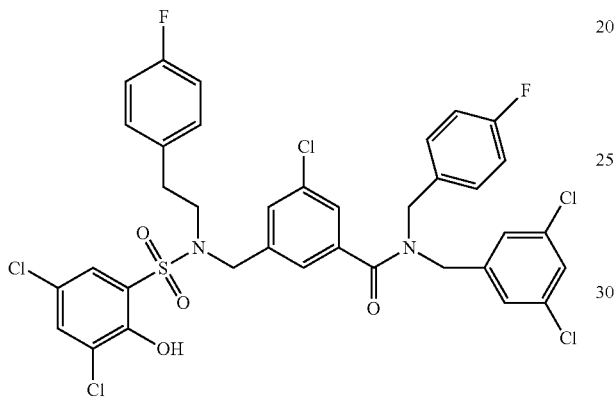

3-Chloro-5-((3,5-dichloro-N-(4-fluorophenethyl)-2-hydroxyphenylsulfonamido)methyl)-N-(3,5-dichlorobenzyl)-N-(4-fluorobenzyl)benzamide The compound was prepared using similar procedures to those described for Examples 95 and 24. MS (ESI): 779.2 (M−H)⁻.

Example 106

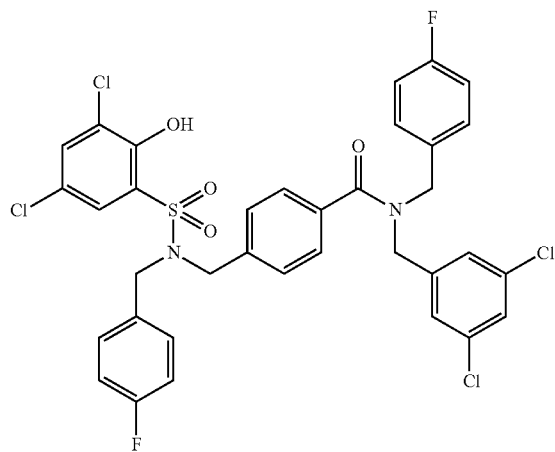 [SMILES: O=C(c1ccc(CN(Cc2ccc(F)cc2)S(=O)(=O)c2cc(Cl)cc(Cl)c2O)cc1)N(Cc1ccc(F)cc1)Cc1cc(Cl)cc(Cl)c1]

4-((3,5-Dichloro-N-(4-fluorobenzyl)-2-hydroxyphenylsulfonamido)methyl)-N-(3,5-dichlorobenzyl)-N-(4-fluorobenzyl)benzamide

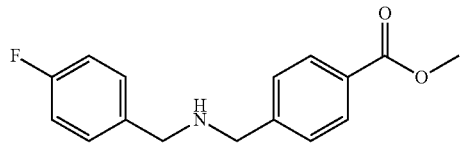 [SMILES: COC(=O)c1ccc(CNCc2ccc(F)cc2)cc1]

A) Methyl 4-((4-fluorobenzylamino)methyl)benzoate

To a solution of 4-fluorobenzaldehyde (2.482 g, 20.00 mmol, Aldrich) in a mixed solvent (20 mL of methylene chloride and 20 mL of i-propanol) at room temperature was added a mixture of 4-(methoxycarbonyl)phenyl)methanaminium chloride (4.03 g, 20 mmol, Aldrich) with triethylamine (2.79 mL, 20 mmol). The reaction mixture was stirred at rt for 1 h, treated with sodium triacetoxyhydroborate (6.36 g, 30.0 mmol, 1.5 eq) and stirred at room temperature overnight. The reaction was quenched by the addition of 10 mL of MeOH and 10 mL of saturated aq. NaHCO₃ solution. The resulting mixture was extracted with EtOAc (3×100 mL). The combined organic extracts were dried over MgSO₄ and concentrated. The residue was purified by flash column chromatography (ISCO system, eluting with CH₂Cl₂/EtOAc with 10% MeOH) to give the desired compound (3.88 g, 71%) as a white solid. ¹H NMR (CDCl₃) δ 7.99 (d, 2H, J=7.7 Hz), 7.39 (d, 2H, J=7.7 Hz), 7.28 (m, 2H), 7.00 (t, 2H, J=8.3 Hz), 5.53 (br, 1H), 3.90 (s, 3H), 3.85 (s, 2H), 3.77 (s, 2H). MS (ESI): 274.1 (M+H)⁺.

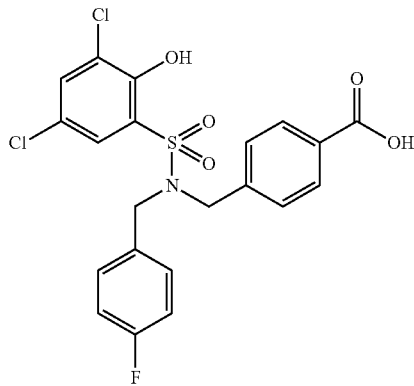 [SMILES: O=C(O)c1ccc(CN(Cc2ccc(F)cc2)S(=O)(=O)c2cc(Cl)cc(Cl)c2O)cc1]

B) 4-#3,5-Dichloro-N-(4-fluorobenzyl)-2-hydroxyphenylsulfonamido)methyl)-benzoic acid To a solution of methyl 4-((4-fluorobenzylamino)methyl) benzoate (1.367 g, 5 mmol) in THF (20 mL) at rt, was added 3,5-dichloro-2-hydroxybenzene-1-sulfonyl chloride (1.438 g, 5.50 mmol) followed by the addition of triethylamine (2.09 mL, 15.0 mmol). The reaction mixture was stirred at room temperature for 2 h. A solid formed, which was removed by filtration. The filtrate was concentrated and dissolved in a mixed solvent (15 mL of MeOH and 15 mL of THF). To this mixture was added 2 N NaOH (25 mL). The reaction mixture was stirred at room temperature for 3 h, cooled to 0° C. and neutralized with 1 N aq. HCl solution to pH 3-4. The solid that formed was collected by filtration and dried under vacuum to give a light yellow solid as the desired product (1.5 g, 62%). $^1$H NMR (CD$_3$OD) δ 7.91 (d, 2H, J=8.3 Hz), 7.39 (d, 2H, J=8.3 Hz), 7.34 (m, 3H), 7.24 (d, 1H, J=2.6 Hz), 7.04 (t, 2H, J=8.8 Hz), 4.13 (s, 2H), 4.08 (s, 2H). MS (ESI): 483.8 (M+H)$^+$.

C) 4-((3,5-Dichloro-N-(4-fluorobenzyl)-2-hydroxyphenylsulfonamido)methyl)-N-(3,5-dichlorobenzyl)-N-(4-fluorobenzyl)benzamide To a solution of 4-((3,5-dichloro-N-(4-fluorobenzyl)-2-hydroxyphenylsulfonamido)methyl)benzoic acid (48 mg, 0.10 mol) in DMF, were added. N-(3,5-dichlorobenzyl)-1-(4-fluorophenyl)methanamine (28 mg, 0.1 mmol), HATU (48 mg, 0.15 mmol), and DIPEA (0.052 mL, 0.30 mmol). The reaction mixture was stirred at room temperature for 2 h and purified by preparative HPLC (Column YMC S5 ODS C18 20×100 mm; Solvent A=10% MeOH-90% H$_2$O with 0.1% TFA; Solvent B=10% H$_2$O-90% MeOH with 0.1% TFA). The desired fractions were combined, concentrated and lyophilized to give the title compound (40 mg, 51%) as a white solid. $^1$H NMR (CD$_3$OD) δ 7.71 (d, 1H, J=2.5 Hz), 7.54 (d, 1H, J=2.5 Hz), 7.37-7.05 (m, 13H), 6.85 (t, 2H, J=8.8 Hz), 4.70 (br, 1H), 4.64 (br, 1H), 4.54 (s, 2H), 4.50 (s, 2H), 4.46 (br, 1H), 4.42 (br, 1H). MS (ESI): 750.8 (M+H)$^+$.

Examples 107-165

The following examples were prepared using similar procedures to those described for Example 106:

| Ex. No. | Structure | Name | HPLC t$_R$ (minute)* | LCMS |
|---|---|---|---|---|
| 107 | 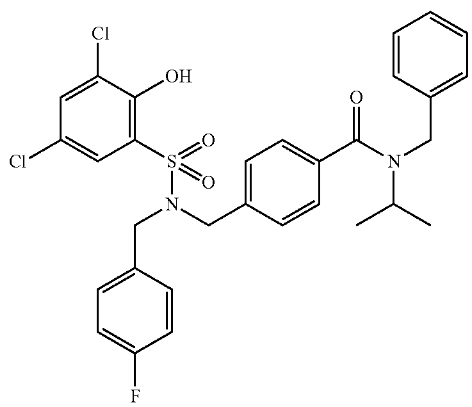 [SMILES: CC(C)N(Cc1ccccc1)C(=O)c1ccc(CN(Cc2ccc(F)cc2)S(=O)(=O)c2cc(Cl)cc(Cl)c2O)cc1] | N-Benzyl-4-((3,5-dichloro-N-(4-fluorobenzyl)-2-hydroxyphenylsulfonamido)methyl)-N-isopropylbenzamide | A 4.07 | (M + H)$^+$ 614.9 |
| 108 | 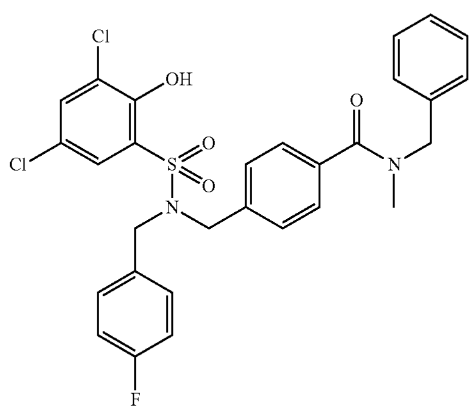 [SMILES: CN(Cc1ccccc1)C(=O)c1ccc(CN(Cc2ccc(F)cc2)S(=O)(=O)c2cc(Cl)cc(Cl)c2O)cc1] | N-Benzyl-4-((3,5-dichloro-N-(4-fluorobenzyl)-2-hydroxyphenylsulfonamido)methyl)-N-methylbenzamide | A 3.94 | (M + H)$^+$ 586.9 |

| Ex. No. | Structure | Name | HPLC $t_R$ (minute)* | LCMS |
|---|---|---|---|---|
| 109 | 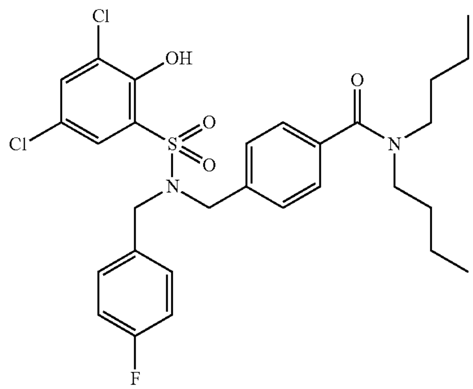 [SMILES: CCCCN(CCCC)C(=O)c1ccc(CN(Cc2ccc(F)cc2)S(=O)(=O)c2cc(Cl)cc(Cl)c2O)cc1] | N,N-Dibutyl-4-((3,5-dichloro-N-(4-fluorobenzyl)-2-hydroxyphenylsulfonamido)methyl)-benzamide | A 4.07 | $(M + H)^+$ 594.9 |
| 110 | 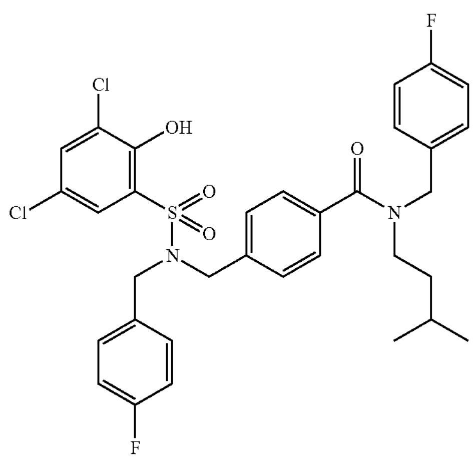 [SMILES: CC(C)CCN(Cc1ccc(F)cc1)C(=O)c1ccc(CN(Cc2ccc(F)cc2)S(=O)(=O)c2cc(Cl)cc(Cl)c2O)cc1] | 4-((3,5-Dichloro-N-(4-fluorobenzyl)-2-hydroxyphenylsulfonamido)methyl)-N-(4-fluorobenzyl)-N-isopentylbenzamide | B 22.579 | $(M - H)^-$ 660 |
| 111 | 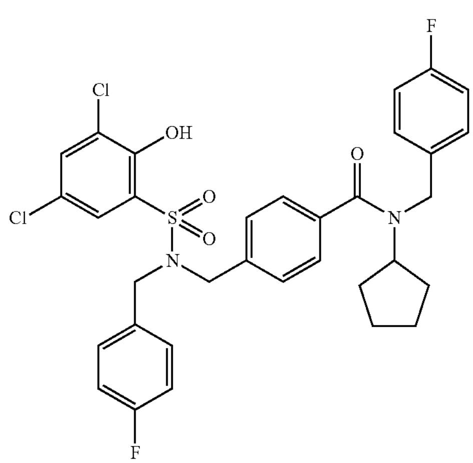 [SMILES: O=C(c1ccc(CN(Cc2ccc(F)cc2)S(=O)(=O)c2cc(Cl)cc(Cl)c2O)cc1)N(Cc1ccc(F)cc1)C1CCCC1] | N-Cyclopentyl-4-((3,5-dichloro-N-(4-fluorobenzyl)-2-hydroxyphenylsulfonamido)methyl)-N-(4-fluorobenzyl)benzamide | B 22.461 | $(M - H)^-$ 657 |

-continued

| Ex. No. | Structure | Name | HPLC t$_R$ (minute)* | LCMS |
|---|---|---|---|---|
| 112 | 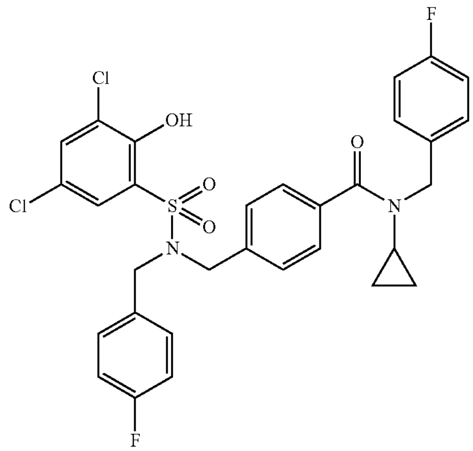 [SMILES: O=C(c1ccc(CN(Cc2ccc(F)cc2)S(=O)(=O)c2cc(Cl)cc(Cl)c2O)cc1)N(Cc1ccc(F)cc1)C1CC1] | N-Cyclopropyl-4-((3,5-dichloro-N-(4-fluorobenzyl)-2-hydroxyphenylsulfonamido)methyl)-N-(4-fluorobenzyl)benzamide | B 21.173 | (M − H)⁻ 630 |
| 113 | 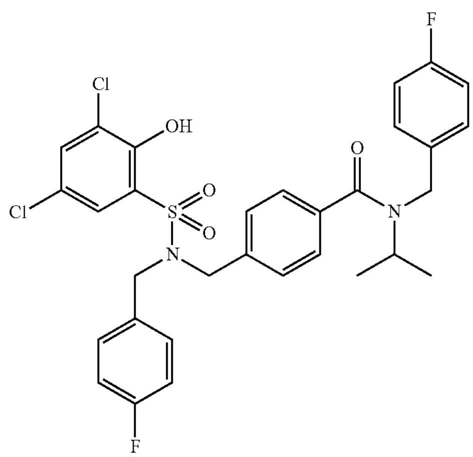 [SMILES: CC(C)N(Cc1ccc(F)cc1)C(=O)c1ccc(CN(Cc2ccc(F)cc2)S(=O)(=O)c2cc(Cl)cc(Cl)c2O)cc1] | 4-((3,5-Dichloro-N-(4-fluorobenzyl)-2-hydroxyphenylsulfonamido)methyl)-N-(4-fluorobenzyl)-N-isopropylbenzamide | B 21.315 | (M − H)⁻ 633 |
| 114 | 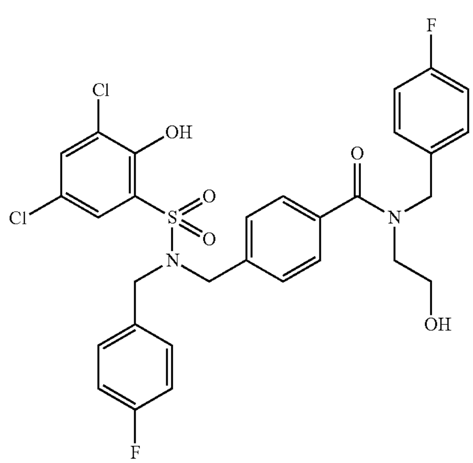 [SMILES: O=C(c1ccc(CN(Cc2ccc(F)cc2)S(=O)(=O)c2cc(Cl)cc(Cl)c2O)cc1)N(CCO)Cc1ccc(F)cc1] | 4-((3,5-Dichloro-N-(4-fluorobenzyl)-2-hydroxyphenylsulfonamido)methyl)-N-(4-fluorobenzyl)-N-(2-hydroxyethyl)benzamide | B 18.546 | (M − H)⁻ 635 |

| Ex. No. | Structure | Name | HPLC t$_R$ (minute)* | LCMS |
|---|---|---|---|---|
| 115 | 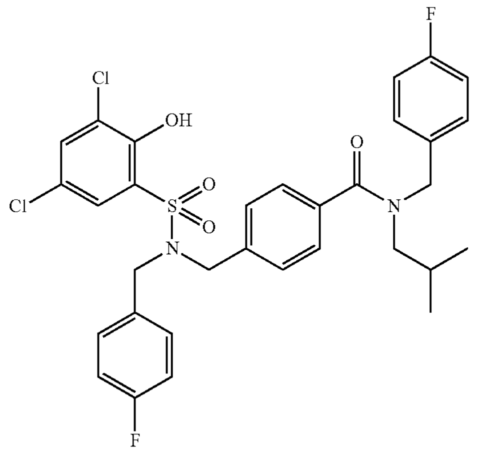 [SMILES: CC(C)CN(Cc1ccc(F)cc1)C(=O)c1ccc(CN(Cc2ccc(F)cc2)S(=O)(=O)c2cc(Cl)cc(Cl)c2O)cc1] | 4-((3,5-Dichloro-N-(4-fluorobenzyl)-2-hydroxyphenylsulfonamido)methyl)-N-(4-fluorobenzyl)-N-isobutylbenzamide | B 22.288 | (M − H)⁻ 646.5 |
| 116 | 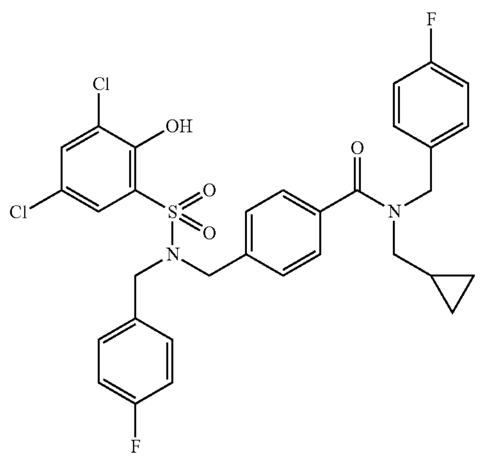 [SMILES: O=C(c1ccc(CN(Cc2ccc(F)cc2)S(=O)(=O)c2cc(Cl)cc(Cl)c2O)cc1)N(Cc1ccc(F)cc1)CC1CC1] | N-(Cyclopropylmethyl)-4-((3,5-dichloro-N-(4-fluorobenzyl)-2-hydroxyphenylsulfonamido)methyl)-N-(4-fluorobenzyl)benzamide | B 21.257 | (M − H)⁻ 644.5 |
| 117 | 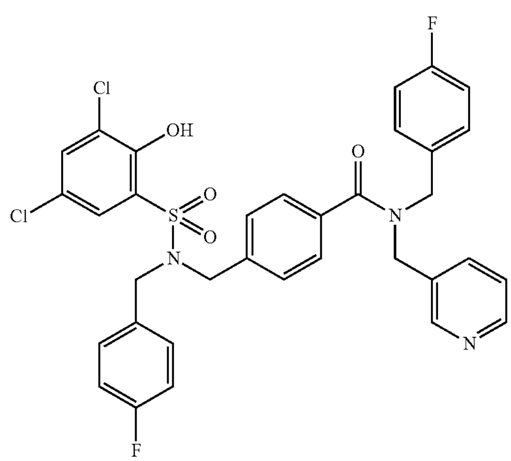 [SMILES: O=C(c1ccc(CN(Cc2ccc(F)cc2)S(=O)(=O)c2cc(Cl)cc(Cl)c2O)cc1)N(Cc1ccc(F)cc1)Cc1cccnc1] | 4-((3,5-Dichloro-N-(4-fluorobenzyl)-2-hydroxyphenylsulfonamido)methyl)-N-(4-fluorobenzyl)-N-(pyridin-3-ylmethyl)benzamide | B 21.361 | (M + H)⁺ 683.6 |

| Ex. No. | Structure | Name | HPLC t$_R$ (minute)* | LCMS |
|---|---|---|---|---|
| 118 | 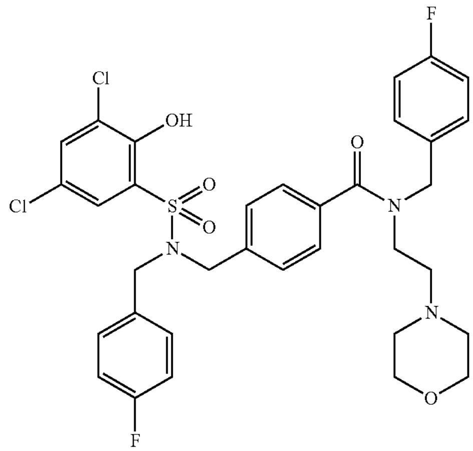 [SMILES: O=C(c1ccc(CN(Cc2ccc(F)cc2)S(=O)(=O)c2cc(Cl)cc(Cl)c2O)cc1)N(CCN1CCOCC1)Cc1ccc(F)cc1] | 4-((3,5-Dichloro-N-(4-fluorobenzyl)-2-hydroxyphenylsulfonamido)methyl)-N-(4-fluorobenzyl)-N-(2-morpholinoethyl)benzamide | B 16.564 | (M − H)⁻ 703.6 |
| 119 | 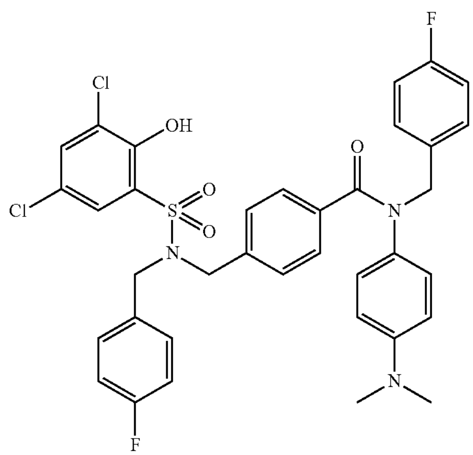 [SMILES: CN(C)c1ccc(N(Cc2ccc(F)cc2)C(=O)c2ccc(CN(Cc3ccc(F)cc3)S(=O)(=O)c3cc(Cl)cc(Cl)c3O)cc2)cc1] | 4-((3,5-Dichloro-N-(4-fluorobenzyl)-2-hydroxyphenylsulfonamido)methyl)-N-(4-(dimethylamino)phenyl)-N-(4-fluorobenzyl)benzamide | B 21.852 | (M − H)⁻ 709.6 |
| 120 | 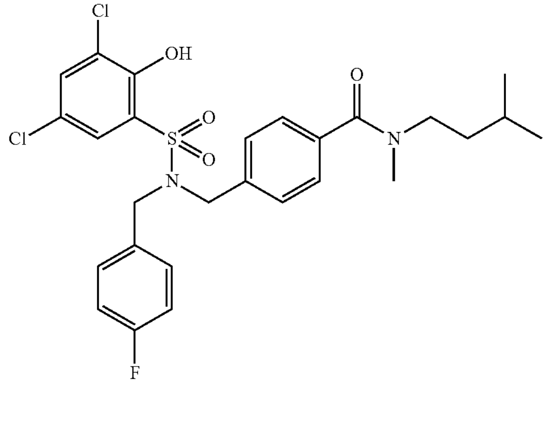 [SMILES: CC(C)CCN(C)C(=O)c1ccc(CN(Cc2ccc(F)cc2)S(=O)(=O)c2cc(Cl)cc(Cl)c2O)cc1] | 4-((3,5-Dichloro-N-(4-fluorobenzyl)-2-hydroxyphenylsulfonamido)methyl)-N-isopentyl-N-methylbenzamide | C 3.385 | (M − H)⁻ 566.8 |

-continued

| Ex. No. | Structure | Name | HPLC t$_R$ (minute)* | LCMS |
|---|---|---|---|---|
| 121 | 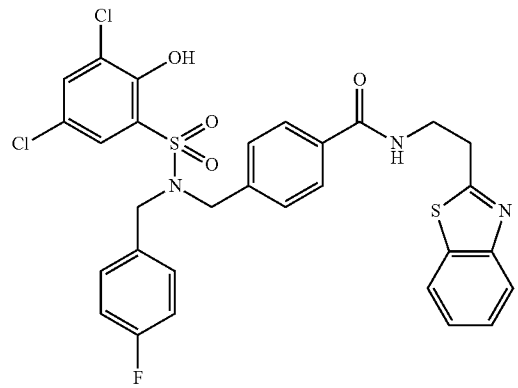 [SMILES: O=C(NCCc1nc2ccccc2s1)c1ccc(CN(Cc2ccc(F)cc2)S(=O)(=O)c2cc(Cl)cc(Cl)c2O)cc1] | N-(2-(Benzo[d]thiazol-2-yl)ethyl)-4-((3,5-dichloro-N-(4-fluorobenzyl)-2-hydroxyphenylsulfonamido)methyl)-benzamide | C 3.282 | (M − H)⁻ 643.7 |
| 122 | 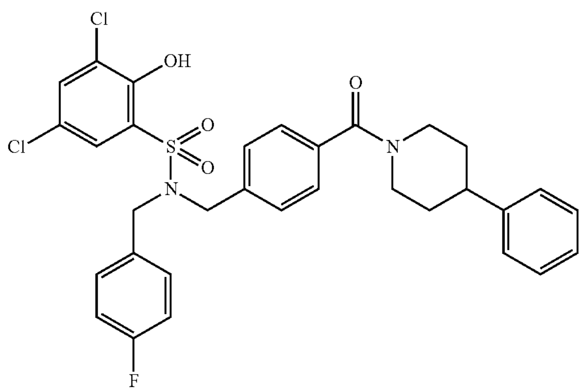 | 3,5-Dichloro-N-(4-fluorobenzyl)-2-hydroxy-N-(4-(4-phenylpiperidine-1-carbonyl)benzyl)benzenesulfonamide | C 3.507 | (M − H)⁻ 626.8 |
| 123 | 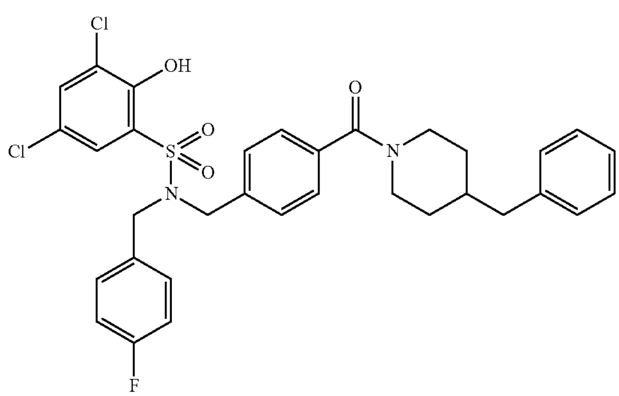 [SMILES: O=C(c1ccc(CN(Cc2ccc(F)cc2)S(=O)(=O)c2cc(Cl)cc(Cl)c2O)cc1)N1CCC(Cc2ccccc2)CC1] | N-(4-(4-Benzylpiperidine-1-carbonyl)benzyl)-3,5-dichloro-N-(4-fluorobenzyl)-2-hydroxybenzenesulfonamide | C 3.675 | (M − H)⁻ 640.8 |
| 124 | 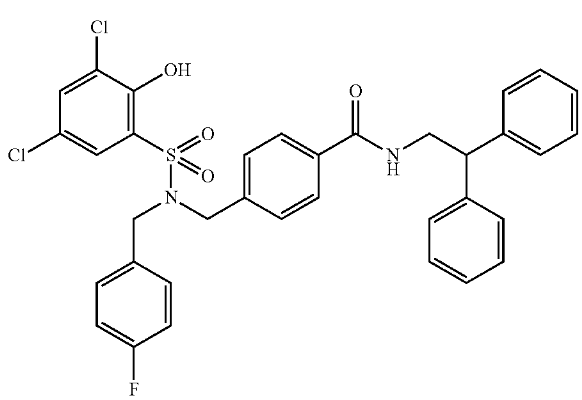 [SMILES: O=C(NCC(c1ccccc1)c1ccccc1)c1ccc(CN(Cc2ccc(F)cc2)S(=O)(=O)c2cc(Cl)cc(Cl)c2O)cc1] | 4-((3,5-Dichloro-N-(4-fluorobenzyl)-2-hydroxyphenylsulfonamido)methyl)-N-(2,2-diphenylethyl)benzamide | C 3.587 | (M − H)⁻ 662.8 |

| Ex. No. | Structure | Name | HPLC $t_R$ (minute)* | LCMS |
|---|---|---|---|---|
| 125 | 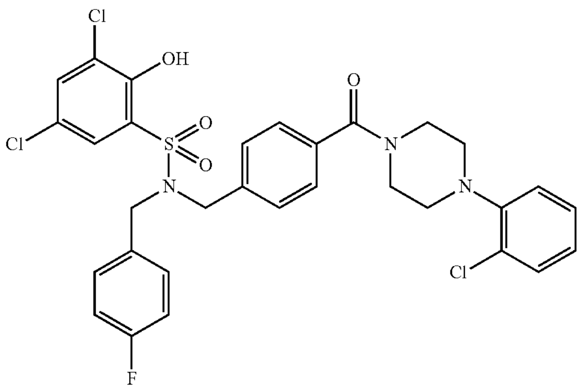 [SMILES: O=C(c1ccc(CN(Cc2ccc(F)cc2)S(=O)(=O)c2cc(Cl)cc(Cl)c2O)cc1)N1CCN(c2ccccc2Cl)CC1] | 3,5-Dichloro-N-(4-(4-(2-chlorophenyl)piperazine-1-carbonyl)benzyl)-N-(4-fluorobenzyl)-2-hydroxybenzenesulfonamide | C 3.588 | (M − H)⁻ 661.7 |
| 126 | 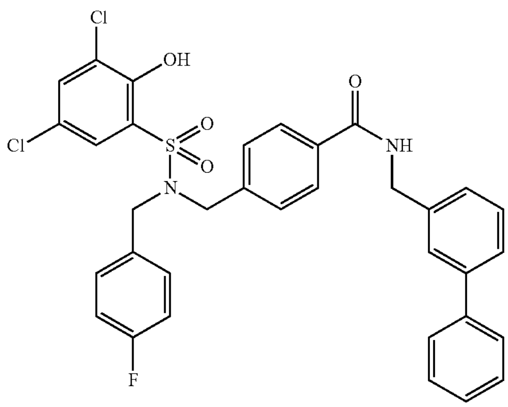 [SMILES: O=C(NCc1cccc(-c2ccccc2)c1)c1ccc(CN(Cc2ccc(F)cc2)S(=O)(=O)c2cc(Cl)cc(Cl)c2O)cc1] | N-(Biphenyl-3-ylmethyl)-4-((3,5-dichloro-N-(4-fluorobenzyl)-2-hydroxyphenylsulfonamido)methyl)-benzamide | C 3.598 | (M − H)⁻ 648.8 |
| 127 | 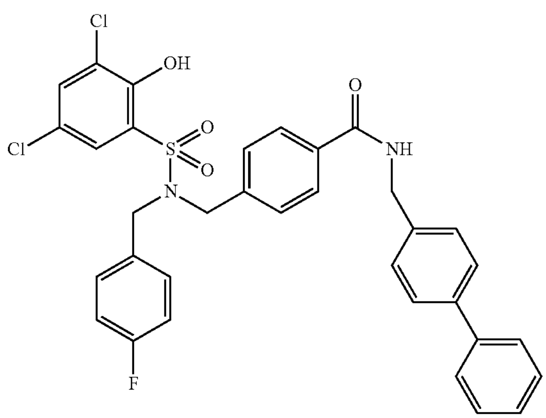 [SMILES: O=C(NCc1ccc(-c2ccccc2)cc1)c1ccc(CN(Cc2ccc(F)cc2)S(=O)(=O)c2cc(Cl)cc(Cl)c2O)cc1] | N-(Biphenyl-4-ylmethyl)-4-((3,5-dichloro-N-(4-fluorobenzyl)-2-hydroxyphenylsulfonamido)methyl)-benzamide | C 3.593 | (M − H)⁻ 648.8 |
| 128 | 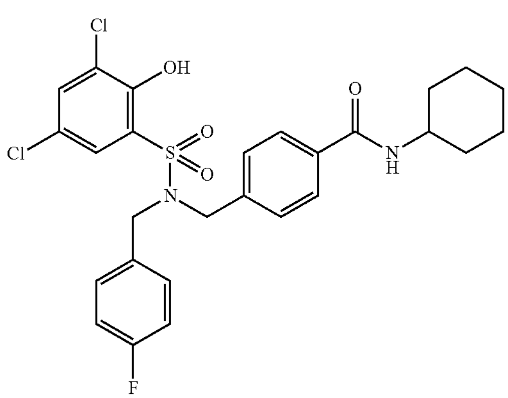 [SMILES: O=C(NC1CCCCC1)c1ccc(CN(Cc2ccc(F)cc2)S(=O)(=O)c2cc(Cl)cc(Cl)c2O)cc1] | N-Cyclohexyl-4-((3,5-dichloro-N-(4-fluorobenzyl)-2-hydroxyphenylsulfonamido)methyl)-benzamide | C 3.252 | (M − H)⁻ 564.8 |

-continued

| Ex. No. | Structure | Name | HPLC t_R (minute)* | LCMS |
|---|---|---|---|---|
| 129 | 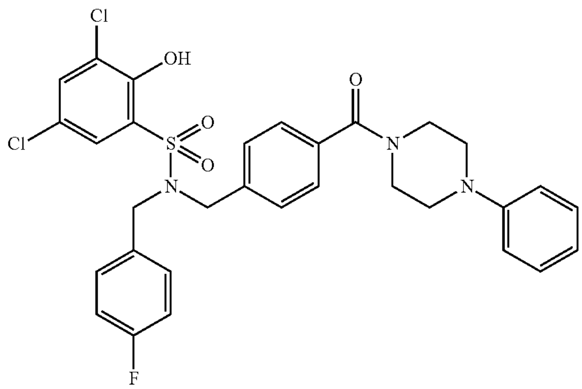 [SMILES: O=C(c1ccc(CN(Cc2ccc(F)cc2)S(=O)(=O)c2cc(Cl)cc(Cl)c2O)cc1)N1CCN(c2ccccc2)CC1] | 3,5-Dichloro-N-(4-fluorobenzyl)-2-hydroxy-N-(4-(4-phenylpiperazine-1-carbonyl)benzyl)benzenesulfonamide | C 3.320 | (M − H)⁻ 627.8 |
| 130 | 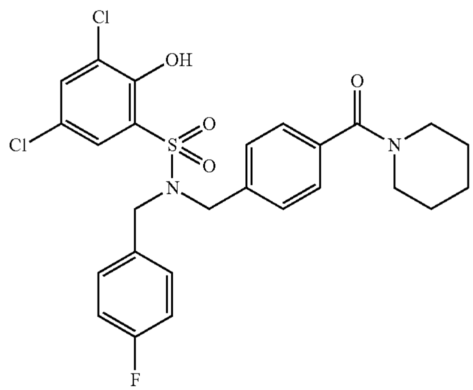 [SMILES: O=C(c1ccc(CN(Cc2ccc(F)cc2)S(=O)(=O)c2cc(Cl)cc(Cl)c2O)cc1)N1CCCCC1] | 3,5-Dichloro-N-(4-fluorobenzyl)-2-hydroxy-N-(4-piperidine-1-carbonyl)benzyl)benzenesulfonamide | C 3.053 | (M − H)⁻ 550.8 |
| 131 | 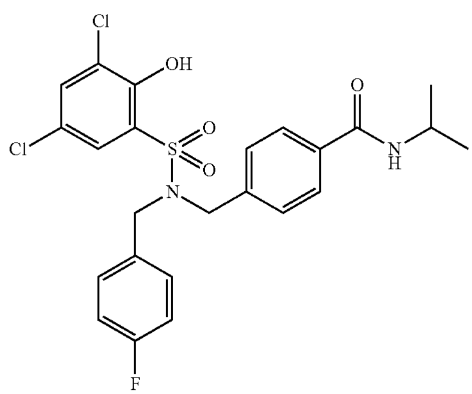 [SMILES: CC(C)NC(=O)c1ccc(CN(Cc2ccc(F)cc2)S(=O)(=O)c2cc(Cl)cc(Cl)c2O)cc1] | 4-((3,5-Dichloro-N-(4-fluorobenzyl)-2-hydroxyphenylsulfonamido)methyl)-N-isopropylbenzamide | C 2.868 | (M − H)⁻ 524.7 |
| 132 | 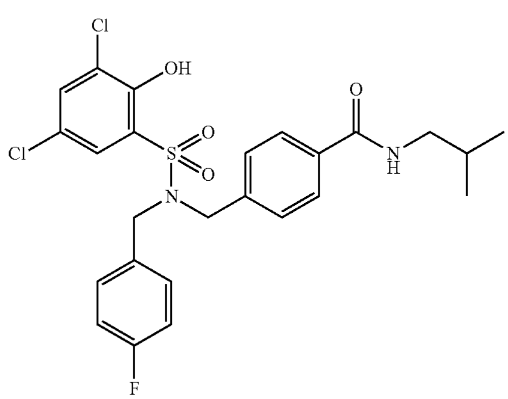 [SMILES: CC(C)CNC(=O)c1ccc(CN(Cc2ccc(F)cc2)S(=O)(=O)c2cc(Cl)cc(Cl)c2O)cc1] | 4-((3,5-Dichloro-N-(4-fluorobenzyl)-2-hydroxyphenylsulfonamido)methyl)-N-isobutylbenzamide | C 3.030 | (M − H)⁻ 538.7 |

| Ex. No. | Structure | Name | HPLC t$_R$ (minute)* | LCMS |
|---|---|---|---|---|
| 133 | 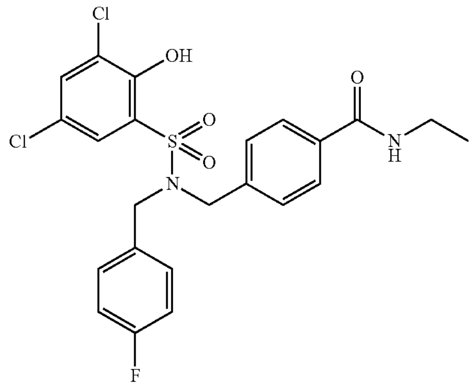 [SMILES: CCNC(=O)c1ccc(CN(Cc2ccc(F)cc2)S(=O)(=O)c2cc(Cl)cc(Cl)c2O)cc1] | 4-((3,5-Dichloro-N-(4-fluorobenzyl)-2-hydroxyphenylsulfonamido)methyl)-N-ethylbenzamide | C 2.687 | (M − H)⁻ 510.7 |
| 134 | 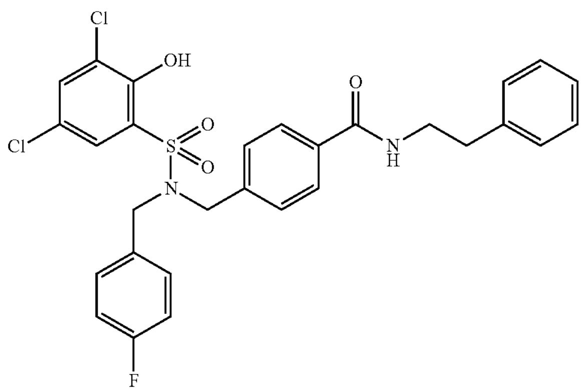 [SMILES: O=C(NCCc1ccccc1)c1ccc(CN(Cc2ccc(F)cc2)S(=O)(=O)c2cc(Cl)cc(Cl)c2O)cc1] | 4-((3,5-Dichloro-N-(4-fluorobenzyl)-2-hydroxyphenylsulfonamido)methyl)-N-phenethylbenzamide | C 3.207 | (M − H)⁻ 586.7 |
| 135 | 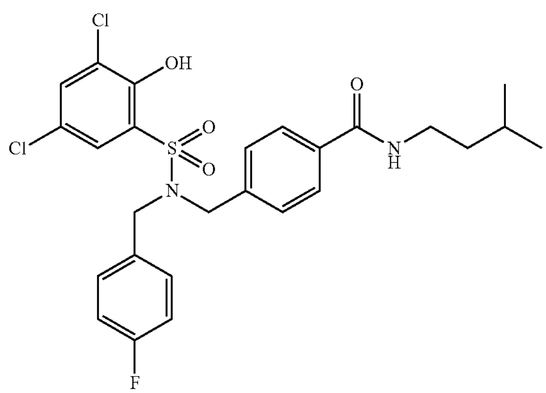 [SMILES: CC(C)CCNC(=O)c1ccc(CN(Cc2ccc(F)cc2)S(=O)(=O)c2cc(Cl)cc(Cl)c2O)cc1] | 4-((3,5-Dichloro-N-(4-fluorobenzyl)-2-hydroxyphenylsulfonamido)methyl)-N-isopentylbenzamide | C 3.227 | (M − H)⁻ 552.7 |
| 136 | 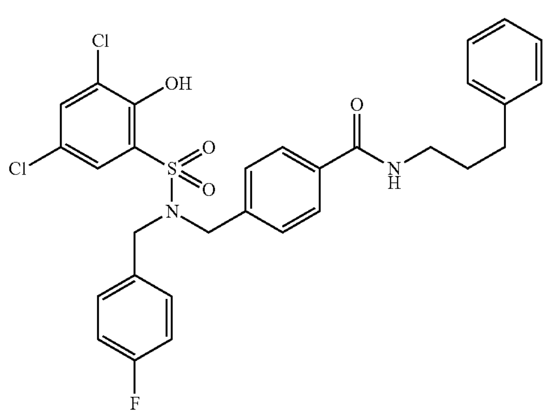 [SMILES: O=C(NCCCc1ccccc1)c1ccc(CN(Cc2ccc(F)cc2)S(=O)(=O)c2cc(Cl)cc(Cl)c2O)cc1] | 4-((3,5-Dichloro-N-(4-fluorobenzyl)-2-hydroxyphenylsulfonamido)methyl)-N-(3-phenylpropyl)benzamide | C 3.350 | (M − H)⁻ 600.7 |

-continued

| Ex. No. | Structure | Name | HPLC t$_R$ (minute)* | LCMS |
|---|---|---|---|---|
| 137 | 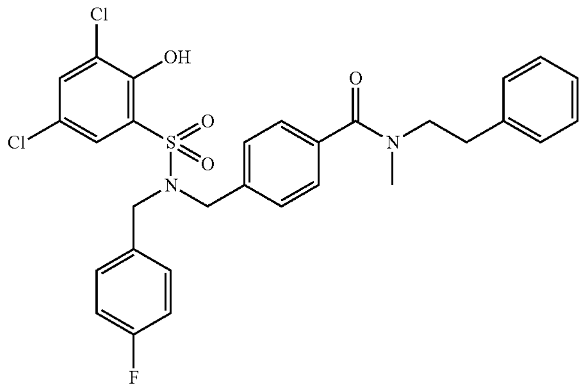 [SMILES: CN(CCc1ccccc1)C(=O)c1ccc(CN(Cc2ccc(F)cc2)S(=O)(=O)c2cc(Cl)cc(Cl)c2O)cc1] | 4-((3,5-Dichloro-N-(4-fluorobenzyl)-2-hydroxyphenylsulfonamido)methyl)-N-methyl-N-phenethylbenzamide | C 3.318 | (M − H)⁻ 600.7 |
| 138 | 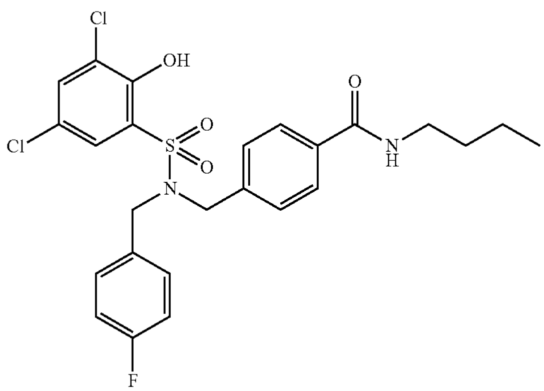 [SMILES: CCCCNC(=O)c1ccc(CN(Cc2ccc(F)cc2)S(=O)(=O)c2cc(Cl)cc(Cl)c2O)cc1] | N-Butyl-4-((3,5-dichloro-N-(4-fluorobenzyl)-2-hydroxyphenylsulfonamido)methyl)-benzamide | C 3.050 | (M − H)⁻ 538.7 |
| 139 | 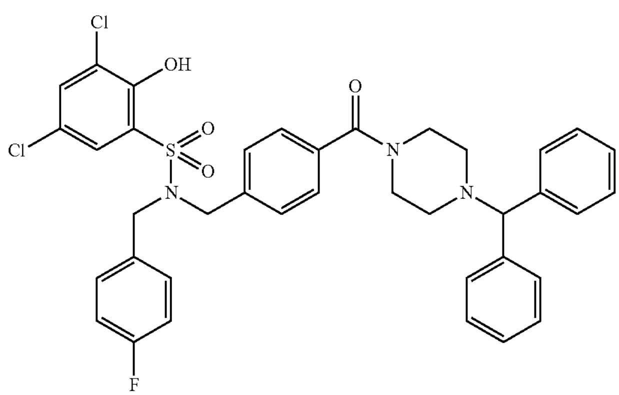 [SMILES: O=C(c1ccc(CN(Cc2ccc(F)cc2)S(=O)(=O)c2cc(Cl)cc(Cl)c2O)cc1)N1CCN(C(c2ccccc2)c2ccccc2)CC1] | N-(4-(4-Benzhydrylpiperazine-1-carbonyl)benzyl)-3,5-dichloro-N-(4-fluorobenzyl)-2-hydroxybenzenesulfonamide | C 3.873 | (M − H)⁻ 717.8 |
| 140 | 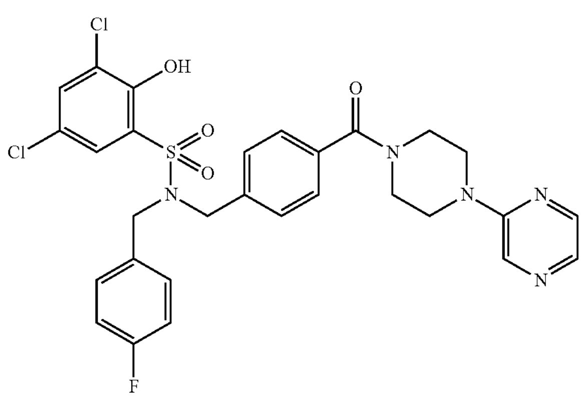 [SMILES: O=C(c1ccc(CN(Cc2ccc(F)cc2)S(=O)(=O)c2cc(Cl)cc(Cl)c2O)cc1)N1CCN(c2cnccn2)CC1] | 3,5-Dichloro-N-(4-fluorobenzyl)-2-hydroxy-N-(4-(4-(pyrazin-2-yl)piperazine-1-carbonyl)benzyl)benzenesulfonamide | C 2.742 | (M − H)⁻ 629.7 |

| Ex. No. | Structure | Name | HPLC $t_R$ (minute)* | LCMS |
|---|---|---|---|---|
| 141 | 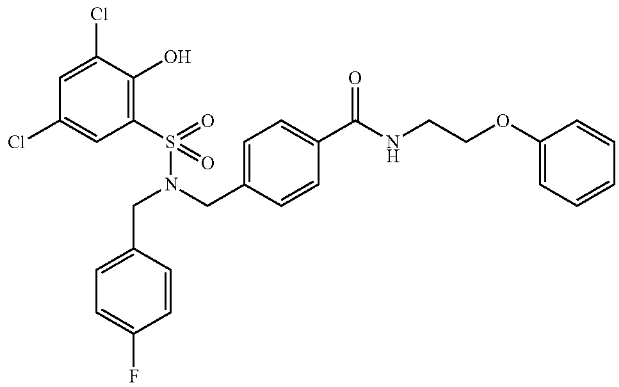 [SMILES: O=C(NCCOc1ccccc1)c1ccc(CN(Cc2ccc(F)cc2)S(=O)(=O)c2cc(Cl)cc(Cl)c2O)cc1] | 4-((3,5-Dichloro-N-(4-fluorobenzyl)-2-hydroxyphenylsulfonamido)methyl)-N-(2-phenoxyethyl)benzamide | C 3.202 | (M − H)⁻ 602.7 |
| 142 | 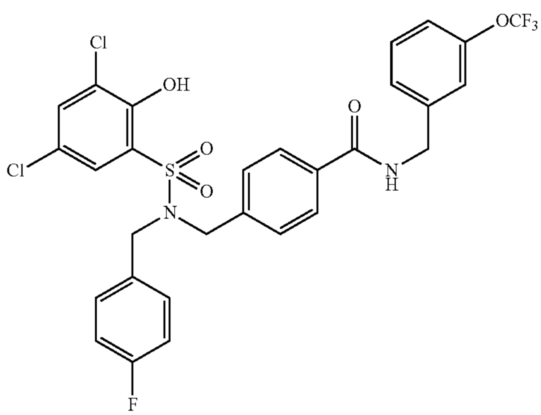 [SMILES: O=C(NCc1cccc(OC(F)(F)F)c1)c1ccc(CN(Cc2ccc(F)cc2)S(=O)(=O)c2cc(Cl)cc(Cl)c2O)cc1] | 4-((3,5-Dichloro-N-(4-fluorobenzyl)-2-hydroxyphenylsulfonamido)methyl)-N-(3-(trifluoromethoxy)benzyl)benzamide | C 3.468 | (M − H)⁻ 656.7 |
| 143 | 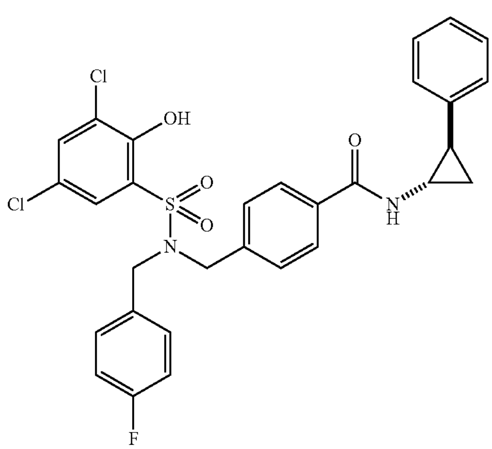 [SMILES: O=C(N[C@H]1C[C@@H]1c1ccccc1)c1ccc(CN(Cc2ccc(F)cc2)S(=O)(=O)c2cc(Cl)cc(Cl)c2O)cc1] | 4-((3,5-Dichloro-N-(4-fluorobenzyl)-2-hydroxyphenylsulfonamido)methyl)-N-((1S,2R)-2-phenylcyclopropyl)benzamide | C 3.300 | (M − H)⁻ 598.7 |

| Ex. No. | Structure | Name | HPLC t$_R$ (minute)* | LCMS |
|---|---|---|---|---|
| 144 | 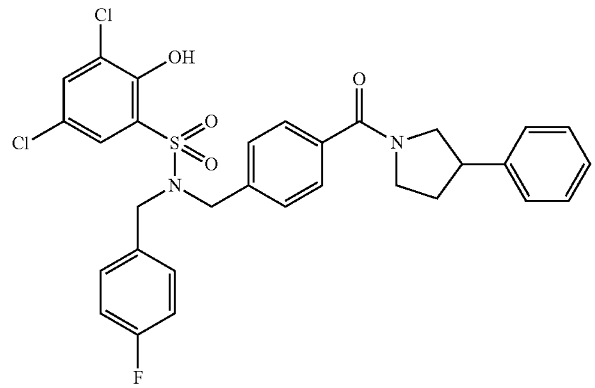 [SMILES: O=C(c1ccc(CN(Cc2ccc(F)cc2)S(=O)(=O)c2cc(Cl)cc(Cl)c2O)cc1)N1CCC(c2ccccc2)C1] | 3,5-Dichloro-N-(4-fluorobenzyl)-2-hydroxy-N-(4-(3-phenylpyrrolidine-1-carbonyl)benzyl)benzenesulfonamide | C 3.360 | (M − H)⁻ 612.7 |
| 145 | 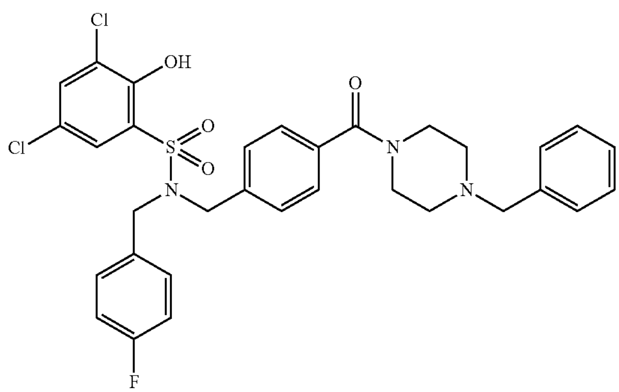 [SMILES: O=C(c1ccc(CN(Cc2ccc(F)cc2)S(=O)(=O)c2cc(Cl)cc(Cl)c2O)cc1)N1CCN(Cc2ccccc2)CC1] | N-(4-(4-Benzylpiperazine-1-carbonyl)benzyl)-3,5-dichloro-N-(4-fluorobenzyl)-2-hydroxybenzenesulfonamide | C 3.278 | (M − H)⁻ 641.8 |
| 146 | 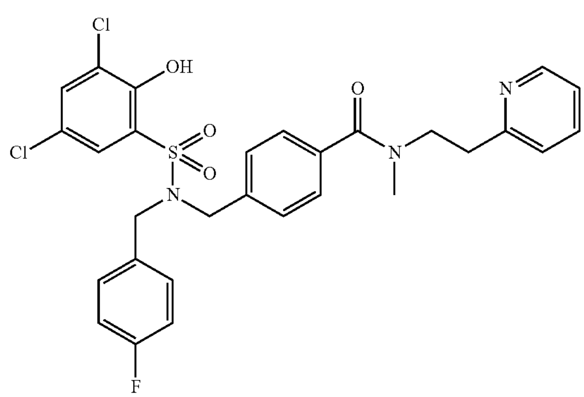 [SMILES: CN(CCc1ccccn1)C(=O)c1ccc(CN(Cc2ccc(F)cc2)S(=O)(=O)c2cc(Cl)cc(Cl)c2O)cc1] | 4-((3,5-Dichloro-N-(4-fluorobenzyl)-2-hydroxyphenylsulfonamido)methyl)-N-methyl-N-(2-(pyridin-2-yl)ethyl)benzamide | C 2.770 | (M − H)⁻ 601.8 |

| Ex. No. | Structure | Name | HPLC $t_R$ (minute)* | LCMS |
|---|---|---|---|---|
| 147 | 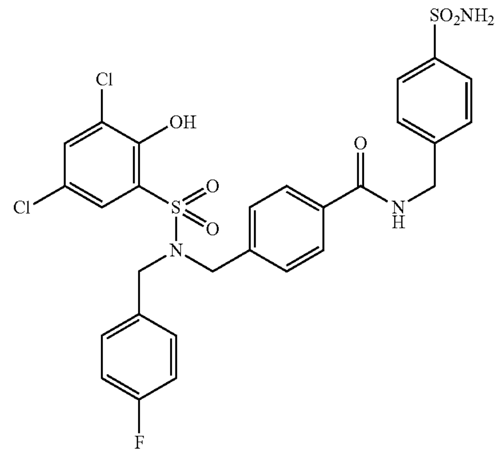 [SMILES: NS(=O)(=O)c1ccc(CNC(=O)c2ccc(CN(Cc3ccc(F)cc3)S(=O)(=O)c3cc(Cl)cc(Cl)c3O)cc2)cc1] | 4-((3,5-Dichloro-N-(4-fluorobenzyl)-2-hydroxyphenylsulfonamido)methyl)-N-(4-sulfamoylbenzyl)benzamide | C 2.620 | (M − H)⁻ 651.7 |
| 148 | 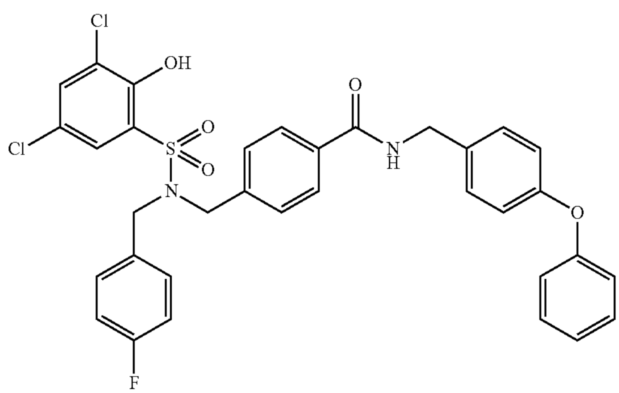 [SMILES: O=C(NCc1ccc(Oc2ccccc2)cc1)c1ccc(CN(Cc2ccc(F)cc2)S(=O)(=O)c2cc(Cl)cc(Cl)c2O)cc1] | 4-((3,5-Dichloro-N-(4-fluorobenzyl)-2-hydroxyphenylsulfonamido)methyl)-N-(4-phenoxybenzyl)benzamide | C 3.585 | (M − H)⁻ 664.7 |
| 149 | 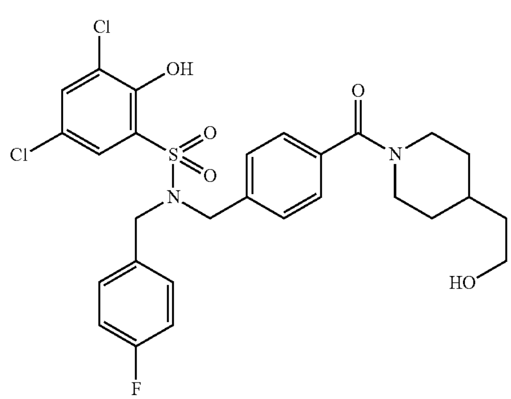 [SMILES: O=C(c1ccc(CN(Cc2ccc(F)cc2)S(=O)(=O)c2cc(Cl)cc(Cl)c2O)cc1)N1CCC(CCO)CC1] | 3,5-Dichloro-N-(4-fluorobenzyl)-2-hydroxy-N-(4-(4-(2-hydroxyethyl)piperidine-1-carbonyl)benzyl)benzenesulfonamide | C 2.573 | (M − H)⁻ 594.8 |

-continued

| Ex. No. | Structure | Name | HPLC t$_R$ (minute)* | LCMS |
|---|---|---|---|---|
| 150 | 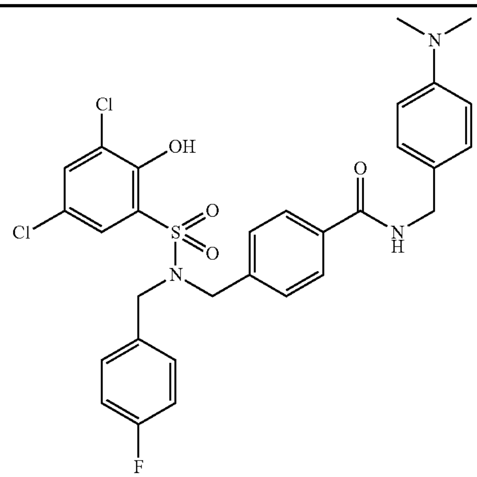 | 4-((3,5-Dichloro-N-(4-fluorobenzyl)-2-hydroxyphenylsulfonamido)methyl)-N-(4-(dimethylamino)benzyl)benzamide | C 3.212 | (M − H)⁻ 615.8 |
| 151 | 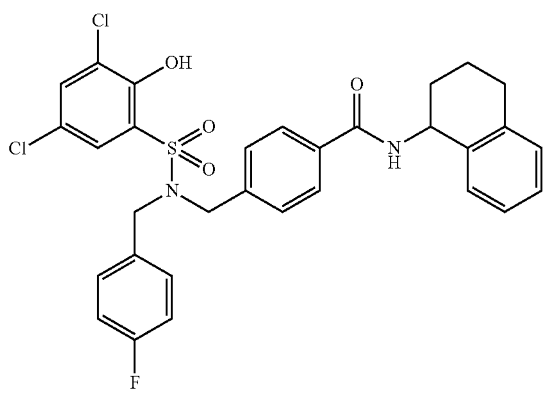 [SMILES: O=C(NC1CCCc2ccccc21)c1ccc(CN(Cc2ccc(F)cc2)S(=O)(=O)c2cc(Cl)cc(Cl)c2O)cc1] | 4-((3,5-Dichloro-N-(4-fluorobenzyl)-2-hydroxyphenylsulfonamido)methyl)-N-(1,2,3,4-tetrahydronaphthalen-1-yl)benzamide | D 3.442 | (M − H)⁻ 612.8 |
| 152 | 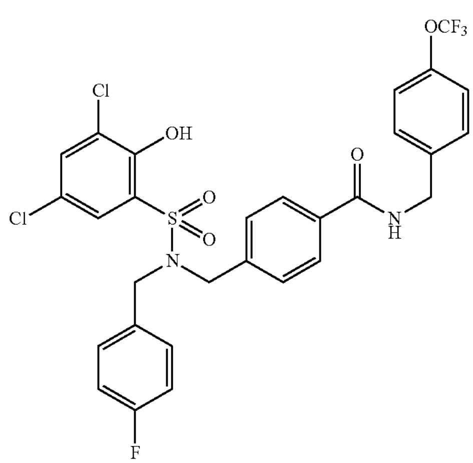 [SMILES: O=C(NCc1ccc(OC(F)(F)F)cc1)c1ccc(CN(Cc2ccc(F)cc2)S(=O)(=O)c2cc(Cl)cc(Cl)c2O)cc1] | 4-((3,5-Dichloro-N-(4-fluorobenzyl)-2-hydroxyphenylsulfonamido)methyl)-N-(4-(trifluorometboxy)benzyl)benzamide | D 3.480 | (M − H)⁻ 656.7 |

| Ex. No. | Structure | Name | HPLC $t_R$ (minute)* | LCMS |
|---|---|---|---|---|
| 153 | 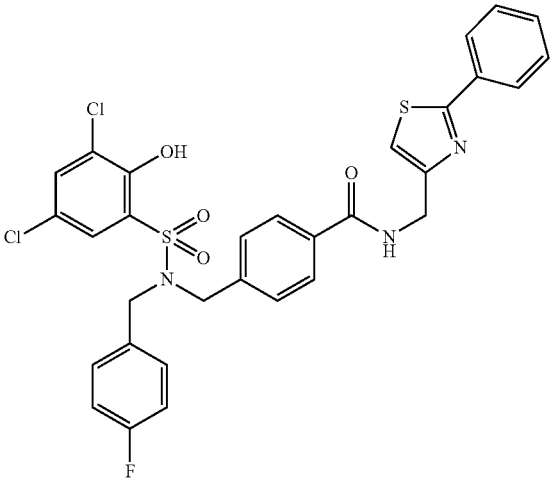 [SMILES: O=C(NCc1csc(-c2ccccc2)n1)c1ccc(CN(Cc2ccc(F)cc2)S(=O)(=O)c2cc(Cl)cc(Cl)c2O)cc1] | 4-((3,5-Dichloro-N-(4-fluorobenzyl)-2-hydroxyphenylsulfonamido)methyl)-N-((2-phenylthiazol-4-yl)methyl)benzamide | D 3.340 | (M − H)⁻ 655.7 |
| 154 | 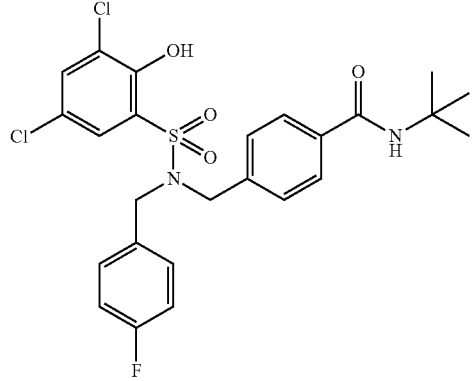 [SMILES: CC(C)(C)NC(=O)c1ccc(CN(Cc2ccc(F)cc2)S(=O)(=O)c2cc(Cl)cc(Cl)c2O)cc1] | N-tert-Butyl-4-((3,5-dichloro-N-(4-fluorobenzyl)-2-hydroxyphenylsulfonamido)methyl)-benzamide | D 3.157 | (M − H)⁻ 538.8 |
| 155 | 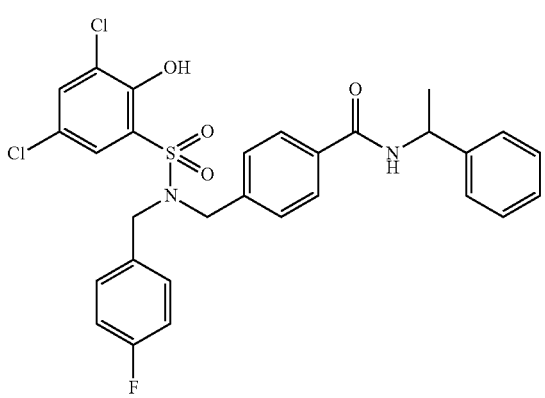 [SMILES: CC(NC(=O)c1ccc(CN(Cc2ccc(F)cc2)S(=O)(=O)c2cc(Cl)cc(Cl)c2O)cc1)c1ccccc1] | 4-((3,5-Dichloro-N-(4-fluorobenzyl)-2-hydroxyphenylsulfonamido)methyl)-N-(1-phenylethyl)benzamide | D 3.240 | (M − H)⁻ 586.8 |

-continued

| Ex. No. | Structure | Name | HPLC t_R (minute)* | LCMS |
|---|---|---|---|---|
| 156 | 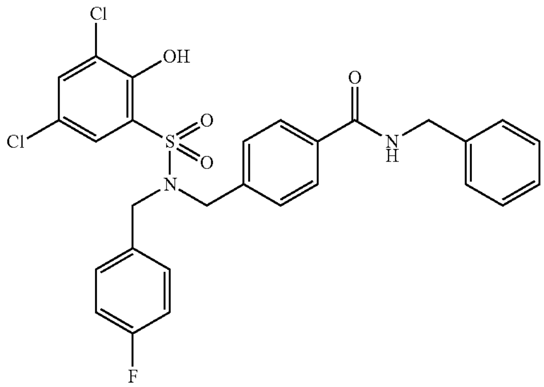 [SMILES: O=C(NCc1ccccc1)c1ccc(CN(Cc2ccc(F)cc2)S(=O)(=O)c2cc(Cl)cc(Cl)c2O)cc1] | N-Benzyl-4-((3,5-dichloro-N-(4-fluorobenzyl)-2-hydroxyphenylsulfonamido)methyl)-benzamide | D 3.115 | (M − H)⁻ 572.7 |
| 157 | 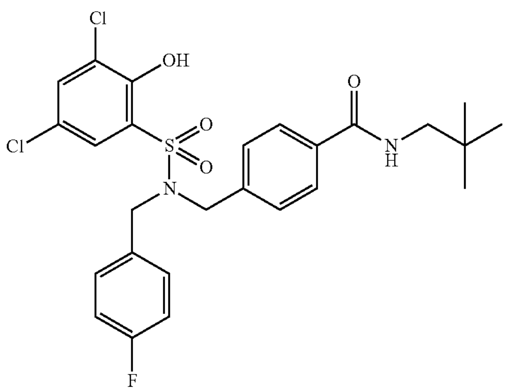 | 4-((3,5-Dichloro-N-(4-fluorobenzyl)-2-hydroxyphenylsulfonamido)methyl)-N-neopentylbenzamide | D 3.208 | (M − H)⁻ 552.8 |
| 158 | 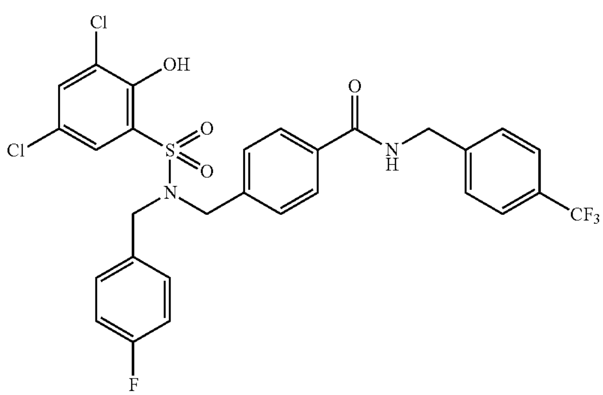 [SMILES: O=C(NCc1ccc(C(F)(F)F)cc1)c1ccc(CN(Cc2ccc(F)cc2)S(=O)(=O)c2cc(Cl)cc(Cl)c2O)cc1] | 4-((3,5-Dichloro-N-(4-fluorobenzyl)-2-hydroxyphenylsulfonamido)methyl)-N-(4-(trifluoromethyl)benzyl)benzamide | D 3.398 | (M − H)⁻ 640.7 |
| 159 | 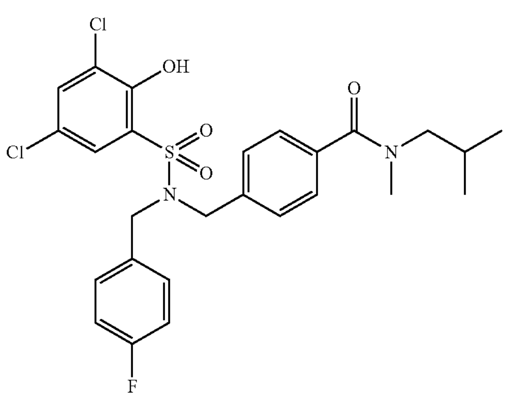 [SMILES: CC(C)CN(C)C(=O)c1ccc(CN(Cc2ccc(F)cc2)S(=O)(=O)c2cc(Cl)cc(Cl)c2O)cc1] | 4-((3,5-Dichloro-N-(4-fluorobenzyl)-2-hydroxyphenylsulfonamido)methyl)-N-isobutyl-N-methylbenzamide | D 3.202 | (M − H)⁻ 552.8 |

-continued

| Ex. No. | Structure | Name | HPLC t$_R$ (minute)* | LCMS |
|---|---|---|---|---|
| 160 | 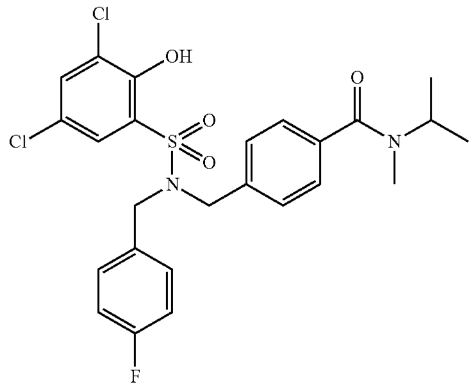 [SMILES: CC(C)N(C)C(=O)c1ccc(CN(Cc2ccc(F)cc2)S(=O)(=O)c2cc(Cl)cc(Cl)c2O)cc1] | 4-((3,5-Dichloro-N-(4-fluorobenzyl)-2-hydroxyphenylsulfonamido)methyl)-N-isopropyl-N-methylbenzamide | D 2.972 | (M − H)⁻ 538.8 |
| 161 | 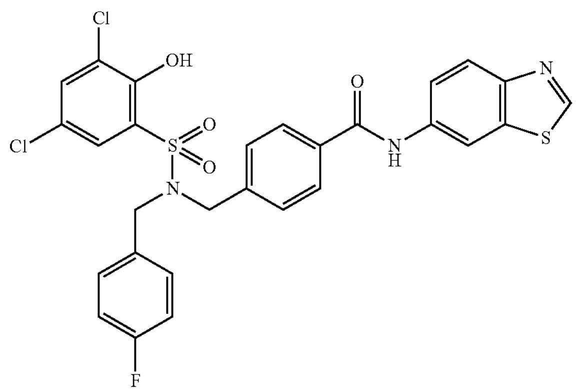 [SMILES: O=C(Nc1ccc2ncsc2c1)c1ccc(CN(Cc2ccc(F)cc2)S(=O)(=O)c2cc(Cl)cc(Cl)c2O)cc1] | N-(Benzo[d]thiazol-6-yl)-4-((3,5-dichloro-N-(4-fluorobenzyl)-2-hydroxyphenylsulfonamido)methyl)-benzamide | D 3.025 | (M − H)⁻ 615.7 |
| 162 | 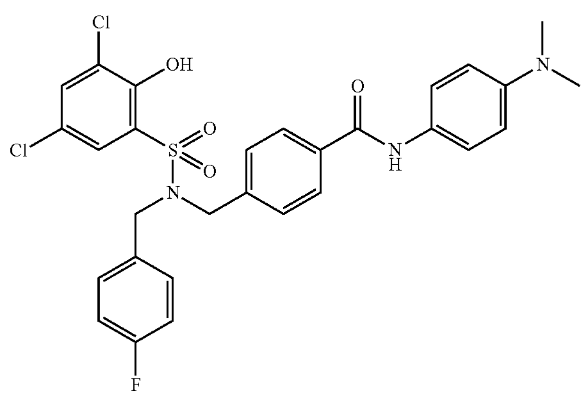 [SMILES: CN(C)c1ccc(NC(=O)c2ccc(CN(Cc3ccc(F)cc3)S(=O)(=O)c3cc(Cl)cc(Cl)c3O)cc2)cc1] | 4-((3,5-Dichloro-N-(4-fluorobenzyl)-2-hydroxyphenylsulfonamido)methyl)-N-(4-(dimethylamino)phenyl)benzamide | D 3.237 | (M − H)⁻ 601.8 |
| 163 | 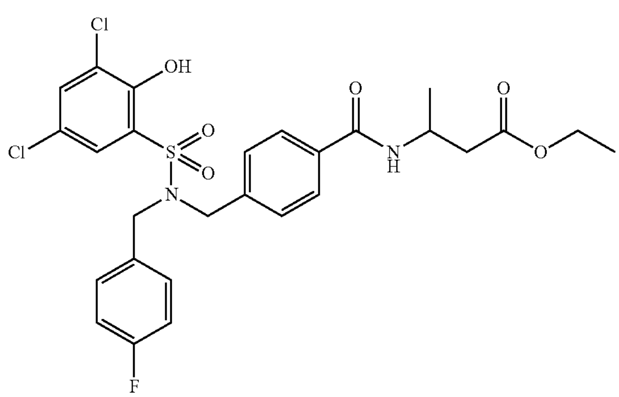 [SMILES: CCOC(=O)CC(C)NC(=O)c1ccc(CN(Cc2ccc(F)cc2)S(=O)(=O)c2cc(Cl)cc(Cl)c2O)cc1] | Ethyl 3-(4-((3,5-dichloro-N-(4-fluorobenzyl)-2-hydroxyphenylsulfonamido)methyl)-benzamido)butanoate | D 2.952 | (M − H)⁻ 596.8 |

| Ex. No. | Structure | Name | HPLC $t_R$ (minute)* | LCMS |
|---|---|---|---|---|
| 164 | 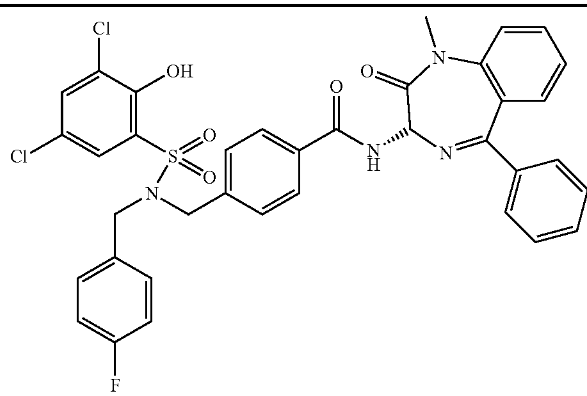 | (S,Z)-4-((3,5-Dichloro-N-(4-fluorobenzyl)-2-hydroxyphenylsulfonamido)methyl)-N-(1-methyl-2-oxo-5-phenyl-2,3-dihydro-1H-benzo[e][1,4]diazepin-3-yl)benzamide | A 3.64 | $(M + H)^+$ 731.0 |
| 165 | 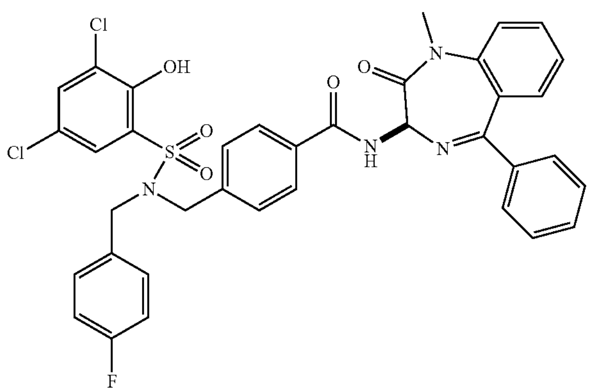 [SMILES: CN1C(=O)[C@H](NC(=O)c2ccc(CN(Cc3ccc(F)cc3)S(=O)(=O)c3cc(Cl)cc(Cl)c3O)cc2)N=C(c2ccccc2)c2ccccc21] | (R,Z)-4-((3,5-Dichloro-N-(4-fluorobenzyl)-2-hydroxyphenylsulfonamido)methyl)-N-(1-methyl-2-oxo-5-phenyl-2,3-dihydro-1H-benzo[e][1,4]diazepin-3-yl)benzamide | A 3.58 | $(M + H)^+$ 730.9 |

*HPLC conditions:
A) YMC S5 ODS, 4.6 × 50 mm Ballistic column: 6 minute run with 4 minute gradient from 10-90% aqueous MeOH with 0.2% $H_3PO_4$.
B) XBridge Phenyl, 4.6 × 150 mm, 3.5μ, column: 35 minute run with 25 minute gradient from 14 to 95% aq. MeCN with 0.05% TFA.
C) Supelco Ascentis Express C-18 4.6 × 50 mm column, 2.7 um; 5.3 min gradient from 0% B to 100% B; flow rate 3 mL/min; A = 5% MeOH − 95% H2O − 0.1% TFA, B = 95% MeOH − 5% $H_2O$ − 0.1% TFA.
D) Supelco Ascentis Express C-18 4.6 × 50 mm column, 2.7 um; 5.3 min gradient from 0% B to 100% B; flow rate 3 mL/min; A = 5% MeCN − 95% $H_2O$ − 10 mM $NH_4OAc$, B = 95% MeCN − 5% $H_2O$ − 10 mM $NH_4OAc$.

Example 166

4-((3,5-Dichloro-N-(4-fluorobenzyl)-2-hydroxyphenylsulfonamido)methyl)-N-(3,5-dichlorobenzyl)-N-(4-fluorobenzyl)-3-methoxybenzamide

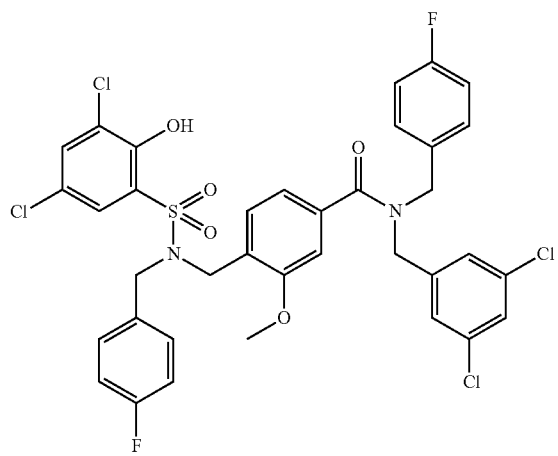 [SMILES: COc1cc(C(=O)N(Cc2ccc(F)cc2)Cc2cc(Cl)cc(Cl)c2)ccc1CN(Cc1ccc(F)cc1)S(=O)(=O)c1cc(Cl)cc(Cl)c1O]

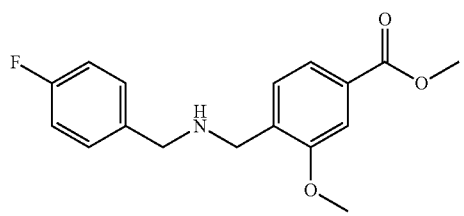 [SMILES: COC(=O)c1ccc(CNCc2ccc(F)cc2)c(OC)c1]

A) Methyl 4-((4-fluorobenzylamino)methyl)-3-methoxybenzoate

To a solution of methyl 4-(bromomethyl)-3-methoxybenzoate (0.518 g, 2 mmol, Trans World Chemicals) in THF (10 mL) at room temperature was added (4-fluorophenyl)methanamine (1.00 g, 8.00 mmol, Aldrich) and triethylamine (0.56 mL, 4 mmol). The reaction mixture was stirred at rt for 1 h and quenched by the addition of 5 mL of saturated aq. NaHCO$_3$ solution. The resulting mixture was extracted with DCM (3×50 mL). The combined organic extracts were dried over MgSO$_4$ and concentrated. The residue was purified by flash column chromatography (ISCO system, eluting with CH$_2$Cl$_2$/EtOAc) to give the desired compound (0.35 g, 57%) as a white solid. $^1$H NMR (CD$_3$OD) δ 7.64 (d, 1H, J=6.0 Hz), 7.60 (s, 1H), 7.40 (d, 2H, J=7.7 Hz), 7.36 (d, 1H, J=6.0 Hz), 7.08 (t, 2H, J=7.7 Hz), 3.97 (s, 3H), 3.96 (s, 3H), 3.82 (s, 2H), 3.76 (s, 2H). MS (ESI): 304.1 (M+H)$^+$.

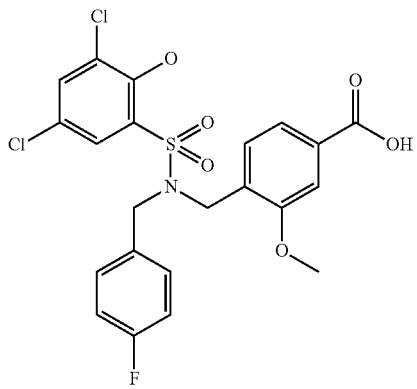 [SMILES: COc1cc(C(=O)O)ccc1CN(Cc1ccc(F)cc1)S(=O)(=O)c1cc(Cl)cc(Cl)c1O]

B) 4-((3,5-Dichloro-N-(4-fluorobenzyl)-2-hydroxyphenylsulfonamido)methyl)-3-methoxybenzoic acid The compound was prepared using a similar procedure as described for Step B of Example 106. MS (ESI): 513.8 (M+H)$^+$.

C) 4-((3,5-Dichloro-N-(4-fluorobenzyl)-2-hydroxyphenylsulfonamido)methyl)-N-(3,5-dichlorobenzyl)-N-(4-fluorobenzyl)-3-methoxybenzamide The compound was prepared using a similar procedure as described for Step C of Example 106. HPLC t$_R$=4.27 min; MS (ESI): 780.8 (M+H)$^+$.

Example 167

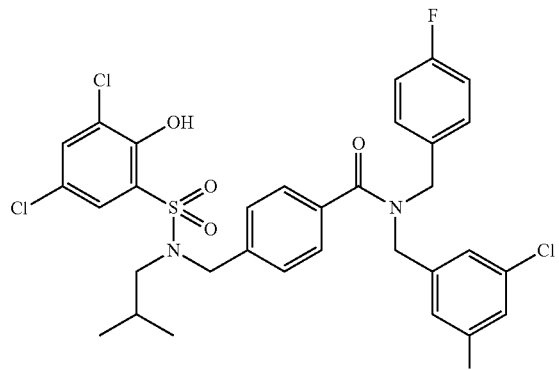

4-((3,5-Dichloro-2-hydroxy-N-isobutylphenylsulfonamido)methyl)-N-(3,5-dichlorobenzyl)-N-(4-fluorobenzyl)benzamide The compound was prepared using similar procedures to those described for Example 106, however, isobutyraldehyde was substituted for 4-fluorobenzaldehyde in Step A. HPLC t$_R$=4.19 min; MS (ESI): 698.8 (M+H)$^+$.

Examples 168-174

The following examples were prepared using similar procedures to those described for Example 167 and 106:

| Ex. No. | Structure | Name | HPLC t$_R$ (minute)* | LCMS (M + H)$^+$ |
|---|---|---|---|---|
| 168 | ![structure] | 4-((3,5-Dichloro-2-hydroxy-N-isopentylphenylsulfonamido)methyl)-N-(3,5-dichlorobenzyl)-N-(4-fluorobenzyl)benzamide | 4.27 | 712.8 |

-continued

| Ex. No. | Structure | Name | HPLC $t_R$ (minute)* | LCMS $(M + H)^+$ |
|---|---|---|---|---|
| 169 | 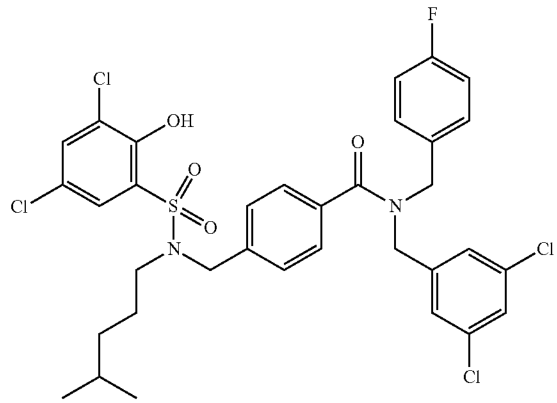 [SMILES: CC(C)CCCN(Cc1ccc(C(=O)N(Cc2ccc(F)cc2)Cc2cc(Cl)cc(Cl)c2)cc1)S(=O)(=O)c1cc(Cl)cc(Cl)c1O] | 4-((3,5-Dichloro-2-hydroxy-N-(4-methylpentyl)phenylsulfonamido)meth-yl)-N-(3,5-dichlorobenzyl)-N-(4-fluorobenzyl)benzamide | 4.34 | 726.8 |
| 170 | 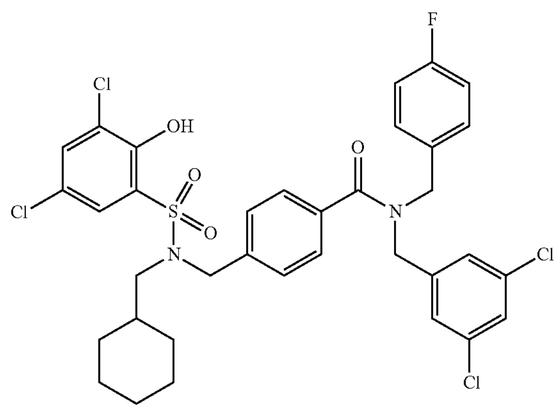 [SMILES: O=C(c1ccc(CN(CC2CCCCC2)S(=O)(=O)c2cc(Cl)cc(Cl)c2O)cc1)N(Cc1ccc(F)cc1)Cc1cc(Cl)cc(Cl)c1] | 4-((3,5-Dichloro-N-(cyclohexylmethyl)-2-hydroxyphenylsulfonamido)methyl)-N-(3,5-dichlorobenzyl)-N-(4-fluorobenzyl)benzamide | 4.35 | 738.8 |
| 171 | 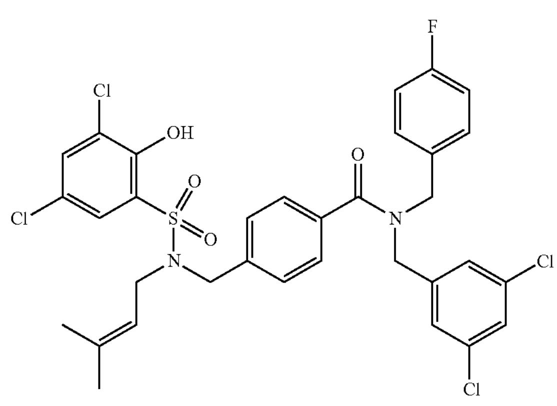 [SMILES: CC(C)=CCN(Cc1ccc(C(=O)N(Cc2ccc(F)cc2)Cc2cc(Cl)cc(Cl)c2)cc1)S(=O)(=O)c1cc(Cl)cc(Cl)c1O] | 4-((3,5-Dichloro-2-hydroxy-N-(3-methylbut-2-enyl)phenylsulfonamido)methyl)-N-(3,5-dichlorobenzyl)-N-(4-fluorobenzyl)benzamide | 4.25 | 710.8 |

| Ex. No. | Structure | Name | HPLC $t_R$ (minute)* | LCMS $(M + H)^+$ |
|---|---|---|---|---|
| 172 | 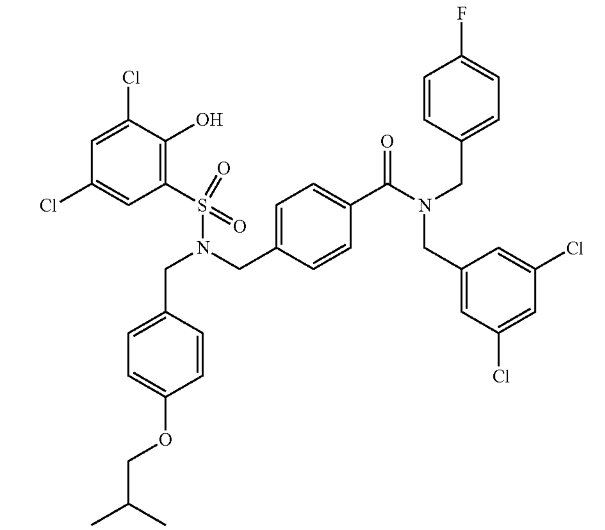 [SMILES: CC(C)COc1ccc(CN(Cc2ccc(C(=O)N(Cc3ccc(F)cc3)Cc3cc(Cl)cc(Cl)c3)cc2)S(=O)(=O)c2cc(Cl)cc(Cl)c2O)cc1] | 4-((3,5-Dichloro-2-hydroxy-N-(4-isobutoxybenzyl) phenylsulfonamido)-methyl)-N-(3,5-dichlorobenzyl)-N-(4-fluorobenzyl)benzamide | 4.45 | 804.9 |
| 173 | 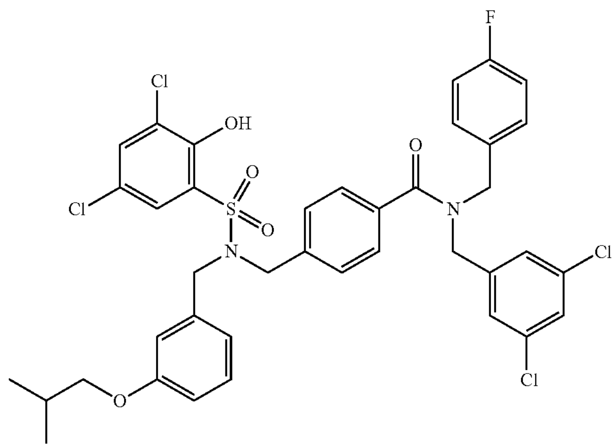 [SMILES: CC(C)COc1cccc(CN(Cc2ccc(C(=O)N(Cc3ccc(F)cc3)Cc3cc(Cl)cc(Cl)c3)cc2)S(=O)(=O)c2cc(Cl)cc(Cl)c2O)c1] | 4-((3,5-Dichloro-2-hydroxy-N-(3-isobutoxybenzyl) phenylsulfonamido)-methyl)-N-(3,5-dichlorobenzyl)-N-(4-fluorobenzyl)benzamide | 4.45 | 804.9 |
| 174 | 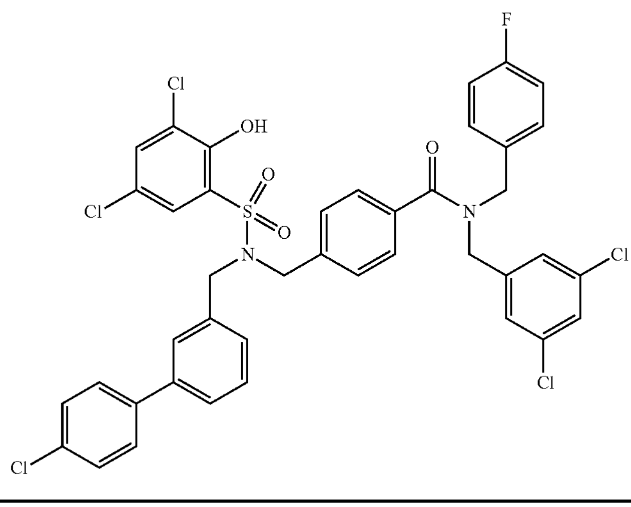 | 4-((3,5-Dichloro-N-((4'-chlorobiphenyl-3-yl)methyl)-2-hydroxyphenylsulfonamido) methyl)-N-(3,5-dichlorobenzyl)-N-(4-fluorobenzyl)benzamide | 4.26 | 842.8 |

*HPLC conditions: YMC S5 ODS, 4.6 × 50 mm Ballistic column: 6 minute run with 4 minute gradient from 10-90% aqueous MeOH with 0.2% $H_3PO_4$

Example 175

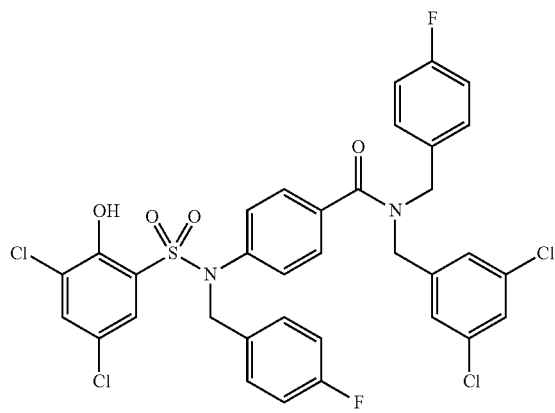 [SMILES: O=C(c1ccc(N(Cc2ccc(F)cc2)S(=O)(=O)c2cc(Cl)cc(Cl)c2O)cc1)N(Cc1ccc(F)cc1)Cc1cc(Cl)cc(Cl)c1]

4-(3,5-Dichloro-N-(4-fluorobenzyl)-2-hydroxyphenylsulfonamido)-N-(3,5-dichlorobenzyl)-N-(4-fluorobenzyl)benzamide The compound was prepared using procedures similar to those described for Example 106, however, methyl 4-aminobenzoate was substituted for the methyl 4-(aminomethyl)benzoate. HPLC $t_R$=4.19 min; MS (ESI): 734.7 (M+H)$^+$.

Example 176

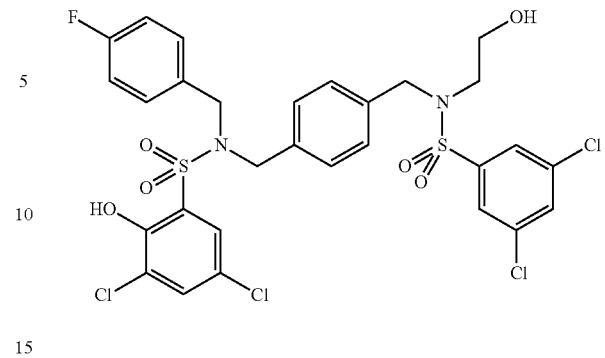

3,5-Dichloro-N-(4-(3,5-dichloro-N-(2-hydroxyethyl)phenylsulfonamido)methyl)benzyl)-N-(4-fluorobenzyl)-2-hydroxybenzenesulfonamide The compound was prepared using a procedure similar to that described for Example 100, however, 2-(tert-butyldimethylsilyloxy)acetaldehyde was used. Deprotection of the intermediate tert-butyldimethylsilyl ether was carried out using 1N HCl in MeOH. HPLC $t_R$=4.21 min; MS (ESI): 720.8 (M+H)$^+$.

Examples 177-179

The following examples were prepared using the corresponding aldehydes and sulfonylchlorides with similar procedures to those described for Example 100:

| Ex. No. | Structure | Name | HPLC $t_R$ (minute) | LCMS (M + H)$^+$ |
|---|---|---|---|---|
| 177 | 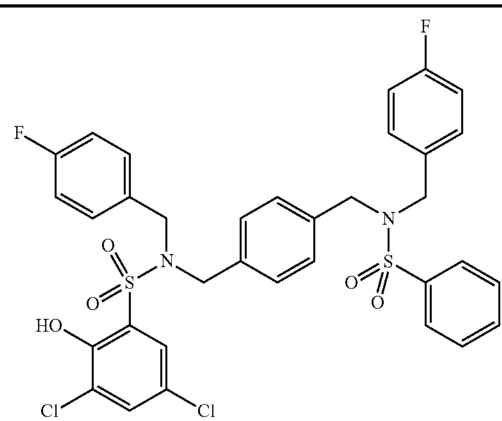 | 3,5-Dichloro-N-(4-fluorobenzyl)-N-(4-((N-(4-fluorobenzyl)phenylsulfonamido)methyl)benzyl)-2-hydroxybenzenesulfonamide | 4.35 | 717.0 |
| 178 | 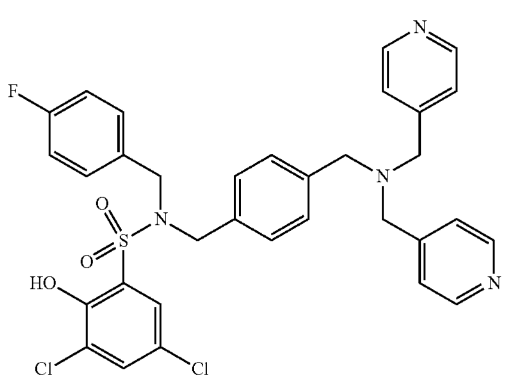 [SMILES: O=S(=O)(c1cc(Cl)cc(Cl)c1O)N(Cc1ccc(F)cc1)Cc1ccc(CN(Cc2ccncc2)Cc2ccncc2)cc1] | N-(4-((Bis(pyridin-4-ylmethyl)amino)methyl)benzyl)-3,5-dichloro-N-(4-fluorobenzyl)-2-hydroxybenzenesulfonamide | 3.21 | 650.9 |

| Ex. No. | Structure | Name | HPLC $t_R$ (minute) | LCMS $(M + H)^+$ |
|---|---|---|---|---|
| 179 | 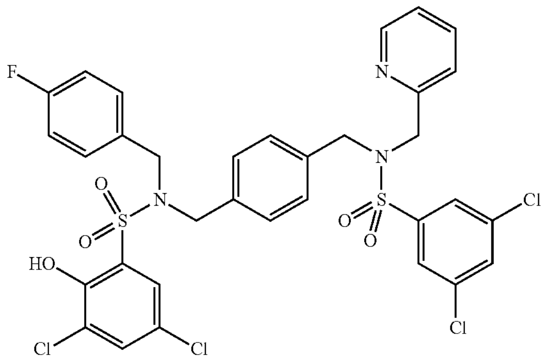 [SMILES: O=S(=O)(c1cc(Cl)cc(Cl)c1)N(Cc1ccc(CN(Cc2ccc(F)cc2)S(=O)(=O)c2cc(Cl)cc(Cl)c2O)cc1)Cc1ccccn1] | 3,5-Dichloro-N-((3,5-dichloro-N-(pyridin-2-ylmethyl)phenylsulfonamido)methyl)-benzyl)-N-(4-fluorobenzyl)-2-hydroxybenzenesulfonamide | 4.51 | 770.1 |

Example 180

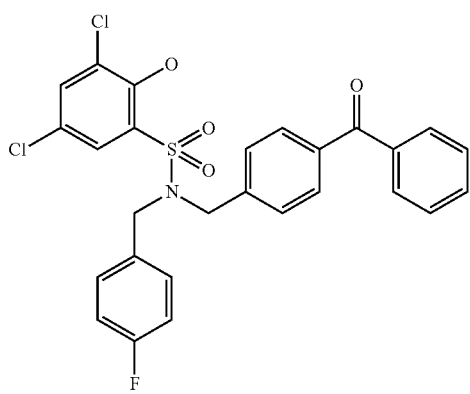 [SMILES: O=C(c1ccccc1)c1ccc(CN(Cc2ccc(F)cc2)S(=O)(=O)c2cc(Cl)cc(Cl)c2O)cc1]

N-(4-Benzoylbenzyl)-3,5-dichloro-N-(4-fluorobenzyl)-2-hydroxybenzenesulfonamide

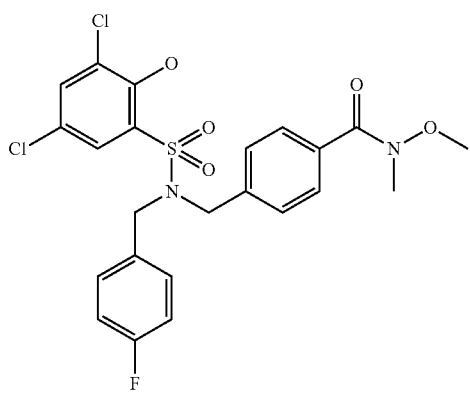 [SMILES: CON(C)C(=O)c1ccc(CN(Cc2ccc(F)cc2)S(=O)(=O)c2cc(Cl)cc(Cl)c2O)cc1]

A) 4-((3,5-Dichloro-N-(4-fluorobenzyl)-2-hydroxyphenylsulfonamido)methyl)-N-methoxy-N-methyl-benzamide To a suspension of 4-((3,5-dichloro-N-(4-fluorobenzyl)-2-hydroxyphenylsulfonamido)methyl)benzoic acid (0.726 g, 1.5 mmol) in DCM (20 mL) at rt was added oxalyl chloride (0.394 mL, 4.50 mmol) and a few drops of DMF. The mixture was stirred at rt to give a yellow solution. The reaction mixture was concentrated and the residue was dissolved in DCM. At 0° C., a mixture of N,O-dimethylhydroxylamine hydrochloride (0.439 g, 4.50 mmol) and TEA (1.045 mL, 7.50 mmol) were added. The resulting mixture was stirred at rt for 1 h. The mixture was diluted with DCM and washed with water and brine. The organic extract was dried, concentrated and purified by flash column chromatography (ISCO system, eluting with DCM/EtOAc) to give the desired product (0.516 g, 62%) as a light yellow solid. MS (ESI): 527.1 (M+H)$^+$.

B) N-(4-Benzoylbenzyl)-3,5-dichloro-N-(4-fluorobenzyl)-2-hydroxybenzenesulfonamide To a solution of 4-((3,5-dichloro-N-(4-fluorobenzyl)-2-hydroxyphenylsulfonamido)methyl)-N-methoxy-N-methyl-benzamide (0.105 g, 0.20 mmol) in THF (2 mL) was added phenylmagnesium bromide (3M in ether, 0.267 mL, 0.800 mmol). The resulting mixture was stirred at rt overnight. The mixture was quenched by adding cold saturated aq. NH$_4$Ac solution and extracted with DCM. The combined organic extracts were dried and concentrated. The residue was purified by preparative HPLC. The desired fractions were combined, concentrated and lyophilized to dryness to give the title compound (46 mg, 42%) as a tan solid. MS (ESI): 544.1 (M+H)$^+$.

Example 181

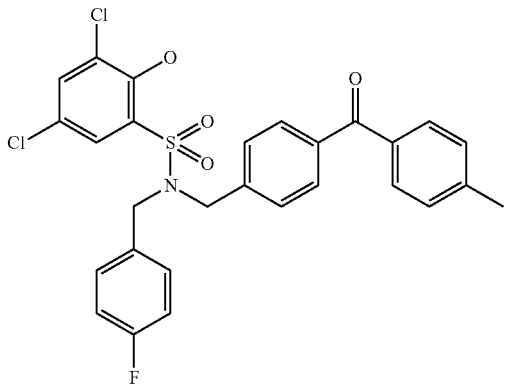 [SMILES: Cc1ccc(C(=O)c2ccc(CN(Cc3ccc(F)cc3)S(=O)(=O)c3cc(Cl)cc(Cl)c3O)cc2)cc1]

3,5-Dichloro-N-(4-fluorobenzyl)-2-hydroxy-N-(4-(4-methylbenzoyl)benzyl)benzenesulfonamide)

The compound was prepared using a procedure similar to that described in Step B of Example 180, however, p-tolylmagnesium was substituted for phenylmagnesium bromide.

Example 182

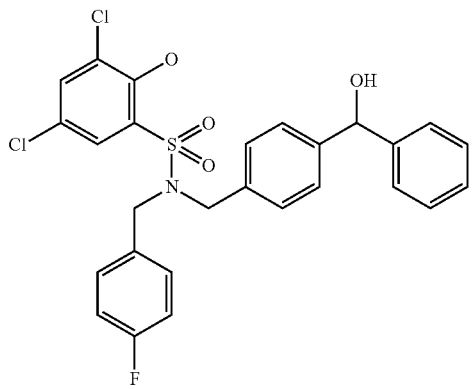 [SMILES: O=S(=O)(c1cc(Cl)cc(Cl)c1O)N(Cc1ccc(F)cc1)Cc1ccc(C(O)c2ccccc2)cc1]

3,5-Dichloro-N-(4-fluorobenzyl)-2-hydroxy-N-(4-(hydroxy(phenyl)methyl)benzyl)benzenesulfonamide To a solution of N-(4-benzoylbenzyl)-3,5-dichloro-N-(4-fluorobenzyl)-2-hydroxybenzenesulfonamide (15 mg, 0.028 mmol) in THF (0.15 mL) and ethanol (0.15 mL) at 0° C. was added sodium borohydride (4 mg, 0.11 mmol). The reaction mixture was stirred at 0° C. for 1 h. The solvents were removed in vacuo and resulting residue was purified by preparative HPLC to give the title compound (14 mg) as a white solid. MS (ESI): 527.9 (M-H$_2$O)$^+$.

Example 183

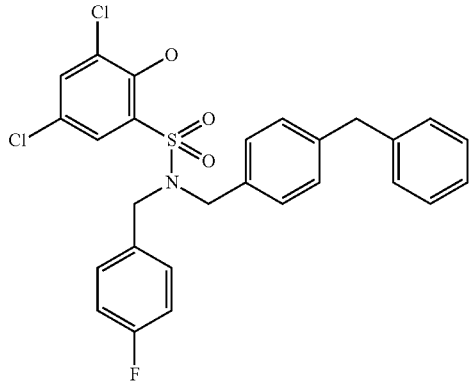 [SMILES: O=S(=O)(c1cc(Cl)cc(Cl)c1O)N(Cc1ccc(F)cc1)Cc1ccc(Cc2ccccc2)cc1]

N-(4-Benzylbenzyl)-3,5-dichloro-N-(4-fluorobenzyl)-2-hydroxybenzenesulfonamide To a solution of TFA (1 mL) at 0° C. was added sodium borohydride (14 mg, 0.037 mmol), followed by 3,5-dichloro-N-(4-fluorobenzyl)-2-hydroxy-N-(4-(hydroxy(phenyl)methyl)benzyl)benzenesulfonamide (10 mg, 0.018 mmol) in DCM (0.5 mL). The resulting mixture was stirred at 0° C. for 0.5 h. The solvent was removed and the residue was carefully quenched by the addition of MeOH. The mixture was purified by preparative HPLC to give the title compound (6 mg) as a white solid. MS (ESI): 530.1 (M+H)$^+$.

Example 184

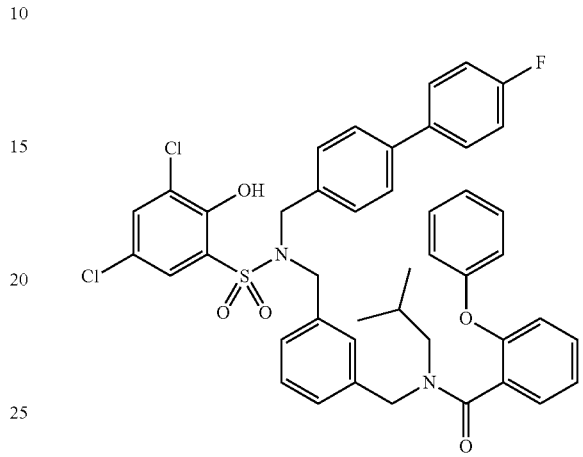

N-(3-((3,5-Dichloro-N-((4'-fluorobiphenyl-4-yl)methyl)-2-hydroxyphenylsulfonamido)methyl)benzyl)-N-isobutyl-2-phenoxybenzamide

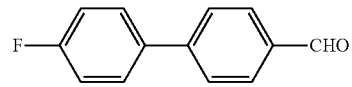

A) 4'-Fluorobiphenyl-4-carbaldehyde

A solution of 4-bromobenzaldehyde (1.0 g, 5.4 mmol, 1.0 eq) and 4-fluorophenylboronic acid (0.75 g, 5.4 mmol, 1.0 eq) in toluene was purged with nitrogen for 15 minutes and degassed under vacuum. Dry K$_2$CO$_3$ (1.12 g, 8.12 mmol, 1.5 eq) and tetrakis catalyst (0.3 g, 0.27 mmol, 0.05 eq) were added under nitrogen. The reaction mixture was refluxed under nitrogen for 12 h, quenched with ice water and extracted with ethyl acetate. The organic layer was dried over sodium sulphate and concentrated under vacuum. The residue was purified by silica gel (60-120) column chromatography using 5-10% ethyl acetate/hexane as the eluent to afford the desired compound (0.75 g, 75%) as a white solid. $^1$H NMR (400 MHz, DMSO-d$_6$) δ 7.29-7.35 (t, 2H), 7.77-7.83 (t, 2H), 7.86-7.88 (d, 2H), 7.96-7.98 (d, 2H), 10.03 (s, 1H). MS (ESI): 201.2 (M+H)$^+$.

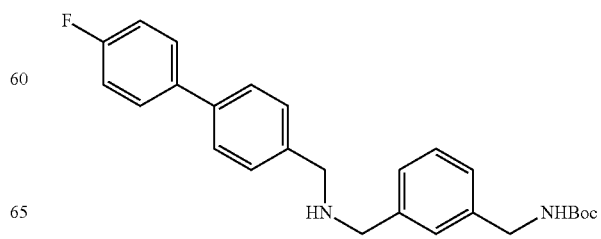

B) tert-Butyl 3-(((4'-fluorobiphenyl-4-yl)methylamino)methyl)benzylcarbamate 4'-Fluorobiphenyl-4-carbaldehyde (1.0 g, 5 mmol, 1.0 eq) and tert-butyl 3-(amino methyl)benzylcarbamate (1.18 g, 5 mmol, 1 eq) were dissolved in dry methanol under nitrogen and refluxed for 4 h. The reaction mass was cooled to 0° C. and sodium borohydride (570 mg, 15 mmol, 3 eq) was added portionwise at 0° C. over 20-30 minutes. The mixture was stirred for 1 h at 0° C. and then the reaction was quenched with 10% aq. sodium bicarbonate solution. The mixture was stirred at room temperature for 1 h. The resulting solution was completely evaporated under vacuum and the aqueous layer was extracted with ethyl acetate. The organic layer was dried over anhydrous $Na_2SO_4$ and evaporated under reduced pressure. The residue was purified by silica gel (60-120) column chromatography using 5-10% methanol dichloromethane as the eluent to afford the desired compound (1.8 g, 85%) as a light yellow liquid. $^1$H NMR (400 MHz, DMSO-$d_6$) δ 1.30-1.37 (d, 9H), 3.66-3.69 (d, 4H), 4.09-4.11 (d, 2H), 7.07-7.09 (d, 1H), 7.18-7.29 (m, 6H), 7.36-7.42 (m, 1H), 7.56-7.59 (m, 2H), 7.65-7.67 (d, 2H), 7.68-7.70 (m, 2H). MS (ESI): 421.0 (M+H)$^+$.

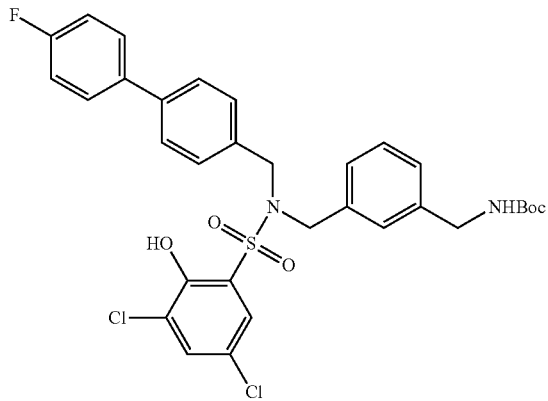 [SMILES: CC(C)(C)OC(=O)NCc1cccc(CN(Cc2ccc(-c3ccc(F)cc3)cc2)S(=O)(=O)c2cc(Cl)cc(Cl)c2O)c1]

C) tert-Butyl 3-((3,5-dichloro-N-((4'-fluorobiphenyl-4-yl)methyl)-2-hydroxyphenylsulfonamido)methyl)benzylcarbamate tert-Butyl 3-(((4'-fluorobiphenyl-4-yl)methylamino)methyl)benzylcarbamate (1.8 g, 4.28 mmol, 1.0 eq) was dissolved in dichloromethane and cooled 0° C. Triethylamine (1.85 mL, 12.8 mmol, 3.0 eq) was added slowly over 5-10 minutes and the mixture was stirred for 10 minutes at 0° C. 3,5-Dichloro-2-hydroxybenzene-1-sulfonyl chloride (1.2 g, 4.7 mmol, 1.1 eq) was dissolved in DCM and added slowly to the above mixture at 0° C. After 2 h, the reaction mixture was concentrated under vacuum at low temperature and the white precipitate that formed was removed. The solution was purified by silica gel (60-120) column chromatography using 15-20% ethyl acetate/hexane as the eluent to afford the desired product (2.3 g, 85%). $^1$H NMR (400 MHz, CD$_3$OD) δ 1.45 (d, 9H), 4.11-4.15 (d, 2H) 4.49-4.52 (d, 4H), 7.07-7.19 (m, 8H), 7.42-7.44 (d, 2H), 7.56-7.59 (m, 3H), 7.65-7.66 (d, 1H). MS (ESI): 644.0 (M−H)$^-$.

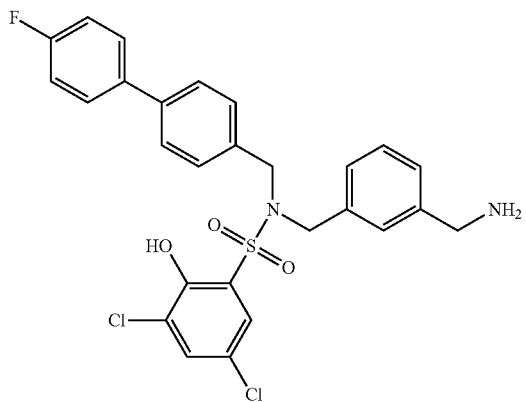 [SMILES: NCc1cccc(CN(Cc2ccc(-c3ccc(F)cc3)cc2)S(=O)(=O)c2cc(Cl)cc(Cl)c2O)c1]

D) N-(3-(Aminomethyl)benzyl)-3,5-dichloro-N-((4'-fluorobiphenyl-4-yl)methyl)-2-hydroxybenzenesulfonamide tert-Butyl 3-[(3,5-dichloro-N-((4'-fluorobiphenyl-4-yl)methyl]-2-hydroxyphenylsulfonamido) methyl)benzylcarbamate (1.0 g, 1.5 mmol, 1 eq) was dissolved in dry DCM, stirred for 10 minutes and cooled to 0° C. Trifluoroacetic acid (3.5 g, 309 mmol 20 eq) was added slowly at 0° C. The reaction mixture was stirred for 10 min and slowly brought to rt. After 4 h, the solvent was evaporated under reduced pressure, and ethyl acetate and 10% aq. NaHCO$_3$ solution were added. The mixture was stirred for 10 minutes and the aqueous mixture was extracted with ethyl acetate. The organic layer was dried with anhydrous Na$_2$SO$_4$ and evaporated under reduced pressure. The crude salt (0.7 g, 82%) was used immediately in the next step. $^1$H NMR (400 MHz, DMSO-$d_6$) δ 3.52 (s, 2H), 4.44 (s, 2H), 4.46 (s, 2H), 6.9-6.99 (t, 2H), 7.08-7.10 (d, 2H), 7.17-7.20 (m, 4H), 7.22-7.27 (m, 2H), 7.44-7.46 (d, 2H), 7.6-7.65 (t, 2H). MS (ESI): 546.0 (M+H)$^+$.

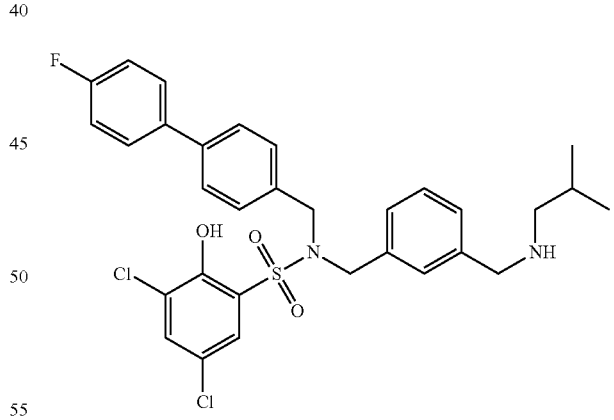

E) 3,5-Dichloro-N-((4'-fluorobiphenyl-4-yl)methyl)-2-hydroxy-N-(3-((isobutyl amino)methyl)benzyl)benzene sulfonamide N-(3-(Aminomethyl)benzyl)-3,5-dichloro-N-((4'-fluorobiphenyl-4-yl)methyl)-2-hydroxybenzenesulfonamide (1.0 g, 1.8 mmol, 1.0 eq) was dissolved in dry methanol. The solution was stirred for 10 minutes and treated with isobutyraldehyde (145 mg, 2 mmol, 1.1 eq). The resulting mixture was stirred for 10 minutes at ambient temperature, refluxed for 3 h, cooled to 0° C. and treated with NaBH₄ (210 mg, 5.5 mmol, 3 eq). The mixture was stirred for 30 min at 0° C., quenched by the addition of 10% aq. NaHCO₃ solution and stirred for 1 h at ambient temperature. The solvent was evaporated under reduced pressure and ethyl acetate was added. The organic layer was washed with water and dried with anhydrous Na₂SO₄ and concentrated under reduced pressure. The residue was purified by silica gel (240-280) column chromatography using 10-20% ethyl acetate/hexane as the eluent to afford the desired product (1 g, 90%). ¹H NMR (400 MHz, DMSO-d₆) δ 0.92-0.94 (s, 6H), 2.0 (t, 1H), 2.67-2.69 (d, 2H), 4.0 (s, 2H), 4.43-4.44 (s, 4H), 7.15-7.16 (d, 2H), 7.22-7.30 (m, 6H), 7.35 (s, 1H), 7.48-7.53 (d, 2H), 7.63-7.64 (d, 1H), 7.65-7.67 (t, 2H). MS (ESI): 602.2 (M+H)⁺.

F) N-(3-((3,5-Dichloro-N-((4'-fluorobiphenyl-4-yl)methyl)-2-hydroxyphenylsulfonamido)methyl)benzyl)-N-Isobutyl-2-phenoxybenzamide 3,5-Dichloro-N-((4'-fluorobiphenyl-4-yl)methyl)-2-hydroxy-N-(3-((isobutyl amino)methyl)benzyl)benzene sulfonamide (0.04 g, 0.066 mmol, 1 eq) was dissolved in acetonitrile. DIPEA (0.034 mL, 0.198 mmol, 3 eq) was added to the solution followed by 2-phenoxy benzoic acid (0.014 g, 0.066 mmol, 1 eq), EDCI (0.018 g, 0.099 mmol, 1.5 eq) and HOIST (0.013 g, 0.099 mmol, 1.5 eq). The reaction mixture was stirred at ambient temperature for 12 h and concentrated to remove all the volatiles. The residue obtained was dissolved in ethyl acetate and the organic layer was washed with water. The organic layer was dried over anhydrous Na₂SO₄ and concentrated under reduced pressure. The residue was purified by preparative HPLC to afford the title compound (0.025 g, 50%). ¹H NMR (400 MHz, DMSO-d₆) δ 0.64-0.65 (d, 3H), 0.74-0.78 (t, 3H), 1.74 (s, 1H), 1.9 (t, 1H), 3.6 (t, 1H), 3.8 (t, 1H), 4.2 (m, 2H), 4.41-4.45 (m, 4H), 6.86-6.93 (m, 3H), 6.92-6.99 (m, 3H), 7.00-7.13 (m, 7H), 7.14-7.26 (m, 3H), 7.28-7.39 (m, 5H), 7.44-7.47 (d, 1H), 7.54-7.61 (m, 3H), 7.73-7.74 (d, 1H), 7.83-7.84 (d, 1H). MS (ESI): 798.7 (M+H)⁺.

Example 185

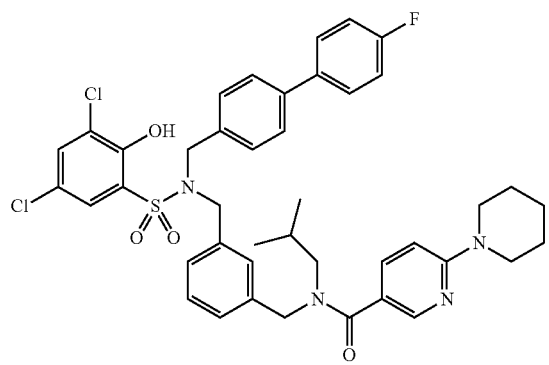 [SMILES: CC(C)CN(Cc1cccc(CN(Cc2ccc(-c3ccc(F)cc3)cc2)S(=O)(=O)c2cc(Cl)cc(Cl)c2O)c1)C(=O)c1ccc(N2CCCCC2)nc1]

N-(3-((3,5-Dichloro-N-((4'-fluorobiphenyl-4-yl)methyl)-2-hydroxyphenylsulfonamido) methyl)benzyl)-N-isobutyl-6-(piperidin-1-yl)nicotinamide 3,5-Dichloro-N-((4'-fluorobiphenyl-4-yl)methyl)-2-hydroxy-N-(3-((isobutyl amino)methyl)benzyl)benzene sulfonamide (Compound E of Example 184, 0.04 g, 0.066 mmol, 1 eq) was dissolved in acetonitrile. DIPEA (0.034 mL, 0.198 mmol, 3 eq) was added followed by 6-(piperidin-1-yl)nicotinic acid (0.013 g, 0.066 mmol, 1 eq), EDCI (0.018 g, 0.099 mmol, 1.5 eq) and HOBT (0.013 g, 0.099 mmol, 1.5 eq). The reaction mixture was stirred at ambient temperature for 12 h and concentrated to remove the volatiles. The residue obtained was dissolved in ethyl acetate. The organic layer was washed with water, dried over anhydrous Na₂SO₄ and concentrated under reduced pressure. The residue was purified by preparative HPLC to afford the title compound (0.03 g, 60%). ¹H NMR (400 MHz, DMSO-d₆) δ 0.74 (t, 6H), 1.50-1.59 (m, 6H), 1.9-2.0 (s, 1H), 3.03-3.04 (t, 2H), 3.54-3.55 (t, 4H), 4.45-4.49 (m, 6H), 6.82-6.84 (d, 1H), 6.9 (t, 1H), 7.03-7.05 (m, 2H), 7.14-7.28 (m, 6H), 7.42-7.44 (d, 2H), 7.53-7.61 (m, 4H), 7.80 (s, 1H), 8.12 (s, 1H). MS (ESI): 788.6 (M–H)⁻.

Examples 186-193

The following examples were prepared using similar procedures to those described above for Example 185:

| Ex. No. | Structure | Name | HPLC t$_R$ (minute)* | LCMS |
|---|---|---|---|---|
| 186 | 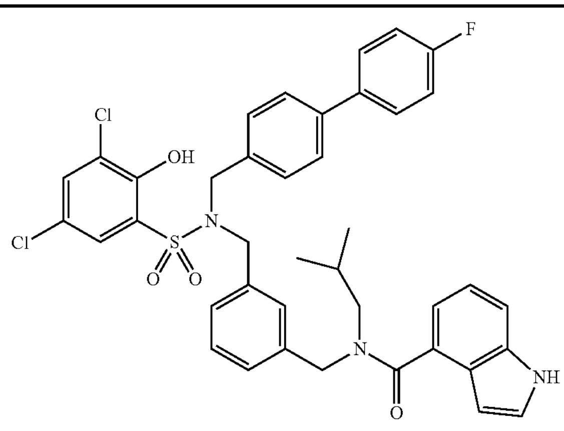 | N-(3-((3,5-Dichloro-N-((4'-fluorobiphenyl-4-yl)methyl)-2-hydroxyphenylsulfonamido)methyl)-benzyl)-N-isobutyl-1H-indole-4-carboxamide | A 22.383 | (M – H)⁻ 742 |

-continued

| Ex. No. | Structure | Name | HPLC t$_R$ (minute)* | LCMS |
|---|---|---|---|---|
| 187 | 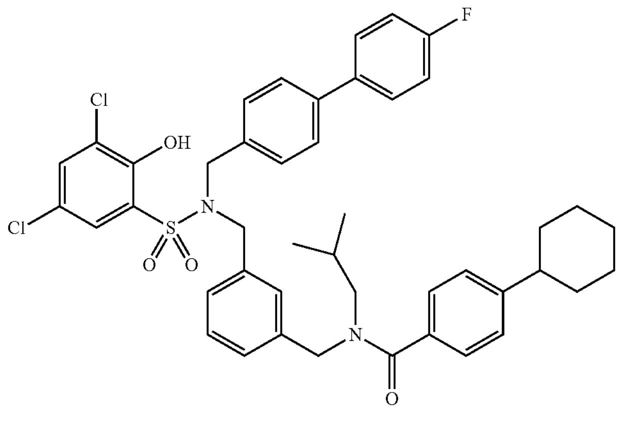 [SMILES: CC(C)CN(Cc1cccc(CN(Cc2ccc(-c3ccc(F)cc3)cc2)S(=O)(=O)c2cc(Cl)cc(Cl)c2O)c1)C(=O)c1ccc(C2CCCCC2)cc1] | 4-Cyclohexyl-N-(3-((3,5-dichloro-N-((4'-fluorobiphenyl-4-yl)methyl)-2-hydroxyphenylsulfonamido)methyl)-benzyl)-N-isobutylbenzamide | A 25.891 | (M − H)$^-$ 786 |
| 188 | 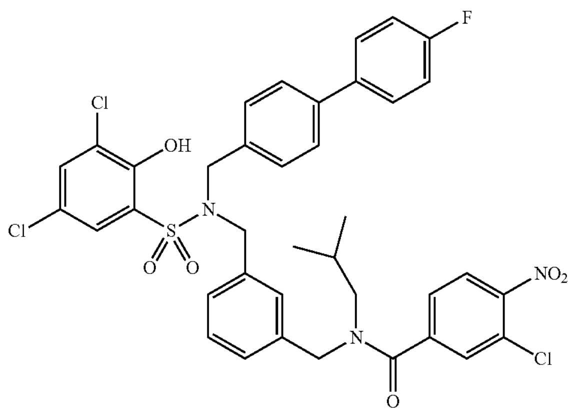 [SMILES: CC(C)CN(Cc1cccc(CN(Cc2ccc(-c3ccc(F)cc3)cc2)S(=O)(=O)c2cc(Cl)cc(Cl)c2O)c1)C(=O)c1ccc([N+](=O)[O-])c(Cl)c1] | 3-Chloro-N-(3-((3,5-dichloro-N-((4'-fluorobiphenyl-4-yl)methyl)-hydroxyphenylsulfonamido)methyl)-benzyl)-N-isobutyl-4-nitrobenzamide | A 23.689 | (M − H)$^-$ 782 |
| 189 | 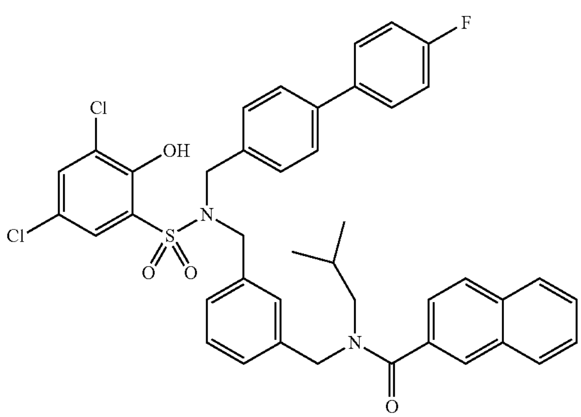 [SMILES: CC(C)CN(Cc1cccc(CN(Cc2ccc(-c3ccc(F)cc3)cc2)S(=O)(=O)c2cc(Cl)cc(Cl)c2O)c1)C(=O)c1ccc2ccccc2c1] | N-(3-((3,5-Dichloro-N-((4'-fluorobiphenyl-4-yl)methyl)-2-hydroxyphenylsulfonamido)methyl)-benzyl)-N-isobutyl-2-naphthamide | A 24.079 | (M − H)$^-$ 754 |

-continued

| Ex. No. | Structure | Name | HPLC $t_R$ (minute)* | LCMS |
|---|---|---|---|---|
| 190 | 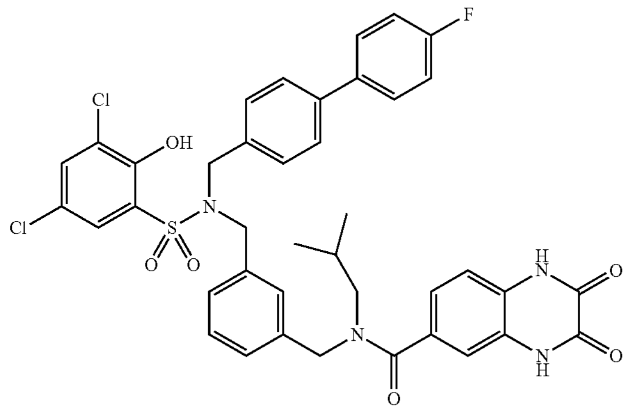 [SMILES: CC(C)CN(Cc1cccc(CN(Cc2ccc(-c3ccc(F)cc3)cc2)S(=O)(=O)c2cc(Cl)cc(Cl)c2O)c1)C(=O)c1ccc2[nH]c(=O)c(=O)[nH]c2c1] | N-(3-((3,5-Dichloro-N-((4'-fluorobiphenyl-4-yl)methyl)-2-hydroxyphenylsulfonamido)methyl)-benzyl)-N-isobutyl-2,3-dioxo-1,2,3,4-tetrahydroquinoxaline-6-carboxamide | A 19.105 | (M − H)− 787 |
| 191 | 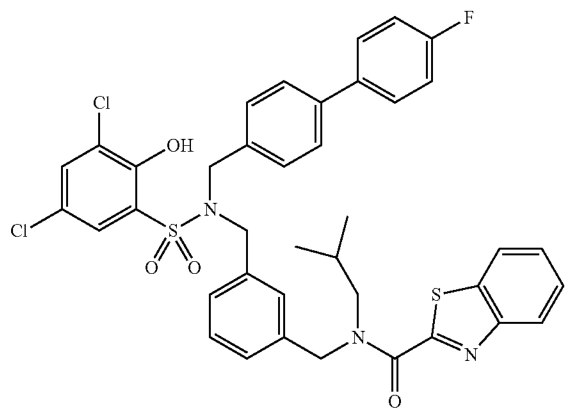 [SMILES: CC(C)CN(Cc1cccc(CN(Cc2ccc(-c3ccc(F)cc3)cc2)S(=O)(=O)c2cc(Cl)cc(Cl)c2O)c1)C(=O)c1nc2ccccc2s1] | N-(3-((3,5-Dichloro-N-((4'-fluorobiphenyl-4-yl)methyl)-2-hydroxyphenylsulfonamido)methyl)-benzyl)-N-isobutylbenzo[d]thiazole-2-carboxamide | A 24.796 | (M − H)− 762 |
| 192 | 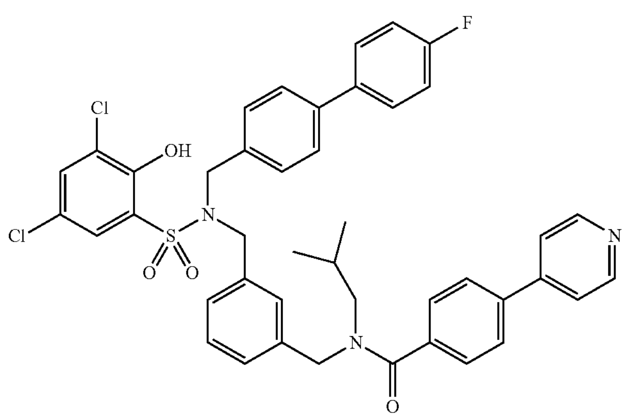 [SMILES: CC(C)CN(Cc1cccc(CN(Cc2ccc(-c3ccc(F)cc3)cc2)S(=O)(=O)c2cc(Cl)cc(Cl)c2O)c1)C(=O)c1ccc(-c2ccncc2)cc1] | N-(3-((3,5-Dichloro-N-((4'-fluorobiphenyl-4-yl)methyl)-2-hydroxyphenylsulfonamido)methyl)-benzyl)-N-isobutyl-4-(pyridin-4-yl)benzamide | B 13.365 | (M − H)− 781 |

| Ex. No. | Structure | Name | HPLC $t_R$ (minute)* | LCMS |
|---|---|---|---|---|
| 193 | 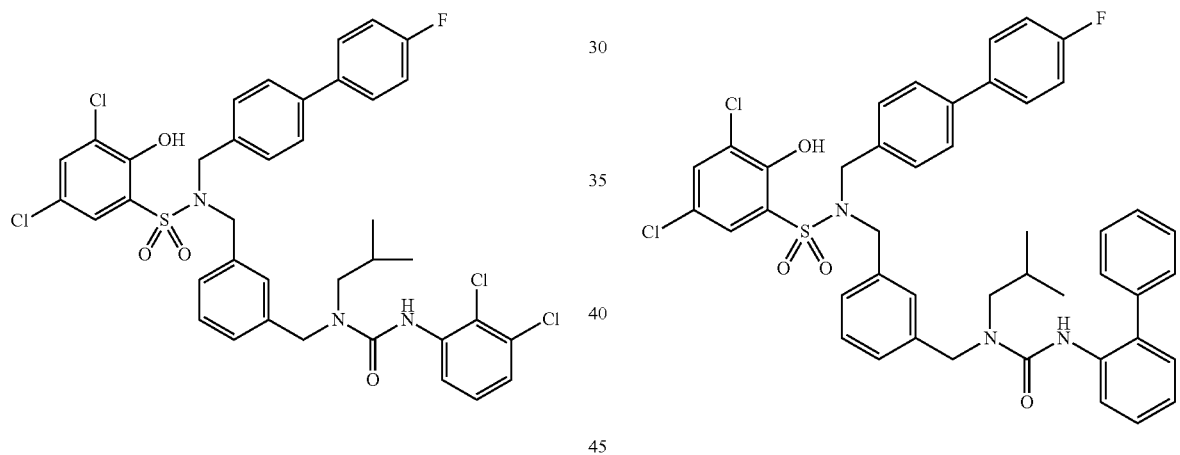 | N-(3-((3,5-Dichloro-N-((4'-fluorobiphenyl-4-yl)methyl)-2-hydroxyphenylsulfonamido)methyl)-benzyl)-N-isobutylbiphenyl-4-carboxamide | A 24.767 | (M − H)⁻ 780 |

*HPLC conditions:
A) XBridge Phenyl, 4.6 × 150 mm, 3.5μ column: 35 minute run with 25 minute gradient from 14 to 95% aq. MeCN with 0.05% TFA.
B) XBridge Phenyl, 4.6 × 150 mm, 3.5μ column: 33 minute run with 15 minute gradient from 14 to 95% aq. MeCN with 0.05% TFA Example 194

3,5-Dichloro-N-(3-((3-(2,3-dichlorophenyl)-1-isobutylureido)methyl)benzyl)-N-((4'-fluorobiphenyl-4-yl)methyl)-2-hydroxybenzenesulfonamide To a solution of 3,5-dichloro-N-((4'-fluorobiphenyl-4-yl)methyl)-2-hydroxy-N-(3-((isobutyl amino)methyl)benzyl)benzene sulfonamide (Compound E of Example 184, 0.04 g, 0.0667 wool, 1.0 eq) in 25 mL of dry THF at 0° C. was added 2,3-dichlorophenyl isocyanate (0.012 g, 0.0667 mmol, 1.0 eq). The reaction mixture was stirred at ambient temperature for 15 min and concentrated. The residue was purified by preparative HPLC to afford the title compound (0.02 g, 40%). $^1$H NMR (400 MHz, DMSO-$d_6$) δ 0.85-0.87 (d, 6H), 2.0 (m, 1H), 3.09-3.11 (d, 2H), 4.44-4.46 (m, 3H), 4.49 (s, 4H), 7.03-7.05 (d, 2H), 7.13-7.15 (d, 3H), 7.21-7.29 (m, 4H), 7.33-7.35 (m, 1H), 7.43-7.45 (d, 2H), 7.56-7.62 (m, 4H), 7.80 (s, 1H), 8.00 (s, 1H). MS (EP: 788.0 (M−H)⁻.

Example 195

N-(3-((3-(Biphenyl-2-yl)-1-isobutylureido)methyl)benzyl)-3,5-dichloro-N-((4'-fluorobiphenyl-4-yl)methyl)-2-hydroxybenzenesulfonamide To a solution of 3,5-dichloro-N-((4'-fluorobiphenyl-4-yl)methyl)-2-hydroxy-N-(3-((isobutyl amino)methyl)benzyl)benzene sulfonamide (Compound E of Example 184, 0.04 g, 0.0667 mmol, 1.0 eq) in a 5 mL of THF at 0° C. was added 2-biphenyl isocyanate (0.013 g, 0.0667 mmol, 1.0 eq). The reaction mixture was stirred at ambient temperature for 15 min and concentrated to remove the volatiles. The residue was purified by preparative HPLC to afford the title compound (0.03 g, 60%). $^1$H NMR (400 MHz, DMSO-$d_6$) δ 0.66-0.68 (d, 6H), 1.7 (m, 1H), 2.82-2.84 (d, 2H), 4.30 (s, 2H), 4.43 (d, 4H), 6.84-6.89 (t, 2H), 6.99 (d, 1H), 7.14-7.20 (m, 4H), 7.23 (m, 4H), 7.25-7.34 (m, 5H), 7.44-7.46 (d, 3H), 7.57-7.62 (m, 4H), 7.80 (s, 1H). MS (HD: 796.1 (M−H)⁻.

Examples 196-205

The following examples were prepared using similar procedures to those described above for Example 195:

| Ex. No. | Structure | Name | HPLC t_R (minute)* | LCMS |
|---|---|---|---|---|
| 196 | 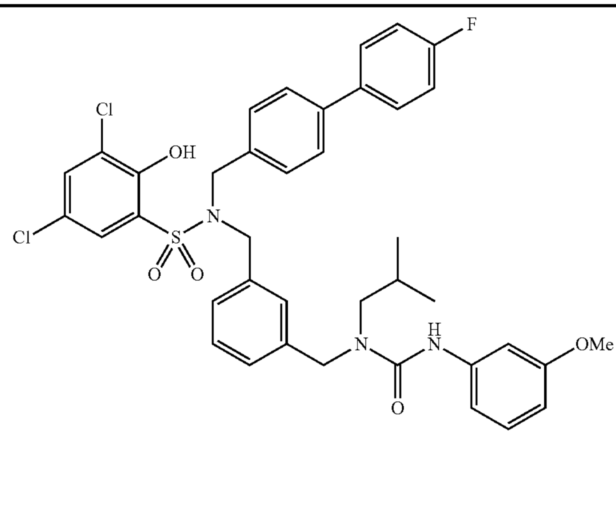 | 3,5-Dichloro-N-((4'-fluorobiphenyl-4-yl)methyl)-2-hydroxy-N-(3-((1-isobutyl-3-(3-methoxyphenyl)ureido)methyl)-benzyl)benzenesulfonamide | A 23.013 | (M − H)⁻ 748 |
| 197 | 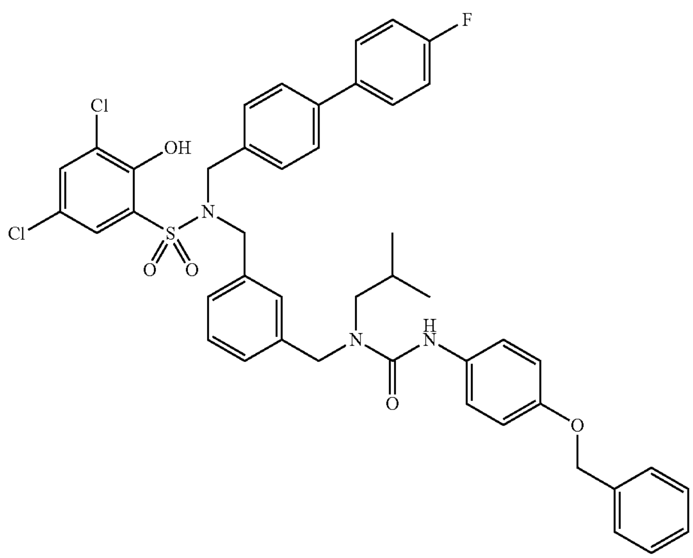 [SMILES: CC(C)CN(Cc1cccc(CN(Cc2ccc(-c3ccc(F)cc3)cc2)S(=O)(=O)c2cc(Cl)cc(Cl)c2O)c1)C(=O)Nc1ccc(OCc2ccccc2)cc1] | N-(3-((3-(4-(Benzyloxy)phenyl)-1-isobutylureido)methyl)benzyl)-3,5-dichloro-((4'-fluorobiphenyl-4-yl)methyl)-2-hydroxybenzenesulfonamide | A 24.294 | (M − H)⁻ 824 |
| 198 | 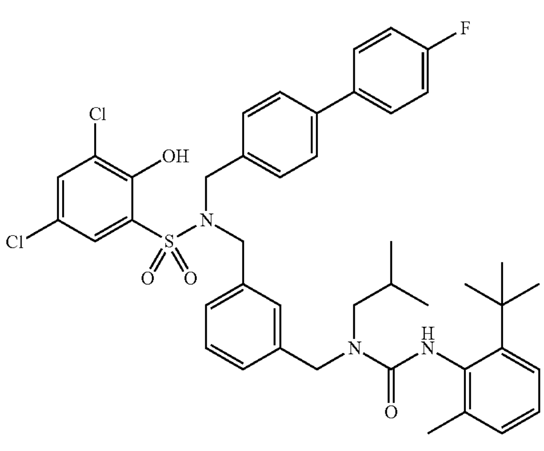 [SMILES: Cc1cccc(C(C)(C)C)c1NC(=O)N(Cc1cccc(CN(Cc2ccc(-c3ccc(F)cc3)cc2)S(=O)(=O)c2cc(Cl)cc(Cl)c2O)c1)CC(C)C] | N-(3-((3-(2-tert-Butyl-6-methylphenyl)-1-isobutylureido)methyl)benzyl)-3,5-dichloro-N-((4'-fluorobiphenyl-4-yl)methyl)-2-hydroxybenzenesulfonamide | A 24.158 | (M − H)⁻ 789 |

| Ex. No. | Structure | Name | HPLC $t_R$ (minute)* | LCMS |
|---|---|---|---|---|
| 199 | 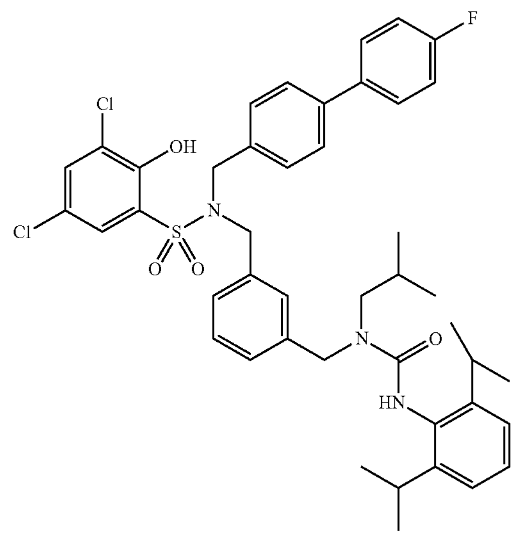 [SMILES: CC(C)CN(Cc1cccc(CN(Cc2ccc(-c3ccc(F)cc3)cc2)S(=O)(=O)c2cc(Cl)cc(Cl)c2O)c1)C(=O)Nc1c(C(C)C)cccc1C(C)C] | 3,5-Dichloro-N-(3-((3-(2,6-diisopropylphenyl)-1-isobutylureido)methyl)benzyl)-N-((4'-fluorobiphenyl-4-yl)methyl)-2-hydroxybenzenesulfonamide | A 24.479 | (M − H)⁻ 803 |
| 200 | 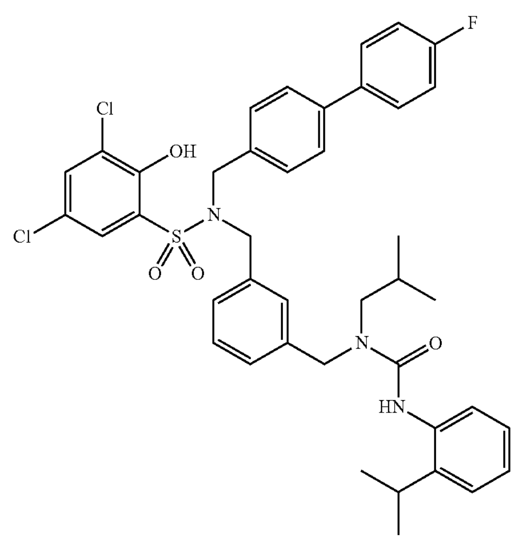 [SMILES: CC(C)CN(Cc1cccc(CN(Cc2ccc(-c3ccc(F)cc3)cc2)S(=O)(=O)c2cc(Cl)cc(Cl)c2O)c1)C(=O)Nc1ccccc1C(C)C] | 3,5-Dichloro-N-((4'-fluorobiphenyl-4-yl)methyl)-2-hydroxy-N-(3-((1-isobutyl-3-(2-isopropylphenyl)ureido)methyl)-benzyl)benzenesulfonamide | A 23.013 | (M − H)⁻ 761 |
| 201 | 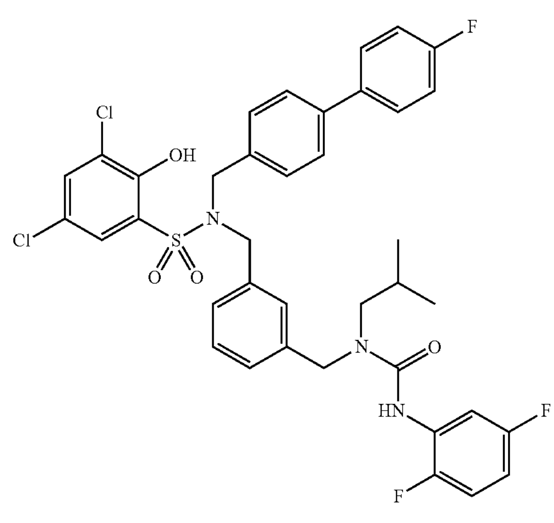 [SMILES: CC(C)CN(Cc1cccc(CN(Cc2ccc(-c3ccc(F)cc3)cc2)S(=O)(=O)c2cc(Cl)cc(Cl)c2O)c1)C(=O)Nc1cc(F)ccc1F] | 3,5-Dichloro-N-(3-((3-(2,5-difluorophenyl)-1-isobutylureido)methyl)benzyl)-N-((4'-fluorobiphenyl-4-yl)methyl)-2-hydroxybenzenesulfonamide | A 23.612 | (M − H)⁻ 754 |

-continued

| Ex. No. | Structure | Name | HPLC t$_R$ (minute)* | LCMS |
|---|---|---|---|---|
| 202 | 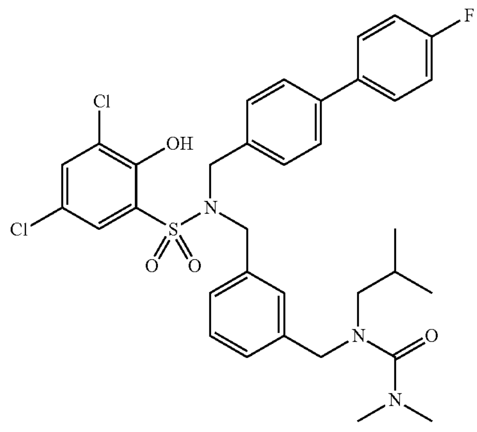 [SMILES: CC(C)CN(Cc1cccc(CN(Cc2ccc(-c3ccc(F)cc3)cc2)S(=O)(=O)c2cc(Cl)cc(Cl)c2O)c1)C(=O)N(C)C] | 3,5-Dichloro-N-((4'-fluorobiphenyl-4-yl)methyl)-2-hydroxy-N-(3-((1-isobutyl-3,3-dimethylureido)methyl)benzyl)-benzenesulfonamide | A 22.151 | (M − H)$^-$ 670 |
| 203 | 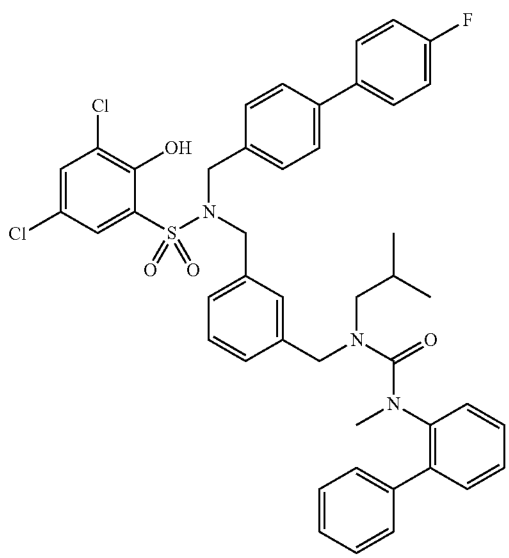 [SMILES: CC(C)CN(Cc1cccc(CN(Cc2ccc(-c3ccc(F)cc3)cc2)S(=O)(=O)c2cc(Cl)cc(Cl)c2O)c1)C(=O)N(C)c1ccccc1-c1ccccc1] | N-(3-((3-(Biphenyl-2-yl)-1-isobutyl-3-methylureido)methyl)benzyl)-3,5-dichloro-N-((4'-fluorobiphenyl-4-yl)methyl)-2-hydroxybenzenesulfonamide | A 25.043 | (M − H)$^-$ 809 |
| 204 | 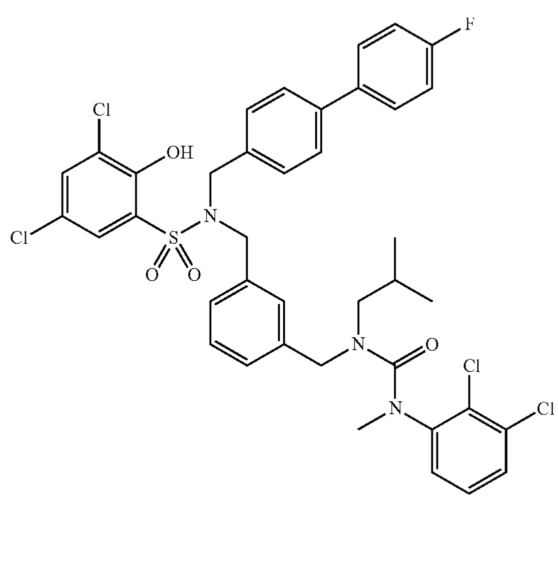 [SMILES: CC(C)CN(Cc1cccc(CN(Cc2ccc(-c3ccc(F)cc3)cc2)S(=O)(=O)c2cc(Cl)cc(Cl)c2O)c1)C(=O)N(C)c1cccc(Cl)c1Cl] | 3,5-Dichloro-N-(3-((3-(2,3-dichlorophenyl)-1-isobutyl-3-methylureido)methyl)benzyl)-N-((4'-fluorobiphenyl-4-yl)methyl)-2-hydroxybenzenesulfonamide | A 25.182 | (M − H)$^-$ 800 |

| Ex. No. | Structure | Name | HPLC $t_R$ (minute)* | LCMS |
|---|---|---|---|---|
| 205 | 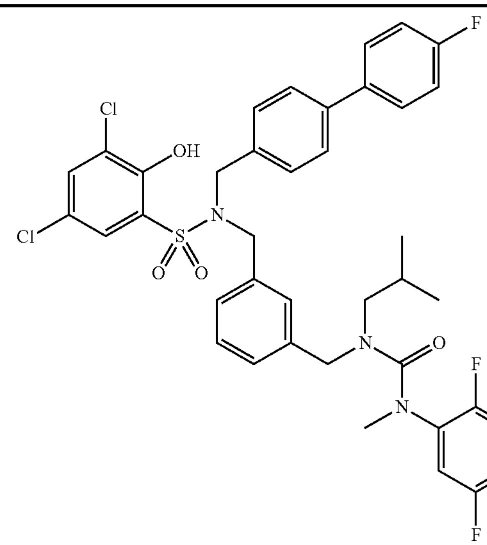 | 3,5-Dichloro-N-(3-((3-(2,5-difluorophenyl)-1-isobutyl-3-methylureido)methyl)benzyl)-N-((4'-fluorobiphenyl-4-yl)methyl)-2-hydroxybenzenesulfonamide | A 23.899 | (M − H)⁻ 771 |

*HPLC conditions:
A) XBridge Phenyl, 4.6 × 150 mm, 3.5µ column: 35 minute run with 25 minute gradient from 14 to 95% aq. MeCN with 0.05% TFA.
B) XBridge Phenyl, 4.6 × 150 mm, 3.5µ column: 35 minute run with 12 minute gradient from 14 to 95% aq. MeCN with 0.05% TFA.

Example 206

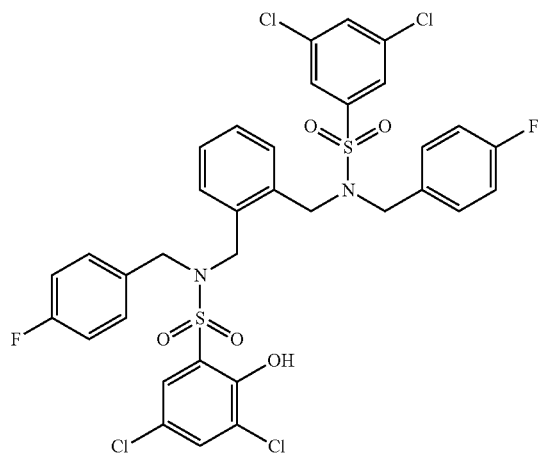 [SMILES: O=S(=O)(c1cc(Cl)cc(Cl)c1)N(Cc1ccc(F)cc1)Cc1ccccc1CN(Cc1ccc(F)cc1)S(=O)(=O)c1cc(Cl)cc(Cl)c1O]

3,5-Dichloro-N-(2-((3,5-dichloro-N-(4-fluorobenzyl)phenylsulfonamido)-methyl)benzyl)-N-(4-fluorobenzyl)-2-hydroxybenzenesulfonamide

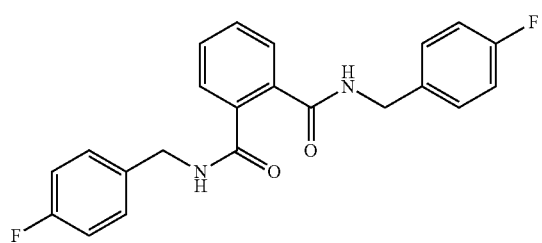 [SMILES: O=C(NCc1ccc(F)cc1)c1ccccc1C(=O)NCc1ccc(F)cc1]

A) N¹,N²-Bis(4-fluorobenzyl)phthalamide

To a mixture of phthaloyl dichloride (3 g, 15 mmol, 1 eq) in toluene (HPLC grade, 20 mL), cooled to 0° C., was added slowly a solution of 4-fluorobenzylamine (4.62 g, 37 mmol, 2.2 eq) in toluene (5 mL). After stirring at ambient temperature for 24 h, the reaction mixture was concentrated in vacuo to remove toluene. The resultant residue was dissolved in DCM, washed with brine and dried over Na$_2$SO$_4$. The organic layer was evaporated under reduced pressure. Recrystallization from DCM:hexane afforded the desired compound (4.6 g, 82%). $^1$H NMR (400 MHz, DMSO-d$_6$) δ 9.3 (s, 2H), 9.1 (s, 2H), 8.64 (s, 1H), 7.39-7.34 (m, 4H), 7.17-7.12 (m, 4H), 4.48-4.46 (d, 4H). MS (ESI): 381.2 (M+H)⁺.

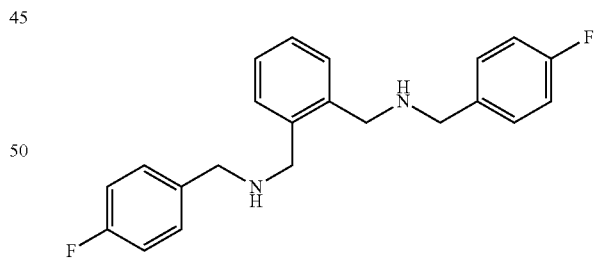

B) N,N'-(1,2-Phenylenebis(methylene))bis(1-(4 fluorphenyl)methanamine)

To a 500 mL 3-neck round bottom flask fitted with condenser and nitrogen tube, was added N¹,N²-bis(4-fluorobenzyl)phthalamide (2 g, 5.2 mmol, 1 eq) and THF (HPLC grade 100 mL). The clear solution was cooled to 0° C., before borondimethylsulphide (12 g, 15 mL, 164 mmol, 30 eq) was added slowly. The reaction mixture refluxed for 36 h, cooled to −10° C. to −15° C. and treated with methanol slowly through a dropping funnel until frothing stopped (50 mL).

The reaction mixture concentrated to dryness and once again cooled to 0° C., before methanol (100 mL) was added slowly, The reaction mixture was refluxed for 40 h and concentrated under vacuum to dryness to give the crude product (1.5 g, 85%) as a solid, which was used without further purification. $^1$H NMR (400 MHz, DMSO-d$_6$) δ 7.32-7.28 (m 6H), 7.22-7.19 (m, 2H), 7.10-7.05 (m, 4H), 3.72-3.64 (m, 8H). MS (ESI): 353.2 (M+H)$^+$.

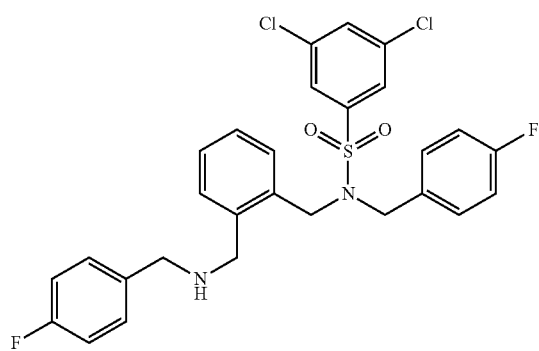 [SMILES: O=S(=O)(c1cc(Cl)cc(Cl)c1)N(Cc1ccc(F)cc1)Cc1ccccc1CNCc1ccc(F)cc1]

C) 3,5-Dichloro-N-(4-fluorobenzyl)-N-(2-((4-fluorobenzylamino)methyl)benzyl)-benzenesulfonamide To a mixture of N,N'-(1,2-phenylenebis(methylene))bis(1-(4-fluorophenyl)methanamine) (1 g, 2.8 mmol, 1 eq) in DCM (HPLC grade 50 mL) at 0° C. was added triethylamine (0.87 g, 8.6 mmol, 3 eq) followed by 3,5-dichlorobenzenesulfonyl chloride (0.52 g, 2.1 mmol, 0.75 eq). The mixture was stirred at 0° C. for 1 h, before being concentrated to dryness. Water was added to the residue and the aqueous mixture was extracted with ethyl acetate. The organic layer was dried over anhydrous Na$_2$SO$_4$ before being evaporated under reduced pressure. The resulting residue was purified by silica gel (230-400) column chromatography eluting with 6% ethyl acetate in hexane to afford the desired product (0.8 g, 53%). $^1$H NMR (400 MHz, CD$_3$OD) δ 7.76-7.72 (m, 1H), 7.33-7.23 (m, 2H), 7.20-7.17 (m, 2H), 7.13-7.10 (m, 4H), 7.03-6.95 (m, 4H), 6.80-6.77 (m, 2H), 4.80 (s, 2H), 4.30 (s, 2H), 3.70 (s, 2H), 3.60 (s, 2H). MS (ESI): 562.0 (M+H)$^+$.

D) 3,5-Dichloro-N-(2-((3,5-dichloro-N-(4-fluorobenzyl)phenylsulfonamido)methyl)-benzyl)-N-(4-fluorobenzyl)-2-hydroxybenzenesulfonamide To a mixture of 3,5-dichloro-N-(4-fluorobenzyl)-N-(2-(4-fluorobenzylamino)methyl)-benzyl)benzene sulfonamide (0.25 g, 0.4 mmol, 1 eq) in DCM (HPLC grade 20 mL) at 0° C. was added triethylamine (0.0.138 g, 1.36 mmol, 3 eq) followed by 3,5-dichloro-2-hydroxybenzenesulfonyl chloride (0.116 g, 0.4 mmol, 1 eq). The reaction mixture was stirred at ambient temperature for 12 h before being concentrated in vacuo. The residue was purified by preparative HPLC to afford the title compound (100 mg, 28.5%). $^1$H NMR (400 MHz, CD$_3$OD) δ 7.73-7.72 (t, 1H), 7.62-7.60 (m, 3H), 7.54-7.53 (d, 1H), 7.12-7.08 (m, 3H), 7.05-6.96 (m, 5H), 6.86-6.80 (m, 4H), 4.39 (s, 2H), 4.37-4.29 (s, 2H), 4.24-4.23 (d, 4H). MS (ESI): 785.0 (M–H)$^-$.

Example 207

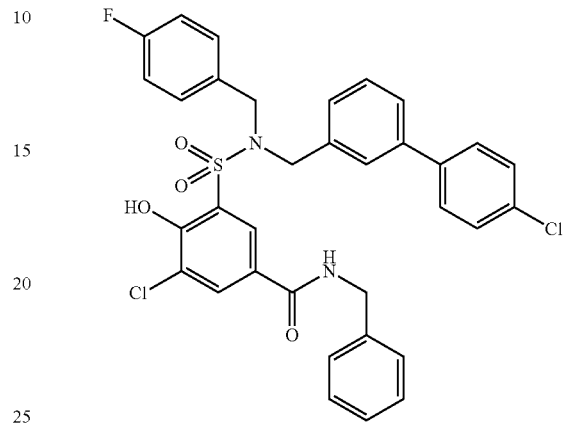

N-Benzyl-3-chloro-5-(N-((4'-chlorobiphenyl-3-yl)methyl)-N-(4-fluorobenzyl)sulfamoyl)-4-hydroxybenzamide

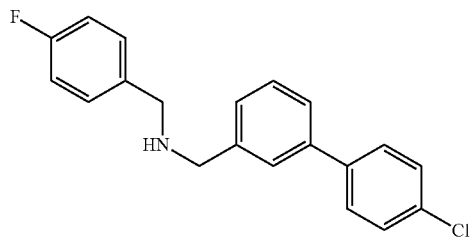 [SMILES: Fc1ccc(CNCc2cccc(-c3ccc(Cl)cc3)c2)cc1]

A) 1-(4'-Chlorobiphenyl-3-yl)-N-(4-fluorobenzyl)methanamine

To a homogeneous mixture of (4-fluorophenyl)methanamine (2.5 mL, 21.8 mmol) and 4'-chlorobiphenyl-3-carbaldehyde (Aldrich, 3.6 g, 16.8 mmol) in anhydrous dichloroethane (25 mL), under nitrogen atmosphere, was added acetic acid (1.2 mL, 21.0 mmol). The mixture was stirred at room temperature for 13.5 h before sodium triacetoxyborohydride (5.0 g, 23.5 mmol) was added. After 4 h, (4-fluorophenyl)methanamine (2.5 mL, 21.8 mmol) was added and the stirring continued. After an additional 5 h of stirring, the reaction was quenched with 1 N aq. NaOH solution (50 mL) then extracted twice with chloroform. The organic extracts were combined, washed with saturated aqueous NaHCO$_3$ and brine, dried over anhydrous MgSO$_4$, filtered and concentrated in vacuo. The residue was purified by silica gel flash chromatography (Merck KGaA, 230-400 mesh particle size) eluting with 0-70% ethyl acetate in hexane, to afford the title compound (3.43 g, 59%) as a colorless oil. MS (ESI): 326.1 (M+H)$^+$.

219

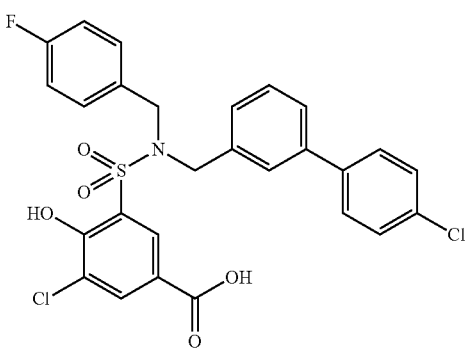

B) 3-Chloro-5-(N-((4'-chlorobiphenyl-3-yl)methyl-N-(4-fluorobenzyl)sulfamoyl)-4-hydroxybenzoic acid To a flask charged with chlorosulfonic acid (13.9 mL, 209.0 mmol) was added 3-chloro-4-hydroxybenzoic acid (6.0 g, 34.8 mmol) portionwise over ten minutes. The mixture was then heated for 2 h at 65° C. under a nitrogen atmosphere. After cooling the mixture to room temperature, the reaction mixture was carefully poured over crushed ice with vigorous stirring, and extracted with Et$_2$O until no further product remained in the aqueous layer. The combined organic extracts were dried over anhydrous Na$_2$SO$_4$, filtered and concentrated in vacuo to afford 3-chloro-5-(chlorosulfonyl)-4-hydroxybenzoic acid as a white solid (7.0 g, 74%) which was used without further purification.

To a heterogeneous mixture of 3-chloro-5-(chlorosulfonyl)-4-hydroxybenzoic acid (0.47 g, 1.8 mmol) in anhydrous dichloromethane (20 mL), at room temperature under nitrogen, was added triethylamine (0.49 mL, 3.5 mmol). To the resulting homogeneous mixture was added a solution of 1-(4'-chlorobiphenyl-3-yl)-N-(4-fluoro-benzyl)methanamine (1.1 g, 3.5 mmol) in anhydrous DCM (5 mL). The resulting mixture was stirred for 15 h before 3-chloro-5-(chlorosulfonyl)-4-hydroxybenzoic acid (0.47 g, 1.8 mmol) was added. After 3.5 h, triethylamine (0.49 mL, 3.5 mmol) was added and the reaction mixture was warwed to 40° C. After 6 h, the reaction mixture was concentrated in vacuo to remove volatiles and treated with saturated aqueous NaHCO$_3$ solution. The resulting mixture was washed twice with Et$_2$O and the organic washings were discarded. The aqueous layer was acidified with 1 N HCl until pH 1-2 (EMD color PHast pH 0-14 pH strips) and extracted three times with ethyl acetate. The combined organic extracts were washed with brine, dried over anhydrous Na$_2$SO$_4$, filtered and concentrated in vacuo to afford an off-white solid. The crude product was purified by preparative HPLC (YMC-Pack, ODS-A, 50×500 mm, 30 minute gradient from 50% to 90% aqueous methanol with 0.1% TFA) to afford the desired compound (254 mg, 26%) as a white solid. $^1$H NMR (DMSO-d$_6$) δ 13.25 (bs, 1H), 8.20 (d, J=2.0 Hz, 1H), 8.02 (d, J=2.0 Hz, 1H), 7.57-7.46 (m, 5H), 7.38-7.05 (m, 7H), 4.54 (s, 2H), 4.50 (s, 2H). MS (ESI): 558.2 (M−H)$^-$.

C) N-Benzyl-3-chloro-5-(N-((4'-chlorobiphenyl-3-yl)methyl)-N-(4-fluorobenzyl)-sulfamoyl)-4-hydroxybenzamide To a homogeneous mixture of 3-chloro-5-(N-((4'-chlorobiphenyl-3-yl)methyl-N-(4-fluorobenzyl)sulfamoyl)-4-hy-

220 droxybenzoic acid (60.8 mg, 0.11 mmol) in anhydrous THF (2 mL) at room temperature under nitrogen was added oxalyl chloride (0.01 mL, 0.15 mmol) followed by anhydrous DMF (one drop). The mixture was stirred for 15 minutes before being concentrated in vacuo to afford 3-chloro-5-(N-((4'-chlorobiphenyl-3-yl)methyl)-N-(4-fluorobenzyl)sulfamoyl)-4-hydroxybenzoyl chloride as a colorless residue.

To a homogeneous mixture of the acid chloride in anhydrous DCM was added phenylmethanamine (0.1 mL, 0.91 mmol). After 2.5 h, the reaction mixture was concentrated in vacuo to afford a gold glass which was purified by preparative HPLC(YMC S5 ODS, 250×20 mm, 30 minute gradient from 58% to 90% aqueous methanol with 0.1% TFA) to afford the title compound (23.1 mg, 66%) as a white solid. $^1$H NMR (DMSO-d$_6$) δ 11.61 (bs, 1H), 9.21-9.14 (m, 1H), 8.30 (d, J=2.0 Hz, 1H), 8.16 (d, J=2.0 Hz, 1H), 7.56-7.43 (m, 5H), 7.39-7.03 (m, 12H), 4.57-4.43 (m, 6H). MS (ESI): 649.1 (M+H)$^+$.

Example 208

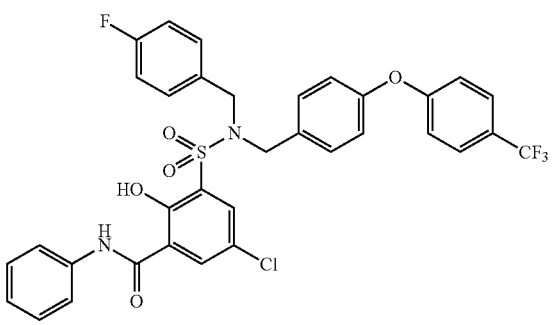 [SMILES: O=C(Nc1ccccc1)c1cc(Cl)cc(S(=O)(=O)N(Cc2ccc(F)cc2)Cc2ccc(Oc3ccc(C(F)(F)F)cc3)cc2)c1O]

5-Chloro-3-(N-(4-fluorobenzyl)-N-(4-(4-(trifluoromethyl)phenoxy)benzyl)sulfamoyl)-2-hydroxy-N-phenylbenzamide

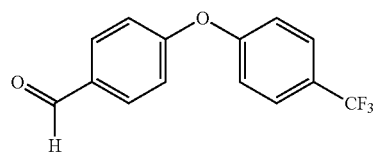 [SMILES: O=Cc1ccc(Oc2ccc(C(F)(F)F)cc2)cc1]

A) 4-(4-(Trifluoromethyl)phenoxy)benzaldehyde

To a homogeneous mixture of 4-(trifluoromethyl)phenol (1.2 g, 7.5 mmol) and 4-fluorobenzaldehyde (0.8 mL, 7.5 mmol) in anhydrous DMF (15 mL), under an argon atmosphere, was added potassium carbonate (1.04 g, 7.5 mmol). The mixture was heated at 150° C. for 4 h before being poured over ice. The resultant precipitate was isolated by vacuum filtration, washed thoroughly with water, dried under vacuum to afford the desired compound (1.4 g, 70%) as a cream colored solid, which was used without further purification. MS (ESI): 267.1 (M+H)$^+$.

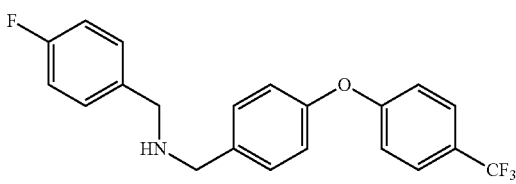 [SMILES: Fc1ccc(CNCc2ccc(Oc3ccc(C(F)(F)F)cc3)cc2)cc1]

B) N-(4-Fluorobenzyl)-1-(4-(4-(trifluoromethyl)phenoxy)phenyl)methanamine

To a mixture of 4-(4-(trifluoromethyl)phenoxy)benzaldehyde (1.4 g, 5.2 mmol) in anhydrous dichloroethane (10 mL), at room temperature under nitrogen, was added (4-fluorophenyl)methanamine (0.6 mL, 52 mmol). The mixture was stirred for 3 minutes before acetic acid (0.42 mL, 7.3 mmol) was added dropwise via syringe. After an additional 30 minutes, sodium triacetoxyborohydride (1.6 g, 7.3 mmol) was added to the reaction mixture. After 20 h, the reaction was quenched with 1 N aqueous NaOH (30 mL) then extracted with chloroform. The organic extracts were combined, washed with saturated aqueous NaHCO$_3$ and brine, dried over anhydrous MgSO$_4$, filtered and concentrated in vacuo. The residue was purified by silica gel flash chromatography (ISCO system, eluting with 0-5% MeOH in CHCl$_3$) to afford the desired compound (0.51 g, 24%) as a colorless oil. MS (ESI): 376.1 (M+H)$^+$.

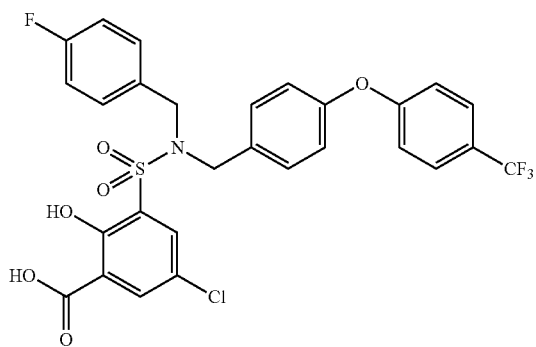 [SMILES: O=C(O)c1cc(Cl)cc(S(=O)(=O)N(Cc2ccc(F)cc2)Cc2ccc(Oc3ccc(C(F)(F)F)cc3)cc2)c1O]

C) 5-Chloro-3-(N-(4-fluorobenzyl)-N-(4-(4-(trifluoromethyl)phenoxy)-benzyl)sulfamoyl)-2-hydroxybenzoic acid N-(4-Fluorobenzyl)-1-(4-(4-(trifluoromethyl)phenoxy)phenyl)methanamine (0.10 g, 0.27 mmol) was converted to the desired compound (0.17 g, 87%) in a manner similar to the preparation of 3-chloro-5-(N-((4'-chlorobiphenyl-3-yl)methyl-N-(4-fluorobenzyl)-sulfamoyl)-4-hydroxybenzoic acid (Compound B of Example 207), except that 5-chloro-2-hydroxybenzoic acid (Alfa Aesar) was used instead of 3-chloro-4-hydroxybenzoic acid and N-(4-fluorobenzyl)-1-(4-(4-(trifluoromethyl)phenoxy)phenyl)-methanamine (0.10 g, 0.27 mmol) was used instead of 1-(4'-chlorobiphenyl-3-yl)-N-(4-fluorobenzyl)-methanamine. $^1$H NMR (DMSO-d$_6$) δ 8.25 (s, 1H), 7.71 (d, J=3.0 Hz, 1H), 7.64 (d, J=8.5 Hz, 2H), 7.55 (d, J=3.0 Hz, 1H), 7.17-7.09 (m, 4H), 6.98-6.78 (m, 6H), 4.41 (s, 2H), 4.36 (s, 2H). MS (ESI): 608.1 (M-H)$^-$.

D) 5-Chloro-3-(N-(4-fluorobenzyl)-N-(4-(4-(trifluoromethyl)phenoxy)benzyl)-sulfamoyl)-2-hydroxy-N-phenylbenzamide 5-Chloro-3-(N-(4-fluorobenzyl)-N-(4-(4-(trifluoromethyl)phenoxy)benzyl)sulfamoyl)-2-hydroxybenzoic acid (0.08 g, 0.14 mmol) was converted to the title compound (0.04 g, 37%) in a manner similar to the preparation of N-benzyl-3-chloro-5-(N-((4'-chloro-biphenyl-3-yl)methyl-N-(4-fluorobenzyl)sulfamoyl)-4-hydroxybenzamide (Compound C of Example 207), except that 5-chloro-3-(N-(4-fluorobenzyl)-N-(4-(4-(trifluoromethyl)-phenoxy)benzyl)sulfamoyl)-2-hydroxybenzoic acid was used instead of 3-chloro-5-(N-((4'-chlorobiphenyl-3-yl)methyl-N-(4-fluorobenzyl)sulfamoyl)-4-hydroxybenzoic acid and aniline (0.2 mL, 2.2 mmol) was used instead of phenylmethanamine. $^1$H NMR (DMSO-d$_6$) δ 8.48 (bs, 1H), 7.88 (s, 1H), 7.72 (m, 4H), 7.45 (t, J=8.0 Hz, 2H), 7.28-7.20 (m, 5H), 7.07 (t, J=8.8 Hz, 2H), 7.01 (d, J=8.3 Hz, 2H), 6.96 (d, J=8.3 Hz, 2H), 4.54 (s, 2H), 4.52 (s, 2H). MS (ESI): 685.1 (M+H)$^+$.

Example 209

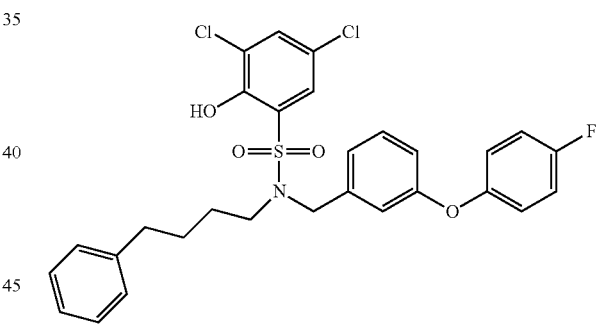

3,5-Dichloro-N-(3-(4-fluorophenoxy)benzyl)-2-hydroxy-N-(4-phenylbutyl)benzenesulfonamide

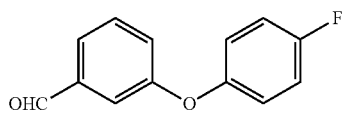 [SMILES: O=Cc1cccc(Oc2ccc(F)cc2)c1]

A) 3-(4-Fluorophenoxy)benzaldehyde

To a mixture of 3-hydroxybenzaldehyde (5.0 g, 40.9 mmol, 1.0 eq) and 4-fluorobromobenzene (14.3 g, 81.7 mmol, 2 eq) in pyridine was added K$_2$CO$_3$ (8.5 g, 61.4 mmol, 1.5 eq) followed by copper powder (1.3 g, 20.5 mmol, 0.5 eq). The reaction mixture was refluxed for 60 h before being filtered to remove the copper powder. The filtrate was then distilled under reduced pressure to remove pyridine. The resultant residue was taken in ethyl acetate and washed with water. The organic layer was dried over anhydrous $Na_2SO_4$ and concentrated under in vacuo. The residue was purified by silica gel column chromatography eluting with 10-20% ethyl acetate in hexane to afford the desired compound (3.0 g, 35%). $^1H$ NMR (400 MHz, $CDCl_3$) δ 9.96 (s, 1H), 7.61-7.58 (t, 1H), 7.50-7.48 (t, 1H), 7.42-7.41 (t, 1H), 7.28-7.24 (m, 1H), 7.11-6.99 (m, 4H). MS (ESI): 218.0 $(M+H)^+$.

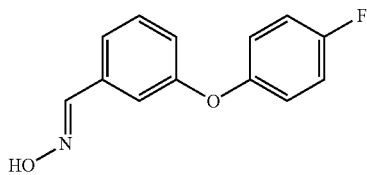 [SMILES: O/N=C/c1cccc(Oc2ccc(F)cc2)c1]

B) (E)-3-(4-Fluorophenoxy)benzaldehyde oxime

To a mixture of 3-(4-fluorophenoxy)benzaldehyde (3.0 g, 13.8 mmol, 1.0 eq) in methanol was added hydroxylamine hydrochloride (1.06 g, 15.2 mmol, 1.1 eq). The reaction mixture was stirred at ambient temperature for 12 h, before being concentrated in vacuo. The residue was taken in ethyl acetate and washed with water. The organic layer was dried with anhydrous $Na_2SO_4$ and concentrated to obtain the desired product (3 g, 94%). $^1H$ NMR (400 MHz, DMSO-$d_6$) δ 8.12 (s, 1H), 7.42-7.38 (t, 1H), 7.32-7.31 (d, 1H), 7.27-7.23 (t, 2H), 7.16 (s, 1H), 7.13-7.10 (m, 2H), 7.01-6.99 (m, 1H). MS (ESI): 232.2 $(M+H)^+$.

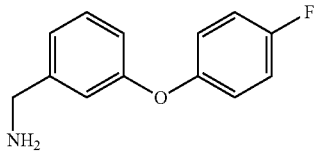 [SMILES: NCc1cccc(Oc2ccc(F)cc2)c1]

C) (3-(4-Fluorophenoxy)phenyl)methanamine

To a mixture of (E)-3-(4-fluorophenoxy)benzaldehyde oxime (3.0 g, 12.9 mmol, 1.0 eq) in ethanol, was added Raney nickel (300 mg, 10% wt/wt) followed by aqueous ammonia (10% in volume). The reaction mixture was stirred at ambient temperature under hydrogen pressure for 4 h, before being filtered. The filtrate was concentrated under high vacuum to obtain the desired compound (1.8 g, 64%). $^1H$ NMR (400 MHz, DMSO-$d_6$) δ 7.30-7.17 (m, 3H), 7.07-6.80 (m, 4H), 6.79-6.76 (t, 1H), 3.67 (s, 1H). MS (ESI): 218.2 $(M+H)^+$.

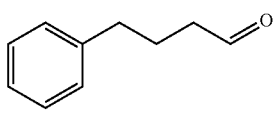 [SMILES: O=CCCCc1ccccc1]

D) 4-Phenylbutanal

To a mixture of 4-phenylbutan-1-ol (1.0 g, 6.6 mmol, 1.0 g) in DCM, cooled to 0° C. was added Dess Martin periodinane (8.4 g, 19.9 mmol, 3.0 eq). The reaction mixture was stirred at ambient temperature for 2 h, before being diluted with DCM and washed with 10% aq. $NaHCO_3$ solution. The organic layer was dried over anhydrous $Na_2SO_4$ and concentrated under reduced pressure to obtain the desired product (600 mg, 61%); $^1H$ NMR (400 MHz, $CDCl_3$) δ 9.77-9.76 (s, 1H), 7.32-7.27 (m, 2H), 7.23-7.18 (m, 3H), 2.69-2.65 (t, 2H), 2.45-2.49 (t, 2H), 1.94-2.00 (m, 3H). MS (ESI): 166.2 $(M+H)^+$.

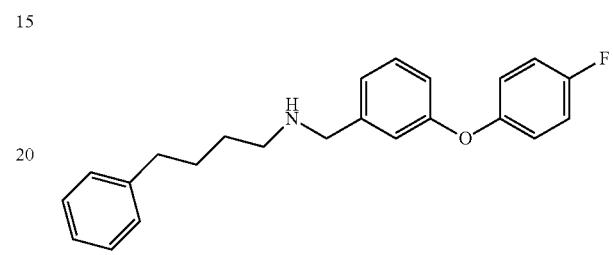

E) N-(3-(4-Fluorophenoxy)benzyl)-4-phenylbutan-1-amine

To a mixture of (3-(4-fluorophenoxy)phenyl)methanamine (200 mg, 0.092 mmol, 1.0 eq) in methanol was added 4-phenylbutanal (136 mg, 0.92 mmol, 1.0 eq). The mixture was refluxed for 2 h, then cooled to 0° C., before adding $NaBH_4$ (105 mg, 2.76 mmol, 3.0 eq) portion wise. The mixture was stirred for 15 minutes before being quenched with 10% aq. $NaHCO_3$ solution. The volatiles were evaporated under reduced pressure and the aqueous solution obtained was extracted with ethyl acetate. The organic layer was dried over anhydrous $Na_2SO_4$ and concentrated under reduced pressure to obtain the desired compound (200 mg, 62%); $^1H$ NMR (400 MHz, $CD_3OD$) δ 7.33-6.86 (m, 13H), 3.72-3.50 (s, 2H), 2.63-2.50 (m, 4H), 1.65-1.54 (m, 4H). MS (ESI): 350.2 $(M+H)^+$.

F) 3,5-Dichloro-N-(3-(4-fluorophenoxy)benzyl)-2-hydroxy-N-(4-phenylbutyl)-benzene sulfonamide To a mixture of N-(3-(4-fluorophenoxy)benzyl)-4-phenylbutan-1-amine (100 mg, 28.6 mmol, 1.0 eq) in DCM (5 mL), was added triethylamine (86 mg, 85 mmol, 3 eq) followed by 2-hydroxy-3,5-dichlorobenzenesulfonyl chloride (75 mg, 28.6 mmol, 1.0 eq). The reaction mixture was stirred at ambient temperature for 4 h before being diluted with DCM (100 mL) and washed with water. The organic layer was dried over anhydrous $Na_2SO_4$ and evaporated under reduced pressure. The residue was purified by preparative HPLC to afford the title compound (45 mg, 28%); $^1H$ NMR (400 MHz, $CD_3OD$) δ 7.67-7.66 (d, 1H), 7.58-7.57 (d, 1H), 7.30-7.26 (t, 1H), 7.23-7.20 (t, 2H), 7.15-7.00 (m, 6H), 6.97-6.94 (m, 2H), 6.88-6.84 (m, 2H), 4.47 (s, 2H), 3.26-3.22 (t, 2H), 2.46-2.43 (t, 2H), 1.42-1.34 (m, 4H). MS (ESI): 574.0 $(M-H)^-$.

Examples 210-229

The following examples were prepared using similar procedures to those for Examples 208 and 209:

| Ex. No. | Structure | Name | HPLC t_R (minute)* | LCMS |
|---|---|---|---|---|
| 210 | 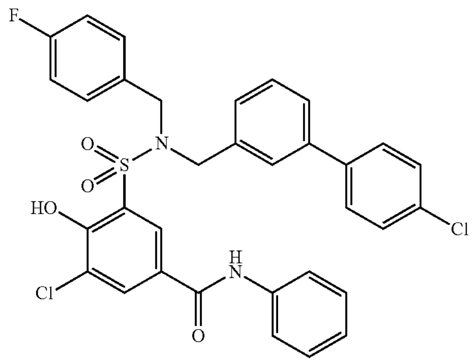 [SMILES: O=C(Nc1ccccc1)c1cc(Cl)c(O)c(S(=O)(=O)N(Cc2ccc(F)cc2)Cc2cccc(-c3ccc(Cl)cc3)c2)c1] | 3-Chloro-5-(N-((4'-chlorobiphenyl-3-yl)methyl)-N-(4-fluorobenzyl)-sulfamoyl)-4-hydroxy-N-phenylbenzamide | A 3.99 | (M + H)+ 635.1 |
| 211 | 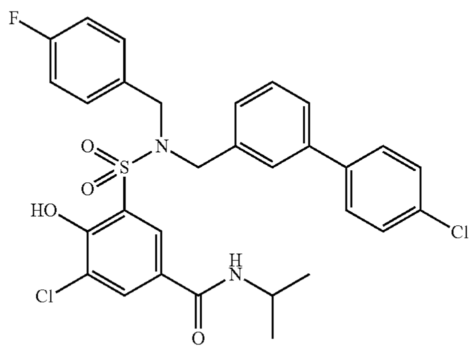 [SMILES: CC(C)NC(=O)c1cc(Cl)c(O)c(S(=O)(=O)N(Cc2ccc(F)cc2)Cc2cccc(-c3ccc(Cl)cc3)c2)c1] | 3-Chloro-5-(N-((4'-chlorobiphenyl-3-yl)methyl)-N-(4-fluorobenzyl)-sulfamoyl)-4-hydroxy-N-isopropylbenzamide | A 3.87 | (M + H)+ 601.1 |
| 212 | 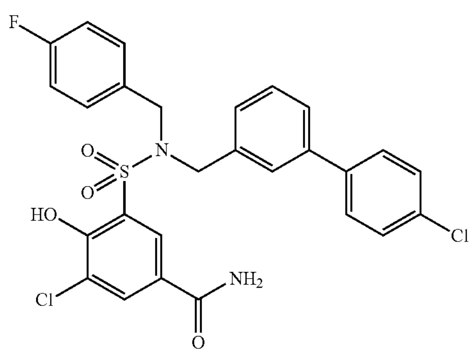 [SMILES: NC(=O)c1cc(Cl)c(O)c(S(=O)(=O)N(Cc2ccc(F)cc2)Cc2cccc(-c3ccc(Cl)cc3)c2)c1] | 3-Chloro-5-(N-((4'-chlorobiphenyl-3-yl)methyl)-N-(4-fluorobenzyl)-sulfamoyl)-4-hydroxybenzamide | B 4.54 | (M + H)+ 559.0 |
| 213 | 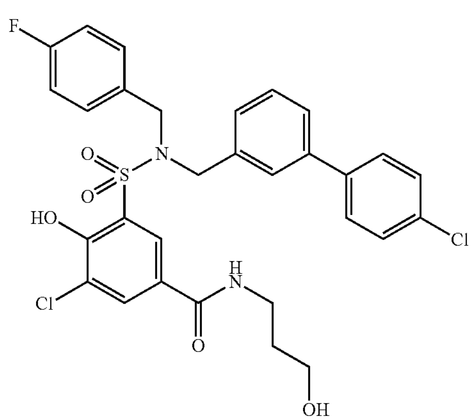 [SMILES: O=C(NCCCO)c1cc(Cl)c(O)c(S(=O)(=O)N(Cc2ccc(F)cc2)Cc2cccc(-c3ccc(Cl)cc3)c2)c1] | 3-Chloro-5-(N-((4'-chlorobiphenyl-3-yl)methyl)-N-(4-fluorobenzyl)-sulfamoyl)-4-hydroxy-N-(3-hydroxypropyl)benzamide | B 4.48 | (M + H)+ 617.1 |

-continued

| Ex. No. | Structure | Name | HPLC t$_R$ (minute)* | LCMS |
|---|---|---|---|---|
| 214 | 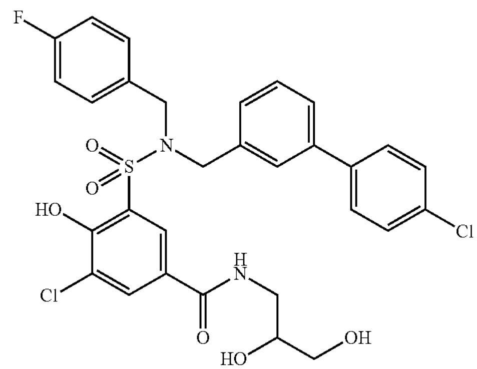 [SMILES: O=C(NCC(O)CO)c1cc(Cl)c(O)c(S(=O)(=O)N(Cc2ccc(F)cc2)Cc2cccc(-c3ccc(Cl)cc3)c2)c1] | 3-Chloro-5-(N-((4'-chlorobiphenyl-3-yl)methyl)-N-(4-fluorobenzyl)-sulfamoyl)-N-(2,3-dihydroxypropyl)-4-hydroxybenzamide | B 3.63 | (M + H)$^+$ 633.1 |
| 215 | 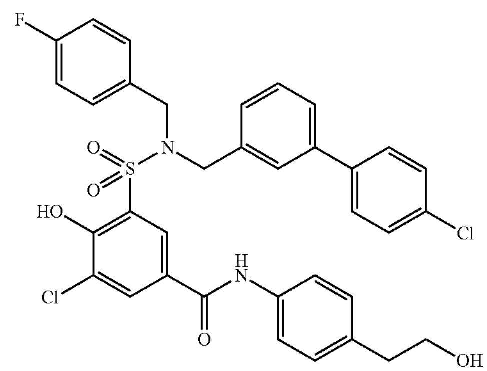 [SMILES: O=C(Nc1ccc(CCO)cc1)c1cc(Cl)c(O)c(S(=O)(=O)N(Cc2ccc(F)cc2)Cc2cccc(-c3ccc(Cl)cc3)c2)c1] | 3-Chloro-5-(N-((4'-chlorobiphenyl-3-yl)methyl)-N-(4-fluorobenzyl)-sulfamoyl)-4-hydroxy-N-(4-(2-hydroxyethyl)phenyl)benzamide | B 4.50 | (M + H)$^+$ 679.17 |
| 216 | 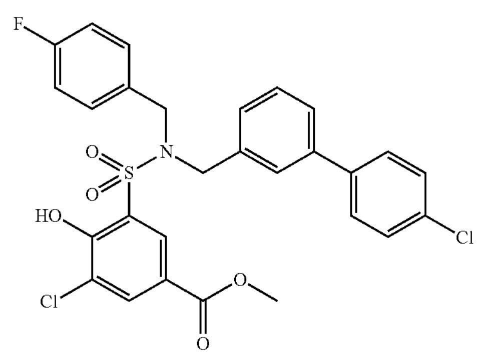 [SMILES: COC(=O)c1cc(Cl)c(O)c(S(=O)(=O)N(Cc2ccc(F)cc2)Cc2cccc(-c3ccc(Cl)cc3)c2)c1] | Methyl 3-chloro-5-(N-((4'-chloro-biphenyl-3-yl)methyl)-N-(4-fluorobenzyl)sulfamoyl)-4-hydroxybenzoate | B 4.83 | (M − H)$^-$ 572.2 |
| 217 | 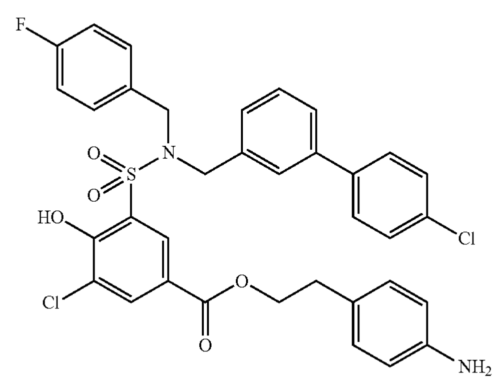 [SMILES: Nc1ccc(CCOC(=O)c2cc(Cl)c(O)c(S(=O)(=O)N(Cc3ccc(F)cc3)Cc3cccc(-c4ccc(Cl)cc4)c3)c2)cc1] | 4-Aminophenethyl 3-chloro-5-(N-((4'-chlorobiphenyl-3-yl)methyl)-N-(4-fluorobenzyl)sulfamoyl)-4-hydroxybenzoate | B 4.15 | (M + H)$^+$ 679.2 |

-continued

| Ex. No. | Structure | Name | HPLC t$_R$ (minute)* | LCMS |
|---|---|---|---|---|
| 218 | 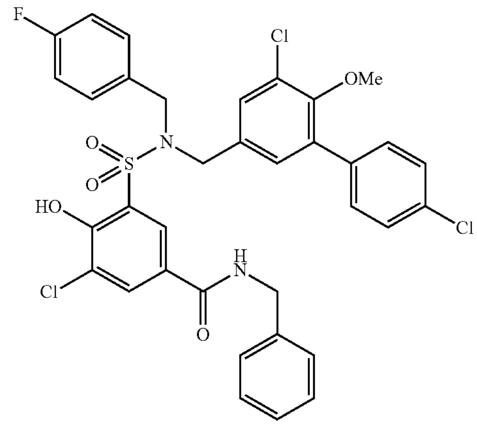 [SMILES: COc1c(Cl)cc(CN(Cc2ccc(F)cc2)S(=O)(=O)c2cc(C(=O)NCc3ccccc3)cc(Cl)c2O)cc1-c1ccc(Cl)cc1] | N-Benzyl-3-chloro-5-(N-((4',5-dichloro-6-methoxybiphenyl-3-yl)methyl)-N-(4-fluorobenzyl)sulfamoyl)-4-hydroxybenzamide | C 22.380 | (M − H)$^-$ 711 |
| 219 | 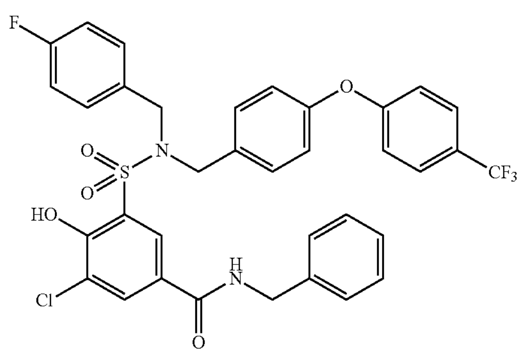 [SMILES: O=C(NCc1ccccc1)c1cc(Cl)c(O)c(S(=O)(=O)N(Cc2ccc(F)cc2)Cc2ccc(Oc3ccc(C(F)(F)F)cc3)cc2)c1] | N-Benzyl-3-chloro-5-(N-(4-fluoro-benzyl)-N-(4-(4-(trifluoromethyl)-phenoxy)benzyl)sulfamoyl)-4-hydroxybenzamide | B 4.76 | (M + H)$^+$ 699.0 |
| 220 | 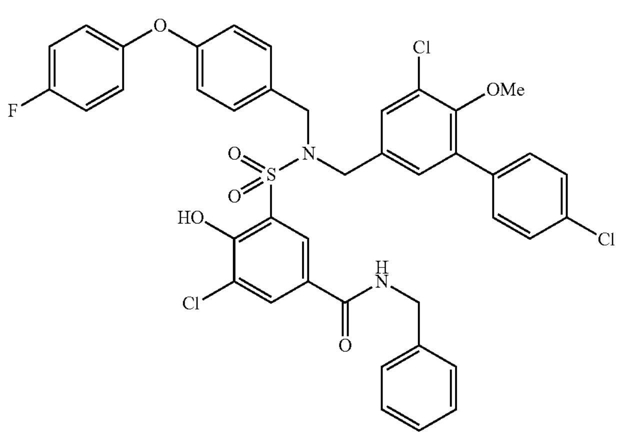 [SMILES: COc1c(Cl)cc(CN(Cc2ccc(Oc3ccc(F)cc3)cc2)S(=O)(=O)c2cc(C(=O)NCc3ccccc3)cc(Cl)c2O)cc1-c1ccc(Cl)cc1] | N-Benzyl-3-chloro-5-(N-((4',5-dichloro-6-methoxybiphenyl-3-yl)methyl)-N-(4-(4-fluorophenoxy)benzyl)sulfamoyl)-4-hydroxybenzamide | C 23.775 | (M − H)$^-$ 803 |

| Ex. No. | Structure | Name | HPLC $t_R$ (minute)* | LCMS |
|---|---|---|---|---|
| 221 | 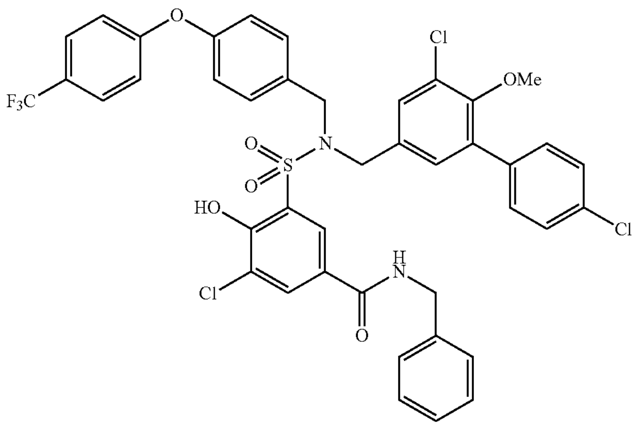 [SMILES: COc1c(Cl)cc(CN(Cc2ccc(Oc3ccc(C(F)(F)F)cc3)cc2)S(=O)(=O)c2cc(C(=O)NCc3ccccc3)cc(Cl)c2O)cc1-c1ccc(Cl)cc1] | N-Benzyl-3-chloro-5-(N-((4',5-dichloro-6-methoxybiphenyl-3-yl)methyl)-N-(4-(4-(trifluoromethyl)phenoxy)benzyl)-sulfamoyl)-4-hydroxybenzamide | C 24.328 | (M − H)⁻ 853 |
| 222 | 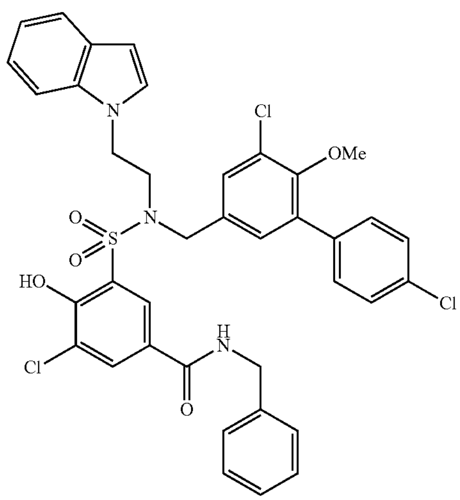 [SMILES: COc1c(Cl)cc(CN(CCn2ccc3ccccc32)S(=O)(=O)c2cc(C(=O)NCc3ccccc3)cc(Cl)c2O)cc1-c1ccc(Cl)cc1] | 3-(N-(2-(1H-Indol-1-yl)ethyl)-N-((4',5-dichloro-6-methoxybiphenyl-3-yl)methyl)sulfamoyl)-N-benzyl-5-chloro-4-hydroxybenzamide | C 24.028 | (M − H)⁻ 746 |
| 223 | 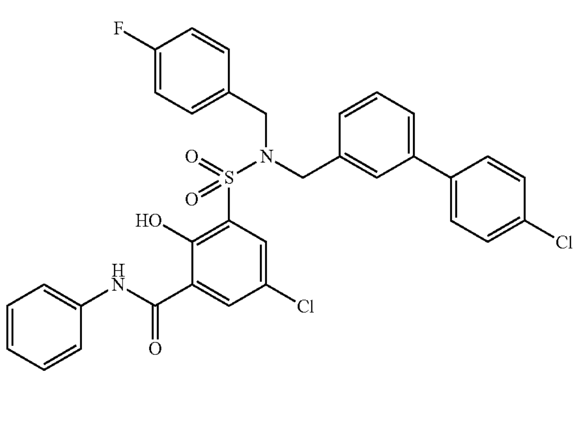 [SMILES: O=C(Nc1ccccc1)c1cc(Cl)cc(S(=O)(=O)N(Cc2ccc(F)cc2)Cc2cccc(-c3ccc(Cl)cc3)c2)c1O] | 5-Chloro-3-(N-((4'-chlorobiphenyl-3-yl)methyl)-N-(4-fluorobenzyl)-sulfamoyl)-2-hydroxy-N-phenylbenzamide | B 5.34 | (M + H)⁺ 635.0 |

| Ex. No. | Structure | Name | HPLC $t_R$ (minute)* | LCMS |
|---|---|---|---|---|
| 224 | 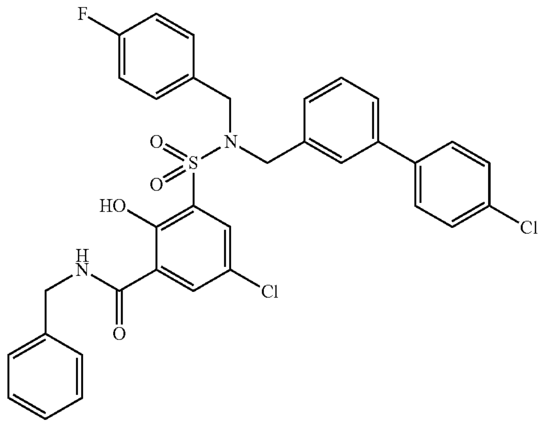 [SMILES: O=C(NCc1ccccc1)c1cc(Cl)cc(S(=O)(=O)N(Cc2ccc(F)cc2)Cc2cccc(-c3ccc(Cl)cc3)c2)c1O] | N-Benzyl-5-chloro-3-(N-((4'-chlorobiphenyl-3-yl)methyl)-N-(4-fluorobenzyl)sulfamoyl)-2-hydroxybenzamide | B 5.15 | $(M + H)^+$ 649.0 |
| 225 | 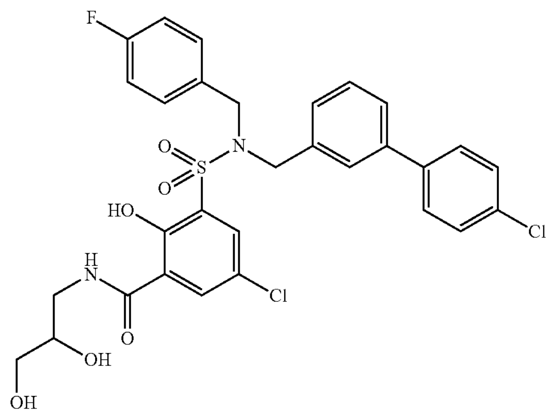 [SMILES: O=C(NCC(O)CO)c1cc(Cl)cc(S(=O)(=O)N(Cc2ccc(F)cc2)Cc2cccc(-c3ccc(Cl)cc3)c2)c1O] | 5-Chloro-3-(N-((4'-chlorobiphenyl-3-yl)methyl)-N-(4-fluorobenzyl)-sulfamoyl)-N-(2,3-dihydroxypropyl)-2-hydroxybenzamide | B 4.71 | $(M + H)^+$ 633.0 |
| 226 | 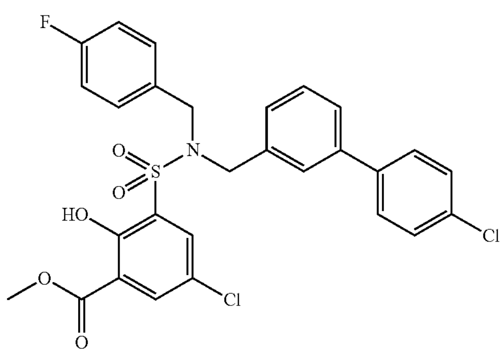 [SMILES: COC(=O)c1cc(Cl)cc(S(=O)(=O)N(Cc2ccc(F)cc2)Cc2cccc(-c3ccc(Cl)cc3)c2)c1O] | Methyl 5-chloro-3-(N-((4'-chloro-biphenyl-3-yl)methyl)-N-(4-fluorobenzyl)sulfamoyl)-2-hydroxybenzoate | B 5.17 | $(M - H)^-$ 572.3 |
| 227 | 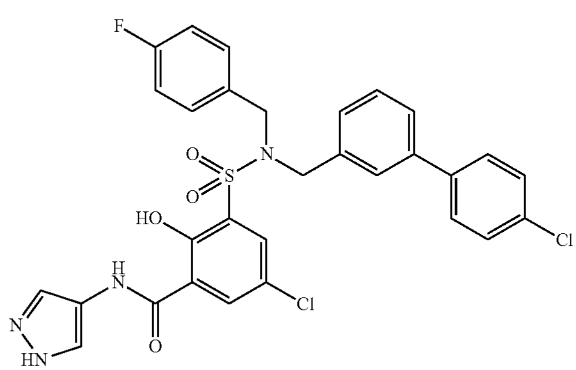 [SMILES: O=C(Nc1cn[nH]c1)c1cc(Cl)cc(S(=O)(=O)N(Cc2ccc(F)cc2)Cc2cccc(-c3ccc(Cl)cc3)c2)c1O] | 5-Chloro-3-(N-((4'-chlorobiphenyl-3-yl)methyl)-N-(4-fluorobenzyl)-sulfamoyl)-2-hydroxy-N-(1H-pyrazol-4-yl)benzamide | B 4.82 | $(M + H)^+$ 625.0 |

| Ex. No. | Structure | Name | HPLC $t_R$ (minute)* | LCMS |
|---|---|---|---|---|
| 228 | 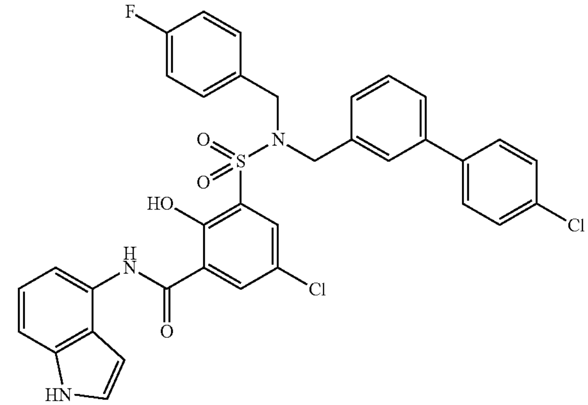 [SMILES: O=C(Nc1cccc2[nH]ccc12)c1cc(Cl)cc(S(=O)(=O)N(Cc2ccc(F)cc2)Cc2cccc(-c3ccc(Cl)cc3)c2)c1O] | 5-Chloro-3-(N-((4'-chlorobiphenyl-3-yl)-methyl)-N-(4-fluorobenzyl)-sulfamoyl)-2-hydroxy-N-(1H-indol-4-yl)benzamide | B 4.92 | (M + H)+ 674.0 |
| 229 | 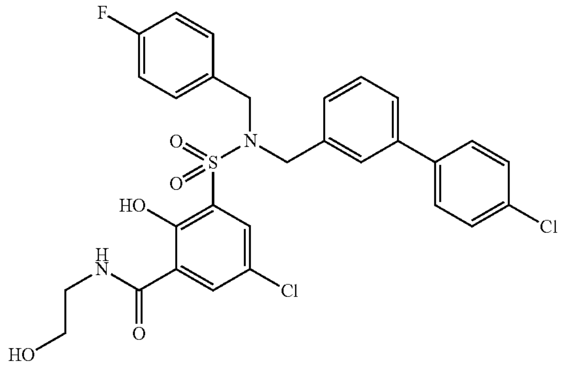 [SMILES: O=C(NCCO)c1cc(Cl)cc(S(=O)(=O)N(Cc2ccc(F)cc2)Cc2cccc(-c3ccc(Cl)cc3)c2)c1O] | 5-Chloro-3-(N-((4'-chlorobiphenyl-3-yl)-methyl)-N-(4-fluorobenzyl)-sulfamoyl)-2-hydroxy-N-(2-hydroxyethyl)benzamide | B 4.79 | (M + H)+ 603.0 |

*HPLC conditions:
A) YMC S5 ODS, 4.6 × 50 mm column: 6 minute run with 4 minute gradient from 10-90% aqueous MeOH with 0.2% H₃PO₄.
B) YMC CombiScreen ODS-A S5, 4.6 × 50 mm column: 6 minute run with 4 minute gradient from 10-90% aqueous MeOH with 0.2% H₃PO₄.
C) XBridge Phenyl, 4.6 × 150 mm, 3.5μ column: 35 minute run with 25 minute gradient from 14 to 95% aq. MCN with 0.05% TFA.

Example 230

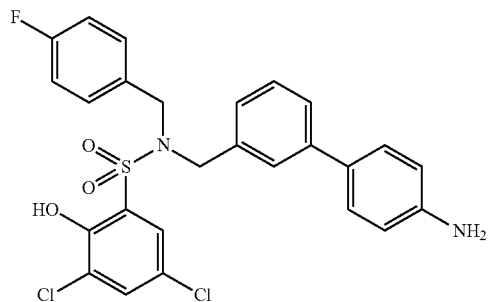

N-((4'-Aminobiphenyl-3-yl)methyl)-3,5-dichloro-N-(4-fluorobenzyl)-2-hydroxybenzenesulfonamide

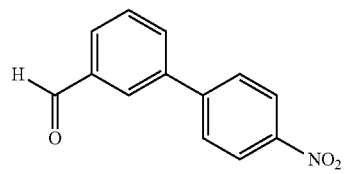

A) 4'-Nitrobiphenyl-3-carbaldehyde

To a sealable flask containing a mixture of 3-bromobenzaldehyde (1.8 mL, 15 mmol) and Na₂CO₃ (1.6 g, 15 mmol) in anhydrous DMF (20 mL) and water (10 mL), were added 4-nitrophenylboronic acid (2.5 g, 15 mmol) then palladium (II) acetate (0.17 g, 0.75 mmol). Argon was bubbled through the mixture before the flask was sealed and the mixture stirred at room temperature. After 4 days, the reaction mixture was partitioned between ethyl acetate and brine before the entire mixture was filtered through a pad of Celite®. The aqueous and organic layers, of the filtrate, were separated and the aqueous layer was extracted twice more with EtOAc. All of the organic layers were combined, washed with brine, dried over anhydrous sodium sulfate, filtered and concentrated in vacuo. Purification by silica gel flash chromatography (ISCO CombiFlash Companion system, 120 g, RediSep normal phase silica flash column, eluting with 10-50% EtOAc in hexane) afforded the desired compound (1.7 g, 47%) as an off-white solid. ¹H NMR (CDCl₃) δ 10.05 (s, 1H), 8.31-8.25 (m, 2H), 8.10-8.06 (m, 1H), 7.93-7.81 (m, 2H), 7.77-7.70 (m, 2H), 7.63 (t, J=7.7 Hz, 1H). MS (ESI): 228.1 (M+H)⁺.

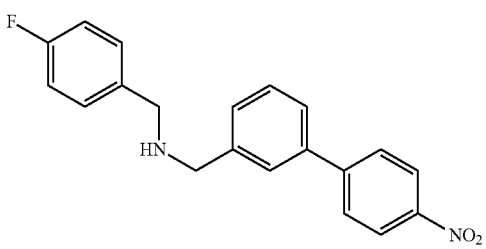 [SMILES: O=[N+]([O-])c1ccc(-c2cccc(CNCc3ccc(F)cc3)c2)cc1]

B) N-(4-Fluorobenzyl)-1-(4'-nitrobiphenyl-3-yl)methanamine

4'-Nitrobiphenyl-3-carbaldehyde (0.73 g, 3.2 mmol) was converted to the desired compound (0.82 g, 71%) in a manner similar to the preparation of 1-(4'-chlorobiphenyl-3-yl)-N-(4-fluorobenzyl)methanamine (Compound A of Example 207). $^1$H NMR (CDCl$_3$) δ 8.34-8.30 (m, 2H), 7.80-7.74 (m, 2H), 7.64 (bs, 1H), 7.58-7.42 (m, 3H), 7.38-7.30 (m, 2H), 7.09-7.00 (m, 2H), 3.91 (s, 2H), 3.84 (s, 2H). MS (ESI): 337.4 (M+H)$^+$.

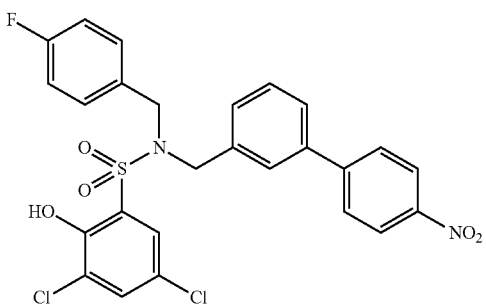 [SMILES: O=[N+]([O-])c1ccc(-c2cccc(CN(Cc3ccc(F)cc3)S(=O)(=O)c3cc(Cl)cc(Cl)c3O)c2)cc1]

C) 3,5-Dichloro-N-(4-fluorobenzyl)-2-hydroxy-N-((4'-nitrobiphenyl-3-yl)methyl)-benzenesulfonamide N-(4-Fluorobenzyl)-1-(4'-nitrobiphenyl-3-yl)methanamine (0.76 g, 2.3 mmol) was converted to the desired compound (0.92 g, 70%) in a manner similar to the preparation of 3-chloro-5-(N-((4'-chlorobiphenyl-3-yl)methyl-N-(4-fluorobenzyl)sulfamoyl)-4-hydroxy-benzoic acid (Compound B of Example 207), except that N-(4-fluorobenzyl)-1-(4'-nitro-biphenyl-3-yl)methanamine was used instead of 1-(4'-chlorobiphenyl-3-yl)-N-(4-fluoro-benzyl)methanamine and 3,5-dichloro-2-hydroxybenzene-1-sulfonyl chloride (0.65 g, 2.5 mmol) was used instead of 3-chloro-5-(chlorosulfonyl)-4-hydroxybenzoic acid. $^1$H NMR (DMSO-d$_6$) δ 8.30 (d, J=8.8 Hz, 2H), 7.78-7.72 (m, 3H), 7.60-7.52 (m, 2H), 7.37 (t, J=7.7 Hz, 1H), 7.33 (s, 1H), 7.28-7.20 (m, 3H), 7.06 (t, J=8.8 Hz, 2H), 4.53 (s, 2H), 4.51 (s, 2H). MS (ESI): 559.2 (M−H)$^−$.

D) N-((4'-Aminobiphenyl-3-yl)methyl)-3,5-dichloro-N-(4-fluorobenzyl)-2-hydroxybenzenesulfonamide A mixture of 3,5-dichloro-N-(4-fluorobenzyl)-2-hydroxy-N-((4'-nitrobiphenyl-3-yl)-methyl)benzenesulfonamide (0.2 g, 0.4 mmol) and iron (0.1 g, 2.1 mmol) in acetic acid (5 mL) was heated at 70° C., under a nitrogen atmosphere. After 40 minutes, the reaction mixture was cooled to room temperature and filtered through a pad of Celite®. The pad was thoroughly rinsed with EtOAc followed by CHCl$_3$. The combined filtrates were concentrated in vacuo. The crude product was dissolved in CHCl$_3$ then passed through a RediSep normal phase silica flash column (12 g) eluting with CHCl$_3$. The appropriate fractions were concentrated in vacuo to afford the title compound (0.18 g, 84%) as an off-white solid. $^1$H NMR (DMSO-d$_6$) δ 7.77 (d, J=2.2 Hz, 1H), 7.58 (d, J=2.7 Hz, 1H), 7.34 (d, J=7.7 Hz, 1H), 7.24-7.03 (m, 8H), 6.93 (d, J=7.7 Hz, 1H), 6.63-6.58 (m, 2H), 4.46 (s, 2H), 4.43 (s, 2H). MS (ESI): 531.0 (M+H)$^+$.

Example 231

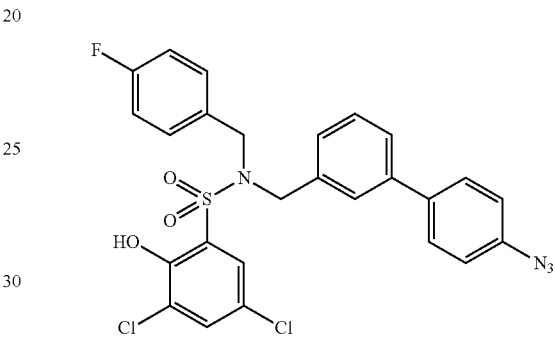

N-((4'-Azidobiphenyl-3-yl)methyl)-3,5-dichloro-N-(4-fluorobenzyl)-2-hydroxybenzenesulfonamide To an ice cold mixture of N-((4'-aminobiphenyl-3-yl)methyl)-3,5-dichloro-N-(4-fluoro-benzyl)-2-hydroxybenzenesulfonamide (0.08 g, 0.15 mmol) in anhydrous acetonitrile (1 mL) and anhydrous THF (1 mL) was added tert-butyl nitrite (0.03 mL, 0.22 mmol) followed by the dropwise addition of azidotrimethylsilane (0.02 mL, 0.17 mmol). The ice bath was removed and the reaction stirred at room temperature. After 1 h, anhydrous THF (0.5 mL) and anhydrous acetonitrile (0.5 mL) were added. After an additional 16 h, the reaction mixture was cooled to 0° C. before tert-butyl nitrite (0.06 mL, 0.44 mmol) and azidotrimethylsilane (0.07 mL, 0.52 mmol) were added. Two hours later, the reaction was quenched with water and extracted twice with chloroform. The combined organic layers were dried over anhydrous sodium sulfate, filtered and concentrated in vacuo. The residue was dissolved in CHCl$_3$ then passed through a RediSep normal phase silica flash column (4 g) eluting with hexane, followed by CHCl$_3$. The appropriate fractions were concentrated in vacuo to afford the title compound (0.04 g, 50%) as a brown glass. $^1$H NMR (DMSO-d$_6$) δ 7.80-7.75 (m, 1H), 7.57 (d, J=2.5 Hz, 1H), 7.56-7.45 (m, 3H), 7.32 (t, J=7.7 Hz, 1H), 7.28-7.18 (m, 5H), 7.15-7.03 (m, 3H), 4.51 (s, 2H), 4.49 (s, 2H). MS (ESI): 555.3 (M−H)$^−$.

Example 232

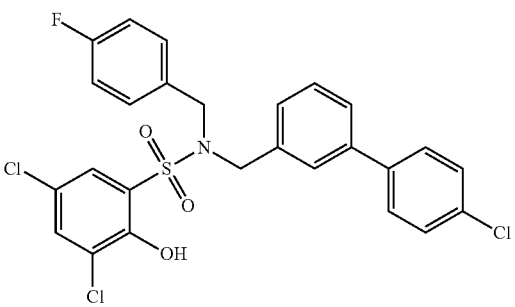 [SMILES: O=S(=O)(c1cc(Cl)cc(Cl)c1O)N(Cc1ccc(F)cc1)Cc1cccc(-c2ccc(Cl)cc2)c1]

3,5-Dichloro-N-((4'-chlorobiphenyl-3-yl)methyl)-N-(4-fluorobenzyl)-2-hydroxybenzenesulfonamide

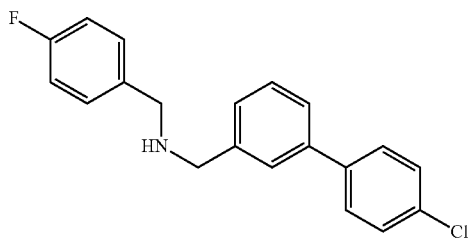 [SMILES: Fc1ccc(CNCc2cccc(-c3ccc(Cl)cc3)c2)cc1]

A) 1-(4'-Chlorobiphenyl-3-yl)-N-(4-fluorobenzyl)methanamine

To a solution of (4'-chlorobiphenyl-3-yl)methanamine HCl salt (Chem-Impex International, Inc., 0.6 g, 2.36 mmol) in CH$_2$Cl$_2$ (6 mL) and 2-propanol (6.00 mL) was added 4-fluorobenzaldehyde (0.28 mL, 2.60 mmol). The resulting reaction mixture was stirred at rt for 1 h. and sodium triacetoxyborohydride (0.75 g, 3.54 mmol) was added under N$_2$. After stirring at rt for 3 h, the reaction mixture was quenched with saturated aqueous NaHCO$_3$, stirred for 10 minutes and concentrated in vacuo. The residue was diluted with ethyl acetate and saturated aqueous NaHCO$_3$ solution. The organic layer was separated, washed with brine, dried over MgSO$_4$, filtered and the filtrate solution was concentrated in vacuo. The residue was purified by flash silica gel chromatography eluting with 0-10% ethyl acetate in CH$_2$Cl$_2$ to afford the desired compound (0.63 g, 73%) as a colorless oil. $^1$H NMR (CDCl$_3$) δ 7.62-7.41 (m, 6H), 7.37-7.32 (m, 3H), 7.09-7.01 (m, 3H), 3.92 (s, 2H), 3.83 (s, 2H). MS (ESI): 326.0 (M+H)$^+$.

B) 3,5-Dichloro-N-((4'-chlorobiphenyl-3-yl)methyl)-N-(4-fluorobenzyl)-2-hydroxybenzenesulfonamide To a solution of 1-(4'-chlorobiphenyl-3-yl)-N-(4-fluorobenzyl)methanamine (70 mg, 0.22 mmol) in THF (4 mL) were added 3,5-dichloro-2-hydroxybenzenesulfonyl chloride (61.8 mg, 0.24 mmol) and TEA (0.08 mL, 0.54 mmol). The resulting mixture was stirred at rt for 1 h and concentrated in vacuo. The residue was dissolved in MeOH and purified by preparative HPLC. Fractions containing the desired product were combined, concentrated, and lyophilized to give the title compound (46 mg, 39%) as a glassy solid. $^1$H NMR (CD$_3$OD) δ 7.59 (d, J=4.0 Hz, 1H), 7.43 (d, J=4.0 Hz, 1H), 7.36-7.35 (m, 5H), 7.22 (t, J=8.0 Hz, 1H), 7.16-7.09 (m, 5H), 7.05-7.03 (t, J=8.0 Hz, 1H), 6.90-6.85 (m, 2H), 4.46 (s, 2H), 4.41 (s, 2H). MS (ESI): 550.0 (M−H)$^−$.

Example 233

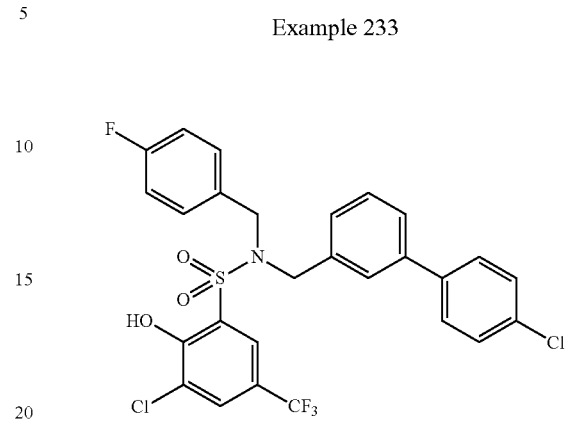

3-Chloro-N-((4'-chlorobiphenyl-3-yl)methyl)-N-(4-fluorobenzyl)-2-hydroxy-5-(trifluoromethyl)benzenesulfonamide 1-(4'-Chlorobiphenyl-3-yl)-N-(4-fluorobenzyl)methanamine (Compound A of Example 232, 200 mg, 0.6 mmol, 1.0 eq) was dissolved in dry DCM (20 mL) then stirred and cooled to 0° C. Triethylamine (186 mg, 1.86 mmol, 3.0 eq) was added slowly and the mixture was stirred for 30 minutes. 3-Chloro-2-hydroxy-5-(trifluoromethyl)benzene-1-sulfonyl chloride (180 mg 0.6 mmol 1.0 eq) dissolved in DCM was added to the above solution and the resulting mixture was stirred for 12 h at ambient temperature. The solution was concentrated under reduced pressure and the residue was purified by silica gel (240-280) column chromatography using 20-30% ethyl acetate/hexane as the eluent to afford the title compound (0.2 g, 56%). $^1$H NMR (400 MHz, CD$_3$OD) δ 7.92 (d, 1H), 7.79 (d, 1H), 7.43 (d, 5H), 7.32-7.29 (t, 1H), 7.27-7.25 (m, 2H), 7.23 (s, 1H), 7.15-7.13 (d, 1H), 6.98-6.94 (t, 2H), 4.89 (s, 1H), 4.58-4.53 (d, 2H). MS (ESI): 585.8 (M+H)$^+$.

Example 234

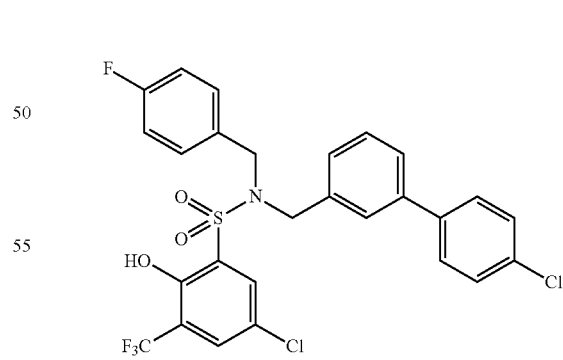

5-Chloro-N-((4'-chlorobiphenyl-3-yl)methyl)-N-(4-fluorobenzyl)-2-hydroxy-3-(trifluoromethyl)benzenesulfonamide The compound was prepared following a similar procedure described for Example 233. MS (ESI): 585.7 (M+H)$^+$,

Example 235

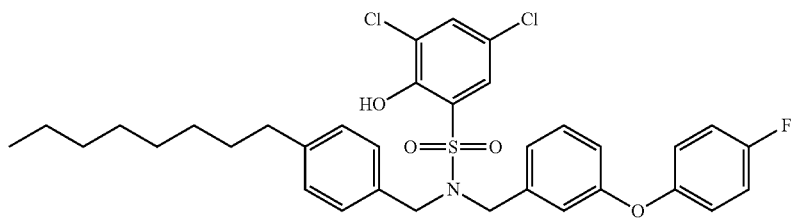 [SMILES: CCCCCCCCc1ccc(CN(Cc2cccc(Oc3ccc(F)cc3)c2)S(=O)(=O)c2cc(Cl)cc(Cl)c2O)cc1]

3,5-Dichloro-N-(3-(4-fluorophenoxy)benzyl)-2-hydroxy-N-(4-octylbenzyl)benzenesulfonamide

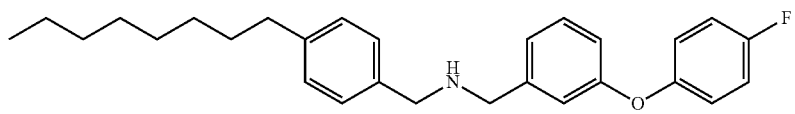 [SMILES: CCCCCCCCc1ccc(CNCc2cccc(Oc3ccc(F)cc3)c2)cc1]

A) N-(3-(4-Fluorophenoxy)benzyl)-1-(4-octylphenyl)methanamine

To a mixture of (3-(4-fluorophenoxy)phenyl)methanamine (Compound C of Example 209, 150 mg, 0.69 mmol, 1.0 eq) in methanol was added 4-octylbenzaldehyde (Apin Chemicals Ltd., 145 mg, 0.69 mmol, 1.0 eq). The mixture was refluxed for 2 h before being cooled to 0° C. and treated, portionwise, with NaBH$_4$ (80 mg, 2.08 mmol, 3.0 eq). After stirring for 15 minutes, the reaction mixture was quenched with 10% aq. NaHCO$_3$ solution. The volatiles were evaporated under reduced pressure and the aqueous solution obtained was extracted with ethyl acetate. The organic layer was dried over Na$_2$SO$_4$ and evaporated under reduced pressure to obtain the desired product (220 mg, 78%). $^1$H NMR (400 MHz, CD$_3$OD) δ 7.33-7.29 (t, 1H), 7.21-7.19 (d, 2H), 7.14-7.06 (m, 5H), 7.02-6.96 (m, 3H), 6.88-6.85 (m, 3.70-3.68 (d, 4H), 2.60-2.57 (t, 2H), 1.59 (m, 2H), 1.31-1.28 (m, 10H), 0.90-0.87 (t, 3H). MS (ESI): 420.2 (M+H)$^+$.

B) 3,5-Dichloro-N-(3-(4-fluorophenoxy)benzyl)-2-hydroxy-N-(4-octylbenzyl)-benzenesulfonamide To a mixture of N-(3-(4-fluorophenoxy)benzyl)-1-(4-octylphenyl)methanamine (100 mg, 0.238 mmol, 1.0 eq) in DCM (10 mL) was added triethylamine (72 mg, 0.72 mmol, 3.0 eq) followed by 2-hydroxy-3,5-dichlorobenzenesulfonyl chloride (62 mg, 0.238 mmol, 1.0 eq). After stirring at ambient temperature for 4 h, the reaction mixture was diluted with 100 mL DCM and washed with water. The organic layer was dried over anhydrous Na$_2$SO$_4$ and evaporated under reduced pressure. The crude residue was purified by preparative HPLC to afford the title compound (25 mg, 16%). $^1$H NMR (400 MHz, CD$_3$OD) δ 7.64-7.63 (d, 1H), 7.55-7.54 (d, 1H), 7.21 (m, 1H), 7.19-7.11 (m, 2H), 7.09-7.02 (m, 4H), 6.95-6.91 (m, 2H), 6.88-6.86 (d, 1H), 6.80-6.78 (d, 1H), 6.68 (s, 1H), 4.43-4.40 (d, 4H), 3.35-3.30 (m, 6H), 2.55-2.51 (t, 2H), 1.57-1.56 (t, 3H), 1.3 (s, 10H), 0.87-0.91 (t, 3H). MS (ESI): 644.0 (M−H)$^-$.

Examples 236-239

The following examples were prepared using similar procedures to those described above:

| Ex. No. | Structure | Name | HPLC tR (minute)* | LCMS |
|---|---|---|---|---|
| 236 | 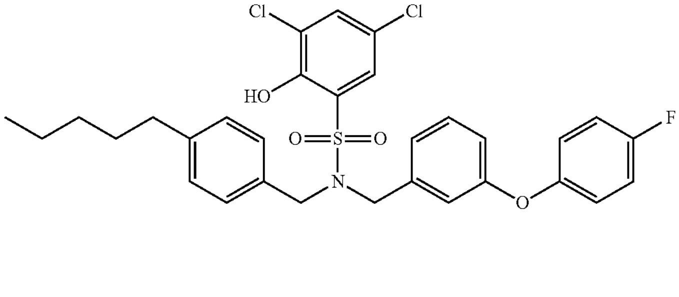 [SMILES: CCCCCc1ccc(CN(Cc2cccc(Oc3ccc(F)cc3)c2)S(=O)(=O)c2cc(Cl)cc(Cl)c2O)cc1] | 3,5-Dichloro-N-(3-(4-fluorophenoxy)-benzyl)-2-hydroxy-N-(4-pentyl-benzyl)benzenesulfonamide | 24.643 | (M − H)$^-$ 602.0 |

-continued

| Ex. No. | Structure | Name | HPLC tR (minute)* | LCMS |
|---|---|---|---|---|
| 237 | 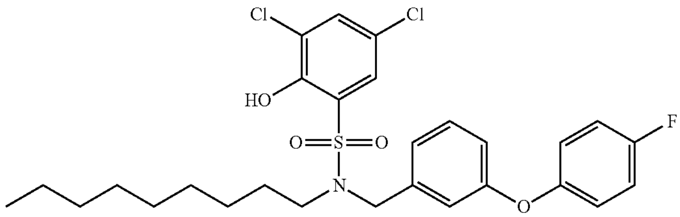 [SMILES: CCCCCCCCCN(Cc1cccc(Oc2ccc(F)cc2)c1)S(=O)(=O)c1cc(Cl)cc(Cl)c1O] | 3,5-Dichloro-N-(3-(4-fluorophenoxy)-benzyl)-2-hydroxy-N-nonyl-benzenesulfonamide | 25.449 | (M − H)⁻ 582.0 |
| 238 | 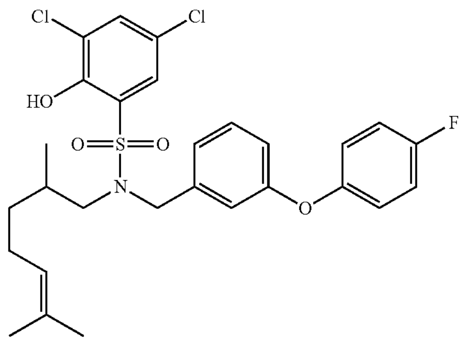 [SMILES: CC(C)=CCCC(C)CN(Cc1cccc(Oc2ccc(F)cc2)c1)S(=O)(=O)c1cc(Cl)cc(Cl)c1O] | 3,5-Dichloro-N-(2,6-dimethylhept-5-enyl)-N-(3-(4-fluorophenoxy)-benzyl)-2-hydroxybenzene-sulfonamide | 24.541 | (M − H)⁻ 580.0 |
| 239 | 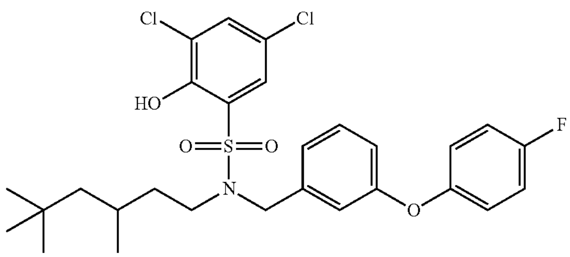 [SMILES: CC(CCN(Cc1cccc(Oc2ccc(F)cc2)c1)S(=O)(=O)c1cc(Cl)cc(Cl)c1O)CC(C)(C)C] | 3,5-Dichloro-N-(3-(4-fluorophenoxy)-benzyl)-2-hydroxy-N-(3,5,5-trimethylhexyl)benzenesulfonamide | 24.263 | (M − H)⁻ 566.0 |

*HPLC conditions: XBridge Phenyl, 4.6 × 150 mm, 3.5μ column: 35 minute run with 25 minute gradient from 14 to 95% aq. MeCN with 0.05% TFA.

Example 240

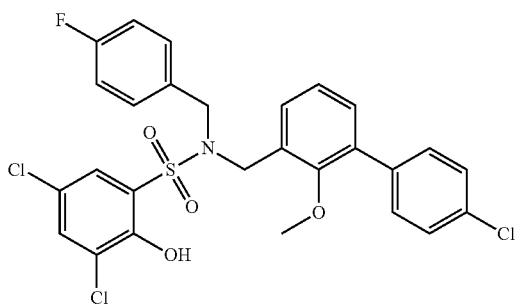 [SMILES: COc1c(CN(Cc2ccc(F)cc2)S(=O)(=O)c2cc(Cl)cc(Cl)c2O)cccc1-c1ccc(Cl)cc1]

3,5-Dichloro-N-((4'-chloro-2-methoxybiphenyl-3-yl)methyl)-N-(4-fluorobenzyl)-2-hydroxybenzene-sulfonamide A) Methyl 3-bromo-2-methoxybenzoate 3-Bromo-2-methoxybenzoic acid (2 g, 8.65 mmol, 1.0 eq) was dissolved in dry DCM and stirred for 10 minutes, cooled to 0° C. and slowly treated with oxalyl chloride (3.3 g, 25.9 mmol, 3 eq). Methanol in pyridine was added dropwise and the reaction mixture was stirred at ambient temperature. The solvents were evaporated under reduced pressure and the reaction mass was diluted with water. The aqueous mixture was extracted with ethyl acetate. The organic layer was dried with anhydrous Na₂SO₄ and concentrated under vacuum to afford the desired product (1.9 g, 90%). ¹H NMR (400 MHz, CDCl₃) δ 3.93 (s, 6H), 7.02-6.06 (t, 1H), 7.72-7.76 (m, 2H). MS (ESI): 247.0 (M+H)⁺.

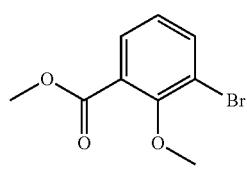

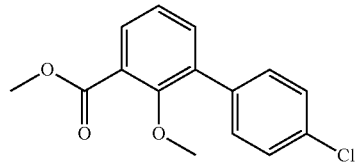 [SMILES: COC(=O)c1cccc(-c2ccc(Cl)cc2)c1OC]

B) Methyl 4'-chloro-2-methoxybiphenyl-3-carboxylate

Methyl 3-bromo-2-methoxybenzoate (1.9 g, 7.75 mmol, 1.0 eq) was dissolved in toluene and treated with 4-chloro phenyl boronic acid (1.2 g, 7.75 mmol, 1 eq). The reaction mixture was stirred for 10 minutes, purged with nitrogen for 10 minutes and degassed with vacuum. Tetrakis triphenylphosphine palladium (0.447 g, 0.387 mmol, 0.05 eq) and $K_2CO_3$ (1.6 g, 11.62 mmol, 1.5 eq) were then added to the mixture. The mixture was heated to reflux for 12 h at 120° C. and cooled to ambient temperature. The solvents were evaporated under reduced pressure and the reaction mass was diluted with water. The aqueous mixture was extracted with ethyl acetate. The organic layer was dried with anhydrous $Na_2SO_4$ and concentrated under vacuum. The residue was purified by silica gel (60-120) column chromatography eluting with 5-10% ethyl acetate/hexane as the eluent to afford the desired product (1.7 g, 80%). $^1$H NMR (400 MHz, $CDCl_3$) δ 3.49 (s, 3H), 3.93-3.95 (s, 3H), 7.20-7.25 (t, 1H), 7.39-7.53 (m, 5H), 7.74-7.78 (t, 1H). MS (ESI): 277.1 (M+H)$^+$.

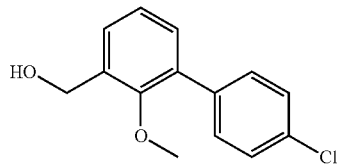 [SMILES: COc1c(CO)cccc1-c1ccc(Cl)cc1]

C) (4'-Chloro-2-methoxybiphenyl-3-yl)methanol

Methyl 4'-chloro-2-methoxybiphenyl-3-carboxylate (1.7 g, 6.14 mmol, 1.0 eq) was dissolved in dry THF under nitrogen and cooled to 0° C. Then 1M LAH solution (0.349 g, 9.22 mmol, 1.5 eq) was slowly added. The reaction mixture was stirred for 1 h at 0° C. Saturated aqueous $NH_4Cl$ solution was added dropwise at 0° C. and the resulting mixture was stirred for 30 minutes. The mixture was further diluted with water and extracted with ethyl acetate. The organic layer was dried with anhydrous $Na_2SO_4$ and concentrated under vacuum to give the desired product (1.4 g, 92%). $^1$H NMR (400 MHz, $CD_3OD$) δ 3.42 (s, 3H), 3.88-3.90 (d, 1H), 4.77-4.78 (m, 2H), 7.18-7.21 (t, 1H), 7.26-7.29 (t, 1H), 7.34-7.43 (m, 3H), 7.51-7.54 (t, 2H). MS (ESI): 248.2 (M+H)$^+$.

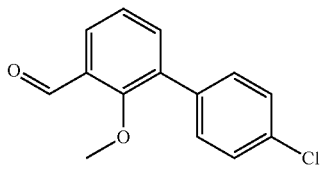 [SMILES: COc1c(C=O)cccc1-c1ccc(Cl)cc1]

D) 4'-Chloro-2-methoxybiphenyl-3-carbaldehyde

To a solution of (4'-chloro-2-methoxybiphenyl-3-yl) methanol (800 mg, 3.21 mmol, 1.0 eq) in dry DCM at 0° C. was added pyridinium chlorochromate (3.0 g, 3.91 mmol, 4.3 eq). The reaction mixture was stirred for 1 h, filtered on a silica pad and washed with DCM. The filtrate was evaporated under reduced pressure and the residue was purified by flash column chromatography on silica gel (60-120) eluting with 5-10% ethyl acetate/hexane to afford the desired product (0.430 g, 54%). $^1$H NMR (400 MHz, $CD_3OD$) δ 3.83-3.94 (s, 3H), 7.02-7.05 (t, 1H), 7.14-7.16 (d, 1H), 7.46-7.48 (t, 1H), 7.57-7.59 (t, 1H), 7.61-7.63 (m, 2H), 7.74-7.76 (d, 1H). MS (ESI): 248.0 (M+H)$^+$.

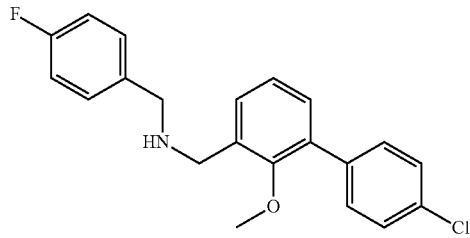 [SMILES: COc1c(CNCc2ccc(F)cc2)cccc1-c1ccc(Cl)cc1]

E) 1-(4'-Chloro-2-methoxybiphenyl-3-yl)-N-(4-fluorobenzyl)methanamine

A solution of 4'-chloro-2-methoxybiphenyl-3-carbaldehyde (400 mg, 1.744 mmol, 1.0 eq) and 4-fluorophenyl) methanamine (190 mg, 1.744 mmol, 1 eq) in dry methanol was stirred for 10 minutes. The reaction mixture was heated to reflux for 2 h and cooled to 0° C. $NaBH_4$ (131 mg, 3.4 mmol, 2 eq) was added slowly and the resulting mixture was stirred for 30 minutes at 0° C. and quenched with 10% aq. $NaHCO_3$ solution at 0° C. The reaction mixture was stirred for an additional 1 h at ambient temperature. The solvents were removed under vacuum and the mixture was extracted with ethyl acetate. The organic layer was dried with anhydrous $Na_2SO_4$ and concentrated under vacuum to afford the desired product (0.590 g, 95%). $^1$H NMR (400 MHz, $CDCl_3$) δ 3.36 (s, 3H), 3.82-3.86 (d, 4H), 7.00-7.05 (t, 3H), 7.14-7.18 (t, 1H), 7.23-7.25 (t, 1H), 7.35-7.40 (d, 4H), 7.51-7.54 (d, 2H). MS (ESI): 356.2 (M+H)$^+$.

F) 3,5-Dichloro-N-((4'-chloro-2-methoxybiphenyl-3-yl)methyl)-N-(4-fluorobenzyl)-2-hydroxybenzenesulfonamide A solution of 1-(4'-chloro-2-methoxybiphenyl-3-yl)-N-(4-fluorobenzyl)methanamine (590 mg, 1.684 mmol, 1.0 eq) in dry DCM under nitrogen at 0° C. and treated slowly with triethylamine (492 mg, 4.8 mmol, 3 eq). The reaction mixture was stirred for 10 minutes and treated with a solution of 3,5-dichloro-2-hydroxybenzene-1-sulfonyl chloride (527 mg, 2.018 mmol, 1.2 eq) dissolved in DCM. The resulting mixture was stirred for 12 h at ambient temperature and concentrated under reduced pressure. The residue was further diluted with water and extracted with ethyl acetate. The organic layer was dried under anhydrous $Na_2SO_4$ and concentrated. The residue was purified by flash column chromatography on silica gel (60-120) eluting with 15-20% ethyl acetate/hexane to afford the title compound (0.400 g, 50%). $^1$H NMR (400 MHz, DMSO-$d_6$) δ 3.32 (s, 3H), 4.52-4.53 (d, 4H), 7.04-7.08 (m, 3H), 7.17-7.24 (m, 4H), 7.43-7.52 (m, 5H), 7.77 (s, 1H). MS (ESI): 577.8 (M−H)$^-$.

Example 241

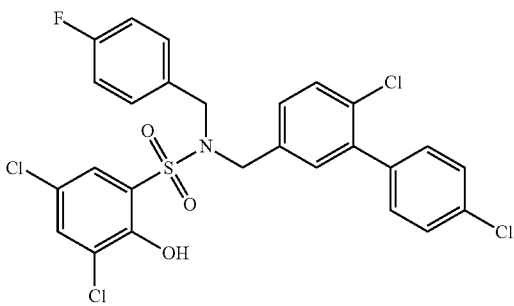 [SMILES: O=S(=O)(c1cc(Cl)cc(Cl)c1O)N(Cc1ccc(F)cc1)Cc1ccc(Cl)c(-c2ccc(Cl)cc2)c1]

3,5-Dichloro-N-((4',6-dichlorobiphenyl-3-yl)methyl)-N-(4-fluorobenzyl)-2-hydroxybenzenesulfonamide

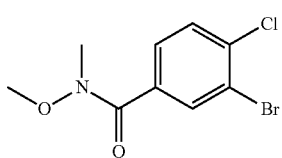

A) 3-Bromo-4-chloro-N-methoxy-N-methylbenzamide

3-Bromo-4-chlorobenzoic acid (1.0 g, 4.24 mmol, 1.0 eq) was dissolved in dry DMF and stirred for 10 minutes. The solution was cooled to 0° C. and treated with N,O-dimethyl hydroxylamine hydrochloride (0.828 mg, 8.48 mmol, 2.0 eq), 1-hydroxybenzotrizole (860 mg, 6.36 mmol, 1.5 eq), N,N-diisopropyl ethylamine (820 mg, 6.37 mmol, 1.5 eq), and EDC HCl (1.2 g, 6.37 mmol, 1.5 eq). The reaction mixture was stirred for 12 h, evaporated under reduced pressure and diluted with water (25 mL). The aqueous layer was extracted with ethyl acetate. The organic layer was dried under anhydrous $Na_2SO_4$ and concentrated under vacuum. The residue was purified by flash column chromatography on silica gel (60-120) eluting with 5-10% ethyl acetate/hexane to afford the desired product (1 g, 85%). $^1$H NMR (400 MHz, $CD_3OD$) δ 3.34 (s, 3H), 3.57 (s, 3H), 7.47-7.49 (d, 1H), 7.71-7.74 (d, 1H), 7.85-7.88 (d, 1H). MS (ESI): 278.2 ($M^+$).

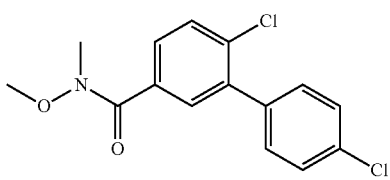 [SMILES: CON(C)C(=O)c1ccc(Cl)c(-c2ccc(Cl)cc2)c1]

B) 4',6-Dichloro-N-methoxy-N-methylbiphenyl-3-carboxamide

3-Bromo-4-chloro-N-methoxy-N-methylbenzamide (1.0 mg, 3.8 mmol, 1.0 eq) and 4-chloro phenyl boronic acid (787 mg, 5 mmol, 1.3 eq) was dissolved in toluene and stirred for 10 minutes. The solution was purged with nitrogen for 10 minutes and degassed under vacuum. Tetrakis triphenylphosphinepalladium (223 mg, 0.19 mmol, 0.05 eq) and $K_2CO_3$ (696 mg, 5 mmol, 1.3 eq) were added to the reaction. The mixture was refluxed for 12 h under nitrogen and the volatiles were removed under reduced pressure. The residue was diluted with water and extracted with ethyl acetate. The organic layer was dried with anhydrous $Na_2SO_4$ and concentrated under vacuum. The residue was purified by flash column chromatography on silica gel (60-120) eluting with 5-10% ethyl acetate/hexane to afford the desired compound (1 g, 90%). $^1$H NMR (400 MHz, $CD_3OD$) δ 3.37-3.39 (s, 3H), 3.60-3.64 (s, 3H), 7.10-7.13 (t, 1H), 7.25-7.27 (t, 1H), 7.43-7.48 (m, 3H), 7.60-7.63 (m, 3H). MS (ESI): 310.2 ($M^+$).

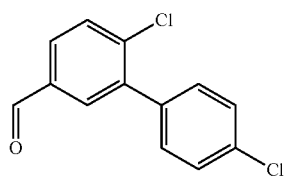 [SMILES: O=Cc1ccc(Cl)c(-c2ccc(Cl)cc2)c1]

C) 4',6-Dichlorobiphenyl-3-carbaldehyde

4',6-Dichloro-N-methoxy-N-methylbiphenyl-3-carboxamide (1.0 g, 3.2 mmol, 1.0 eq) was dissolved in dry THF and stirred for 10 minutes. The solution was cooled to −78° C. and DIBAL-H (1 M solution, 1.83 g, 12.9 mmol, 4 eq, 13 mL) was slowly added over 15-30 minutes. The reaction mixture was stirred for 1 h at −78° C., quenched with saturated $NH_4Cl$ solution at −78° C. and stirred for 30 minutes at ambient temperature. Water and ethyl acetate were added into the reaction mixture. The aqueous layer was separated and extracted twice with ethyl acetate. The organic layer was dried with anhydrous $Na_2SO_4$ and concentrated under vacuum to give the desired product (0.7 g, 87%). $^1$H NMR (400 MHz, $CDCl_3$) δ 7.06-7.09 (d, 2H), 7.24-7.27 (d, 2H), 7.40 (s, 1H), 7.55-7.58 (d, 1H), 7.90-7.95 (m, 1H).

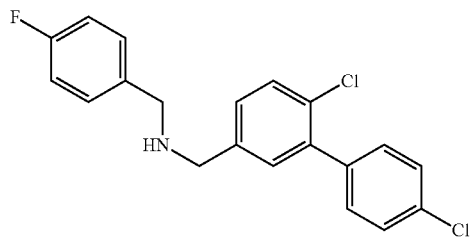 [SMILES: Fc1ccc(CNCc2ccc(Cl)c(-c3ccc(Cl)cc3)c2)cc1]

D) 1-(4',6-Dichlorobiphenyl-3-yl)-N-(4-fluorobenzyl)methanamine

4',6-Dichlorobiphenyl-3-carbaldehyde (1.0 g, 3.98 mmol, 1 eq) and 4-fluorophenyl)methanamine (0.498 g, 3.98 mmol, 1 eq) were dissolved in dry methanol. The resulting solution was stirred for 10 minutes, heated to reflux for 2 h and cooled to 0° C. $NaBH_4$ (0.2945 g, 7.96 mmol, 2 eq) was slowly added and the mixture was stirred for 30 minutes at 0° C. The reaction was quenched by the addition of 10% aq. $NaHCO_3$ solution at 0° C. and the mixture was stirred for 1-2 h at ambient temperature. The volatiles were removed under vacuum and the aqueous mixture was extracted with ethyl acetate. The organic layer was dried with anhydrous $Na_2SO_4$ and concentrated under vacuum to afford the desired product (1.2 g, 86%). $^1$H NMR (400 MHz, $CD_3OD$) δ 3.76-3.81 (s, 4H), 7.00-7.08 (m, 4H), 7.21-7.31 (m, 2H), 7.33-7.39 (m, 4H). MS (ESI): 360.2 ($M^+$).

E) 3,5-Dichloro-N-((4',6-dichlorobiphenyl-3-yl)methyl)-N-(4-fluorobenzyl)-2-hydroxybenzenesulfonamide 1-(4',6-Dichlorobiphenyl-3-yl)-N-(4-fluorobenzyl) methanamine (200 mg, 0.555 mmol, 1.0 eq) was dissolved in dry DCM and the resulting solution was stirred for 10 minutes and cooled to 0° C. Triethylamine (168 mg, 1.6 mmol, 3 eq) was added to the above solution and the mixture was stirred for 10 minutes. 3,5-Dichloro-2-hydroxybenzene-1-sulfonyl chloride dissolved in DCM was added slowly over a period of 10 minutes and the mixture was stirred for 4 h at ambient temperature. The solvent was evaporated under reduced pressure and the residue was purified by flash column chromatography on silica gel (60-120) eluting with 5-10% ethyl acetate/hexane to give the title compound (0.14 g, 46%). $^1$H NMR (400 MHz, $CD_3OD$) δ 4.47 (s, 2H), 4.53 (s, 2H), 6.91-6.98 (m, 3H), 7.12-7.15 (m, 1H), 7.22-7.27 (m, 4H), 7.33-7.35 (d, 1H), 7.43-7.45 (d, 2H), 7.54 (d, 1H), 7.67 (d, 1H). MS (ESI): 583.8 (M−H)$^-$.

Examples 242-266

The following examples were prepared using the similar procedures to those described above:

| Ex. No. | Structure | Name | HPLC $t_R$ (minute)* | LCMS |
|---|---|---|---|---|
| 242 | 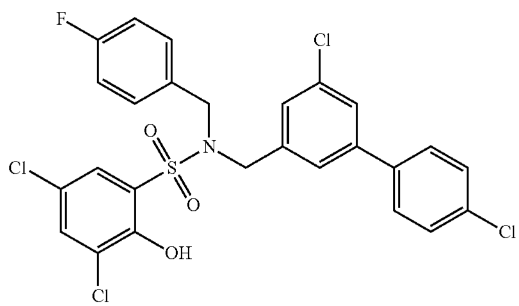 [SMILES: O=S(=O)(c1cc(Cl)cc(Cl)c1O)N(Cc1ccc(F)cc1)Cc1cc(Cl)cc(-c2ccc(Cl)cc2)c1] | 3,5-Dichloro-N-((4',5-dichloro-biphenyl-3-yl)methyl-N-(4-fluorobenzyl)-2-hydroxybenzene-sulfonamide | A 23.588 | (M − H)$^-$ 583.8 |
| 243 | 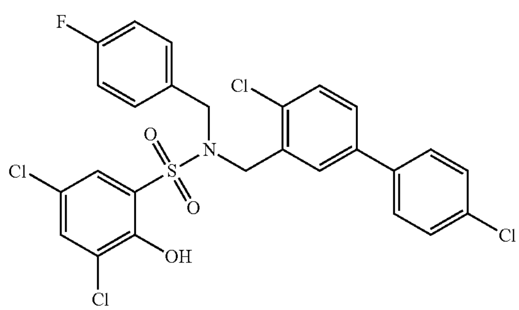 [SMILES: O=S(=O)(c1cc(Cl)cc(Cl)c1O)N(Cc1ccc(F)cc1)Cc1cc(-c2ccc(Cl)cc2)ccc1Cl] | 3,5-Dichloro-N-((4,4'-dichloro-biphenyl-3-yl)methyl-N-(4-fluorobenzyl)-2-hydroxybenzene-sulfonamide | A 23.573 | (M − H)$^-$ 583.8 |
| 244 | 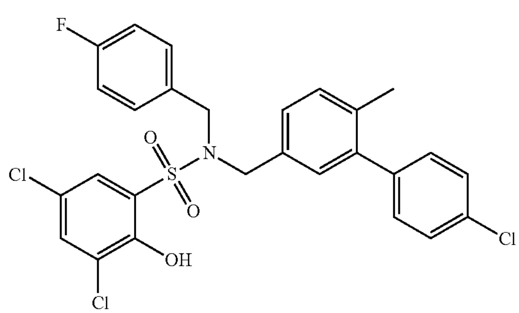 [SMILES: Cc1ccc(CN(Cc2ccc(F)cc2)S(=O)(=O)c2cc(Cl)cc(Cl)c2O)cc1-c1ccc(Cl)cc1] | 3,5-Dichloro-N-((4'-chloro-6-methyl-biphenyl-3-yl)methyl-N-(4-fluorobenzyl)-2-hydroxybenzene-sulfonamide | B 27.519 | (M − H)$^-$ 562.0 |

-continued

| Ex. No. | Structure | Name | HPLC $t_R$ (minute)* | LCMS |
|---|---|---|---|---|
| 245 | 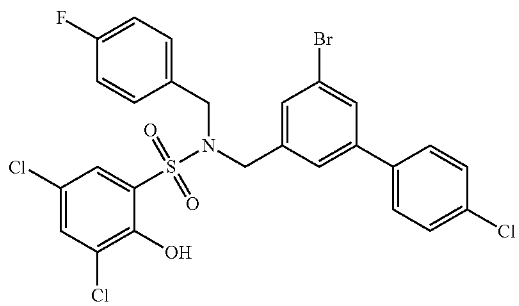 | N-((5-Bromo-4'-chlorobiphenyl-3-yl)methyl-3,5-dichloro-N-(4-fluoro-benzyl)-2-hydroxybenzene-sulfonamide | A 24.116 | $(M-H)^-$ 625.8 |
| 246 | 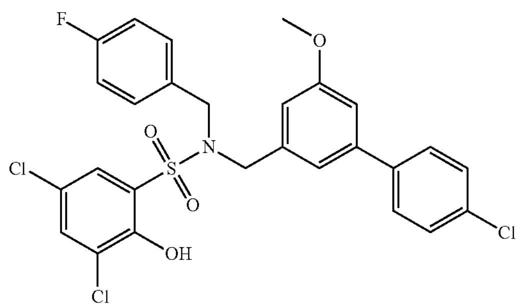 [SMILES: COc1cc(CN(Cc2ccc(F)cc2)S(=O)(=O)c2cc(Cl)cc(Cl)c2O)cc(-c2ccc(Cl)cc2)c1] | 3,5-Dichloro-N-((4'-chloro-5-methoxybiphenyl-3-yl)methyl)-N-(4-fluorobenzyl)-2-hydroxybenzene-sulfonamide | A 22.559 | $(M-H)^-$ 578.0 |
| 247 | 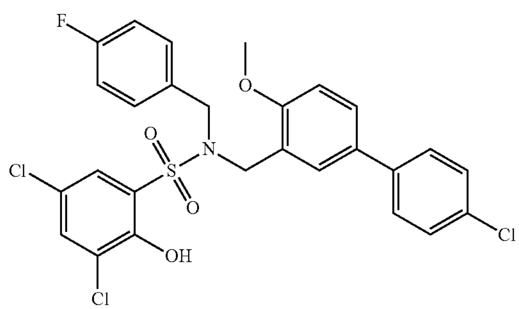 [SMILES: COc1ccc(-c2ccc(Cl)cc2)cc1CN(Cc1ccc(F)cc1)S(=O)(=O)c1cc(Cl)cc(Cl)c1O] | 3,5-Dichloro-N-((4'-chloro-4-methoxybiphenyl-3-yl)methyl)-N-(4-fluorobenzyl)-2-hydroxybenzene-sulfonamide | A 22.691 | $(M-H)^-$ 578.0 |
| 248 | 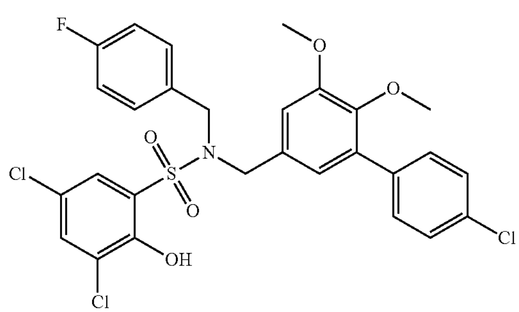 [SMILES: COc1cc(CN(Cc2ccc(F)cc2)S(=O)(=O)c2cc(Cl)cc(Cl)c2O)cc(-c2ccc(Cl)cc2)c1OC] | 3,5-Dichloro-N-((4'-chloro-5,6-dimethoxybiphenyl-3-yl)methyl)-N-(4-fluorobenzyl)-2-hydroxy-benzenesulfonamide | A 22.706 | $(M-H)^-$ 610.0 |
| 249 | 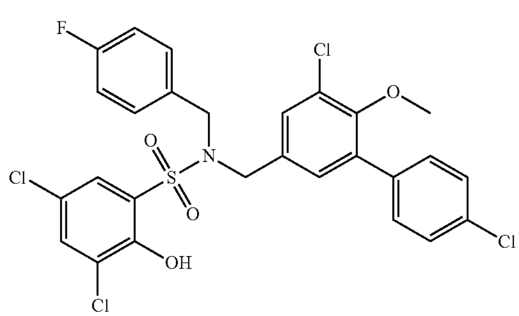 [SMILES: COc1c(Cl)cc(CN(Cc2ccc(F)cc2)S(=O)(=O)c2cc(Cl)cc(Cl)c2O)cc1-c1ccc(Cl)cc1] | 3,5-Dichloro-N-((4',5-chloro-6-methoxybiphenyl-3-yl)methyl)-N-(4-fluorobenzyl)-2-hydroxybenzenesulfonamide | A 23.425 | $(M-H)^-$ 612 |

| Ex. No. | Structure | Name | HPLC $t_R$ (minute)* | LCMS |
|---|---|---|---|---|
| 250 | 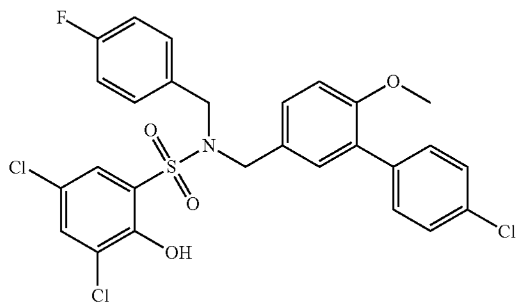 [SMILES: COc1ccc(CN(Cc2ccc(F)cc2)S(=O)(=O)c2cc(Cl)cc(Cl)c2O)cc1-c1ccc(Cl)cc1] | 3,5-Dichloro-N-((4'-chloro-6-methoxybiphenyl-3-yl)methyl)-N-(4-fluorobenzyl)-2-hydroxy-benzenesulfonamide | A 22.879 | (M − H)⁻ 578.0 |
| 251 | 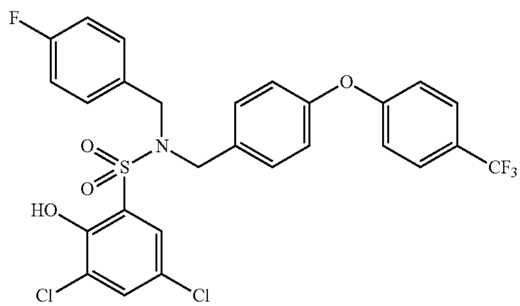 [SMILES: O=S(=O)(c1cc(Cl)cc(Cl)c1O)N(Cc1ccc(F)cc1)Cc1ccc(Oc2ccc(C(F)(F)F)cc2)cc1] | 3,5-Dichloro-N-(4-fluorobenzyl)-2-hydroxy-N-(4-(4-(trifluoromethyl)phenoxy)benzyl)benzene-sulfonamide | A 3.988 | (M − H)⁻ 598.0 |
| 252 | 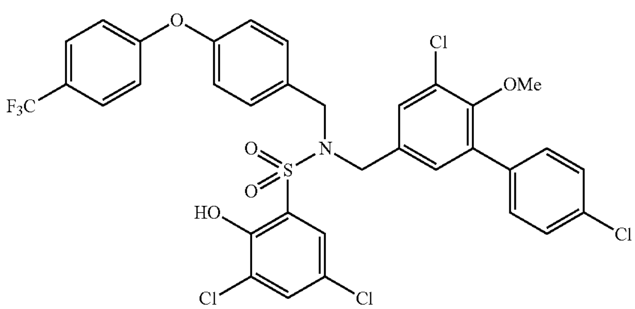 [SMILES: COc1c(Cl)cc(CN(Cc2ccc(Oc3ccc(C(F)(F)F)cc3)cc2)S(=O)(=O)c2cc(Cl)cc(Cl)c2O)cc1-c1ccc(Cl)cc1] | 3,5-Dichloro-N-((4',5-dichloro-6-methoxybiphenyl-3-yl)methyl)-2-hydroxy-N-(4-(4-(trifluoromethyl)phenoxy)benzyl)-benzenesulfonamide | E 14.451 | (M − H)⁻ 754 |
| 253 | 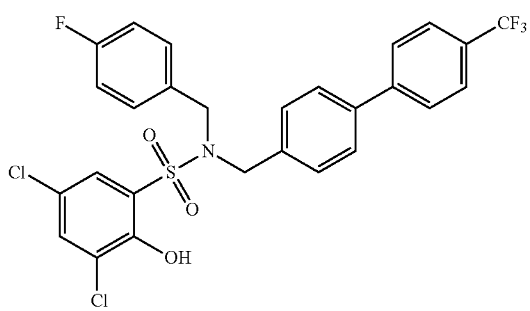 [SMILES: O=S(=O)(c1cc(Cl)cc(Cl)c1O)N(Cc1ccc(F)cc1)Cc1ccc(-c2ccc(C(F)(F)F)cc2)cc1] | 3-5-Dichloro-N-(4-fluorobenzyl)-2-hydroxy-N-((4'-(trifluoromethyl)-biphenyl-4-yl)methyl)benzene-sulfonamide | A 22.976 | (M − H)⁻ 584.0 |
| 254 | 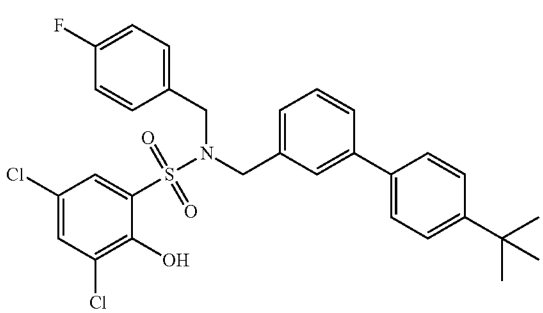 [SMILES: CC(C)(C)c1ccc(-c2cccc(CN(Cc3ccc(F)cc3)S(=O)(=O)c3cc(Cl)cc(Cl)c3O)c2)cc1] | N-((4'-tert-Butylbiphenyl-3-yl)methyl)-3,5-dichloro-N-(4-fluorobenzyl)-2-hydroxybenzene-sulfonamide | B 23.918 | (M − H)⁻ 572.0 |

-continued

| Ex. No. | Structure | Name | HPLC t$_R$ (minute)* | LCMS |
|---|---|---|---|---|
| 255 | 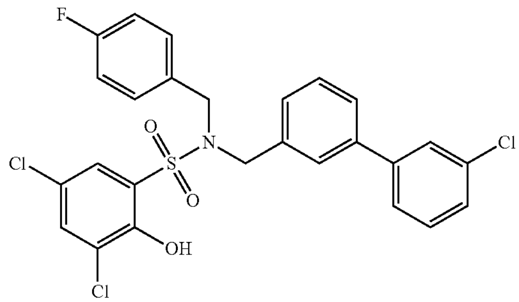 [SMILES: O=S(=O)(c1cc(Cl)cc(Cl)c1O)N(Cc1ccc(F)cc1)Cc1cccc(-c2cccc(Cl)c2)c1] | 3,5-Dichloro-N-((3'-chlorobiphenyl-3-yl)methyl)-N-(4-fluorobenzyl)-2-hydroxybenzenesulfonamide | A 22.870 | (M − H)⁻ 548.0 |
| 256 | 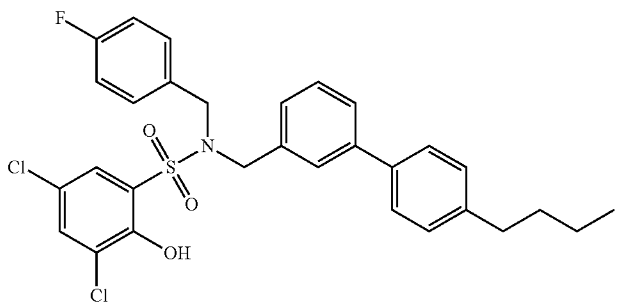 [SMILES: CCCCc1ccc(-c2cccc(CN(Cc3ccc(F)cc3)S(=O)(=O)c3cc(Cl)cc(Cl)c3O)c2)cc1] | N-((4'-Butylbiphenyl-3-yl)methyl)-3,5-dichloro-N-(4-fluorobenzyl)-2-hydroxybenzenesulfonamide | A 24.655 | (M − H)⁻ 571.2 |
| 257 | 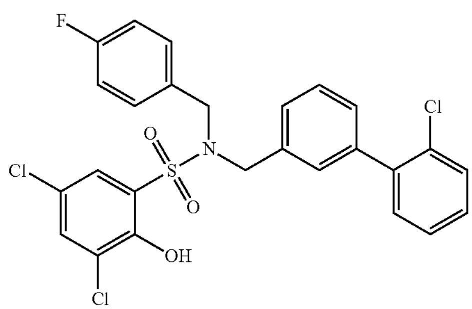 [SMILES: O=S(=O)(c1cc(Cl)cc(Cl)c1O)N(Cc1ccc(F)cc1)Cc1cccc(-c2ccccc2Cl)c1] | 3,5-Dichloro-N-((2'-chlorobiphenyl-3-yl)methyl)-N-(4-fluorobenzyl)-2-hydroxybenzenesulfonamide | B 26.080 | (M + H)⁺ 550.0 |
| 258 | 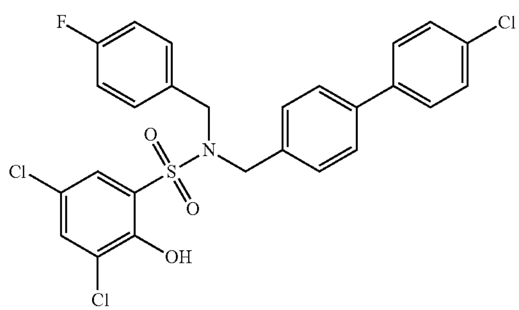 [SMILES: O=S(=O)(c1cc(Cl)cc(Cl)c1O)N(Cc1ccc(F)cc1)Cc1ccc(-c2ccc(Cl)cc2)cc1] | 3,5-Dichloro-N-((4'-chlorobiphenyl-4-yl)methyl)-N-(4-fluorobenzyl)-2-hydroxybenzenesulfonamide | D 4.451 | (M − H)⁻ 549.9 |
| 259 | 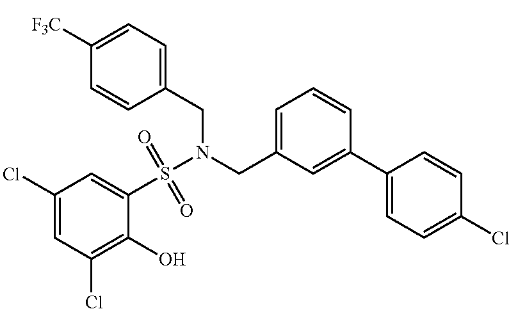 [SMILES: O=S(=O)(c1cc(Cl)cc(Cl)c1O)N(Cc1ccc(C(F)(F)F)cc1)Cc1cccc(-c2ccc(Cl)cc2)c1] | 3,5-Dichloro-N-((4'-chlorobiphenyl-3-yl)methyl)-2-hydroxy-N-(4-(trifluoromethyl)benzyl)benzenesulfonamide | A 23.639 | (M − H)⁻ 598.0 |

| Ex. No. | Structure | Name | HPLC $t_R$ (minute)* | LCMS |
|---|---|---|---|---|
| 260 | 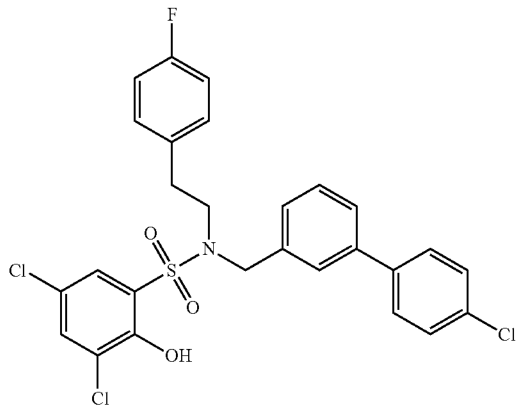 [SMILES: O=S(=O)(c1cc(Cl)cc(Cl)c1O)N(CCc1ccc(F)cc1)Cc1cccc(-c2ccc(Cl)cc2)c1] | 3,5-Dichloro-N-((4'-chlorobiphenyl-3-yl)methyl)-N-(4-fluorophenethyl)-2-hydroxybenzenesulfonamide | D 4.448 | (M − H)⁻ 561.9 |
| 261 | 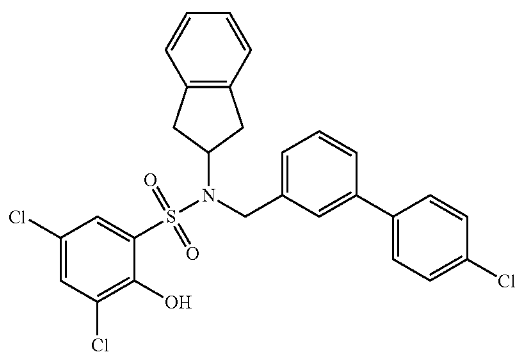 [SMILES: O=S(=O)(c1cc(Cl)cc(Cl)c1O)N(Cc1cccc(-c2ccc(Cl)cc2)c1)C1Cc2ccccc2C1] | 3,5-Dichloro-N-((4'-chlorobiphenyl-3-yl)methyl)-N-(2,3-dihydro-1H-inden-2-yl)-2-hydroxybenzenesulfonamide | D 4.050 | (M + H)⁺ 557.8 |
| 262 | 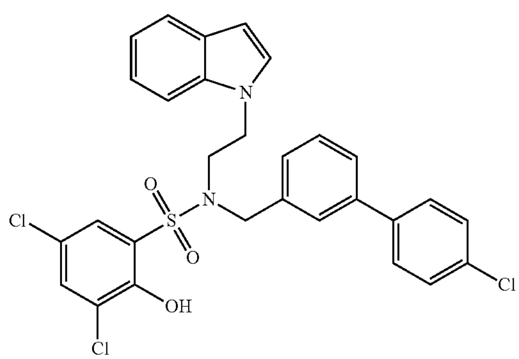 [SMILES: O=S(=O)(c1cc(Cl)cc(Cl)c1O)N(CCn1ccc2ccccc21)Cc1cccc(-c2ccc(Cl)cc2)c1] | N-(2-(1H-Indol-1-yl)ethyl)-3,5-dichloro-N-((4'-chlorobiphenyl-3-yl)methyl)-2-hydroxybenzenesulfonamide | C 4.63 | (M + H)⁺ 587.0 |
| 263 | 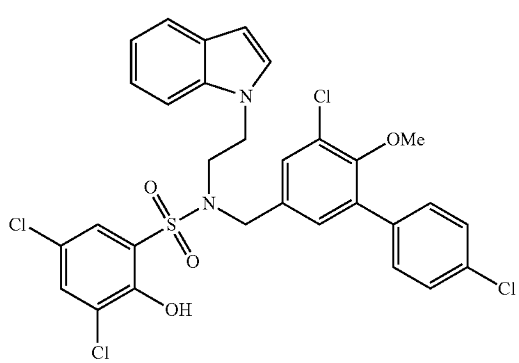 [SMILES: COc1c(Cl)cc(CN(CCn2ccc3ccccc32)S(=O)(=O)c2cc(Cl)cc(Cl)c2O)cc1-c1ccc(Cl)cc1] | N-(2-(1H-Indol-1-yl)ethyl)-3,5-dichloro-N-((4',5-dichloro-6-methoxybiphenyl-3-yl)methyl)-2-hydroxybenzenesulfonamide | A 24.727 | (M − H)⁻ 648 |

| Ex. No. | Structure | Name | HPLC $t_R$ (minute)* | LCMS |
|---|---|---|---|---|
| 264 | 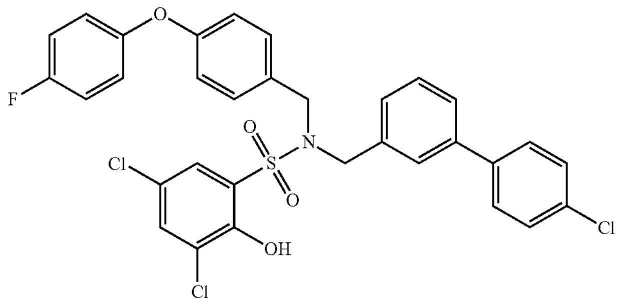 [SMILES: O=S(=O)(c1cc(Cl)cc(Cl)c1O)N(Cc1ccc(Oc2ccc(F)cc2)cc1)Cc1cccc(-c2ccc(Cl)cc2)c1] | 3,5-Dichloro-N-((4'-chlorobiphenyl-3-yl)methyl)N-(4-(4-fluorophenoxy)benzyl)-2-hydroxybenzenesulfonamide | C 4.76 | (M − H)⁻ 641.9 |
| 265 | 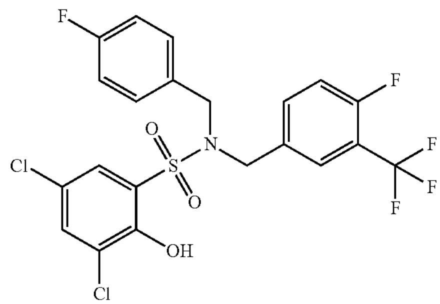 [SMILES: O=S(=O)(c1cc(Cl)cc(Cl)c1O)N(Cc1ccc(F)cc1)Cc1ccc(F)c(C(F)(F)F)c1] | 3,5-Dichloro-N-(4-fluoro-3-(trifluoromethyl)benzyl)-N-(4-fluorobenzyl)-2-hydroxybenzenesulfonamide | C 4.04 | (M + H)⁺ 523.9 |
| 266 | 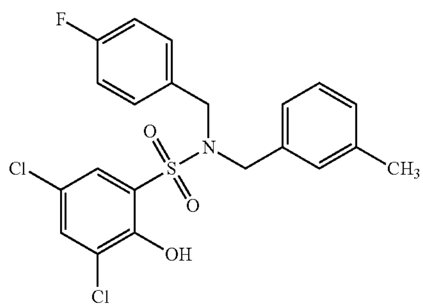 [SMILES: Cc1cccc(CN(Cc2ccc(F)cc2)S(=O)(=O)c2cc(Cl)cc(Cl)c2O)c1] | 3,5-Dichloro-N-(4-fluorobenzyl)-2-hydroxy-N-(3-methylbenzyl)benzenesulfonamide | C 4.09 | (M + H)⁺ 454.0 |

*HPLC conditions:
A) XBridge Phenyl, 4.6 × 150 mm, 3.5μ column: 35 minute run with 25 minute gradient from 14 to 95% aq. MeCN with 0.05% TEA.
B) Sunfire C18, 4.6 × 150 mm, 3.5μ column: 35 minute run with 25 minute gradient from 14 to 95% aq. MeCN with 0.05% TFA.
C) Chromolith S5 ODS, 4.6 × 50 mm column: 5 minute run with 4 minute gradient from 10-90% aqueous MeOH with 0.1% TFA.
D) YMC S5 ODS, 4.6 × 50 mm Ballistic column: 6 minute run with 4 minute gradient from 10-90% aqueous MeOH with 0.2% $H_3PO_4$.
E) XBridge Phenyl, 4.6 × 150 mm, 3.5μ column: 20 minute run with 12 minute gradient from 10 to 100% aq. MeOH with 10 mM aq. $NH_4CO_3$.

Example 267

3,5-Dichloro-N-(4-fluorophenethyl)-2-hydroxy-N-(3-(phenethylthiomethyl)benzyl)benzenesulfonamide

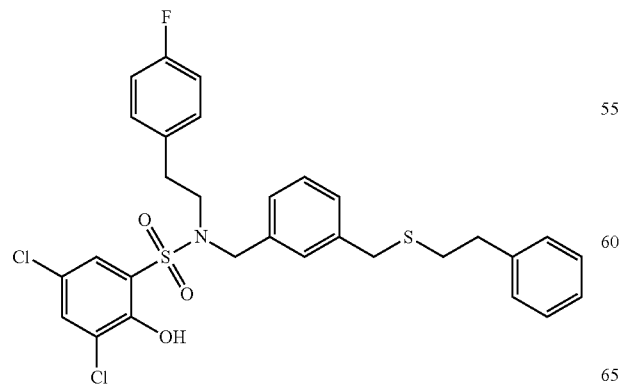

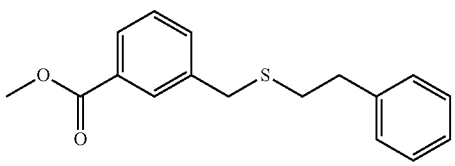 [SMILES: COC(=O)c1cccc(CSCCc2ccccc2)c1]

A) Methyl 3-(phenethylthiomethyl)benzoate

To a solution of phenylethyl mercaptan (0.66 g, 4.80 mmol) and methyl 3-(bromomethyl)benzoate (1.0 g, 4.37 mmol) in DMF (10 mL) was added Cs$_2$CO$_3$ (2.84 g, 8.73 mmol). The suspension was stirred at rt for 3 h. The reaction mixture was then diluted with ethyl acetate and water. The organic layer was separated, washed with brine three times, dried over MgSO$_4$. The filtrate was concentrated in vacuo to give a light yellow oil. The crude product was purified by flash chromatography on silica gel eluting with 30% ethyl acetate in hexane to give the desired product (1.2 g, 96%) as a colorless oil. $^1$H NMR (CDCl$_3$) δ 8.00 (s, 1H), 7.96-7.94 (m, 1H), 7.55-7.53 (m, 1H), 7.42 (t, J=8.0 Hz, 1H), 7.33-7.28 (m, 2H), 7.25-7.17 (m, 3H), 3.95 (s, 3H), 3.76 (s, 2H), 2.89-2.85 (m, 2H), 2.69-2.65 (m, 2H). MS (ESI): 287.1 (M+H)$^-$.

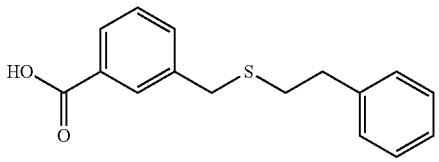 [SMILES: O=C(O)c1cccc(CSCCc2ccccc2)c1]

B) 3-(Phenethylthiomethyl)benzoic acid

To a solution of methyl 3-(phenethylthiomethyl)benzoate (1.15 g, 4.02 mmol) in THF (4 mL) and MeOH (4.00 mL) was added 1 N aqueous NaOH solution (6 mL). The resulting mixture was stirred at rt for overnight. The reaction mixture was concentrated in vacuo and the residue was diluted with 1 N HCl solution. The solid was filtered and vacuum dried to give the desired product (1.05 g, 95%) as a white solid. $^1$H NMR (DMSO-d$_6$) δ 13.07 (s, 1H), 7.93 (s, 1H), 7.83-7.81 (m, 1H), 7.57 (d, J=8.0 Hz, 1H), 7.45 (t, J=8.0 Hz, 1H), 7.29-7.25 (m, 2H), 7.20-7.17 (m, 3H), 3.84 (s, 2H), 2.91-2.78 (m, 2H), 2.63-2.59 (m, 2H). MS (ESI): 273.1 (M+H)$^+$.

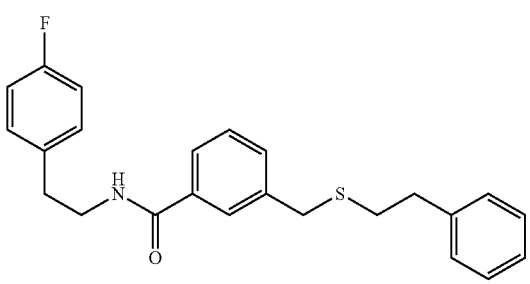 [SMILES: O=C(NCCc1ccc(F)cc1)c1cccc(CSCCc2ccccc2)c1]

C) N-(4-Fluorophenethyl)-3-(phenethylthiomethyl)benzamide

To a solution of 3-(phenethylthiomethyl)benzoic acid (0.5 g, 1.84 mmol) in DMF (8 mL) were added EDC (0.49 g, 2.57 mmol), HOBT (0.28 g, 1.84 mmol) and 4-fluorophenethylamine (0.24 mL, 1.84 mmol). The clear reaction mixture was stirred at rt for 2 h and diluted with ethyl acetate and 1 N aqueous HCl solution. The organic layer was separated, washed with brine and dried over MgSO$_4$. The filtrate was concentrated in vacuo. The residue was dissolved in DCM and purified by flash chromatography on silica gel eluting with 20% ethyl acetate in dichloromethane to give the desired product (0.34 g, 47%) as a white solid. $^1$H NMR (CDCl$_3$) δ 7.61 (s, 1H), 7.52 (d, J=8.0 Hz, 1H), 7.41 (d, J=8.0 Hz, 1H), 7.35 (t, J=8.0 Hz, 1H), 7.24 (d, J=8.0 Hz, 2H), 7.20-7.11 (m, 5H), 6.97 (t, J=8.0 Hz, 2H), 6.11 (s, 1H), 3.69 (s, 2H), 3.67-3.63 (m, 2H), 2.94-2.79 (m, 4H), 2.63-2.61 (m, 2H). MS (ESI): 394.1 (M+H)$^+$.

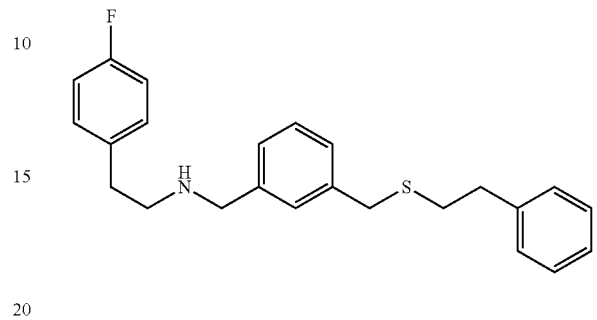

D) 2-(4-Fluorophenyl)-N-(3-(phenethylthiomethyl)benzyl)ethanamine

To a solution of N-(4-fluorophenethyl)-3-(phenethylthiomethyl)benzamide (0.3 g, 0.76 mmol) in THF (5 mL) was added borane-THF complex (1 M solution in THF, 12 mL, 12 mmol). The reaction mixture was stirred at rt for overnight. To the reaction mixture was added MeOH and 2 mL of TFA, and the resulting mixture was stirred for 3 h. The resulting mixture was concentrated and the residue was diluted with saturated NaHCO$_3$ solution and ethyl acetate. The organic layer was separated, washed with brine, and dried over MgSO$_4$. The filtrate was concentrated in vacuo and the residue was purified by flash chromatography silica gel eluting with 20% ethyl acetate in hexanes, which contained 10% of 2 M ammonia in MeOH to give the desired product (0.18 g, 58%) as a colorless oil. $^1$H NMR (CDCl$_3$) δ 7.32-7.14 (m, 11H), 7.01-6.95 (m, 2H), 3.84 (s, 2H), 3.72 (s, 2H), 2.91-2.80 (m, 6H), 2.73-2.64 (m, 2H). MS (ESI): 380.1 (M+H)$^+$.

E) 3,5-Dichloro-N-(4-Fluorophenethyl)-2-hydroxy-N-(3-(phenethylthiomethyl)benzyl)benzenesulfonamide To a solution of 2-(4-fluorophenyl)-N-(3-(phenethylthiomethyl)benzyl)ethanamine (70 mg, 0.184 mmol) in THF (3 mL) were added 3,5-dichloro-2-hydroxybenzenesulfonyl chloride (63 mg, 0.24 mmol) and N,N-diisopropylethylamine (0.1 mL, 0.55 mmol). The resulting reaction mixture was stirred at it for 1.5 h. The reaction mixture was concentrated and the residue was dissolved in MeOH. The mixture was purified by preparative HPLC. Fractions containing the desired product were combined, concentrated in vacuo and lyophilized to give the title compound (50 mg, 44%) as a white solid. $^1$H NMR (CDCl$_3$) δ 9.15 (s, 1H), 7.55 (d, J=4.0 Hz, 1H), 7.45 (d, J=4.0 Hz, 1H), 7.34-7.15 (m, 9H), 6.98-6.89 (m, 4H), 4.40 (s, 2H), 3.70 (s, 2H), 3.35 (t, J=8.0 Hz, 2H), 2.86 (t, J=4.0 Hz, 2H), 2.69-2.63 (m, 4H). MS (ESI): 602.0 (M−H)$^-$.

Examples 268-269

The following examples were prepared using similar procedures to those described for Example 267:

| Ex. No. | Structure | Name | HPLC $t_R$ (minute) | LCMS |
|---|---|---|---|---|
| 268 | 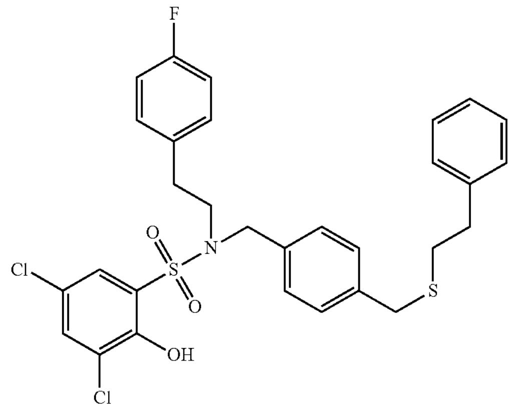 [SMILES: O=S(=O)(c1cc(Cl)cc(Cl)c1O)N(CCc1ccc(F)cc1)Cc1ccc(CSCCc2ccccc2)cc1] | 3,5-Dichloro-N-(4-fluorophenethyl)-2-hydroxy-N-(4-(phenethylthiomethyl)benzyl)-benzenesulfonamide | 4.5 | (M − H)⁻ 602.1 |
| 269 | 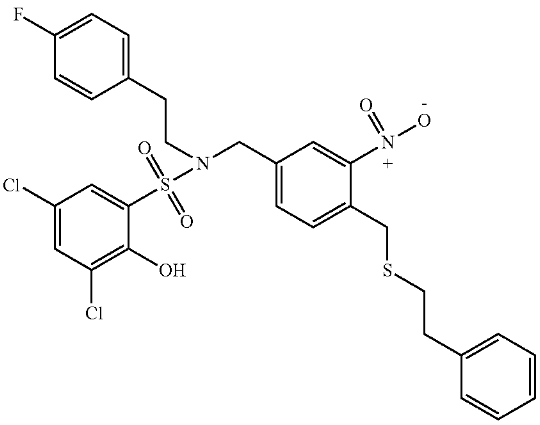 | 3,5-Dichloro-N-(4-fluorophenethyl)-2-hydroxy-N-(3-nitro-4-(phenethylthiomethyl)benzyl)-benzenesulfonamide | 4.30 | (M − H)⁻ 647.2 |

Example 270

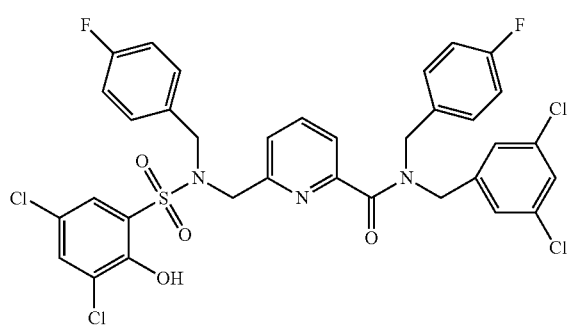 [SMILES: O=C(c1cccc(CN(Cc2ccc(F)cc2)S(=O)(=O)c2cc(Cl)cc(Cl)c2O)n1)N(Cc1ccc(F)cc1)Cc1cc(Cl)cc(Cl)c1]

6-((3,5-Dichloro-N-(4-fluorobenzyl)-2-hydroxyphenylsulfonamido)methyl)-N-(3,5-dichlorobenzyl)-N-(4-fluorobenzyl)picolinamide A) Methyl 6-(hydroxymethyl)picolinate To a solution of 2-ethyl 6-methylpyridine-2,6-dicarboxylate (3.0 g, 14.3 mmol) in MeOH (20 mL) and $CH_2Cl_2$ (10 mL) was added slowly $NaBH_4$ (1.95 g, 51.6 mmol) in several portions at −40° C. After 10 min, the reaction mixture was stirred at rt for 1 h. To the reaction mixture was added 5 mL of 1 N HCl and the mixture was stirred for 20 min. The solvents were removed in vacuo and the residue was diluted with $CHCl_3$ and saturated aqueous $NaHCO_3$ solution (20 mL). The organic layer was separated, dried over $MgSO_4$, filtered and the filtrate solution was concentrated in vacuo to give the desired compound (2.6 g, 54%) as a white solid. $^1H$ NMR (DMSO-$d_6$) δ 8.02 (t, J=8.0 Hz, 1H), 7.92 (d, J=8.0 Hz, 1H), 7.73 (d, J=8.0 Hz, 1H), 4.62 (d, J=8.0 Hz, 2H), 3.88 (s, 3H). MS (ESI): 168.1 (M+H)⁺.

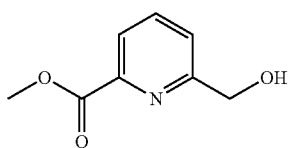

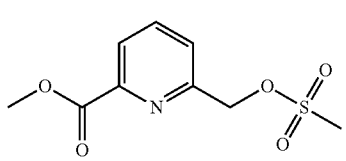

B) Methyl 6-((methylsulfonyloxy)methyl)picolinate

To a solution of methyl 6-(hydroxymethyl)picolinate (2.6 g, 15.5 mmol) in $CH_2Cl_2$ (15 mL) were added methanesulfonyl chloride (1.81 mL, 23.3 mmol) and TEA (5.42 mL, 38.9 mmol) dropwise at 0° C. The reaction mixture was stirred at 0° C. for 1 h and diluted with $CHCl_3$ and saturated aqueous $NaHCO_3$ solution. The organic layer was separated, washed with brine, dried over $MgSO_4$, filtered, and the filtrate was concentrated to give the desired compound (4.2 g, 85%) as a brown oil. $^1H$ NMR ($CDCl_3$) δ 8.15 (d, J=8.0 Hz, 1H), 7.96 (t, J=8.0 Hz, 1H), 7.12 (d, J=8.0 Hz, 1H), 5.46 (s, 2H), 4.04 (s, 3H), 3.20 (s, 3H). MS (ESI): 246.1 (M+H)+.

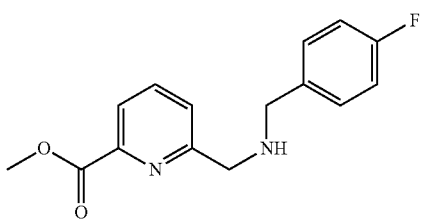 [SMILES: COC(=O)c1cccc(CNCc2ccc(F)cc2)n1]

C) Methyl 6-((4-fluorobenzylamino)methyl)picolinate

To a solution of methyl 6-((methylsulfonyloxy)methyl)picolinate (0.4 g, 1.63 mmol) in $CH_3CN$ (15 mL) were added 4-fluorobenzylamine (0.75 mL, 6.52 mmol) and $Cs_2CO_3$ (0.8 g, 2.45 mmol). The reaction mixture was stirred at rt for 4 h, filtered and the filtrate solution was concentrated in vacuo. The residue was purified by preparative HPLC. Fractions containing the desired product were combined and concentrated to give the desired compound (140 mg, 31%) as an oil. $^1H$ NMR ($CDCl_3$) δ 8.02 (d, J=8.0 Hz, 1H), 7.81 (t, J=8.0 Hz, 1H), 7.59 (d, J=8.0 Hz, 1H), 7.35-7.31 (m, 2H), 7.04-6.99 (m, 2H), 4.02 (s, 2H), 3.99 (s, 3H), 3.82 (s, 2H). MS (ESI): 275.1 (M+H)+.

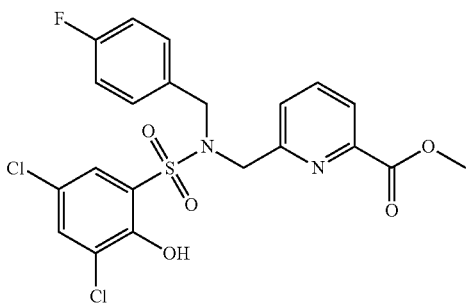 [SMILES: COC(=O)c1cccc(CN(Cc2ccc(F)cc2)S(=O)(=O)c2cc(Cl)cc(Cl)c2O)n1]

D) Methyl 6-((3,5-dichloro-N-(4-fluorobenzyl)-2-hydroxyphenylsulfonamido)-methyl)picolinate To a solution of methyl 6-((4-fluorobenzylamino)methyl)picolinate (140 mg, 0.51 mmol) in THF (3 mL) were added 3,5-dichloro-2-hydroxybenzene-1-sulfonyl chloride (147 mg, 0.56 mmol) and TEA (0.142 mL, 1.02 mmol). The reaction mixture was stirred at rt overnight and concentrated in vacuo. The residue was purified by preparative HPLC. Fractions containing the desired product were combined, concentrated and lyophilized to give the desired product (0.19 g, 74%) as a white solid. $^1H$ NMR ($CD_3OD$) δ 7.93-7.80 (m, 2H), 7.65-7.53 (m, 3H), 7.27-7.25 (m, 2H), 6.94-6.90 (m, 2H), 4.68 (s, 2H), 4.65 (s, 2H), 3.98 (s, 3H). MS (ESI): 499.0 (M+H)+.

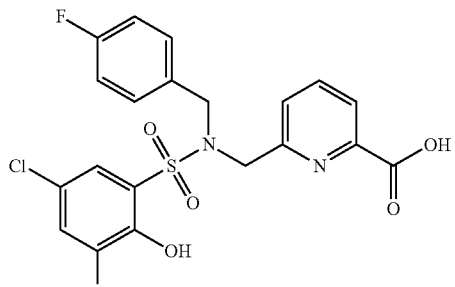

E) 6-((3,5-Dichloro-N-(4-fluorobenzyl)-2-hydroxyphenylsulfonamido)-methyl)picolinic acid A mixture of methyl 6-((3,5-dichloro-N-(4-fluorobenzyl)-2-hydroxyphenylsulfonamido)methyl)picolinate (0.185 g, 0.37 mmol), 1 N NaOH (2 mL), THF (2 mL) and MeOH (2 mL) was stirred at rt overnight. The reaction mixture was concentrated in vacuo and the residue was diluted with ethyl acetate and 1 N HCl. The organic layer was separated, washed with brine, dried over $MgSO_4$, filtered and the filtrate solution was concentrated to give the desired product (0.18 g, 99%) as a colorless oil. $^1H$ NMR ($CDCl_3$) δ 8.12 (d, J=8.0 Hz, 1H), 7.88 (t, J=8.0 Hz, 1H), 7.58 (d, J=4.0 Hz, 1H), 7.55 (d, J=4.0 Hz, 1H), 7.45 (d, J=8.0 Hz, 1H), 7.06-7.03 (m, 2H), 6.93 (t, J=8.0 Hz, 2H), 4.64 (s, 2H), 4.40 (s, 2H). MS (ESI): 485.0 (M+H)+.

F) 6-((3,5-Dichloro-N-(4-fluorobenzyl)-2-hydroxyphenylsulfonamido)methyl)-N-(3,5-dichlorobenzyl)-N-(4-fluorobenzyl)picolinamide To a solution of 6-((3,5-dichloro-N-(4-fluorobenzyl)-2-hydroxyphenylsulfonamido)methyl)picolinic acid, HCl (70 mg, 0.13 mmol) in $CH_2Cl_2$ (2 mL) were added EDC (39 mg, 0.20 mmol) and HOBT (20.5 mg, 0.13 mmol), followed by N-(3,5-dichlorobenzyl)-1-(4-fluorophenyl)methanamine (46 mg, 0.16 mmol) and TEA (0.2 mL, 1.44 mmol). The resulting red color reaction mixture was stirred at rt for 3 h, concentrated and the residue was diluted with ethyl acetate and 1 N NaOH. The organic layer was separated, washed with 1 N HCl, brine and concentrated in vacuo. The residue was dissolved in MeOH and purified by preparative HPLC. Fractions containing the desired product were combined, concentrated, and lyophilized to give the title compound (48 mg, 47.1%) as a white solid. $^1H$ NMR ($CD_3OD$) δ 7.70-7.68 (m, 1H), 7.57-7.54 (m, 1H), 7.50 (m, 1H), 7.44 (d, J=8.0 Hz, 1H), 7.30 (d, J=8.0 Hz, 1H), 724-7.17 (m, 3H), 7.12-7.11 (m, 2H), 6.98-6.89 (m, 4H), 6.69 (t, J=8.0 Hz, 2H), 4.58 (s, 1H), 4.54-4.53 (m, 2H), 4.47-4.46 (m, 3H), 4.37 (s, 1H), 4.31 (s, 1H). MS (ESI): 752.1 (M+H)+.

Examples 271-275

The following examples were prepared using similar procedures to those described above:

| Ex. No. | Structure | Name | HPLC $t_R$ (minute) | LCMS $(M + H)^+$ |
|---|---|---|---|---|
| 271 | 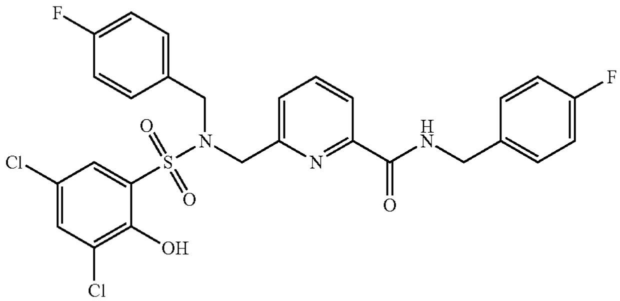 [SMILES: O=C(NCc1ccc(F)cc1)c1cccc(CN(Cc2ccc(F)cc2)S(=O)(=O)c2cc(Cl)cc(Cl)c2O)n1] | 6-((3,5-Dichloro-N-(4-fluorobenzyl)-2-hydroxyphenylsulfonamido)methyl)-N-(4-fluorobenzyl)picolinamide | 3.92 | 592.1 |
| 272 | 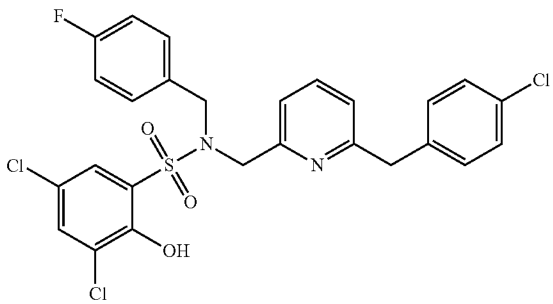 [SMILES: O=S(=O)(c1cc(Cl)cc(Cl)c1O)N(Cc1ccc(F)cc1)Cc1cccc(Cc2ccc(Cl)cc2)n1] | 3,5-Dichloro-N-((6-(4-chlorobenzyl)pyridin-2-yl)methyl)-N-(4-fluorobenzyl)-2-hydroxybenzenesulfonamide | 4.15 | 567.2 |
| 273 | 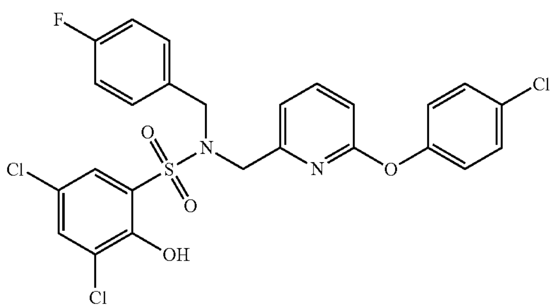 [SMILES: O=S(=O)(c1cc(Cl)cc(Cl)c1O)N(Cc1ccc(F)cc1)Cc1cccc(Oc2ccc(Cl)cc2)n1] | 3,5-Dichloro-N-((6-(4-chlorophenoxy)pyridin-2-yl)methyl)-N-(4-fluorobenzyl)-2-hydroxybenzenesulfonamide | 4.21 | 569.2 |
| 274 | 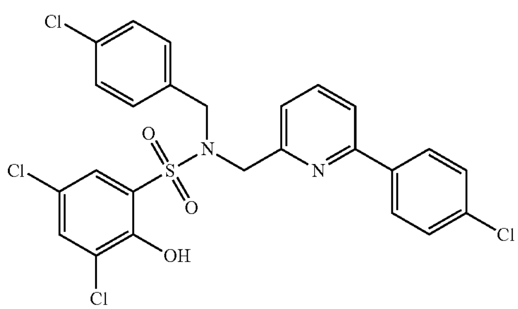 | 3,5-Dichloro-N-(4-chlorobenzyl)-N-((6-(4-chlorophenyl)pyridin-2-yl)methyl)-2-hydroxybenzenesulfonamide | 4.34 | 569.2 |
| 275 | 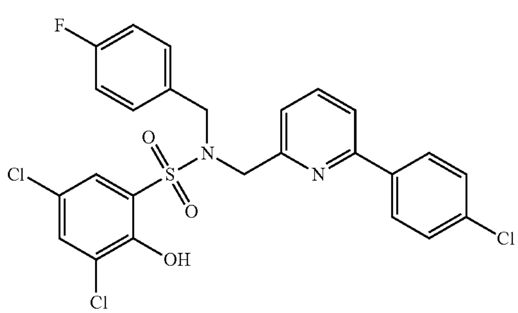 [SMILES: O=S(=O)(c1cc(Cl)cc(Cl)c1O)N(Cc1ccc(Cl)cc1)Cc1cccc(-c2ccc(Cl)cc2)n1] | 3,5-Dichloro-N-((6-(4-chlorophenyl)pyridin-2-yl)methyl)-N-(4-fluorobenzyl)-2-hydroxybenzenesulfonamide | 4.21 | 553.0 |

What is claimed is:

1. A compound of formula I

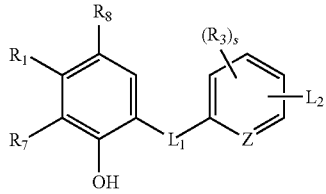

or salt thereof, wherein:

$L_1$ is —$SO_2N(R_2)$—$CH_2$—;

$L_2$ is $C_{3-10}$-carbocyclic residue substituted with 0-5 $R_6$, aryl substituted with 0-5 $R_6$, and heterocyclyl substituted with 0-5 $R_6$, —$(CH_2)_n$—$N(R_4)$—CO—$(CH_2)_l$—$R_5$, —$(CH_2)_n$—$N(R_4)$—CO(O)$C_{1-6}$alkyl, —$CH_2$—N$(R_4)$—$SO_2$—$R_5$, —$CH_2$—$N(R_4)$—CO—$N(R_4)$—$R_5$, —CO—$N(R_4)$—$(CHR)_n$—$R_5$, —$CH_2$—$N(R_4)$—$CH_2$—$R_5$—, —O—$R_{5a}$, —$CH_2$—S—$(CH_2)_l$—$R_5$, —$(CH_2)_n$—$R_{5a}$, or —CO—$R_{5b}$;

n is 0, 1, 2, or 3;

l is 0, 1, 2, or 3;

Z is CH, N or N-oxide;

R at each occurrence, is independently selected from H, $C_{1-6}$ alkyl, $C_{1-6}$ haloalkyl, and/or —$(CH_2)_r$-aryl;

$R_1$ is selected from hydrogen, F, Br, Cl, $NO_2$, CN, $C_{1-6}$ alkyl, —(CHR)$_r$-aryl substituted with 0-2 $R_{1a}$, alkoxy, aryloxy substituted with 0-2 $R_{1a}$, and heterocyclyl substituted with 0-2$R_{1a}$;

$R_{1a}$, at each occurrence, is independently selected from H, $C_{1-6}$ alkyl, $C_{1-6}$ haloalkyl, Cl, Br, F, $NO_2$, CN, (CHR)$_r$OH, (CHR)$_r$SH, (CHR)$_r$OR$_b$, (CHR)$_r$S(O)$_p$R$_b$, (CHR)$_r$C(O)R$_d$, (CHR)$_r$NR$_a$R$_a$, (CHR)$_r$C(O)NR$_a$R$_a$, (CHR)$_r$C(O)NR$_a$OR$_b$, (CHR)$_r$NR$_a$C(O)R$_d$, (CHR)$_r$NR$_a$C(O)OR$_b$, (CHR)$_r$OC(O)NR$_a$R$_a$, (CHR)$_r$C(O)OR$_d$, (CHR)$_r$S(O)$_p$NR$_a$R$_a$, (CHR)$_r$NR$_a$S(O)$_p$R$_b$, and/or a (CHR)$_r$—$C_{3-6}$ carbocyclic residue substituted with 0-5 R$_e$;

$R_2$ is selected from hydrogen, $C_{1-9}$ alkyl, $C_{1-9}$ alkenyl, $C_{1-6}$ haloalkyl, —$(CH_2)_r$-cycloalkyl substituted with 0-5 $R_{2a}$, —$(CH_2)_r$-aryl substituted with 0-5 $R_{2a}$, and —$(CH_2)_r$-heterocycloalkyl substituted with 0-3 $R_{2a}$;

$R_{2a}$, at each occurrence, is independently selected from $C_{1-6}$ alkyl, $C_{2-6}$ alkenyl, $C_{2-6}$ alkynyl, $C_{1-6}$ haloalkyl, $(CH_2)_rC_{3-6}$ cycloalkyl, Cl, Br, F, $NO_2$, CN, (CHR)$_r$OH, (CHR)$_r$SH, (CHR)$_r$OR$_b$, (CHR)$_r$S(O)$_p$R$_b$, (CHR)$_r$C(O)R$_d$, (CHR)$_r$NR$_a$R$_a$, (CHR)$_r$C(O)NR$_a$R$_a$, (CHR)$_r$C(O)NR$_a$OR$_b$, (CHR)$_r$NR$_a$C(O)R$_d$, (CHR)$_r$NR$_a$C(O)OR$_b$, (CHR)$_r$OC(O)NR$_a$R$_a$, (CHR)$_r$C(O)OR$_d$, (CHR)$_r$S(O)$_p$NR$_a$R$_a$, (CHR)$_r$NR$_a$S(O)$_p$R$_b$, and/or a (CHR)$_r$—$C_{3-10}$ carbocyclic residue substituted with 0-5 R$_e$;

$R_3$, at each occurrence, is independently selected from hydrogen, F, Br, Cl, $C_{1-6}$ alkyl, (CHR)$_r$—$C_{3-6}$ cycloalkyl, (CHR)$_r$-aryl substituted with 0-3 $R_{3a}$, —O—$C_{1-6}$alkyl, —O—(CHR)$_r$-aryl substituted with 0-3 $R_{3a}$, and/or heterocycle substituted with 0-2 $R_{3a}$;

$R_{3a}$, at each occurrence, is independently selected from $C_{1-6}$ alkyl, $C_{2-6}$ alkenyl, $C_{2-6}$ alkynyl, $C_{1-6}$ haloalkyl, $(CH_2)_rC_{3-6}$ cycloalkyl, Cl, Br, F, $NO_2$, CN, (CHR)$_r$OH, (CHR)$_r$SH, (CHR)$_r$OR$_b$, (CHR)$_r$S(O)$_p$R$_b$, (CHR)$_r$C(O)R$_d$, (CHR)$_r$NR$_a$R$_a$, (CHR)$_r$C(O)NR$_a$R$_a$, (CHR)$_r$C(O)NR$_a$OR$_b$, (CHR)$_r$NR$_a$C(O)R$_d$, (CHR)$_r$NR$_a$C(O)OR$_b$, (CHR)$_r$OC(O)NR$_a$R$_a$, (CHR)$_r$C(O)OR$_d$, (CHR)$_r$S(O)$_p$NR$_a$R$_a$, (CHR)$_r$NR$_a$S(O)$_p$R$_b$, and/or a (CHR)$_r$—$C_{3-6}$ carbocyclic residue substituted with 0-5 Re;

$R_4$, at each occurrence, is independently selected from hydrogen, $C_{1-6}$ alkyl substituted with 0-3 $R_e$, (CHR)$_r$—$C_{3-6}$cycloalkyl, (CHR)$_r$-aryl substituted with 0-2 $R_{4a}$, and/or (CHR)$_r$-heterocycle substituted with 0-2 $R_{4a}$;

$R_{4a}$, at each occurrence, is independently selected from $C_{1-6}$ alkyl, $C_{2-6}$ alkenyl, $C_{2-6}$ alkynyl, $(CH_2)_rC_{3-6}$ cycloalkyl, Cl, Br, F, $NO_2$, CN, (CHR)$_r$OH, (CHR)$_r$SH, (CHR)$_r$OR$_b$, (CHR)$_r$S(O)$_p$R$_b$, (CHR)$_r$C(O)R$_d$, (CHR)$_r$NR$_a$R$_a$, (CHR)$_r$C(O)NR$_a$R$_a$, (CHR)$_r$C(O)NR$_a$OR$_b$, (CHR)$_r$NR$_a$C(O)R$_d$, (CHR)$_r$NR$_a$C(O)OR$_b$, (CHR)$_r$OC(O)NR$_a$R$_a$, (CHR)$_r$C(O)OR$_d$, (CHR)$_r$S(O)$_p$NR$_a$R$_a$, (CHR)$_r$NR$_a$S(O)$_p$R$_b$, and/or a (CHR)$_r$—$C_{3-6}$ carbocyclic residue substituted with 0-5 $R_e$;

$R_5$ is selected from $C_{1-6}$ alkyl substituted with 0-3 $R_6$, $C_{3-10}$ carbocyclic residue substituted with 0-5 $R_6$, aryl substituted with 0-5 $R_6$, and heterocyclyl substituted with 0-5 $R_6$;

$R_{5a}$ is aryl substituted with 0-5 $R_6$;

$R_{5b}$ is aryl substituted with 0-5 $R_6$ or heterocyclyl substituted with 0-5 $R_6$;

$R_6$, at each occurrence, is independently selected from hydrogen, H, F, Cl, Br, $OCF_3$, $CF_3$, N, $NO_2$, =O, $N_3$, (CHR)$_r$OH, (CHR)$_r$SH, (CHR)$_r$OR$_b$, (CHR)$_r$S(O)$_p$R$_b$, (CHR)$_r$C(O)R$_d$, (CHR)$_r$NR$_a$R$_a$, (CHR)$_r$C(O)NR$_a$R$_a$, (CHR)$_r$C(O)NR$_a$OR$_b$, (CHR)$_r$NR$_a$C(O)R$_d$, (CHR)$_r$NR$_a$C(O)OR$_b$, (CHR)$_r$OC(O)NR$_a$R$_a$, (CHR)$_r$NR$_a$C(O)NR$_a$R$_a$, (CHR)$_r$C(O)OR$_d$, (CHR)$_r$S(O)$_p$NR$_a$R$_a$, (CHR)$_r$NR$_a$S(O)$_p$R$_b$, $SO_2F$, $C_{1-6}$ alkyl substituted with 0-2 $R_e$, $C_{1-6}$ haloalkyl, a (CHR)$_r$—$C_{3-6}$ carbocyclic residue substituted with 0-5 $R_e$, and/or a (CHR)$_r$-heterocyclyl substituted with 0-5 $R_e$;

$R_a$, at each occurrence, is independently selected from H, $C_{1-6}$ alkyl substituted with 0-2 $R_e$, $C_{1-6}$ haloalkyl, $C_{3-6}$ alkenyl substituted with 0-2 $R_e$, $C_{3-6}$ alkynyl substituted with 0-2 $R_e$, a $(CH_2)_r$-$C_{3-10}$ carbocyclic residue substituted with 0-5 $R_e$, and/or a $(CH_2)_r$-heterocyclyl substituted with 0-2 $R_e$;

$R_b$, at each occurrence, is independently selected from $C_{1-6}$ alkyl substituted with 0-2 $R_e$, $C_{1-6}$ haloalkyl, $C_{3-6}$ alkenyl substituted with 0-2 $R_e$, $C_{3-6}$ alkynyl substituted with 0-2 $R_e$, a $(CH_2)_r$—$C_{3-10}$ carbocyclic residue substituted with 0-5 $R_e$, and/or a $(CH_2)_r$-heterocyclyl substituted with 0-2 $R_e$;

$R_d$, at each occurrence, is independently selected from H, $C_{1-6}$ alkyl substituted with 0-2 $R_e$, $C_{1-6}$ haloalkyl, $C_{3-6}$ alkenyl substituted with 0-2 $R_e$, $C_{3-6}$ alkynyl substituted with 0-2 $R_e$, a $(CH_2)_r$—$C_{3-10}$ carbocyclic residue substituted with 0-5 $R_e$, and/or a $(CH_2)_r$-heterocyclyl substituted with 0-2 $R_e$;

$R_e$, at each occurrence, is independently selected from $C_{1-6}$ alkyl, $C_{2-6}$ alkenyl, $C_{2-6}$ alkynyl, $(CH_2)_rC_{3-6}$ cycloalkyl, Cl, F, Br, CN, $NO_2$, $CO_2H$, $CO_2C_{1-5}$alkyl, $(CF_2)_rCF_3$, $(CH_2)_rOC_{1-5}$ alkyl, OH, SH, $(CH_2)_rSC_{1-5}$ alkyl, $(CH_2)_rNR_fR_f$, and/or $(CH_2)_r$phenyl;

$R_f$, at each occurrence, is independently selected from H, $C_{1-5}$ alkyl, $C_{3-6}$ cycloalkyl, and/or phenyl;

$R_7$ is selected from F, Cl, $CF_3$, C(O)NR$_a$R$_a$, and C(O)OR$_b$;

$R_8$ is selected from hydrogen, F, Cl, $CF_3$, C(O)NR$_a$R$_a$, and C(O)OR$_b$;

p, at each occurrence, is independently selected from 0, 1, and/or 2;

r, at each occurrence, is independently selected from 0, 1, 2, 3, and/or 4; and s is selected from 0, 1, and 2.

2. The compound of claim 1, wherein:
   $R_1$ is selected from hydrogen, F, Br, Cl, $C_{1-6}$ alkyl, and —(CHR)$_r$-phenyl substituted with 0-2 $R_{1a}$;
   $R_2$ is selected from hydrogen, $C_{1-9}$ alkyl, $C_{1-9}$ alkenyl, —(CH$_2$)$_r$-cyclohexyl substituted with 0-5 $R_{2a}$, —(CH$_2$)$_r$phenyl substituted with 0-5 $R_{2a}$, and indolinyl substituted with 0-1 $R_{2a}$; and
   $R_{2a}$, at each occurrence, is independently selected from $C_{1-6}$ alkyl, $C_{1-6}$ haloalkyl, (CH$_2$)$_r$C$_{3-6}$ cycloalkyl, Cl, Br, F, NO$_2$, CN, (CHR)$_r$OH, (CHR)$_r$OR$_b$, (CHR)$_r$S(O)$_p$R$_b$, and/or a (CHR)$_r$—C$_{3-6}$ carbocyclic residue substituted with 0-5 $R_e$.

3. The compound of claim 1, wherein:
   $R_3$, at each occurrence, is independently selected from hydrogen, F, Br, Cl, (CH$_2$)$_r$-phenyl substituted with 0-3 $R_{3a}$, —O—C$_{1-6}$alkyl, and/or —O(CH$_2$)$_r$-phenyl substituted with 0-3 $R_{3a}$;
   $R_{3a}$, at each occurrence, is independently selected from $C_{1-6}$ alkyl, (CH$_2$)$_r$C$_{3-6}$ cycloalkyl, CF$_3$, Cl, Br, F, NO$_2$, and/or CN;
   $R_4$, at each occurrence, is independently selected from hydrogen, $C_{1-6}$ alkyl substituted with 0-1 $R_e$, cyclopropyl, cyclopentyl, cyclohexyl, (CH$_2$)$_r$-phenyl substituted with 0-2 $R_{4a}$, and/or (CHR)$_r$-heterocycle substituted with 0-2 $R_{4a}$; and
   $R_{4a}$, at each occurrence, is independently selected from $C_{1-6}$ alkyl, (CH$_2$)$_r$C$_{3-6}$ cycloalkyl, Cl, Br, F, NO$_2$, CN, (CH$_2$)$_r$S(O)$_p$R$_b$, (CHR)$_r$C(O)R$_d$, and/or a (CHR)$_r$—C$_{3-6}$ carbocyclic residue substituted with 0-5 $R_e$.

4. The compound of claim 1, wherein:
   $R_1$ is hydrogen;
   $R_2$ is selected from hydrogen, $C_{1-9}$ alkyl, —(CH$_2$)$_r$-cyclohexyl substituted with 0-5 $R_{2a}$, —(CH$_2$)$_r$-phenyl substituted with 0-2 $R_{2a}$, and indolinyl; and
   $R_{2a}$, at each occurrence is independently selected from $C_{1-6}$ alkyl, $C_{1-2}$ haloalkyl, Cl, Br, F, NO$_2$, CN, (CH$_2$)$_r$OH, (CH$_2$)$_r$OR$_b$, (CH$_2$)$_r$S(O)$_p$R$_b$, and/or a (CHR)$_r$—C$_{3-6}$ carbocyclic residue substituted with 0-2 $R_e$.

5. The compound of claim 4, wherein:
   $R_3$, at each occurrence, is independently selected from hydrogen, F, Br, Cl, (CH$_2$)$_r$-phenyl substituted with 0-1 $R_{3a}$, and/or —O(CH$_2$)$_r$-phenyl substituted with 0-1 $R_{3a}$;
   $R_4$, at each occurrence, is independently selected from hydrogen, $C_{1-6}$ alkyl, and/or (CH$_2$)$_r$-phenyl substituted with 0-2 $R_{4a}$; and
   $R_{4a}$, at each occurrence, is independently selected from $C_{1-6}$ alkyl, Cl, Br, F, NO$_2$, CN, (CH$_2$)$_r$S(O)$_p$R$_b$, (CHR)$_r$C(O)R$_d$, and/or a (CHR)$_r$—C$_{3-6}$ carbocyclic residue substituted with 0-5 $R_e$.

6. The compound of claim 5, wherein:
   $R_5$ is selected from $C_{1-6}$ alkyl substituted with 0-3 $R_6$, cyclopropyl substituted with 0-3 $R_6$, aryl substituted with 0-3 $R_6$, wherein the aryl is selected from phenyl and naphthyl, and heterocyclyl substituted with 0-3 $R_6$, wherein the heterocyclyl is selected from pyrrolidinyl, piperidinyl, morpholinyl, pyridinyl, pyridinyl N-oxide, piperazinyl, thiazolyl, benzothiazolyl, benzodiazepinonyl, indolyl, and quinoxaline-dionyl;
   $R_{5a}$ is phenyl substituted with 0-3 $R_6$ or napthyl substituted with 0-3 $R_6$; and
   $R_{5b}$ is phenyl substituted with 0-3 $R_6$ or heterocyclyl substituted with 0-3 $R_6$, wherein the heterocyclyl is selected from piperidinyl, piperazinyl, morpholinyl and pyrrolidinyl.

7. The compound of claim 1, wherein:
   $R_6$, at each occurrence, is independently selected from hydrogen, F, Cl, Br, OCF$_3$, CF$_3$, CN, NO$_2$, =O, N$_3$, (CHR)$_r$OH, (CH$_2$)$_r$OR$_b$, (CH$_2$)$_r$S(O)$_p$R$_b$, (CH$_2$)$_r$C(O)R$_d$, (CH$_2$)$_r$NR$_a$R$_a$, (CH$_2$)$_r$C(O)NR$_a$R$_a$, (CH$_2$)$_r$NR$_a$C(O)R$_d$, (CH$_2$)$_r$NR$_a$C(O)OR$_b$, (CH$_2$)$_r$OC(O)NR$_a$R$_a$, (CH$_2$)$_r$NR$_a$C(O)NR$_a$R$_a$, (CH$_2$)$_r$C(O)OR$_d$, (CH$_2$)$_r$S(O)$_p$NR$_a$R$_a$, (CH$_2$)$_r$NR$_a$S(O)$_p$R$_b$, SO$_2$F, $C_{1-6}$ alkyl substituted with 0-2 $R_e$, a (CHR)$_r$—C$_{3-6}$ carbocyclic residue substituted with 0-5 $R_e$, wherein the carbocyclic residue is selected from phenyl and cyclohexyl, and/or a (CHR)$_r$-heterocyclyl substituted with 0-5 $R_e$, wherein the heterocyclyl is selected from piperidinyl, pyrazinyl, and pyridinyl.

8. The compound of claim 1, wherein:
   $R_6$, at each occurrence, is independently selected from hydrogen, F, Cl, Br, OCF$_3$, CF$_3$, CN, NO$_2$, =O, N$_3$, (CHR)$_r$OH, (CH$_2$)$_r$OR$_b$, S(O)$_p$R$_b$, NR$_a$R$_a$, NR$_a$C(O)NR$_a$R$_a$, C(O)OR$_d$, S(O)$_p$NR$_a$R$_a$, SO$_2$F, $C_{1-6}$ alkyl substituted with 0-2 $R_e$ wherein alkyl is selected from methyl, ethyl, propyl, i-propyl and t-butyl, a (CHR)$_r$—C$_{3-6}$ carbocyclic residue substituted with 0-5 $R_e$, wherein the carbocyclic residue is selected from phenyl and cyclohexyl, and/or a (CHR)$_r$-heterocyclyl substituted with 0-5 $R_e$, wherein the heterocyclyl is selected from piperidinyl, pyrazinyl, and pyridinyl.

9. The compound of claim 1, wherein:
   $R_7$ is selected from Cl, CF$_3$, C(O)NR$_a$R$_a$, and C(O)OR$_b$;
   $R_8$ is selected from hydrogen, Cl, CF$_3$, C(O)NR$_a$R$_a$, and C(O)OR$_b$;
   $R_a$, at each occurrence, is independently selected from H, $C_{1-6}$ alkyl substituted with 0-2 $R_e$, $C_{1-6}$ haloalkyl, a (CH$_2$)$_r$C$_{3-6}$ carbocyclic residue substituted with 0-3 $R_e$ wherein the carbocyclic residue is selected from phenyl and cyclohexyl, (CH$_2$)$_r$-indolyl, and/or (CH$_2$)$_r$-pyrazolyl;
   $R_b$, at each occurrence, is independently selected from $C_{1-6}$ alkyl substituted with 0-2 $R_e$, CF$_3$, and/or a (CH$_2$)$_r$—C$_{3-6}$ carbocyclic residue substituted with 0-3 $R_e$, wherein the carbocyclic residue is selected from phenyl and cyclohexyl;
   $R_d$, at each occurrence, is independently selected from H, $C_{1-6}$ alkyl substituted with 0-2 $R_e$, CF$_3$, and/or a (CH$_2$)$_r$—C$_{3-6}$ carbocyclic residue substituted with 0-3 $R_e$, wherein the carbocyclic residue is selected from phenyl and cyclohexyl; and
   $R_e$, at each occurrence, is independently selected from $C_{1-6}$ alkyl, $C_{2-6}$ alkenyl, $C_{2-6}$ alkynyl, (CH$_2$)$_r$C$_{3-6}$ cycloalkyl, Cl, F, Br, CN, NO$_2$, CO$_2$H, CO$_2$C$_{1-5}$alkyl, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$_f$R$_f$ and/or (CH$_2$)$_r$phenyl.

10. The compounds of claim 1, wherein:
    $R_2$ is selected from $C_{1-9}$ alkyl, —(CH$_2$)$_r$-cyclohexyl substituted with 0-5 $R_{2a}$, —(CH$_2$)$_r$-phenyl substituted with 0-2 $R_{2a}$, and/or indolinyl.

11. The compound of claim 1 or pharmaceutically acceptable salt thereof, wherein said compound is selected from: 3,5-Dichloro-N-(3-((3,5-dichloro-2-hydroxyphenylsulfonamido)methyl)benzyl)-N-(4-fluorobenzyl)-2-hydroxybenzenesulfonamide (1); N-(3-((3,5-Dichloro-N-(4-fluorobenzyl)-2-hydroxyphenylsulfonamido)methyl)benzyl)-2,6-dihydroxyisonicotinamide (2); N-(Biphenyl-4-ylmethyl)-3,5-dichloro-N-(3-((3,5-dichloro-2-hydroxyphenylsulfonamido)methyl)benzyl)-2-hydroxybenzenesulfonamide (3); N-(Biphenyl-4-ylmethyl)-3,5-dichloro-N-(3-((4-cyanophenylsulfonamido)methyl)benzyl)-2-hydroxybenzenesulfonamide (4); 3,5-Dichloro-N-(4-(4-fluorophenoxy)benzyl)-2-hydroxy-N-(3-((4-methylphenylsulfonamido)methyl)benzyl)benzenesulfonamide (5); 3,5-Dichloro-N-(3-((3,5-dichloro- 2-hydroxyphenylsulfonamido)methyl)benzyl)-2-hydroxy-N-(3-(trifluoromethoxy)benzyl)benzenesulfonamide (6); 3,5-Dichloro-N-(3-((3,5-dichloro-N-isobutylphenylsulfonamido) methyl)-5-(4-fluorophenoxy)benzyl)-N-(4-fluorobenzyl)-2-hydroxybenzenesulfonamide (7); 3,5-Dichloro-N-(4-fluorobenzyl)-N-(3-(4-fluorophenoxy)-5-((N-isobutyl-4-methylphenylsulfonamido) methyl)benzyl)-2-hydroxybenzenesulfonamide (8); N-(3-((N-(Biphenyl-4-ylmethyl)-3,5-dichloro-2-hydroxyphenylsulfonamido) methyl)benzyl)-3,4,5-trihydroxybenzamide (9); 3,5-Dichloro-N-(3-((3-(2,4-difluorophenyl)ureido)methyl) benzyl)-2-hydroxy-N-(4-(trifluoromethyl)benzyl) benzenesulfonamide (10); N-(3-((3-Biphenyl-4-ylureido) methyl)benzyl)-3,5-dichloro-2-hydroxy-N-(4-(trifluoromethyl)benzyl)benzenesulfonamide (11); 4-(2-Chlorophenyl)-N-(3-((3,5-dichloro-2-hydroxy-N-(4-(trifluoromethyl)benzyl)phenylsulfonamido)methyl)benzyl) piperazine-1-carboxamide (12); 3,5-Dichloro-N-((4'-fluoro-5-((N-(4-fluorobenzyl)-4-methylphenylsulfonamido) methyl)biphenyl-3-yl)methyl)-2-hydroxybenzenesulfonamide (13); N,N'-(5-Cyclopropyl-1,3-phenylene)bis(methylene)bis(3,5-dichloro-N-(4-fluorobenzyl)-2-hydroxybenzenesulfonamide (14); tert-Butyl 3-chloro-5-((3,5-dichloro-2-hydroxy-N-isobutylphenylsulfonamido)methyl)benzyl (isobutyl)carbamate (15); 3,5-Dichloro-N-(3-chloro-5-((N-isobutyl-4-methylphenylsulfonamido) methyl)benzyl)-2-hydroxy-N-isobutylbenzenesulfonamide (16); 6-Chloro-N-(3-chloro-5-((3,5-dichloro-2-hydroxy-N-isobutylphenylsulfonamido)methyl)benzyl)-N-isobutylnicotinamide (17); 3,5-Dichloro-N-(3-((3,5-dichloro-2-hydroxyphenylsulfonamido)methyl)-5-(4-fluorophenoxy)benzyl)-N-(4-fluorobenzyl)-2-hydroxybenzenesulfonamide (18); N-(3-((3,5-Dichloro-N-(4-fluorobenzyl)-2-hydroxyphenylsulfonamido)methyl)-5-(4-fluorophenoxy)benzyl)-N-isobutylnicotinamide (19); 3-((3-((3,5-Dichloro-N-(4-fluorobenzyl)-2-hydroxyphenylsulfonamido)methyl)-5-(4-fluorophenoxy)benzyl) (isobutyl) carbamoyl)pyridine 1-oxide (20); 3,5-Dichloro-N-(3-((3-(2, 4-difluorophenyl)ureido)methyl)-5-(4-fluorophenoxy) benzyl)-N-(4-fluorobenzyl)-2-hydroxybenzenesulfonamide (21); N-(4-Fluoro-benzyl)-N-(3-{[(4-fluoro-benzyl)-(3,5-dichloro-2-hydroxybenzene)sulfonyl-amino]-methyl}-benzyl)-3,5-dichloro-2-hydroxybenzenesulfonamide (22); N-(4-Fluoro-benzyl)-N-(4-{[(4-fluoro-benzyl)-(3,5-dichloro-2-hydroxybenzene)carbamoyl]-methyl}-benzyl)-3,5-dichloro-2-hydroxybenzeamide (23); N-(4-Fluoro-benzyl)-N-(3-chloro-5-{[(4-fluoro-benzyl)-(3,5-dichloro-2-hydroxybenzene)sulfonyl-amino]-methyl}-benzyl)-3,5-dichloro-2-hydroxybenzenesulfonamide (24); 5-(N-(3-((N-(Biphenyl-4-ylmethyl)-3,5-dichloro-2-hydroxyphenylsulfonamido)methyl)benzyl) sulfamoyl)-2-methylbenzoic acid (25); N-(3-((3,5-dichloro-2-hydroxyphenylsulfonamido)methyl)benzyl)-N-(4-fluorobenzyl)-2,6-dihydroxyisonicotinamide (26); N-(3-((3, 5-dichloro-2-hydroxy-N-(4-(trifluoromethyl)benzyl) benzamide) methyl)benzyl)-2,6-dihydroxyisonicotinamide (27); N-(3-((3,5-dichloro-2-hydroxy-N-(4-(trifluoromethyl) benzyl)phenylsulfonamido)methyl)benzyl)-2,3-dioxo-1,2,3,4-tetrahydroquinoxaline-6-carboxamide (28); 3,5-dichloro-N-(3-((5-chloro-2-methoxyphenylsulfonamido)methyl)-5-(4-fluorophenoxy)benzyl)-N-(4-fluorobenzyl)-2-hydroxybenzenesulfonamide (29); tert-butyl 3-((3,5-dichloro-N-(4-fluorobenzyl)-2-hydroxyphenylsulfonamido) methyl)benzylcarbamate (30); tert-butyl 3-((N-(biphenyl-4-ylmethyl)-3,5-dichloro-2-hydroxyphenylsulfonamido) methyl)benzylcarbamate (31); N-(3-((3,5-dichloro-N-(4-fluorobenzyl)-2-hydroxyphenylsulfonamido)methyl) benzyl)-3,4,5-trihydroxybenzamide (32); N-(biphenyl-4-ylmethyl)-3,5-dichloro-2-hydroxy-N-(3-((4-(pyridin-4-yloxy)phenylsulfonamido) methyl)benzyl) benzenesulfonamide (33); 5-(N-(3-((N-(biphenyl-4-ylmethyl)-3,5-dichloro-2-hydroxyphenylsulfonamido) methyl)benzyl)sulfamoyl)-2-hydroxybenzoic acid (34); 3-(N-(3-((N-(biphenyl-4-ylmethyl)-3,5-dichloro-2-hydroxyphenylsulfonamido) methyl)benzyl)sulfamoyl)benzoic acid (35); N1-(3-((N-(biphenyl-4-ylmethyl)-3,5-dichloro-2-hydroxyphenylsulfonamido)methyl)benzyl)-4-chlorobenzene-1,3-disulfonamide (36); N-(biphenyl-4-ylmethyl)-3,5-dichloro-2-hydroxy-N-(3-((3-(1,3,3-trimethylureido) phenylsulfonamido)methyl)benzyl)benzenesulfonamide (37); N-(3-((N-(biphenyl-4-ylmethyl)-3,5-dichloro-2-hydroxyphenylsulfonamido)methyl)benzyl)-4-((1,3-dihydroxypropan-2-ylamino)methyl)benzamide (38); N-(3-((N-(biphenyl-4-ylmethyl)-3,5-dichloro-2-hydroxyphenylsulfonamido)methyl)benzyl)-2-methoxy-5-sulfamoylbenzamide (39); N-(biphenyl-4-ylmethyl)-3,5-dichloro-2-hydroxy-N-(3-((4-(pyridin-3-yloxy) phenylsulfonamido)methyl)benzyl)benzenesulfonamide (40); 3,5-dichloro-N-(3-((3,5-dichloro-N-(4-fluorobenzyl)-2-hydroxyphenylsulfonamido)methyl)benzyl)-N-(4-fluorophenethyl)-2-hydroxybenzenesulfonamide (41); 3,5-dichloro-N-(3-((3,5-dichloro-2-hydroxy-N-isobutylphenylsulfonamido)methyl)benzyl)-N-(4-fluorophenethyl)-2-hydroxybenzenesulfonamide (42); (R)-tert-butyl 1-(3-((5-chloro-N-(4-fluorobenzyl)-2-methoxyphenylsulfonamido)methyl)benzylamino)-1-oxo-3-phenylpropan-2-ylcarbamate (43); 3,5-dichloro-N-(4-fluorobenzyl)-2-hydroxy-N-(3-((4-methylphenylsulfonamido) methyl)benzyl) benzenesulfonamide (44); N-(3-((3,5-dichloro-N-(4-fluorobenzyl)-2-hydroxyphenylsulfonamido)methyl) benzyl)-4-methylbenzamide (45); N-(3-((N-(biphenyl-4-ylmethyl)-3,5-dichloro-2-hydroxyphenylsulfonamido) methyl)benzyl)-3,5-dichloro-2-hydroxybenzamide (46); N-(biphenyl-4-ylmethyl)-3,5-dichloro-N-(3-((3,5-dichlorophenylsulfonamido)methyl)benzyl)-2-hydroxybenzenesulfonamide (47); N-(3-((N-(biphenyl-4-ylmethyl)-3,5-dichloro-2-hydroxyphenylsulfonamido)methyl)benzyl) naphthalene-2-sulfonamide (48); 4-(N-(3-((N-(biphenyl-4-ylmethyl)-3,5-dichloro-2-hydroxyphenylsulfonamido) methyl)benzyl)sulfamoyl)benzoic acid (49); 3,5-dichloro-N-(3-((3,5-dichloro-2-hydroxyphenylsulfonamido)methyl) benzyl)-N-(4-(4-fluorophenoxy)benzyl)-2-hydroxybenzenesulfonamide (50); 3,5-dichloro-N-(3-((3,5-dichloro-2-hydroxyphenylsulfonamido) methyl)benzyl)-N-(4-(difluoromethoxy)benzyl)-2-hydroxybenzenesulfonamide (51); N-(biphenyl-4-ylmethyl)-3,5-dichloro-2-hydroxy-N-(3-(phenylsulfonamidomethyl)benzyl)benzenesulfonamide (52); 3,5-dichloro-N-(3-((3,5-dichloro-2-hydroxyphenylsulfonamido)methyl)benzyl)-2-hydroxy-N-(4-(methylthio) benzyl)benzenesulfonamide (53); 3,5-dichloro-N-(3-((3,5-dichloro-2-hydroxyphenylsulfonamido)methyl)benzyl)-N-(3-ethoxybenzyl)-2-hydroxybenzenesulfonamide (54); 3-(N-(3-((N-(biphenyl-4-ylmethyl)-3,5-dichloro-2-hydroxyphenylsulfonamido)methyl)benzyl)sulfamoyl)-4-chlorobenzoic acid (55); 3,5-dichloro-N-(3-((3,5-dichloro-2-hydroxyphenylsulfonamido)methyl)benzyl)-2-hydroxy-N-(4-(methylsulfonyl)benzyl)benzenesulfonamide (56); 5-(N-(3-((N-(biphenyl-4-ylmethyl)-3,5-dichloro-2-hydroxyphenylsulfonamido)methyl)benzyl) sulfamoyl)-2-chloro-4-fluorobenzoic acid (57); 3,5-dichloro-N-(3-((3,5-dichloro-2-hydroxyphenylsulfonamido)methyl)benzyl)-2-hydroxy-N-(3-(2-hydroxyethoxy)benzyl) benzenesulfonamide (58); 3,5-dichloro-N-(3-((3,5-dichloro- 2-hydroxyphenylsulfonamido)methyl)benzyl)-2-hydroxy-N-(3,4,5-trimethoxybenzyl)benzenesulfonamide (59); 2-chloro-5-(N-(3-chloro-5-((3,5-dichloro-N-(4-fluorobenzyl)-2-hydroxyphenylsulfonamido)methyl)benzyl)-N-(4-fluorobenzyl) sulfamoyl)-4-fluorobenzoic acid (60); 3,5-dichloro-N-(3-((3,5-dichloro-2-hydroxyphenylsulfonamido)methyl)benzyl)-N-(4-(2-(diethylamino) ethoxy)benzyl)-2-hydroxybenzenesulfonamide (61); 2-(3-((3,5-dichloro-N-(3-((3,5-dichloro-2-hydroxyphenylsulfonamido)methyl) benzyl)-2-hydroxyphenylsulfonamido)methyl)phenoxy) acetic acid (62); N-(3-((N-(biphenyl-4-ylmethyl)-3,5-dichloro-2-hydroxyphenylsulfonamido)methyl)benzyl)-4-(trifluoromethylthio)benzamide (63); 3,5-dichloro-N-(3-((3,5-dichloro-2-hydroxyphenylsulfonamido)methyl)benzyl)-2-hydroxy-N-(2-(trifluoromethylthio)benzyl) benzenesulfonamide (64); 3,5-dichloro-N-(3-((3,5-dichloro-2-hydroxyphenylsulfonamido)methyl)benzyl)-2-hydroxy-N-(3-(trifluoromethylthio)benzyl)benzenesulfonamide (65); N-(biphenyl-4-ylmethyl)-3,5-dichloro-N-(3-((4-fluoro-3-(trifluoromethylsulfonyl)phenylsulfonamido)methyl)benzyl)-2-hydroxybenzenesulfonamide (66); N,N'-(5-chloro-1,3-phenylene)bis(methylene)bis(3,5-dichloro-2-hydroxy-N-isobutylbenzenesulfonamide (67); 4-(N-(3-((N-(biphenyl-4-ylmethyl)-3,5-dichloro-2-hydroxyphenylsulfonamido) methyl)benzyl)sulfamoyl)-3-(trifluoromethylsulfonyl) benzene-1-sulfonyl fluoride (68); 3,5-dichloro-N-(3-chloro-5-((N-(4-fluorobenzyl)-4-methylphenylsulfonamido) methyl)benzyl)-N-(4-fluorobenzyl)-2-hydroxybenzenesulfonamide (69); 3,5-dichloro-N-(3-chloro-5-((3-cyano-N-(4-fluorobenzyl)phenylsulfonamido) methyl)benzyl)-N-(4-fluorobenzyl)-2-hydroxybenzenesulfonamide (70); N-(3-chloro-5-((3,5-dichloro-2-hydroxy-N-isobutylphenylsulfonamido)methyl) benzyl)-N-isobutyl-4-(trifluoromethylthio)benzamide (71); N-(3-chloro-5-((3,5-dichloro-2-hydroxy-N-isobutylphenylsulfonamido)methyl)benzyl)-N-isobutyl-3-(trifluoromethylthio)benzamide (72); N-(3-chloro-5-((3,5-dichloro-2-hydroxy-N-isobutylphenylsulfonamido)methyl)benzyl)-N-isobutyl-3-(trifluoromethylsulfonyl)benzamide (73); 3,5-dichloro-N-(3-((3-cyanophenylsulfonamido)methyl)-5-(4-fluorophenoxy)benzyl)-2-hydroxy-N-(3-(methylsulfonyl) benzyl)benzenesulfonamide (74); 3,5-dichloro-N-(3-(4-fluorophenoxy)-5-((4-methylphenylsulfonamido)methyl) benzyl)-2-hydroxy-N-(3-(methylsulfonyl)benzyl) benzenesulfonamide (75); N-(3-((3,5-dichloro-2-hydroxy-N-(3-(methylsulfonyl)benzyl)phenylsulfonamido)methyl)-5-(4-fluorophenoxy)benzyl)-2-fluoro-3-methoxybenzamide (76); N-(3-((3,5-dichloro-2-hydroxy-N-(3-(methylsulfonyl) benzyl)phenylsulfonamido)methyl)-5-(4-fluorophenoxy) benzyl)-3-phenoxybenzamide (77); N-(3-((3,5-dichloro-2-hydroxy-N-(4-(methylsulfonyl)benzyl)phenylsulfonamido) methyl)-5-(4-fluorophenoxy)benzyl)-3-phenoxybenzamide (78); N-(3-((3,5-dichloro-2-hydroxy-N-(4-(methylsulfonyl) benzyl)phenylsulfonamido)methyl)-5-(4-fluorophenoxy) benzyl)-2-fluoro-3-methoxybenzamide (79); 3,5-dichloro-N-(3-((3-cyanophenylsulfonamido)methyl)-5-(4-fluorophenoxy)benzyl)-2-hydroxy-N-(4-(methylsulfonyl) benzyl)benzenesulfonamide (80); 3,5-dichloro-N-(3-(4-fluorophenoxy)-5-((4-methylphenylsulfonamido) methyl) benzyl)-2-hydroxy-N-(4-(methylsulfonyl)benzyl) benzenesulfonamide (81); N-(3-((3,5-dichloro-2-hydroxy-N-(4-(methylsulfonyl)benzyl)phenylsulfonamido)methyl)-5-(4-fluorophenoxy)benzyl)-3-(trifluoromethylsulfonyl) benzamide (82); N-(3-((3,5-dichloro-N-(4-fluorobenzyl)-2-hydroxyphenylsulfonamido)methyl)-5-(4-fluorophenoxy) benzyl)-N-(4-(methylsulfonyl)benzyl)-3-(trifluoromethylthio)benzamide (83); 3,5-dichloro-N-(3-((3, 5-dichloro-2-hydroxyphenylsulfonamido)methyl)-5-(4-fluorophenoxy)benzyl)-2-hydroxy-N-(4-(methylsulfonyl) benzyl)benzenesulfonamide (84); N-(3-((3,5-dichloro-N-(4-fluorobenzyl)-2-hydroxyphenylsulfonamido)methyl)-5-(4-fluorophenoxy)benzyl)-N-(4-(methylsulfonyl)benzyl)-3-(trifluoromethylthio)benzamide (85); N-(3-((3,5-dichloro-N-(4-fluorobenzyl)-2-hydroxyphenylsulfonamido)methyl)-5-(4-fluorophenoxy)benzyl)-N-(4-(methylsulfonyl)benzyl)-3-(trifluoromethylsulfinyl)benzamide (86); 6-chloro-N-(3-((3,5-dichloro-N-(4-fluorobenzyl)-2-hydroxyphenylsulfonamido)methyl)-5-(4-fluorophenoxy) benzyl)-N-isobutylnicotinamide (87); N-(3-((3,5-dichloro-N-(4-fluorobenzyl)-2-hydroxyphenylsulfonamido)methyl)-5-(4-fluorophenoxy)benzyl)nicotinamide (88); 3-(3-((3,5-dichloro-N-(4-fluorobenzyl)-2-hydroxyphenylsulfonamido) methyl)-5-(4-fluorophenoxy)benzylcarbamoyl)pyridine 1-oxide (89); 3,5-dichloro-N-(3-chloro-5-((3,5-dichloro-N-(4-fluorobenzyl)phenylsulfonamido)methyl)benzyl)-N-(4-fluorobenzyl)-2-hydroxybenzenesulfonamide (90); 3,5-dichloro-N-((6-((3,5-dichloro-N-(4-fluorobenzyl) phenylsulfonamido) methyl)pyridin-2-yl)methyl)-N-(4-fluorobenzyl)-2-hydroxybenzenesulfonamide (91); 2-((3,5-dichloro-N-(4-fluorobenzyl)-2-hydroxyphenylsulfonamido) methyl)-6-((3,5-dichloro-N-(4-fluorobenzyl) phenylsulfonamido) methyl)pyridine 1-oxide (92); 3,5-dichloro-N-(3-((3,5-dichloro-N-isobutylphenylsulfonamido) methyl)benzyl)-N-((4'-fluorobiphenyl-4-yl)methyl)-2-hydroxybenzenesulfonamide (93); 3,5-Dichloro-N-(3-(N-(3,5-dichlorobenzyl)-N-(4-fluorobenzyl)sulfamoyl)benzyl)-N-(4-fluorobenzyl)-2-hydroxybenzenesulfonamide (94); 3-((3,5-Dichloro-N-(4-fluorobenzyl)-2-hydroxyphenylsulfonamido)methyl)-N-(3,5-dichlorobenzyl)-N-(4-fluorobenzyl)benzamide (95); N-(4-Fluoro-benzyl)-N-(4-{[(4-fluoro-benzyl)-(3,5-dichloro-2-hydroxybenzene)sulfonyl-amino]-methyl}-benzyl)-3,5-dichloro-2-hydroxybenzenesulfonamide (96); N-Isobutyl-N-{4-[(isobutyl-(3,5-dichloro-2-hydroxybenzene)sulfonyl-amino)-methyl]-benzyl}-(3,5-dichloro-2-hydroxybenzene) sulfonamide (97); 3,5-Dichloro-N-(4-((3,5-dichlorophenylsulfonamido)methyl)benzyl)-N-(4-fluorobenzyl)-2-hydroxybenzenesulfonamide (98); 3,5-Dichloro-N-(4-((3,5-dichloro-N-(4-fluorobenzyl)phenylsulfonamido)methyl) benzyl)-N-(4-fluorobenzyl)-2-hydroxybenzenesulfonamide (99); N-(4-((3,5-Dichloro-N-(4-fluorobenzyl)-2-hydroxyphenylsulfonamido)methyl)benzyl)-N-(4-fluorobenzyl)-6-(trifluoromethyl)pyridine-3-sulfonamide (100); N-(Biphenyl-4-ylmethyl)-3,5-dichloro-2-hydroxy-N-(3-((4-methylphenylsulfonamido)methyl)benzyl) benzenesulfonamide (101); 3,5-Dichloro-N-(3-((3,5-dichloro-N-(4-fluorobenzyl)phenylsulfonamido)-methyl) benzyl)-2-hydroxy-N-(naphthalen-1-ylmethyl)-benzenesulfonamide (102); 3-Chloro-5-((3,5-dichloro-N-(4-fluorophenethyl)-2-hydroxyphenylsulfonamido)methyl)-N-(3,5-dichlorobenzyl)-N-(4-fluorobenzyl)benzamide (105); 4-((3,5-Dichloro-N-(4-fluorobenzyl)-2-hydroxyphenylsulfonamido)methyl)-N-(3,5-dichlorobenzyl)-N-(4-fluorobenzyl)benzamide (106); N-Benzyl-4-((3,5-dichloro-N-(4-fluorobenzyl)-2-hydroxyphenylsulfonamido)methyl)-N-isopropylbenzamide (107); N-Benzyl-4-((3,5-dichloro-N-(4-fluorobenzyl)-2-hydroxyphenylsulfonamido)methyl)-N-methylbenzamide (108); N,N-Dibutyl-4-((3,5-dichloro-N-(4-fluorobenzyl)-2-hydroxyphenylsulfonamido)methyl) benzamide (109); 4-((3,5-Dichloro-N-(4-fluorobenzyl)-2-hydroxyphenylsulfonamido)methyl)-N-(4-fluorobenzyl)-N-isopentylbenzamide (110); N-Cyclopentyl-4-((3,5-dichloro-N-(4-fluorobenzyl)-2-hydroxyphenylsulfonamido)methyl)-N-(4-fluorobenzyl)benzamide (111); N-Cyclopropyl-4-((3, 5-dichloro-N-(4-fluorobenzyl)-2-hydroxyphenylsulfonamido)methyl)-N-(4-fluorobenzyl)benzamide (112); 4-((3,5-Dichloro-N-(4-fluorobenzyl)-2-hydroxyphenylsulfonamido)methyl)-N-(4-fluorobenzyl)-N-isopropylbenzamide (113); 4-((3,5-Dichloro-N-(4-fluorobenzyl)-2-hydroxyphenylsulfonamido)methyl)-N-(4-fluorobenzyl)-N-(2-hydroxyethyl)benzamide (114); 4-((3,5-Dichloro-N-(4-fluorobenzyl)-2-hydroxyphenylsulfonamido)methyl)-N-(4-fluorobenzyl)-N-isobutylbenzamide (115); N-(Cyclopropylmethyl)-4-((3,5-dichloro-N-(4-fluorobenzyl)-2-hydroxyphenylsulfonamido)methyl)-N-(4-fluorobenzyl)benzamide (116); 4-((3,5-Dichloro-N-(4-fluorobenzyl)-2-hydroxyphenylsulfonamido)methyl)-N-(4-fluorobenzyl)-N-(pyridin-3-ylmethyl)benzamide (117); 4-((3,5-Dichloro-N-(4-fluorobenzyl)-2-hydroxyphenylsulfonamido)methyl)-N-(4-fluorobenzyl)-N-(2-morpholinoethyl)benzamide (118); 4-((3,5-Dichloro-N-(4-fluorobenzyl)-2-hydroxyphenylsulfonamido)methyl)-N-(4-(dimethylamino)phenyl)-N-(4-fluorobenzyl)benzamide (119); 4-((3,5-Dichloro-N-(4-fluorobenzyl)-2-hydroxyphenylsulfonamido)methyl)-N-isopentyl-N-methylbenzamide (120); N-(2-(Benzo[d]thiazol-2-yl)ethyl)-4-((3,5-dichloro-N-(4-fluorobenzyl)-2-hydroxyphenylsulfonamido)methyl)-benzamide (121); 3,5-Dichloro-N-(4-fluorobenzyl)-2-hydroxy-N-(4-(4-phenylpiperidine-1-carbonyl)benzyl)benzenesulfonamide (122); N-(4-(4-Benzylpiperidine-1-carbonyl)benzyl)-3,5-dichloro-N-(4-fluorobenzyl)-2-hydroxybenzenesulfonamide (123); 4-((3,5-Dichloro-N-(4-fluorobenzyl)-2-hydroxyphenylsulfonamido)methyl)-N-(2,2-diphenylethyl)benzamide (124); 3,5-Dichloro-N-(4-(4-(2-chlorophenyl)piperazine-1-carbonyl)benzyl)-N-(4-fluorobenzyl)-2-hydroxybenzenesulfonamide (125); N-(Biphenyl-3-ylmethyl)-4-((3,5-dichloro-N-(4-fluorobenzyl)-2-hydroxyphenylsulfonamido)methyl)-benzamide (126); N-(Biphenyl-4-ylmethyl)-4-((3,5-dichloro-N-(4-fluorobenzyl)-2-hydroxyphenylsulfonamido)methyl)-benzamide (127); N-Cyclohexyl-4-((3,5-dichloro-N-(4-fluorobenzyl)-2-hydroxyphenylsulfonamido)methyl)-benzamide (128); 3,5-Dichloro-N-(4-fluorobenzyl)-2-hydroxy-N-(4-(4-phenylpiperazine-1-carbonyl)benzyl)benzenesulfonamide (129); 3,5-Dichloro-N-(4-fluorobenzyl)-2-hydroxy-N-(4-(piperidine-1-carbonyl)benzyl)benzenesulfonamide (130); 4-((3,5-Dichloro-N-(4-fluorobenzyl)-2-hydroxyphenylsulfonamido)methyl)-N-isopropylbenzamide (131); 4-((3,5-Dichloro-N-(4-fluorobenzyl)-2-hydroxyphenylsulfonamido)methyl)-N-isobutylbenzamide (132); 4-((3,5-Dichloro-N-(4-fluorobenzyl)-2-hydroxyphenylsulfonamido)methyl)-N-ethylbenzamide (133); 4-((3,5-Dichloro-N-(4-fluorobenzyl)-2-hydroxyphenylsulfonamido)methyl)-N-phenethylbenzamide (134); 4-((3,5-Dichloro-N-(4-fluorobenzyl)-2-hydroxyphenylsulfonamido)methyl)-N-isopentylbenzamide (135); 4-((3,5-Dichloro-N-(4-fluorobenzyl)-2-hydroxyphenylsulfonamido)methyl)-N-(3-phenylpropyl)benzamide (136); 4-((3,5-Dichloro-N-(4-fluorobenzyl)-2-hydroxyphenylsulfonamido)methyl)-N-methyl-N-phenethylbenzamide (137); N-Butyl-4-((3,5-dichloro-N-(4-fluorobenzyl)-2-hydroxyphenylsulfonamido)methyl)-benzamide (138); N-(4-(4-Benzhydrylpiperazine-1-carbonyl)benzyl)-3,5-dichloro-N-(4-fluorobenzyl)-2-hydroxybenzenesulfonamide (139); 3,5-Dichloro-N-(4-fluorobenzyl)-2-hydroxy-N-(4-(4-(pyrazin-2-yl)piperazine-1-carbonyl)benzyl)benzenesulfonamide (140); 4-((3,5-Dichloro-N-(4-fluorobenzyl)-2-hydroxyphenylsulfonamido) methyl)-N-(2-phenoxyethyl)benzamide (141); 4-((3,5-Dichloro-N-(4-fluorobenzyl)-2-hydroxyphenylsulfonamido)methyl)-N-(3-(trifluoromethoxy)benzyl)benzamide (142); 4-((3,5-Dichloro-N-(4-fluorobenzyl)-2-hydroxyphenylsulfonamido)methyl)-N-((1S,2R)-2-phenylcyclopropyl)benzamide (143); 3,5-Dichloro-N-(4-fluorobenzyl)-2-hydroxy-N-(4-(3-phenylpyrrolidine-1-carbonyl)benzyl)benzenesulfonamide (144); N-(4-(4-Benzylpiperazine-1-carbonyl)benzyl)-3,5-dichloro-N-(4-fluorobenzyl)-2-hydroxybenzenesulfonamide (145); 4-((3,5-Dichloro-N-(4-fluorobenzyl)-2-hydroxyphenylsulfonamido)methyl)-N-methyl-N-(2-(pyridin-2-yl)ethyl)benzamide (146); 4-((3,5-Dichloro-N-(4-fluorobenzyl)-2-hydroxyphenylsulfonamido) methyl)-N-(4-sulfamoylbenzyl)benzamide (147); 4-((3,5-Dichloro-N-(4-fluorobenzyl)-2-hydroxyphenylsulfonamido)methyl)-N-(4-phenoxybenzyl)benzamide (148); 3,5-Dichloro-N-(4-fluorobenzyl)-2-hydroxy-N-(4-(4-(2-hydroxyethyl)piperidine-1-carbonyl)benzyl)benzenesulfonamide (149); 4-((3,5-Dichloro-N-(4-fluorobenzyl)-2-hydroxyphenylsulfonamido) methyl)-N-(4-(dimethylamino)benzyl)benzamide (150); 4-((3,5-Dichloro-N-(4-fluorobenzyl)-2-hydroxyphenylsulfonamido)methyl)-N-(1,2,3,4-tetrahydronaphthalen-1-yl)benzamide (151); 4-((3,5-Dichloro-N-(4-fluorobenzyl)-2-hydroxyphenylsulfonamido)methyl)-N-(4-(trifluoromethoxy)benzyl)benzamide (152); 4-((3,5-Dichloro-N-(4-fluorobenzyl)-2-hydroxyphenylsulfonamido)methyl)-N-((2-phenylthiazol-4-yl)methyl)benzamide (153); N-tert-Butyl-4-((3,5-dichloro-N-(4-fluorobenzyl)-2-hydroxyphenylsulfonamido)methyl)-benzamide (154); 4-((3,5-Dichloro-N-(4-fluorobenzyl)-2-hydroxyphenylsulfonamido)methyl)-N-(1-phenylethyl)benzamide (155); N-Benzyl-4-((3,5-dichloro-N-(4-fluorobenzyl)-2-hydroxyphenylsulfonamido) methyl)-benzamide (156); 4-((3,5-Dichloro-N-(4-fluorobenzyl)-2-hydroxyphenylsulfonamido)methyl)-N-neopentylbenzamide (157); 4-((3,5-Dichloro-N-(4-fluorobenzyl)-2-hydroxyphenylsulfonamido)methyl)-N-(4-(trifluoromethyl)benzyl)benzamide (158); 4-((3,5-Dichloro-N-(4-fluorobenzyl)-2-hydroxyphenylsulfonamido) methyl)-N-isobutyl-N-methylbenzamide (159); 4-((3,5-Dichloro-N-(4-fluorobenzyl)-2-hydroxyphenylsulfonamido)methyl)-N-isopropyl-N-methylbenzamide (160); N-(Benzo[d]thiazol-6-yl)-4-((3,5-dichloro-N-(4-fluorobenzyl)-2-hydroxyphenylsulfonamido)methyl)-benzamide (161); 4-((3,5-Dichloro-N-(4-fluorobenzyl)-2-hydroxyphenylsulfonamido)methyl)-N-(4-(dimethylamino) phenyl)benzamide (162); Ethyl 3-(4-((3,5-dichloro-N-(4-fluorobenzyl)-2-hydroxyphenylsulfonamido)methyl)-benzamido)butanoate (163); (S,Z)-4-((3,5-Dichloro-N-(4-fluorobenzyl)-2-hydroxyphenylsulfonamido)methyl)-N-(1-methyl-2-oxo-5-phenyl-2,3-dihydro-1H-benzo[e][1,4]diazepin-3-yl)benzamide (164); (R,Z)-4-((3,5-Dichloro-N-(4-fluorobenzyl)-2-hydroxyphenylsulfonamido)methyl)-N-(1-methyl-2-oxo-5-phenyl-2,3-dihydro-1H-benzo[e][1,4]diazepin-3-yl)benzamide (165); 4-((3,5-Dichloro-N-(4-fluorobenzyl)-2-hydroxyphenylsulfonamido) methyl)-N-(3,5-dichlorobenzyl)-N-(4-fluorobenzyl)-3-methoxybenzamide (166); 4-((3,5-Dichloro-2-hydroxy-N-isobutylphenylsulfonamido)methyl)-N-(3,5-dichlorobenzyl)-N-(4-fluorobenzyl)benzamide (167); 4-((3,5-Dichloro-2-hydroxy-N-isopentylphenylsulfonamido)methyl)-N-(3,5-dichlorobenzyl)-N-(4-fluorobenzyl)benzamide (168); 4-((3,5-Dichloro-2-hydroxy-N-(4-methylpentyl)phenylsulfonamido)meth-yl)-N-(3,5-dichlorobenzyl)-N-(4-fluorobenzyl)benzamide (169); 4-((3,5-Dichloro-N-(cyclohexylmethyl)-2-hydroxyphenylsulfonamido)methyl)-N-(3,5-dichlorobenzyl)-N-(4-fluorobenzyl)benzamide (170); 4-((3,5-Dichloro-2-hydroxy- N-(3-methylbut-2-enyl)phenylsulfonamido)methyl)-N-(3,5-dichlorobenzyl)-N-(4-fluorobenzyl)benzamide (171); 4-((3,5-Dichloro-2-hydroxy-N-(4-isobutoxybenzyl)phenylsulfonamido)-methyl)-N-(3,5-dichlorobenzyl)-N-(4-fluorobenzyl)benzamide (172); 4-((3,5-Dichloro-2-hydroxy-N-(3-isobutoxybenzyl)phenylsulfonamido)-methyl)-N-(3,5-dichlorobenzyl)-N-(4-fluorobenzyl)benzamide (173); 4-((3,5-Dichloro-N-((4'-chlorobiphenyl-3-yl)methyl)-2-hydroxyphenylsulfonamido)methyl)-N-(3,5-dichlorobenzyl)-N-(4-fluorobenzyl)benzamide (174); 4-(3,5-Dichloro-N-(4-fluorobenzyl)-2-hydroxyphenylsulfonamido)-N-(3,5-dichlorobenzyl)-N-(4-fluorobenzyl)benzamide (175); 3,5-Dichloro-N-(4-((3,5-dichloro-N-(2-hydroxyethyl)phenylsulfonamido)methyl)benzyl)-N-(4-fluorobenzyl)-2-hydroxybenzenesulfonamide (176); 3,5-Dichloro-N-(4-fluorobenzyl)-N-(4-((N-(4-fluorobenzyl)phenylsulfonamido)-methyl)benzyl)-2-hydroxybenzenesulfonamide (177); N-(4-((Bis(pyridin-4-ylmethyl)amino)methyl)benzyl)-3,5-dichloro-N-(4-fluorobenzyl)-2-hydroxybenzenesulfonamide (178); 3,5-Dichloro-N-(4-((3,5-dichloro-N-(pyridin-2-ylmethyl)phenylsulfonamido)methyl)-benzyl)-N-(4-fluorobenzyl)-2-hydroxybenzenesulfonamide (179); N-(4-Benzoylbenzyl)-3,5-dichloro-N-(4-fluorobenzyl)-2-hydroxybenzenesulfonamide (180); 3,5-Dichloro-N-(4-fluorobenzyl)-2-hydroxy-N-(4-(4-methylbenzoyl)benzyl)benzenesulfonamide (181); 3,5-Dichloro-N-(4-fluorobenzyl)-2-hydroxy-N-(4-(hydroxy(phenyl)methyl)benzyl)benzenesulfonamide (182); N-(4-Benzylbenzyl)-3,5-dichloro-N-(4-fluorobenzyl)-2-hydroxybenzenesulfonamide (183); N-(3-((3,5-Dichloro-N-((4'-fluorobiphenyl-4-yl)methyl)-2-hydroxyphenylsulfonamido)methyl)benzyl)-N-isobutyl-2-phenoxybenzamide (184); N-(3-((3,5-Dichloro-N-((4'-fluorobiphenyl-4-yl)methyl)-2-hydroxyphenylsulfonamido) methyl)benzyl)-N-isobutyl-6-(piperidin-1-yl)nicotinamide (185); N-(3-((3,5-Dichloro-N-((4'-fluorobiphenyl-4-yl)methyl)-2-hydroxyphenylsulfonamido)methyl)-benzyl)-N-isobutyl-1H-indole-4-carboxamide (186); 4-Cyclohexyl-N-(3-((3,5-dichloro-N-((4'-fluorobiphenyl-4-yl)methyl)-2-hydroxyphenylsulfonamido)methyl)-benzyl)-N-isobutylbenzamide (187); 3-Chloro-N-(3-((3,5-dichloro-N-((4'-fluorobiphenyl-4-yl)methyl)-2-hydroxyphenylsulfonamido) methyl)-benzyl)-N-isobutyl-4-nitrobenzamide (188); N-(3-((3,5-Dichloro-N-((4'-fluorobiphenyl-4-yl)methyl)-2-hydroxyphenylsulfonamido)methyl)-benzyl)-N-isobutyl-2-naphthamide (189); N-(3-((3,5-Dichloro-N-((4'-fluorobiphenyl-4-yl)methyl)-2-hydroxyphenylsulfonamido)methyl)-benzyl)-N-isobutyl-2,3-dioxo-1,2,3,4-tetrahydroquinoxaline-6-carboxamide (190); N-(3-((3,5-Dichloro-N-((4'-fluorobiphenyl-4-yl)methyl)-2-hydroxyphenylsulfonamido)methyl)-benzyl)-N-isobutylbenzo[d]thiazole-2-carboxamide (191); N-(3-((3,5-Dichloro-N-((4'-fluorobiphenyl-4-yl)methyl)-2-hydroxyphenylsulfonamido)methyl)-benzyl)-N-isobutyl-4-(pyridin-4-yl)benzamide (192); N-(3-((3,5-Dichloro-N-((4'-fluorobiphenyl-4-yl)methyl)-2-hydroxyphenylsulfonamido)methyl)-benzyl)-N-isobutylbiphenyl-4-carboxamide (193); 3,5-Dichloro-N-(3-((3-(2,3-dichlorophenyl)-1-isobutylureido) methyl)benzyl)-N-((4'-fluorobiphenyl-4-yl)methyl)-2-hydroxybenzenesulfonamide (194); N-(3-((3-(Biphenyl-2-O-1-isobutylureido) methyl)benzyl)-3,5-dichloro-N-((4'-fluorobiphenyl-4-yl)methyl)-2-hydroxybenzenesulfonamide (195); 3,5-Dichloro-N-((4'-fluorobiphenyl-4-yl)methyl)-2-hydroxy-N-(3-((1-isobutyl-3-(3-methoxyphenyl) ureido) methyl)-benzyl)benzenesulfonamide (196); N-(3-((3-(4-(Benzyloxy)phenyl)-1-isobutylureido)methyl)benzyl)-3,5-dichloro-N-((4'-fluorobiphenyl-4-yl)methyl)-2-hydroxybenzenesulfonamide (197); N-(3-((3-(2-tert-Butyl-6-methylphenyl)-1-isobutylureido)methyl)benzyl)-3,5-dichloro-N-((4'-fluorobiphenyl-4-yl)methyl)-2-hydroxybenzenesulfonamide (198); 3,5-Dichloro-N-(3-((3-(2,6-diisopropylphenyl)-1-isobutylureido)methyl)benzyl)-N-((4'-fluorobiphenyl-4-yl)methyl)-2-hydroxybenzenesulfonamide (199); 3,5-Dichloro-N-((4'-fluorobiphenyl-4-yl)methyl)-2-hydroxy-N-(3-((1-isobutyl-3-(2-isopropylphenyl)ureido)methyl)-benzyl) benzenesulfonamide (200); 3,5-Dichloro-N-(3-((3-(2,5-difluorophenyl)-1-isobutylureido)methyl)benzyl)-N-((4'-fluorobiphenyl-4-yl)methyl)-2-hydroxybenzenesulfonamide (201); 3,5-Dichloro-N-((4'-fluorobiphenyl-4-yl)methyl)-2-hydroxy-N-(3-((1-isobutyl-3,3-dimethylureido)methyl)benzyl)-benzenesulfonamide (202); N-(3-((3-(Biphenyl-2-yl)-1-isobutyl-3-methylureido)methyl)benzyl)-3,5-dichloro-N-((4'-fluorobiphenyl-4-yl)methyl)-2-hydroxybenzenesulfonamide (203); 3,5-Dichloro-N-(3-((3-(2,3-dichlorophenyl)-1-isobutyl-3-methylureido)methyl) benzyl)-N-((4'-fluorobiphenyl-4-yl)methyl)-2-hydroxybenzenesulfonamide (204); 3,5-Dichloro-N-(3-((3-(2,5-difluorophenyl)-1-isobutyl-3-methylureido)methyl) benzyl)-N-((4'-fluorobiphenyl-4-yl)methyl)-2-hydroxybenzenesulfonamide (205); 3,5-Dichloro-N-(2-((3,5-dichloro-N-(4-fluorobenzyl)phenylsulfonamido)-methyl)benzyl)-N-(4-fluorobenzyl)-2-hydroxybenzenesulfonamide (206); N-Benzyl-3-chloro-5-(N-((4'-chlorobiphenyl-3-yl)methyl)-N-(4-fluorobenzyl)sulfamoyl)-4-hydroxybenzamide (207); 5-Chloro-3-(N-(4-fluorobenzyl)-N-(4-(4-(trifluoromethyl)phenoxy)benzyl) sulfamoyl)-2-hydroxy-N-phenylbenzamide (208); 3,5-Dichloro-N-(3-(4-fluorophenoxy)benzyl)-2-hydroxy-N-(4-phenylbutyl)benzenesulfonamide (209); 3-Chloro-5-(N-((4'-chlorobiphenyl-3-yl)methyl)-N-(4-fluorobenzyl)-sulfamoyl)-4-hydroxy-N-phenylbenzamide (210); 3-Chloro-5-(N-((4'-chlorobiphenyl-3-yl)methyl)-N-(4-fluorobenzyl)-sulfamoyl)-4-hydroxy-N-isopropylbenzamide (211); 3-Chloro-5-(N-((4'-chlorobiphenyl-3-yl)methyl)-N-(4-fluorobenzyl)-sulfamoyl)-4-hydroxybenzamide (212); 3-Chloro-5-(N-((4'-chlorobiphenyl-3-yl)methyl)-N-(4-fluorobenzyl)-sulfamoyl)-4-hydroxy-N-(3-hydroxypropyl)benzamide (213); 3-Chloro-5-(N-((4'-chlorobiphenyl-3-yl)methyl)-N-(4-fluorobenzyl)-sulfamoyl)-N-(2,3-dihydroxypropyl)-4-hydroxybenzamide (214); 3-Chloro-5-(N-((4'-chlorobiphenyl-3-yl)methyl)-N-(4-fluorobenzyl)-sulfamoyl)-4-hydroxy-N-(4-(2-hydroxyethyl)phenyl)benzamide (215); Methyl 3-chloro-5-(N-((4'-chloro-biphenyl-3-yl)methyl)-N-(4-fluorobenzyl)sulfamoyl)-4-hydroxybenzoate (216); 4-Aminophenethyl 3-chloro-5-(N-((4'-chlorobiphenyl-3-yl)methyl)-N-(4-fluorobenzyl)sulfamoyl)-4-hydroxybenzoate (217); N-Benzyl-3-chloro-5-(N-((4',5-dichloro-6-methoxybiphenyl-3-yl)methyl)-N-(4-fluorobenzyl)sulfamoyl)-4-hydroxybenzamide (218); N-Benzyl-3-chloro-5-(N-(4-fluorobenzyl)-N-(4-(4-(trifluoromethyl)-phenoxy)benzyl)sulfamoyl)-4-hydroxybenzamide (219); N-Benzyl-3-chloro-5-(N-((4',5-dichloro-6-methoxybiphenyl-3-yl)methyl)-N-(4-(4-fluorophenoxy)benzyl)sulfamoyl)-4-hydroxybenzamide (220); N-Benzyl-3-chloro-5-(N-((4',5-dichloro-6-methoxybiphenyl-3-yl)methyl)-N-(4-(4-(trifluoromethyl)phenoxy)benzyl)-sulfamoyl)-4-hydroxybenzamide (221); 3-(N-(2-(1H-Indol-1-yl)ethyl)-N-((4',5-dichloro-6-methoxybiphenyl-3-yl)methyl)sulfamoyl)-N-benzyl-5-chloro-4-hydroxybenzamide (222); 5-Chloro-3-(N-((4'-chlorobiphenyl-3-yl)methyl)-N-(4-fluorobenzyl)-sulfamoyl)-2-hydroxy-N-phenylbenzamide (223); N-Benzyl-5-chloro-3-(N-((4'-chlorobiphenyl-3-yl)methyl)-

N-(4-fluorobenzyl)sulfamoyl)-2-hydroxybenzamide (224); 5-Chloro-3-(N-((4'-chlorobiphenyl-3-yl)methyl)-N-(4-fluorobenzyl)-sulfamoyl)-N-(2,3-dihydroxypropyl)-2-hydroxybenzamide (225); Methyl 5-chloro-3-(N-((4'-chloro-biphenyl-3-yl)methyl)-N-(4-fluorobenzyl)sulfamoyl)-2-hydroxybenzoate (226); 5-Chloro-3-(N-((4'-chlorobiphenyl-3-yl)methyl)-N-(4-fluorobenzyl)-sulfamoyl)-2-hydroxy-N-(1H-pyrazol-4-yl)benzamide (227); 5-Chloro-3-(N-((4'-chlorobiphenyl-3-yl)methyl)-N-(4-fluorobenzyl)-sulfamoyl)-2-hydroxy-N-(1H-indol-4-yl)benzamide (228); 5-Chloro-3-(N-((4'-chlorobiphenyl-3-yl)methyl)-N-(4-fluorobenzyl)-sulfamoyl)-2-hydroxy-N-(2-hydroxyethyl)benzamide (229); N-((4'-Aminobiphenyl-3-yl)methyl)-3,5-dichloro-N-(4-fluorobenzyl)-2-hydroxybenzenesulfonamide (230); N-((4'-Azidobiphenyl-3-yl)methyl)-3,5-dichloro-N-(4-fluorobenzyl)-2-hydroxybenzenesulfonamide (231); 3,5-Dichloro-N-((4'-chlorobiphenyl-3-yl)methyl)-N-(4-fluorobenzyl)-2-hydroxybenzenesulfonamide (232); 3-Chloro-N-((4'-chlorobiphenyl-3-yl)methyl)-N-(4-fluorobenzyl)-2-hydroxy-5-(trifluoromethyl)benzenesulfonamide (233); 5-Chloro-N-((4'-chlorobiphenyl-3-yl)methyl)-N-(4-fluorobenzyl)-2-hydroxy-3-(trifluoromethyl)benzenesulfonamide (234); 3,5-Dichloro-N-(3-(4-fluorophenoxy)benzyl)-2-hydroxy-N-(4-octylbenzyl)benzenesulfonamide (235); 3,5-Dichloro-N-(3-(4-fluorophenoxy)-benzyl)-2-hydroxy-N-(4-pentyl-benzyl)benzenesulfonamide (236); 3,5-Dichloro-N-(3-(4-fluorophenoxy)-benzyl)-2-hydroxy-N-nonyl-benzenesulfonamide (237); 3,5-Dichloro-N-(2,6-dimethylhept-5-enyl)-N-(3-(4-fluorophenoxy)-benzyl)-2-hydroxybenzene-sulfonamide (238); 3,5-Dichloro-N-(3-(4-fluorophenoxy)-benzyl)-2-hydroxy-N-(3,5,5-trimethylhexyl)benzenesulfonamide (239); 3,5-Dichloro-N-((4'-chloro-2-methoxybiphenyl-3-yl)methyl)-N-(4-fluorobenzyl)-2-hydroxybenzenesulfonamide (240); 3,5-Dichloro-N-((4',6-dichlorobiphenyl-3-yl)methyl)-N-(4-fluorobenzyl)-2-hydroxybenzenesulfonamide (241); 3,5-Dichloro-N-((4',5-dichloro-biphenyl-3-yl)methyl)-N-(4-fluorobenzyl)-2-hydroxybenzene-sulfonamide (242); 3,5-Dichloro-N-((4,4'-dichloro-biphenyl-3-yl)methyl)-N-(4-fluorobenzyl)-2-hydroxybenzene-sulfonamide (243); 3,5-Dichloro-N-((4'-chloro-6-methyl-biphenyl-3-yl)methyl)-N-(4-fluorobenzyl)-2-hydroxybenzene-sulfonamide (244); N-((5-Bromo-4'-chlorobiphenyl-3-yl)methyl)-3,5-dichloro-N-(4-fluoro-benzyl)-2-hydroxybenzene-sulfonamide (245); 3,5-Dichloro-N-((4'-chloro-5-methoxybiphenyl-3-yl)methyl)-N-(4-fluorobenzyl)-2-hydroxybenzene-sulfonamide (246); 3,5-Dichloro-N-((4'-chloro-4-methoxybiphenyl-3-yl)methyl)-N-(4-fluorobenzyl)-2-hydroxybenzene-sulfonamide (247); 3,5-Dichloro-N-((4'-chloro-5,6-dimethoxybiphenyl-3-yl)methyl)-N-(4-fluorobenzyl)-2-hydroxy-benzenesulfonamide (248); 3,5-Dichloro-N-((4',5-dichloro-6-methoxybiphenyl-3-yl)methyl)-N-(4-fluorobenzyl)-2-hydroxybenzenesulfonamide (249); 3,5-Dichloro-N-((4'-chloro-6-methoxybiphenyl-3-yl)methyl)-N-(4-fluorobenzyl)-2-hydroxy-benzenesulfonamide (250); 3,5-Dichloro-N-(4-fluorobenzyl)-2-hydroxy-N-(4-(4-(trifluoromethyl)phenoxy)benzyl)benzene-sulfonamide (251); 3,5-Dichloro-N-((4',5-dichloro-6-methoxybiphenyl-3-yl)methyl)-2-hydroxy-N-(4-(4-(trifluoromethyl)phenoxy)benzyl)-benzenesulfonamide (252); 3,5-Dichloro-N-(4-fluorobenzyl)-2-hydroxy-N-((4'-(trifluoromethyl)-biphenyl-4-yl)methyl)benzene-sulfonamide (253); N-((4'-tert-Butylbiphenyl-3-yl)methyl)-3,5-dichloro-N-(4-fluorobenzyl)-2-hydroxybenzene-sulfonamide (254); 3,5-Dichloro-N-((3'-chlorobiphenyl-3-yl)methyl)-N-(4-fluorobenzyl)-2-hydroxybenzenesulfonamide (255); N-((4'-Butylbiphenyl-3-yl)methyl)-3,5-dichloro-N-(4-fluorobenzyl)-2-hydroxybenzenesulfonamide (256); 3,5-Dichloro-N-((2'-chlorobiphenyl-3-yl)methyl)-N-(4-fluorobenzyl)-2-hydroxybenzenesulfonamide (257); 3,5-Dichloro-N-((4'-chlorobiphenyl-4-yl)methyl)-N-(4-fluorobenzyl)-2-hydroxybenzenesulfonamide (258); 3,5-Dichloro-N-((4'-chlorobiphenyl-3-yl)methyl)-2-hydroxy-N-(4-(trifluoromethyl)benzyl)benzene-sulfonamide (259); 3,5-Dichloro-N-((4'-chlorobiphenyl-3-yl)methyl)-N-(4-fluorophenethyl)-2-hydroxybenzenesulfonamide (260); 3,5-Dichloro-N-((4'-chlorobiphenyl-3-yl)methyl)-N-(2,3-dihydro-1H-inden-2-yl)-2-hydroxybenzenesulfonamide (261); N-(2-(1H-Indol-1-yl)ethyl)-3,5-dichloro-N-((4'-chlorobiphenyl-3-yl)methyl)-2-hydroxybenzenesulfonamide (262); N-(2-(1H-Indol-1-yl)ethyl)-3,5-dichloro-N-((4',5-dichloro-6-methoxybiphenyl-3-yl)methyl)-2-hydroxybenzenesulfonamide (263); 3,5-Dichloro-N-((4'-chlorobiphenyl-3-yl)methyl)-N-(4-(4-fluorophenoxy)benzyl)-2-hydroxybenzenesulfonamide (264); 3,5-Dichloro-N-(4-fluoro-3-(trifluoromethyl)benzyl)-N-(4-fluorobenzyl)-2-hydroxybenzenesulfonamide (265); 3,5-Dichloro-N-(4-fluorobenzyl)-2-hydroxy-N-(3-methylbenzyl)benzenesulfonamide (266); 3,5-Dichloro-N-(4-fluorophenethyl)-2-hydroxy-N-(3-(phenethylthiomethyl)benzyl)benzenesulfonamide (267); 3,5-Dichloro-N-(4-fluorophenethyl)-2-hydroxy-N-(4-(phenethylthiomethyl)benzyl)-benzenesulfonamide (268); 3,5-Dichloro-N-(4-fluorophenethyl)-2-hydroxy-N-(3-nitro-4-(phenethylthiomethyl)benzyl)-benzenesulfonamide (269); 6-((3,5-Dichloro-N-(4-fluorobenzyl)-2-hydroxyphenylsulfonamido) methyl)-N-(3,5-dichlorobenzyl)-N-(4-fluorobenzyl)picolinamide (270); 6-((3,5-Dichloro-N-(4-fluorobenzyl)-2-hydroxyphenylsulfonamido)methyl)-N-(4-fluorobenzyl)picolinamide (271); 3,5-Dichloro-N-((6-(4-chlorobenzyl)pyridin-2-yl)methyl)-N-(4-fluorobenzyl)-2-hydroxybenzenesulfonamide (272); 3,5-Dichloro-N-((6-(4-chlorophenoxy)pyridin-2-yl)methyl)-N-(4-fluorobenzyl)-2-hydroxybenzenesulfonamide (273); 3,5-Dichloro-N-(4-chlorobenzyl)-N-((6-(4-chlorophenyl)pyridin-2-yl)methyl)-2-hydroxybenzenesulfonamide (274); and 3,5-Dichloro-N-((6-(4-chlorophenyl)pyridin-2-yl)methyl)-N-(4-fluorobenzyl)-2-hydroxybenzenesulfonamide (275).

12. A pharmaceutical composition, comprising a pharmaceutically acceptable carrier and a compound of claim 1, or pharmaceutically acceptable salts thereof.

* * * * *

UNITED STATES PATENT AND TRADEMARK OFFICE
CERTIFICATE OF CORRECTION

PATENT NO. : 8,501,992 B2
APPLICATION NO. : 13/055056
DATED : August 6, 2013
INVENTOR(S) : Kap-Sun Yeung et al.

Page 1 of 1

It is certified that error appears in the above-identified patent and that said Letters Patent is hereby corrected as shown below:

In the Claims:

Claim 1, col. 269, line 16, delete "$C_{3-10}$-carbocyclic" and insert -- $C_{3-10}$carbocyclic --, therefor.

Claim 1, col. 270, line 2, delete "Re;" and insert -- $R_e$; --, therefor.

Claim 2, col. 271, line 6, delete ")$_r$ phenyl" and insert -- )$_r$-phenyl --, therefor.

Claim 6, col. 271, line 59, delete "napthyl" and insert -- naphthyl --, therefor.

Claim 9, col. 272, line 30, delete "$(CH_2)_rC_{3-6}$" and insert -- $(CH_2)_r$-$C_{3-6}$ --, therefor.

Claim 10, col. 272, line 49, delete "compounds" and insert -- compound --, therefor.

Signed and Sealed this
Thirteenth Day of May, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,501,992 B2 | Page 1 of 1 |
| APPLICATION NO. | : 13/055056 | |
| DATED | : August 6, 2013 | |
| INVENTOR(S) | : Kim et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 171 days.

Signed and Sealed this
Seventeenth Day of February, 2015

Michelle K. Lee
*Deputy Director of the United States Patent and Trademark Office*